(12) United States Patent
Binkowski et al.

(10) Patent No.: US 9,290,794 B2
(45) Date of Patent: *Mar. 22, 2016

(54) MUTANT PROTEASE BIOSENSORS WITH ENHANCED DETECTION CHARACTERISTICS

(71) Applicant: PROMEGA CORPORATION, Madison, WI (US)

(72) Inventors: Brock Binkowski, Sauk City, WI (US); Braeden Butler, Madison, WI (US); Lance P. Encell, Fitchburg, WI (US); Frank Fan, Verona, WI (US); Brad Hook, Baraboo, WI (US); Paul Otto, Madison, WI (US); Kimberly Risma, Cincinnati, OH (US); Gediminas Vidugiris, Fitchburg, WI (US); Susan Wigdal, Belleville, WI (US); Kristopher Zimmerman, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 180 days.

This patent is subject to a terminal disclaimer.

(21) Appl. No.: 13/674,655

(22) Filed: Nov. 12, 2012

(65) Prior Publication Data

US 2014/0030725 A1 Jan. 30, 2014

Related U.S. Application Data

(63) Continuation-in-part of application No. 13/105,648, filed on May 11, 2011, now Pat. No. 8,735,559.

(60) Provisional application No. 61/558,796, filed on Nov. 11, 2011, provisional application No. 61/470,845, filed on Apr. 1, 2011, provisional application No. 61/333,706, filed on May 11, 2010.

(51) Int. Cl.
*C12Q 1/66* (2006.01)
*C12Q 1/37* (2006.01)
*C12N 9/02* (2006.01)

(52) U.S. Cl.
CPC ............... *C12Q 1/66* (2013.01); *C12N 9/0069* (2013.01); *C12Q 1/37* (2013.01)

(58) Field of Classification Search
CPC ........... C12N 9/0069; C12Q 1/66; C12Q 1/37
See application file for complete search history.

(56) References Cited

U.S. PATENT DOCUMENTS

| | | | |
|---|---|---|---|
| 5,097,026 A | 3/1992 | Jahnsen | |
| 6,251,667 B1 | 6/2001 | Habener et al. | |
| 6,270,964 B1 | 8/2001 | Michnick et al. | |
| 6,294,330 B1 | 9/2001 | Michnick et al. | |
| 6,406,856 B1 | 6/2002 | Glover et al. | |
| 6,428,951 B1 | 8/2002 | Michnick et al. | |
| 6,573,059 B1 | 6/2003 | Reymond | |
| 6,602,677 B1 | 8/2003 | Wood et al. | |
| 6,762,026 B1 | 7/2004 | Sugiyama | |
| 6,808,874 B2 | 10/2004 | Griffiths | |
| 6,855,515 B1* | 2/2005 | Rosen et al. | 435/68.1 |
| 6,890,745 B1 | 5/2005 | Leng | |
| 6,936,687 B1* | 8/2005 | Komoriya et al. | 530/300 |
| 7,083,911 B2 | 8/2006 | Wood et al. | |
| 7,241,584 B2 | 7/2007 | Wood et al. | |
| 7,452,663 B2 | 11/2008 | Wood et al. | |
| 7,700,310 B2 | 4/2010 | Somberg et al. | |
| 7,732,128 B2 | 6/2010 | Wood et al. | |
| 7,741,067 B2 | 6/2010 | Hawkins et al. | |
| 7,927,816 B2* | 4/2011 | Reed et al. | 435/7.1 |
| 7,927,871 B2* | 4/2011 | Packard et al. | 435/325 |

(Continued)

FOREIGN PATENT DOCUMENTS

| | | |
|---|---|---|
| EP | 1097992 | 5/2001 |
| EP | 1229330 | 8/2002 |

(Continued)

OTHER PUBLICATIONS

Thornberry, N. A., 1997, "A combinatorial approach defines specificities of members of the caspase family and granzyme B. Functional relationships established for key mediators of apoptosis", The Journal of Biological Chemistry, vol. 272, No. 29, pp. 17907-17911.*
Li, H., et al., 1998, "Cleavage of BID by caspase 8 mediates the mitochondrial damage in the Fas pathway of apoptosis", Cell, vol. 94, pp. 491-501.*
Gross, A., et al., 1999, "Caspase cleaved BID targets mitochondria and is required for cytochrome c release, while BCL-XL prevents this release but not tumor necrosis factor-R1/Fas death", The Journal of Biological Chemistry, vol. 274, No. 2, pp. 1156-1163.*
European Patent Office Action for Application No. 07754666.1 dated Feb. 11, 2014 (5 pages).

(Continued)

*Primary Examiner* — Manjunath Rao
*Assistant Examiner* — William W Moore
(74) *Attorney, Agent, or Firm* — Michael Best & Friedrich LLP

(57) ABSTRACT

A polynucleotide encoding a biosensor polypeptide comprising a modified circularly-permuted thermostable luciferase and a linker linking the C-terminal portion of the thermostable luciferase to the N-terminal portion of the thermostable luciferase. The modified circularly-permuted thermostable luciferase is modified relative to a parental circularly-permuted thermostable luciferase. The linker contains a sensor region capable of interacting with a target molecule in a cell. The modified circularly-permuted thermostable luciferase has an enhanced response after interaction of the biosensor with the target molecule relative to the parental circularly-permuted thermostable luciferase in the presence of the target molecule. Alternatively, the modified circularly-permuted thermostable luciferase has an enhanced response after interaction of the biosensor with the target molecule relative to the modified circularly-permuted thermostable luciferase in the absence of the target molecule.

5 Claims, 43 Drawing Sheets

(56) References Cited

U.S. PATENT DOCUMENTS

| | | | |
|---|---|---|---|
| 8,030,017 B2 | 10/2011 | Wood et al. | |
| 8,183,036 B2 | 5/2012 | Fan et al. | |
| 8,227,572 B2 | 7/2012 | Leitch et al. | |
| 2002/0022220 A1 | 2/2002 | Izevbigie | |
| 2002/0132327 A1* | 9/2002 | Hay et al. | 435/195 |
| 2002/0150885 A1 | 10/2002 | Weber et al. | |
| 2002/0151014 A1 | 10/2002 | Campbell | |
| 2003/0003506 A1 | 1/2003 | Umezawa et al. | |
| 2003/0053995 A1* | 3/2003 | Hung et al. | 424/93.21 |
| 2003/0068801 A1 | 4/2003 | Wood et al. | |
| 2003/0092098 A1 | 5/2003 | Bryan et al. | |
| 2003/0104507 A1 | 6/2003 | Wood et al. | |
| 2003/0170850 A1 | 9/2003 | Cardone et al. | |
| 2003/0203407 A1 | 10/2003 | Craig et al. | |
| 2003/0232404 A1 | 12/2003 | Wood et al. | |
| 2004/0096926 A1* | 5/2004 | Packard et al. | 435/23 |
| 2004/0101922 A1 | 5/2004 | Somberg et al. | |
| 2004/0157272 A1 | 8/2004 | Cardone et al. | |
| 2005/0026171 A1 | 2/2005 | Hawkins et al. | |
| 2005/0054573 A1 | 3/2005 | Werner et al. | |
| 2005/0153310 A1 | 7/2005 | Fan et al. | |
| 2005/0170442 A1 | 8/2005 | Kupcho et al. | |
| 2005/0176071 A1 | 8/2005 | Nikiforov et al. | |
| 2005/0181452 A1 | 8/2005 | Westwick et al. | |
| 2006/0048592 A1 | 3/2006 | Wood et al. | |
| 2006/0110364 A1 | 5/2006 | Harding | |
| 2006/0183212 A1 | 8/2006 | Wood et al. | |
| 2007/0184493 A1* | 8/2007 | Packard et al. | 435/7.2 |
| 2008/0199898 A1* | 8/2008 | Packard et al. | 435/24 |
| 2008/0206798 A1 | 8/2008 | Wood et al. | |
| 2009/0075292 A1* | 3/2009 | Reed et al. | 435/7.1 |
| 2009/0137019 A1 | 5/2009 | Wood et al. | |
| 2009/0215864 A1 | 8/2009 | Feinstein | |
| 2009/0253131 A1 | 10/2009 | Wigdal et al. | |
| 2009/0286299 A1 | 11/2009 | Ronaghi et al. | |
| 2009/0305280 A1 | 12/2009 | Binkowski et al. | |
| 2009/0311769 A1 | 12/2009 | Wood et al. | |
| 2010/0021949 A1 | 1/2010 | Somberg et al. | |
| 2010/0297620 A1* | 11/2010 | Umezawa et al. | 435/6 |
| 2011/0039257 A1 | 2/2011 | Binkowski et al. | |
| 2011/0283373 A1 | 11/2011 | Binkowski et al. | |
| 2012/0009647 A1 | 1/2012 | Wood et al. | |
| 2012/0117667 A1* | 5/2012 | Klaubert et al. | 800/3 |
| 2012/0174242 A1* | 7/2012 | Binkowski et al. | 800/13 |
| 2012/0214677 A1 | 8/2012 | Fan et al. | |
| 2014/0273156 A1* | 9/2014 | Fan | C12N 9/0069 435/189 |
| 2014/0298500 A1* | 10/2014 | Binkowski | C12N 9/0069 800/13 |
| 2014/0308211 A1* | 10/2014 | Binkowski | C12N 9/0069 424/9.6 |

FOREIGN PATENT DOCUMENTS

| | | |
|---|---|---|
| JP | 5501862 | 4/1993 |
| JP | 2002315589 | 10/2002 |
| JP | 2012/090635 | 5/2012 |
| WO | WO 95/18853 | 7/1995 |
| WO | WO 00/14267 | 3/2000 |
| WO | WO 00/24768 | 5/2000 |
| WO | WO 00/75332 | 12/2000 |
| WO | WO 01/20002 | 3/2001 |
| WO | WO 02/06458 | 1/2002 |
| WO | WO 02/08766 | 1/2002 |
| WO | WO 02/16944 | 2/2002 |
| WO | WO 02/059262 | 8/2002 |
| WO | WO 03/066883 | 8/2003 |
| WO | WO 2004/027094 | 4/2004 |
| WO | WO 2004/038039 | 5/2004 |
| WO | WO 2004/043992 | 5/2004 |
| WO | WO 2004/059294 | 7/2004 |
| WO | WO 2004/081189 | 9/2004 |
| WO | WO 2005/015161 | 2/2005 |
| WO | WO 2005/038029 | 4/2005 |
| WO | WO 2005/052186 | 6/2005 |
| WO | WO 2006/023972 | 3/2006 |
| WO | WO 2007/120522 | 10/2007 |
| WO | 2008/030968 | 3/2008 |
| WO | 2009/049892 | 4/2009 |
| WO | WO 2009/142735 | 11/2009 |
| WO | WO 2011/143339 | 11/2011 |
| WO | WO 2013/071237 * | 5/2013 |

OTHER PUBLICATIONS

Japanese Patent Office Action for Application No. 2006-534242 dated Feb. 4, 2014 (8 pages, English translation included).

United States Patent Office Action for U.S. Appl. No. 11/732,105 dated Sep. 4, 2013 (10 pages).

European Patent Office Action for Application No. 11720279.6 dated Sep. 24, 2013 (7 pages).

Japanese Patent Office Action for Application No. 2011-43966 dated Jul. 2, 2014 (7 pages, English translation included).

European Patent Office Action for Application No. 10182746.7 dated Nov. 21, 2013 (3 pages).

De Wet, J.R., et al., 1987, "Firefly luciferase gene: structure and expression in mammalian cells", Molecular and Cellular Biology, vol. 7, No. 2, pp. 725-737.

Tatsumi, H., et al., 1992, "Molecular cloning and expression in *Escherichia coli* of a cDNA clone encoding luciferase of a firefly, Lucio la lateralis", Biochimica et Biophysica Acta, vol. 1131, pp. 161-165.

Devine, J.H., et al., 1993, "Luciferase from the East European firefly *Luciola mingrelica*: cloning and nucleotide sequence of the cDNA, overexpression in *Escherichia coli* and purification of the enzyme", Biochimica et Biophysica Acta, vol. 1173, pp. 121-132.

Sala-Newby, G.B., et al., 1996, "Sequence and biochemical similarities between the luciferases of the glow-worm *Lampyris noctiluca* and the firefly *Photinus pyralis*", Biochemical Journal, vol. 313, pp. 761-767.

Alipour B.S., et al., 2004, "Molecular cloning, sequence analysis, and expression of a cDNA encoding the luciferase from the glow-worm, *Lampyris turkestanicus*", Biochemical and Biophysical Research Communications, vol. 325, pp. 215-222.

Viviani, V. R., et al., 2004, "Cloning and characterization of the cDNA for the Brazilian Cratomorphus distinctus larval firefly luciferase: similarities with European Lampyris noctiluca and Asiatic Pyrocoelia luciferases", Comparative Biochemistry and Physiology, Part B, vol. 139, pp. 151-156.

Li, X., et al., 2006, "Phylogenetic relationship of the firefly, *Diaphanes pectineal* is based on the DNA sequence and gene structure of luciferase", Dong Wu Xue Za Zhi [Zoological Research], vol. 27, No. 4, pp. 367-374.

Oba, Y., et al., 2010, "Identification and characterization of a luciferase isotype in the Japanese firefly, *Luciola cruciata*, involving in the dim glow of firefly eggs", Biochemistry, vol. 49, pp. 10788-10795.

European Patent Office Action for Application No. 10182742.6 dated Oct. 15, 2013 (4 pages).

Japanese Patent Office Action for Application No. 2011-510512 dated Nov. 25, 2013 (Original, 5 pages).

United States Patent Office Notice of Allowance for U.S. Appl. No. 13/105,648 dated Jan. 10, 2014 (12 pages).

European Patent Office Action for Application No. 11155576.9 dated Nov. 20, 2013 (4 pages).

United States Patent Office Action for U.S. Appl. No. 13/454,464 dated Apr. 30, 2013 (8 pages).

Japanese Patent Office Action for Application No. 2011-43966 dated May 1, 2013 (6 pages) English translation.

United States Patent Office Action for U.S. Appl. No. 13/105,648 dated Jun. 20, 2013 (14 pages).

Japanese Patent Office Action for Application No. 2009-504249 dated May 26, 2014 (5 pages, English translation included).

European Patent Office Action for Application No. 10182742.6 dated Apr. 2, 2014 (5 pages).

European Patent Office Action for Application No. 11720279.6 dated May 2, 2014 (5 pages).

(56) References Cited

OTHER PUBLICATIONS

Japanese Patent Office Action for Application No. 2012-248580 dated May 1, 2014 (5 pages, English translation included).
United States Patent Office Action for U.S. Appl. No. 11/732,105 dated May 23, 2014 (10 pages).
United States Patent Office Action for U.S. Appl. No. 12/454,643 dated Jun. 24, 2014 (14 pages).
PCT/US2012/064675 International Search Report and Written Opinion dated Apr. 3, 2013 (19 pages).
Goodsell, "PDB Molecule of the Month: Estrogen Receptor," http://www.rcsb.org/pdb/molecules/pdb45_1.html, (observed Dec. 8, 2003) 2 pages.
Baird, G.S. et al., "Circular permutation and receptor insertion within green fuorescent proteins," Proc. Natl. Acad. Sci. USA (1999) 96:11241-11246.
Berman, H.M.et al., "The cAMP binding domain: an ancient signaling module," Proc. Natl. Acad. Sci. USA (2000) 102(1):45-50.
Binkowski et al., Engineered luciferases for molecular sensing in living cells, Current Opinion in Biotechnology, vol. 20, Iss. 1, Feb. 2009, pp. 14-18.
Bos, J.L., "Epac: a new cAMP target and new avenues in cAMP research," Nat. Rev. Mol. Cell. Biol. (2003) 4:733-738.
Burbelo, P.D. et al., "Detecting protein-protein interactions using renilla luciferase fusion proteins," Biotech. (2002) 33(5):1044-1049.
Chong, S. et al., "Single-column purification of free recombinant proteins using a self-cleavable affinity tag derived from a protein splicing element," Gene (1997) 192:271-281.
Dremier, S. et al., "Search for new cyclic AMP-binding proteins," FEBS Lett. (2003) 546:103-107.
Fan, F. et al., "Novel genetically encoded biosensors using firefly luciferase," ACS Chemical Biology (2008) 3(6):346-351.
Genbank Accession No. AF115480, Sequence ID No. 123, "Mus musculus cAMP-dependent Rap1 guanine-nucleotide exchange factor mRNA, complete cds" (1999) 2 pages.
Genbank Accession No. AF192755, Seq. ID No. 125, "Trypanosoma brucei cyclic nucleotide phophodiesterase (PDE) gene, complete cds" (2002) 2 pages.
Genbank Accession No. NM_002734, "*Homo sapiens* protein kinase, cAMP-dependent, regulatory, type I, alpha (tissue specific extinguished), (PRKAR1A), transcript variant 1, mRNA," (2010) 5 pages.
Genbank Accession No. M124921, "Rat type II cAMP-dependent protein kinase regulatory subunit mRNA, 3' end" (2002) 2 pages.
Graf, R. et al., "Random circular permutation of genes and expressed polypeptide chains: application of the method to the catalytic chains of aspartate transcarbamoylase," Proc. Natl. Acad. Sci. USA (1996) 93:11591-11596.
Greer, L.F. et al., "Imaging of light emission from the expression of luciferases in living cells and organisms: a review," Luminescence (2002) 17(1):43-74.
Hanks, S.K. et al., "The eukaryotic protein kinase super family: kinase (catalytic) domain structure and classification," FASEB J. (1995) 9:576-596.
Heinemann, U. et al., "Circular permutation of polypeptide chains: implications for protein folding and stability," Prog. Biophys. Mol. Biol. (1995) 64(2-3):121-143.
Kaihara, A. et al., "Locating a protein-protein interaction in living cells via split renilla luciferase complementation," Anal. Chem. (2003) 75(16):4176-4181.
Kim et al., Circularly permutated bioluminescent probes for illuminating ligand-activated protein dynamics, Bioconjugate Chem, 2008, 19, pp. 2480-2486.
Laxman, B. et al., "Noninvasive real-time imaging of apoptosis," Proc. Natl. Acad. Sci. USA (2002) 99(26):16551-16555.
Leclerc, G.M. et al., "Development of a destabilized firefly luciferase enzyme for measurement of gene expression," BioTech. (2000) 29(3):590-601.

Lee, J-C., "Development of a cell-based assay for monitoring specific hepatitis C virus NS3/4A protease activity in mammalian cells," Anal. Biochem. (2003) 316(2):162-170.
Li, I.T. et al., "Protein biosensors based on the principle of fluorescene resonance energy transfer for monitoring cellular dynamics," Biotech. Lett. (2006) 28(24):1971-1982.
Littlewood, T.D. et al., "A modified oestrogen receptor ligand-binding domain as an improved switch for the regulation of heterologous proteins," Nucl. Acids Res. (1995) 23(10):1686-1690.
Lorenz, W. et al., "Isolation and expression of a cDNA encoding renilla reniformis luciferase," Proc. Natl. Academ. Sci. USA, May 1991, vol. 88, pp. 4438-4442.
Luker, K.E. et al., "Kinetics of regulated protein-protein interactions revealed with firefly luciferase complementation imaging in cells and living animals," Proc. Natl. Acad. Sci. USA (2004) 101(33):12288-12293.
Lykens et al., "Perforin is a critical physiologic regulator of T-cell activation," Blood, 118:618-626 (2011).
Maldonado, F. et al., "A cDNA clone encoding human cAMP-dependent protein kinase catalytic subunit calpha," Nucl. Acids Res. (1988) 16(16):8189-8190.
Massoud, T.F. et al., "Molecular imaging of homodimeric protein-protein interactions in living subjects," The FASEB Journal (2004) 18:1105-1107.
Mayer, B.J. et al., "Signalling through SH2 and SH3 domains," Trends Cell Biol. (1993) 3:8-13.
Michel, P. et al., "Expression and purification of polyhistidine-tagged firefly luciferase in insect cells—a potential alternative for process scale-up," J. Biotech., Short Technical Reports (2001) 85(1):49-56.
Murray et al. "Codon usage in plant genes" NAR 17: 477-498 (1989).
Nagai, T. et al., "Development of a GFP variant with fast and efficient maturation properties," (2002) 42(6):305308.
Nagai, T. et al., Circularly permuted green fluorescent proteins engineered to sense Ca2+, Proc. Natl. Acad. Sci. USA, 2001, 98, pp. 3197-3202.
Nikolaev, V.O. et al., "Novel single chain cAMP sensors for receptor-induced signal propagation," J. Biol. Chem. (2004) 279(36):37215-37218.
Niles, A.L. et al., "Caspase activity assays," Meth. Mol. Biol. (2008) 414:137-150.
Øyen, O. et al., "Human testis cDNA for the regulatory subunit R11α of cAMP-dependent protein kinase encodes an alternative amino-terminal region," FEBS Lett. (1989) 246(1-2):57-64.
Ozawa, T. et al., "Split luciferase as an optical probe for detecting protein-protein interactions in mammalian cells based on protein splicing," Anal. Chem. (2001) 73(11):2516-2521.
Paulmurugan, R. et al., "An intramolecular folding sensor for imaging estrogen receptor-ligand interactions," Proc. Natl. Acad. Sci. USA (2006) 103(43):15883-15888.
Paulmurugan, R. et al., "Molecular imaging of drug-modulated protein-protein interactions in living subjects," Cancer Res. (2004) 64:2113-2119.
Paulmurugan, R. et al., "Monitoring protein-protein interactions using split synthetic renilla luciferase protein-fragment-assisted complementation," Anal. Chem. (2003) 75(7):1584-1589.
Paulmurugan, R. et al., "Novel fusion protein approach for efficient high-throughput screening of small molecule-mediating protein-protein interactions in cells in living animals," Cancer Res. (2005) 65(16):7413-7420.
Paulmurugan, R. eta l., "Noninvasive imaging of protein-protein interactions in living subjects by using reporter protein complementation and reconsittution strategies," Proc. Natl. Acad. Sci. USA (2002) 99(24):15608-15613.
Plainkum, P. et al., "Creation of a zymogen," Nature Structural Biology (2003) 10(2):115-119.
Qian, Z. et al., "Improving the catalytic activity of candida antarctica lipase B by circular permutation," J. Am. Chem. Soc. (2005) 127:13466-13467.
Sadowski, I. et al., "A noncatalytic domain conserved among cytoplasmic protein-tyrosine kinases modifies the kinase function and transforming activity of fujinami sarcoma virus P130 gaag-fps," Mol. Cell. Biol. (1986) 6:4396-4408.
Sala-Newby, G., "Engineering a bioluminescent indicator for cyclic AMP-dependent protein kinase," Biochem. J. (1991) 279(Part 3):727-732.

(56) References Cited

OTHER PUBLICATIONS

Sala-Newby, G., "Engineering firefly luciferase as an indicator of cyclic AMP-dependent protein kinase in living cells," FEBS Letters (1992) 307(2):241-244.
Siehler, S., "Cell-based assays in GPCR drug discovery," Biotechnol. J. (2008) 3:471-483.
Spotts, J.M. et al., "Time-lapse imaging of a dynamic phosphorylation-dependent protein-protein interaction in mammalian cells," Proc. Natl Acad. Sci. USA (2002) 99(23):15142-15147.
Daugherty et al., "Quantitative analysis of the effect of the mutation frequency on the affinity maturation of single chain Fv antibodies," PNAS USA 97(5):2029-2034 (2000).
Kunkel, "Rapid and efficient site-specific mutagenesis without phenotypic selection," PNAS USA 82(2):488-492 (1985).
Tanenbaum, D.M. et al., "Crystallographic comparison of the estrogen and progesterone receptor's ligand binding domains," Proc. Natl. Acad. Sci. USA (1998) 95:5998-6003.
Umezawa, Y., "Assay and screening methods for bioactive substances based on cellular signalling pathways," Reviews in Mol. Biotech. (2001) 82:357-370.
Wada et al. "Codon usage tabulated from the GenBank genetic sequence data" NAR 18: 2367-2411 (1990).
Wang, X. et al., "Effect of removal of the N-terminal amino acid residues on the activity and conformation of firefly luciferase," Intl. J. Biochem. Cell Biol. (2002) 34(8):983-991.
Waud, J.P. et al., "Engineering the C-terminus of firefly luciferase as an indicator of covalent modification of proteins," Biochim. Biophys. Acta (1996) 1292(1):89-98.
Wigdal, S.S. et al., "A novel bioluminescent protease assay using engineered firefly luciferase," Curr. Chem. Genomics (2008) 2(1):16-28.
Wiley, S.R. et al., "Identification and characterization of a new member of the TNF family that induces apoptosis," Immunity (1995) 3(6):673-682.
Ye, L. et al., "Cloning and sequencing of a cDNA for firefly luciferase from photuris pennsylvanica," Biochimica et Biophysica Acta (1997) 1339:39-52.
Zagotta, W.N. et al., "Structural basis for modulation and agonist specificity of HCN pacemaker channels," Nature (2003) 425:200-205.
Zako, T. et al., "Luminescent and substrate binding activities of firefly luciferase N-terminal domain," Biochim. Biophys. Acta—Proteins & Proteomics (2003) 1649(2):183-189.
Zhang et al., "A Simple Statistical Parameter for Use in Evaluation and Validation of High Throughput Screening Assays," Biomol Screen. 4:67-73 (1999).
Zhang, J. et al., "Creating new fluorescent probes for cell biology," Mol. Cell Biol. (2002) 3:906-918.
Zhao, H. et al., "Emission spectra of bioluminescent reporters and interaction with mammalian tissue determine the sensitivity of detection in vivo," J. Biomed. Optics (2005) 10(4):041230-1-041230-9.
International Search Report and Written Opinion for Application No. PCT/US2007/008176 dated Dec. 27, 2007 (18 pages).
Invitation to Pay Additional Fees and Partial Search Report for Application No. PCT/US2007/008176 dated Feb. 10, 2007 (7 pages).
International Search Report and Written Opinion for Application No. PCT/US2004/032705 dated Dec. 9, 2005 (20 pages).
Invitation to Pay Additional Fees and Partial Search Report for Application No. PCT/US2004/032705 dated May 19, 2005 (9 pages).
International Search Report and Written Opinion for Application No. PCT/US2009/003132 dated Nov. 12, 2009 (10 pages).
International Search Report and Written Opinion for Application No. PCT/US2011/036110 dated Jul. 28, 2011 (15 pages).
PCT/US2012/064675 Invitation to Pay Additional Fees and International Search Report dated Jan. 31, 2013 (9 pages).
United States Patent Office Action for U.S. Appl. No. 10/957,433 dated Jan. 7, 2010 (6 pages).
United States Patent Office Action for U.S. Appl. No. 10/957,433 dated Jul. 21, 2009 (8 pages).
United States Patent Office Action for U.S. Appl. No. 10/957,433 dated Feb. 12, 2009 (5 pages).
United States Patent Office Action for U.S. Appl. No. 10/957,433 dated Sep. 4, 2008 (7 pages).
United States Patent Office Action for U.S. Appl. No. 10/957,433 dated Mar. 21, 2008 (10 pages).
United States Patent Office Action for U.S. Appl. No. 10/957,433 dated Oct. 21, 2007 (9 pages).
United States Patent Office Action for U.S. Appl. No. 10/957,433 dated Mar. 11, 2011 (6 pages).
United States Patent Office Action for U.S. Appl. No. 10/957,433 dated Jan. 31, 2012 (3 pages).
United States Patent Office Action for U.S. Appl. No. 11/732,105 dated Jun. 7, 2011 (22 pages).
United States Patent Office Action for U.S. Appl. No. 11/732,105 dated Nov. 23, 2011 (19 pages).
United States Patent Office Action for U.S. Appl. No. 12/454,643 dated Jan. 31, 2012 (13 pages).
United States Patent Office Final Rejection for U.S. Appl. No. 12/454,643 dated Jun. 15, 2012 (9 pages).
Canadian Patent Office Action for Application No. 2648263 dated Feb. 8, 2011 (4 pages).
Chinese Patent Office Action for Application No. 200780020577.7 dated Jun. 4, 2010 (9 pages) with translation.
European Patent Office Action for Application No. 07754666.1 dated Jan. 11, 2010 (3 pages).
European Patent Office Action for Application No. 07754666.1 dated Feb. 13, 2009 (6 pages).
European Patent Office Action for Application No. 07754666.1 dated Aug. 19, 2011 (4 pages).
European Patent Office Partial Search Report for Application No. 11155576.9 dated May 3, 2011 (7 pages).
European Patent Office Action for Application No. 11155576.9 dated Sep. 9, 2011 (12 pages).
European Patent Office Action for Application No. 07754666.1 dated Jun. 11, 2012 (4 pages).
European Patent Office Action for Application No. 07754666.1 dated Mar. 25, 2013 (4 pages).
European Patent Office Action for Application No. 11155576.9 dated Jul. 13, 2012 (4 pages).
European Patent Office Action for Application No. 04809862.8 dated Mar. 19, 2007 (3 pages).
European Patent Office Examination Report for Application No. 04809862.8 dated Dec. 28, 2007 (3 pages).
European Patent Office Action for Application No. 04809862.8 dated Apr. 8, 2009 (4 pages).
European Patent Office Examination Report for Application No. 04809862.8 dated Dec. 23, 2009 (4 pages).
European Patent Office Action for Application No. 04809862.8 dated Dec. 1, 2010 (4 pages).
European Patent Office Action for Application No. 10182746.7 dated Feb. 10, 2011 (7 pages).
European Patent Office Action for Application No. 10182746.7 dated Jan. 17, 2013 (4 pages).
European Patent Office Action for Application No. 10182742.6 dated Jan. 10, 2013 (5 pages).
European Patent Office Action for Application No. 09750966.5 dated Apr. 19, 2011 (3 pages).
United States Patent Office Action for U.S. Appl. No. 11/732,105 dated Oct. 9, 2014 (11 pages).
Japanese Patent Office Action for Application No. 2009-504249 dated Dec. 8, 2014 (2 pages).
Wilson et al., Annu. Rev. Cell Dev. Biol., 1998, vol. 14, pp. 197-230.
Japanese Patent Office Action for Application No. 2011-043966 dated Feb. 25, 2015 (6 pages—English summary included).
United States Patent Office Notice of Allowance for U.S. Appl. No. 12/454,643 dated Jan. 26, 2015 (19 pages).
United States Patent Office Action for U.S. Appl. No. 14/180,451 dated Feb. 11, 2015 (9 pages).
United States Patent Office Action for U.S. Appl. No. 14/269,669 dated Feb. 2, 2015 (11 pages).
United States Patent Office Action for U.S. Appl. No. 14/269,689 dated Feb. 4, 2015 (16 pages).

(56) References Cited

OTHER PUBLICATIONS

United States Patent Office Final Action for U.S. Appl. No. 14/269,669 dated Jul. 20, 2015 (11 pages).
United States Patent Office Notice of Allownace for U.S. Appl. No. 14/269,689 dated Sep. 25, 2015 (9 pages).
United States Patent Office Final Action for U.S. Appl. No. 14/180,451 dated Jul. 29, 2015 (5 pages).
United States Patent Office Final Action for U.S. Appl. No. 11/732,105 dated Oct. 9, 2015 (11 pages).
United States Patent Office Final Action for U.S. Appl. No. 14/269,669 dated Jan. 13, 2016 (9 pages).

\* cited by examiner

Exp. 1

| Linker | Basal (t=0) | Induced (10 h) | Response (10 h) |
|---|---|---|---|
| 1) SSDEVDGSSG (SEQ ID NO:52) | 342,334 | 2,545,188 | 7.4 |
| 2) SSGSDEVDGSLSSG (SEQ ID NO:53) | 397,954 | 2,715,405 | 6.8 |

Exp. 2

| Linker | Basal (t=0) | Induced (10 h) | Response (10 h) |
|---|---|---|---|
| 2) SSGSDEVDGSLSSG (SEQ ID NO:53) | 113,709 | 3,164,676 | 27.8 |
| 3) SDEVDGSL (SEQ ID NO:54) | 65,548 | 2,486,068 | 37.9 |
| 4) DEVDG (SEQ ID NO:55) | 42,943 | 713,955 | 16.6 |

Fig. 4

000# MUTANT PROTEASE BIOSENSORS WITH ENHANCED DETECTION CHARACTERISTICS

CROSS-REFERENCE TO RELATED APPLICATIONS

This application is a continuation-in-part of U.S. patent application Ser. No. 13/105,648, filed May 11, 2011, which claims the benefit of U.S. Provisional Patent Application Ser. No. 61/333,706, filed May 11, 2010 and U.S. Provisional Patent Application Ser. No. 61/470,845, filed Apr. 1, 2011, each of which is incorporated herein by reference in its entirety. This application also claims priority to U.S. Provisional Application No. 61/558,796, filed Nov. 11, 2011, which is incorporated herein by reference in its entirety.

FIELD OF INVENTION

The present invention relates to the field of biochemical assays and reagents. More specifically, this invention relates to modified luciferases and methods for their use. The present invention relates, in general, to non-radioactive methods for the detection of cell-mediated cytotoxicity. The methods of the present invention can be used to detect cell-mediated cytotoxicity by cytotoxic lymphocyte or natural killer cells, in particular activated cytotoxic lymphocyte and activated natural killer cells. The methods of the present invention can be used in cellular assays to monitor granzyme B activity in cellular processes such as β-arrestin localization. The present invention also provides novel Granzyme B recognition sequences and biosensors as well as methods of their use.

SEQUENCE LISTING

The instant application contains a Sequence Listing which has been submitted in ASCII format via EFS-Web and is hereby incorporated by reference in its entirety. Said ASCII copy, created on Nov. 2, 2012, is named "US01_ASFILED_SequenceListing" and is 153,876 bytes in size.

BACKGROUND

Luciferases are enzymes that catalyze the oxidation of a substrate (e.g., luciferin or coelenterazine) with the concomitant release of photons of light. Luciferases have been isolated from numerous species, including Coleopteran arthropods and many sea creatures as well as bacteria. Because it is easily detectable and its activity can be quantified with high precision, luciferases have been widely used to study gene expression and protein localization. Unlike green fluorescent protein (GFP), which requires up to 30 minutes to form its chromophore, the products of luciferases can be detected immediately upon completion of synthesis of the polypeptide chain (if substrate and oxygen are also present). In addition, no post-translational modifications are required for enzymatic activity, and the enzyme contains no prosthetic groups, bound cofactors, or disulfide bonds. Luciferases are useful reporters in numerous species and in a wide variety of cells.

Luciferases possess additional features that render them particularly useful as reporter molecules for biosensing, i.e., molecules which reveal molecular properties of a system. Most catalytic reactions generate less than the energy of hydrolysis for two molecules of ATP, or about 70 kJ/mole. However, the luminescence elicited by luciferases has much higher energy content. For instance, the reaction catalyzed by firefly luciferase (560 nm) emits 214 kJ/mole of energy. Furthermore, luciferases are also highly efficient at converting chemical energy into photons, i.e., they have high quantum yields. Luciferases are thus extremely efficient for generating detectable signals.

Cytotoxic T lymphocytes (CTLs) and natural killer (NK) cells are effector lymphocytes that share common cytotoxic pathways that are necessary for defense against virus-infected or transformed cells such as tumor cells. NK cells play a major role in the rejection of tumors and cells infected by viruses. They kill cells by releasing, via exocytosis, into target cells small cytoplasmic granules of proteins called perforin and granzyme that cause the target cell to die by apoptosis, i.e., programmed cell death. The granule-exocytosis pathway powerfully activates cell-death pathways that operate through the activation of apoptotic cysteine proteases (caspases), but it also leads to cell death in the absence of activated caspases. Perforin and granzymes induce target-cell apoptosis cooperatively. Granzymes, a family of structurally related serine proteases, are necessary for triggering apoptosis in target cells, but they depend on being appropriately delivered by perforin.

Granzyme B and granzyme B isoforms, which cleave target-cell proteins at specific aspartate residues, is a potent activator of caspase-mediated, as well as caspase-independent cell death. The uptake of granzyme B into target cells is believed to be mediated (at least in part) by endocytosis through the cation-independent mannose 6-phosphate receptor. Granzyme B mainly triggers caspase activation indirectly rather than by direct caspase processing. It achieves this by directly activating pro-apoptotic 'BH3-only' members of the BCL-2 family, such as BH3-interacting domain death agonist (BID), which results in the leakage of pro-apoptotic mitochondrial mediators, such as cytochrome c, into the cytosol. BID-independent pathways for granzyme-mediated apoptosis also seem to exist. Some viruses encode potent granzyme-B inhibitors, and the endogenous granzyme-B inhibitor PI9 might be expressed aberrantly by some cancer cells.

CTLs and NK cells are critical effector cells of the immune system. The components of NK function include: NK numbers, granule number/content, immune synapse formation, polarization toward synapse, docking to membrane, priming, fusion, and delivery of granzyme. Measurement of target cell damage has historically been an important measure of CTL and NK cell function. The gold standard for CTL-mediated cytotoxicity has been the chromium release assay ("[51Cr] release assay"). The [51Cr] release assay involves the labeling of viable cells with [51Cr] which binds tightly to most intracellular proteins. After washing, the cells are incubated with a cytotoxic agent, e.g., effector cells. Labeled proteins are released into the cell media due to damage and/or leakage of the cell membrane caused by the triggering of cell death by the cytotoxic agent. Radioactivity is detected, thereby indicating cell death. As the [51Cr] release assay involves the use of radioactivity, and is time intensive, there exists a need to provide a non-radioactive, sensitive assay for the measurement of cell-mediated cytotoxicity.

SUMMARY

In some embodiments, the invention provides a polynucleotide encoding a biosensor polypeptide comprising a modified circularly-permuted thermostable luciferase and a linker. The linker links the C-terminal portion of the thermostable luciferase to the N-terminal portion of the thermostable luciferase. The modified circularly-permuted thermostable luciferase is modified relative to a parental circularly-permuted thermostable luciferase. The linker comprises a sensor region capable of interacting with a target molecule in a cell. The modified circularly-permuted thermostable luciferase has an enhanced response after interaction of the biosensor with the target molecule relative to the parental circularly-permuted thermostable luciferase in the presence of the target molecule. Alternatively, the modified circularly-permuted thermostable luciferase has an enhanced response after interaction of the biosensor with the target molecule relative to the modified circularly-permuted thermostable luciferase in the absence of the target molecule.

In other embodiments, the invention provides a polynucleotide encoding a biosensor polypeptide comprising a modified circularly-permuted thermostable luciferase and a linker, wherein the modified circularly-permuted thermostable luciferase has a substitution of at least one amino acid at positions 5, 17, 21, 23, 26, 39, 44, 51, 81, 101, 103, 110, 114, 115, 119, 123, 126, 128, 133, 137, 186, 191, 192, 193, 196, 208, 211, 214, 226, 228, 230, 233, 264, 273, 275, 286, 287, 294, 295, 297, 302, 303, 304, 306, 308, 309, 313, 324, 329, 331, 343, 348, 353, 364, 374, 385, 389, 409, 420, 426, 427, 428, 431, 449, 456, 460, 461, 465, 466, 468, 471, 473, 482, 484, 485, 489, 493, 494, 497, 503, 507, 509, 510, 513, 516, 517, 521, 522, 523, 526, 530, 533, 536, 537, 542, or 543 corresponding to SEQ ID NO: 2. The linker links the C-terminal portion of the thermostable luciferase to the N-terminal portion of the thermostable luciferase. The linker has a sensor region capable of interacting with a target molecule in a cell. The modified circularly-permuted thermostable luciferase has an enhanced response after interaction of the biosensor with the target molecule relative to the parental circularly-permuted thermostable luciferase in the presence of the target molecule. Alternatively, the modified circularly-permuted thermostable luciferase has an enhanced response after interaction of the biosensor with the target molecule relative to the modified circularly-permuted thermostable luciferase in the absence of the target molecule. The modified circularly-permuted thermostable luciferase may also have increased luminescence or increased stability relative to an unmodified circularly-permuted thermostable luciferase.

In some aspects, the disclosure relates to a method to detect the presence or activity of a target molecule in a sample, comprising contacting the sample with a polynucleotide encoding a modified circularly-permuted thermostable luciferase biosensor comprising a sensor region for the target molecule and a substrate for the modified circularly-permuted thermostable luciferase and detecting luminescence in the sample.

In some aspects, the disclosure relates to a method to detect the presence or activity of a target molecule in a cell, comprising contacting a cell with a polynucleotide encoding a modified circularly-permuted thermostable luciferase biosensor comprising a sensor region for the target molecule and a substrate for the modified circularly-permuted thermostable luciferase and detecting luminescence in the cell.

In some aspects, the disclosure relates to a method to detect the presence or activity of a target molecule in an animal, comprising contacting an animal with a modified circularly-permuted thermostable luciferase biosensor comprising a sensor region for the target molecule and a substrate for the modified circularly-permuted thermostable luciferase and detecting luminescence in the animal.

In some aspects, the disclosure relates to a method to detect the presence or activity of a target molecule in a sample, comprising immobilizing a modified circularly-permuted thermostable luciferase biosensor comprising a sensor region for the target molecule to a solid support, adding a sample containing the target molecule to the immobilized biosensor, adding a substrate for the modified circularly-permuted thermostable luciferase, and detecting luminescence.

In some aspects, the disclosure relates to a method to detect apoptosis in a sample, comprising contacting the sample with a polynucleotide encoding a modified circularly-permuted thermostable luciferase biosensor comprising a sensor region for a molecule involved in apoptosis and a substrate for the modified circularly-permuted thermostable luciferase and detecting luminescence in the sample.

In some aspects, the disclosure relates to a polynucleotide encoding a biosensor polypeptide comprising a modified circularly-permuted thermostable luciferase and a linker linking the C-terminal portion of the thermostable luciferase to the N-terminal portion of the thermostable luciferase, the modified circularly-permuted thermostable luciferase is modified relative to a parental circularly-permuted thermostable luciferase, the linker comprising a sensor region capable of interacting with a target molecule in a cell wherein the modified circularly-permuted thermostable luciferase has an enhanced response after interaction of the biosensor with the target molecule relative to at least one of: i) the parental circularly-permuted thermostable luciferase in the presence of the target molecule, or ii) the modified circularly-permuted thermostable luciferase in the absence of the target molecule, wherein the linker includes a granzyme B recognition site and the target molecule is granzyme B.

In some embodiments, the disclosure relates to a polynucleotide encoding a circularly-permuted thermostable luciferase comprising a peptide linker linking the original N- and C-termini of a non-permuted thermostable luciferase, wherein the peptide linker comprises a granzyme B recognition site that is recognized and cleaved by a granzyme B or granzyme B isoform, wherein the circularly-permuted thermostable luciferase has increased luminescence following cleavage by granzyme B when compared to an uncleaved circularly-permuted thermostable luciferase.

In some embodiments, the disclosure relates to a method for detecting the presence and/or amount of active granzyme B in a cell or sample. In some embodiments, the method comprises contacting a cell or sample with a polynucleotide, or a polypeptide encoded by said polynucleotide, wherein the polynucleotide encodes a circularly-permuted thermostable luciferase biosensor comprising a peptide linker linking the original N- and C-termini of a non-permuted thermostable luciferase, wherein the peptide linker comprises a granzyme B recognition site that is recognized and cleaved by a granzyme B or granzyme B isoform, and a substrate for the circularly-permuted thermostable luciferase and detecting luminescence in the cell or sample, wherein active granzyme B present in the sample is capable of cleaving the peptide linker in the circularly-permuted thermostable luciferase thereby detecting the presence and/or amount of active granzyme B. In some embodiments, the method comprises contacting a cell or sample with a polynucleotide, or a polypeptide encoded by said polynucleotide, wherein the polynucleotide encodes a circularly-permuted thermostable luciferase comprising a peptide linker linking the original N- and C-termini of a non-permuted thermostable luciferase, and the peptide linker comprises a sequence that is recognized and cleaved by a granzyme B or granzyme B isoform, a substrate for the circularly-permuted thermostable luciferase, and a cytotoxic lymphocyte(s); and detecting luminescence in the cell or sample, wherein active granzyme B present in the sample is capable of cleaving the peptide linker in the circularly-permuted thermostable luciferase thereby detecting the presence and/or amount of active granzyme B. In some embodiments, the cytotoxic lymphocyte(s) is a patient or patient-derived cytotoxic lymphocyte(s) or a cytokine-activated natural killer cell. In some embodiments, the detection of granzyme B determines the cytotoxic function of the cytotoxic lymphocyte. In other embodiments, the detection of granzyme B indicates cell-mediated cytotoxicity. In some embodiments, the screening is performed in high-throughput, e.g., in a multi-well plate.

In some embodiments, the disclosure relates to a method for screening for one or more modulators of granzyme B activity. In some embodiments, the method comprises: contacting a cell or sample with one or more test agents, a polynucleotide, or polypeptide encoded by said polypeptide, wherein the polynucleotide encodes a circularly-permuted thermostable luciferase comprising a peptide linker linking the original N- and C-termini of a non-permuted thermostable luciferase, wherein the peptide linker comprises a sequence that is recognized and cleaved by a granzyme B or granzyme B isoform, a substrate for the circularly-permuted thermostable luciferase; and detecting luminescence in the cell or sample, wherein granzyme B present in the sample is capable of cleaving the peptide linker in the circularly-permuted thermostable luciferase thereby identifying modulators of granzyme B. In some embodiments, the modulator is an inhibitor or an enhancer of granzyme B. In some embodiments, the inhibitor is a siRNA. In some embodiments, the enhancer is a small molecule, peptide, or protein. In some embodiments, the screening is performed in high-throughput, e.g., in a multi-well plate.

In some embodiments, the disclosure relates to a method for screening for one or more modulators of cytotoxic function. In some embodiments, the method comprises contacting a target cell with a polynucleotide encoding a circularly-permuted thermostable luciferase comprising a peptide linker linking the original N- and C-termini of a non-permuted thermostable luciferase, wherein the peptide linker comprises a sequence that is recognized and cleaved by a granzyme B or granzyme B isoform with a substrate for the circularly-permuted thermostable luciferase; contacting the target cells and/or cells mediating cytotoxicity with one or test agents; and detecting luminescence in the cell or sample, wherein granzyme B present released from the cells mediating cytotoxicity is capable of cleaving the peptide linker in the circularly-permuted thermostable luciferase thereby identifying modulators of cytotoxic function. In some embodiments, the modulator is an inhibitor or an enhancer of granzyme B. In some embodiments, the inhibitor is a siRNA. In some embodiments, the enhancer or inhibitor is a small molecule, peptide, or protein. In some embodiments, the cells mediating cytotoxicity is a cytotoxic lymphocyte(s) or a cytokine-activated natural killer (NK) cell(s). In some embodiments, the screening is performed in high-throughput, e.g., in a multi-well plate.

In some embodiments, the disclosure relates to a method for detecting granzyme B activity in a cellular process. In some embodiments, the method comprises contacting a cell or sample with one or more test agents, a polynucleotide encoding a circularly-permuted thermostable luciferase comprising a peptide linker linking the original N- and C-termini of a non-permuted thermostable luciferase, wherein the peptide linker comprises a sequence that is recognized and cleaved by a granzyme B or granzyme B isoform, and a substrate for the circularly-permuted thermostable luciferase; and detecting luminescence in the cell or sample, wherein granzyme B is capable of cleaving the peptide linker in the circularly-permuted thermostable luciferase thereby detecting granzyme B activity. In some embodiments, the screening is performed in high-throughput, e.g., in a multi-well plate.

In some embodiments, the disclosure relates to a polypeptide encoded by a polynucleotide encoding a circularly-permuted thermostable luciferase. The circularly-permuted thermostable luciferase comprises a peptide linker linking the original N- and C-termini of a non-permuted thermostable luciferase, and wherein the peptide linker comprises a sequence that is recognized and cleaved by a granzyme B. In other embodiments, the disclosure relates to a vector comprising a polynucleotide encoding a circularly-permuted thermostable luciferase comprising a peptide linker linking the original N- and C-termini of a non-permuted thermostable luciferase, wherein the peptide linker comprises a sequence that is recognized and cleaved by a granzyme B. In some embodiments, the disclosure relates to a cell comprising a polynucleotide encoding a circularly-permuted thermostable luciferase comprising a peptide linker linking the original N- and C-termini of a non-permuted thermostable luciferase, wherein the peptide linker comprises a sequence that is recognized and cleaved by a granzyme B. In some embodiments, the disclosure relates to a non-human animal comprising a cell comprising a polynucleotide encoding a circularly-permuted thermostable luciferase comprising a peptide linker linking the original N- and C-termini of a non-permuted thermostable luciferase, wherein the peptide linker comprises a sequence that is recognized and cleaved by a granzyme B.

In some embodiments, the disclosure relates to a polynucleotide encoding a circularly-permuted thermostable luciferase comprising a peptide linker linking the original N- and C-termini of a non-permuted thermostable luciferase, wherein the peptide linker comprises a sequence that is recognized and cleaved by caspase-3 and/or caspase-7 isoforms, wherein the circularly-permuted thermostable luciferase has increased luminescence following cleavage by caspase-3 and/or caspase-7 compared to an uncleaved circularly-permuted thermostable luciferase.

In some embodiments, the disclosure relates to a method for screening one or more modulators of cytotoxic function. In some embodiments, the method comprises: contacting a target cell population with a polynucleotide, or a polypeptide encoded by said polynucleotide, wherein the polynucleotide encodes a circularly-permuted thermostable luciferase comprising a peptide linker linking the original N- and C-termini of a non-permuted thermostable luciferase and the peptide linker comprises a sequence that is recognized and cleaved by a caspase-3 and/or caspase-7 isoform, and a substrate for the circularly-permuted thermostable luciferase; contacting the target cells and/or cells mediating cytotoxicity with one or test agents; and detecting luminescence in the cell or sample, wherein the cells mediating cytotoxicity are capable of activating caspase-3 and/or caspase-7, wherein the activated caspase-3 and/or caspase-7 is capable of cleaving the peptide linker and activating the circularly-permuted thermostable luciferase thereby identifying modulators of cytotoxic function. In some embodiments, the modulator is an inhibitor or an enhancer of cytotoxic function. In some embodiments, the inhibitor is a siRNA. In some embodiments, the enhancer or inhibitor is a small molecule, peptide, or protein. In some embodiments, the screening is performed in high-throughput, e.g., in a multi-well plate.

Other aspects of the invention will become apparent by consideration of the detailed description and accompanying drawings.

BRIEF DESCRIPTION OF THE DRAWINGS

FIG. 4 shows the effect of the linker on the performance of the Caspase-3/7 BioSensor (CBS).

DETAILED DESCRIPTION

Figure 1:
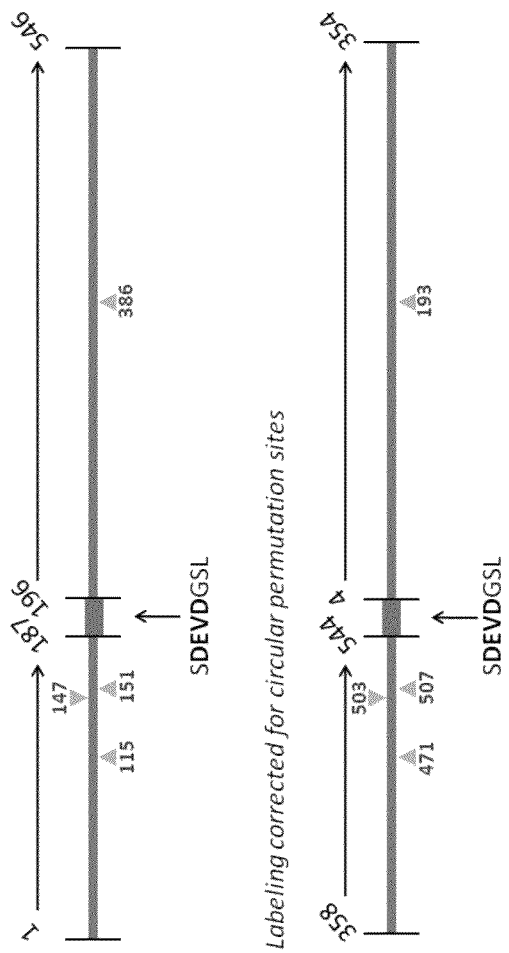
FIG. 1 illustrates the position of the amino acid substitutions, 1471T, S503G, T5071, and S193P in the corresponding starting sequence TL-CP358-DEVD:DD.

Before any embodiments of the invention are explained in detail, it is to be understood that the invention is not limited in its application to details of construction and the arrangement of components set forth in the following description or illustrated in the following drawings. The invention is capable of other embodiments and of being practiced or of being carried out in various ways.

In the following description of the methods of the invention, process steps are carried out at room temperature (about 22° C.) and atmospheric pressure unless otherwise specified. It also is specifically understood that any numerical range recited herein includes all values from the lower value to the upper value. For example, if a concentration range or beneficial effect range is stated as 1% to 50%, it is intended that values such as 2% to 40%, 10% to 30%, or 1% to 3%, etc. are expressly enumerated in this specification. Similarly, if a sequence identity range is given as between, e.g., 60% to <100%, it is intended that 65%, 75%, 90%, etc. are expressly enumerated in this specification. These are only examples of what is specifically intended, and all possible numerical values from the lowest value to the highest value are considered expressly stated in the application.

The term "thermostable luciferase" includes a luciferase that has enhanced stability at a given temperature (e.g., 22° C.) compared to a corresponding wild-type luciferase. For the exemplary embodiments disclosed herein, the term "TL" is used to refer to a thermostable variant of Ppe2, where Ppe2 is a luciferase from *Photuris pennsylvanica*. However, one skilled in the art would recognize that any thermostable luciferase could be used where TL is stated. For example, a luciferase from *Photinus pyralis* may be used, as well as luciferases from *Luciola cruciata, Luciola lateralis, Pyrocoelia miyako, Lampyris noctiluca, Photuris pennsylvanica, Phengodes* sp., *Luciola mingrelica*, and *Photinus pyralis*. (See Ye et al., Biochimica et Biophysica Acta, 1339:39-52 (1997)).

The term "CP" refers to circularly-permuted. For example, "TL-CP" refers to a circularly-permuted thermostable variant of the Ppe2 luciferase from *Photuris pennsylvanica*. The term "DEVD:DD" refers to a linker, i.e., an amino acid sequence that connects the N- and C-terminals of a circularly-permuted luciferase, that contains the DEVD caspase 3/7 recognition site and the three amino acids, GSL, that are on the C-terminal side of the DEVD caspase recognition site.

The term "biosensor" refers to an amino acid sequence containing a sensor region which can interact with a target molecule. When the target molecule interacts with the sensor region, molecular properties of a system are revealed.

The terms "Caspase-3/7 BioSensor" and "CBS" refers to a biosensor comprising a thermostable variant of the Ppe2 luciferase from *Photuris pennsylvanica* circularly-permuted with a caspase-3/7 recognition site, i.e., one containing the caspase-3/7 recognition site, DEVD, at the junction between the modified TL fragments. For example, "TL-CP358-DEVD:DD" refers to a CBS circularly-permuted at position 358 relative to SEQ ID NO:2 and comprises the DEVD:DD linker connecting the N- and C-terminal ends of the circularly-permuted thermostable luciferase. The term "CBS variant" refers to a CBS with one or more amino acid substitutions relative to CBS.

The amino acid numbering used throughout this application to identify substituted residues is specified relative to the positions in the polypeptide sequence of the wild-type Ppe2 luciferase from *Photuris pennsylvanica*, i.e., SEQ ID NO:2, or the thermostable variant of the Ppe2 luciferase from *Photuris pennsylvanica* polypeptide sequence, i.e., SEQ ID NO:4. In addition, other mutants than that shown in SEQ ID NO:4 can be used.

The term "caspase-3 or caspase-7 recognition site" refers to a peptide sequence that is recognized and cleaved by either a caspase-3 or caspase-7 isoform. For example, the caspase-3 or caspase-7 recognition site may include DEVDG (SEQ ID NO:55).

The term "granzyme B recognition site" refers to a peptide sequence that is recognized and cleaved by a granzyme B isoform. For example, the granzyme B recognition site may include GRIEADSE (SEQ ID NO:80) or KSVGPDFG (SEQ ID NO:81).

The term "target molecule" refers to a molecule of interest that interacts with the biosensor, e.g., a protease, a kinase, a G-protein coupled receptor, cAMP, cGMP, enzyme cofactors, ions (e.g., calcium ion; hydrogen ion for use as a pH sensor), an antibody, a peptide, or a sugar that causes the biosensor to reveal molecular properties of a system.

The term "identity" in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. Methods of alignment of sequence for comparison are well-known in the art.

The terms "cell," "cell line," and "host cell," as used herein, are used interchangeably, and all such designations include progeny or potential progeny of these designations. The term "transformed cell" refers to a cell into which (or into an ancestor of which) has been introduced a nucleic acid molecule of the invention. Optionally, a nucleic acid molecule of the invention may be introduced into a suitable cell line so as to create a stably-transfected cell line capable of producing the protein or polypeptide encoded by the nucleic acid molecule of the invention. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

As used herein, the term "heterologous" nucleic acid sequence or protein refers to a sequence that, relative to a reference sequence, has a different source, e.g., originates from a foreign species, or, if from the same species, it may be substantially modified from the original form. The term "homology" refers to a degree of complementarity between two or more sequences. There may be partial homology or complete homology (i.e., identity).

The term "nucleic acid molecule," "polynucleotide," or "nucleic acid sequence" as used herein, refers to nucleic acid, DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A polynucleotide encoding a protein or polypeptide means a nucleic acid sequence comprising the coding region of a gene, or in other words, the nucleic acid sequence encodes a gene product. The coding region may be present in a cDNA, genomic DNA or RNA form. When present in a DNA form, the oligonucleotide may be single stranded (i.e., the sense strand) or double stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Other control or regulatory elements include, but are not limited to, transcription factor binding sites, splicing signals, polyadenylation signals, termination signals, and enhancer elements.

As used herein, "parental" refers to the starting amino acid or nucleotide sequence that is used to generate the variants with further manipulations of the present invention. For example a wild-type *Photuris pennsylvanica* Ppe2 luciferase (SEQ ID NO:2), a thermostable variant of the Ppe2 luciferase from *Photuris pennsylvanica*, such as SEQ ID NO:4, or a circularly-permuted thermostable variant of the Ppe2 luciferase from *Photuris pennsylvanica*, such as SEQ ID NO:6, can be used as the starting sequence to generate the variants described in the present invention. In addition, other variants besides those shown in SEQ ID NOs:4 or 6 can be used as the parental sequence.

By "peptide," "protein" and "polypeptide" is meant any chain of amino acids, regardless of length or post-translational modification (e.g., glycosylation or phosphorylation). The nucleic acid molecules of the invention may also encode a variant of a naturally-occurring protein or polypeptide fragment thereof, which has an amino acid sequence that is at least 60%, 70%, 80%, 85%, 90%, 95% or 99% identical to the amino acid sequence of the naturally-occurring (native or wild-type) protein from which it is derived. For example, a coleopteran luciferase has at least 60%, 70%, 80%, 85%, 90%, 95% or 99% amino acid sequence identity to SEQ ID NO:2; a firefly luciferase has at least 60%, 70%, 80%, 85%, 90%, 95% or 99% amino acid sequence identity to one of SEQ ID NO:2 or 4 or the luciferases on which SEQ ID NOs:6, 8, 10, 12, 14, 18, 20, 22, 58, 60, 62, 64, 66, 68, 70, 72, or 74 are based.

As used herein, "pure" means an object species is the predominant species present (i.e., on a molar basis it is more abundant than any other individual species in the composition), and in one embodiment a substantially purified fraction is a composition wherein the object species comprises at least about 50% (on a molar basis) of all macromolecular species present. Generally, a "substantially pure" composition will comprise more than about 80% of all macromolecular species present in the composition, in one embodiment more than about 85%, about 90%, about 95%, or about 99%. In one embodiment, the object species is purified to essential homogeneity (contaminant species cannot be detected in the composition by conventional detection methods) wherein the composition consists essentially of a single macromolecular species.

Nucleic acids are known to contain different types of mutations. A "substitution" refers to an alteration in the sequence of a nucleotide at one or more base position(s) from the parental sequence. Mutations may also refer to insertion or deletion of one or more bases, so that the nucleic acid sequence differs from a parental sequence (e.g., a wild-type) or has a replacement stop codon.

The term "responsivity" refers to the alteration in luminescence, e.g., increased or decreased luminescence, due to the interaction of the biosensor with the target molecule.

As used herein, a "sample" may refer to a cell, an animal, cell lysate, or an in vitro transcription/translation mixture.

The term "vector" refers to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The term "wild-type" as used herein, refers to a gene or gene product that has the characteristics of that gene or gene product isolated from a naturally occurring source. The gene or gene product can be naturally occurring or synthetic. A wild-type gene is that which is most frequently observed in a population and is thus arbitrarily designated the "wild-type" form of the gene. In contrast, the term "mutant" or "variant" refers to a gene or gene product that displays modifications in sequence and/or functional properties (i.e., altered characteristics) when compared to the wild-type gene or gene product. It is noted that naturally-occurring and synthetic mutants can be isolated and are identified by the fact that they have altered characteristics when compared to the wild-type gene or gene product.

Luminescence refers to the light output of a luciferase polypeptide under appropriate conditions, e.g., in the presence of a suitable substrate such as a luciferin. The light output may be measured as an instantaneous or near-instantaneous measure of light output (which is sometimes referred to as "T=0" luminescence or "flash") upon start of the luminescence reaction, which may start upon addition of the luciferin substrate. The luminescence reaction in various embodiments is carried out in a solution containing lysate, for example, from the cells in a prokaryotic or eukaryotic expression system. In other embodiments, expression occurs in an in vitro system, or the luciferase protein is secreted into an extracellular medium, such that, in this latter case, it is not necessary to produce a lysate. In other embodiments, the luciferase is expressed in a whole cell(s) or in vivo, e.g., in animals. In some embodiments, the reaction is started by injecting appropriate materials, e.g., luciferin, into a reaction chamber (e.g., a well of a multiwell plate such as a 96-well plate) containing the luciferase protein. The reaction chamber may be situated in a reading device which can measure the light output, e.g., using a luminometer or photomultiplier. When the luciferase is expressed in whole cell(s) or in an animal, the reaction is started by the administration of a luciferase substrate, e.g., luciferin. For a whole cell(s), this administration may include addition of the luciferase substrate into the cell media. For animals, administration of the luciferase substrate may include injection or oral administration, e.g., inclusion of the substrate into the animal's food or water. The light output or luminescence may also be measured over time, for example in the same reaction chamber, cell(s) or animal, for a period of seconds, minutes, hours, etc. The light output or luminescence may be reported as the average over time, the half-life of decay of signal, the sum of the signal over a period of time, or as the peak output. Luminescence can also be detected via imaging, e.g., in vivo imaging.

Enhanced response includes the differential activity before and after the TL-CP biosensor interacts with a target molecule. The basal activity of the TL-CP biosensor is defined as the activity at assay time (O), before the biosensor interacts with a target molecule. The induced activity is defined as the activity at some later time (t) after the TL-CP biosensor has been interacted with a target molecule. The response or fold increase in activity is the ratio of induced to basal activity.

Enhanced luminescence includes increased light output as determined by suitable comparison of comparably-obtained measurements. As disclosed herein, one or more suitable amino acid substitutions to the TL-CP biosensor sequence produce TL-CP biosensor polypeptides which exhibit enhanced luminescence. Changes in the nucleotide sequence from the parental thermostable luciferase nucleotide sequence may contribute to enhanced luminescence by leading to an amino acid substitution and/or by enhancing protein expression.

Enhanced signal stability includes an increase in how long the signal from a luciferase continues to luminescence, for example, as measured by the half-life of decay of the signal in a time-course.

Enhanced protein stability includes increased thermostability (e.g., stability at elevated temperatures) and chemical stability (e.g., stability in the presence of denaturants such as detergents, including e.g., Triton X-100).

Luciferase biosensors have been previously described, see e.g., U.S. Patent Publication No. 2005/0153310, the disclosure of which are incorporated by reference herein. The sensor regions are cloned into a circularly-permuted luciferase such that when the luciferase biosensor interacts with a target molecule, an enhanced or increased luminescence is generated relative to a luciferase biosensor which has not been contact with a target molecule. Alternatively, the sensor regions are cloned into a circularly-permuted luciferase such that when the luciferase biosensor interacts with a target molecule, a decrease or no luminescence is generated relative to a luciferase biosensor which has not been in contact with a target molecule. The sensor regions may be useful for detecting the activity of a protease, the binding of cyclic nucleotides such as cAMP and cGMP, the presence or concentration of calcium, other ions or antibodies, the presence or concentrations of one or more G-protein coupled receptor ligands, a change in pH, the activity of a phosphatase or kinase or other enzymes, binding proteins or molecules of interest such as a peptide or a sugar known to those of skill in the art.

In some embodiments, a polynucleotide of the invention is optimized for expression in a particular host. As used herein, optimization includes codon optimization as well as, in eukaryotic cells, introduction of a Kozak sequence, and/or one or more introns. Thus, a nucleic acid molecule may have a codon composition that differs from that of a wild-type nucleic acid sequence encoding an unmodified luciferase at more than 30%, 35%, 40% or more than 45%, e.g., 50%, 55%, 60% or more of the codons.

In some embodiments of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In some embodiments of the invention, the majority of the codons which differ are ones that are preferred codons in a desired host cell, as those optimized sequences can increase the strength of the signal for luciferase. Preferred codons for mammals (e.g., humans) and plants are known to the art (e.g., Wada et al. NAR 18: 2367 (1990); Murray et al. NAR 17: 477 (1989); WO 02/16944).

In some embodiments, the corresponding wild-type luciferase is from a Coleopteran species, e.g., *Luciola cruciata, Luciola lateralis, Pyrocoelia miyako, Lampyris noctiluca, Photuris pennsylvanica, Phengodes* sp., *Luciola mingrelica*, and *Photinus pyralis*. (See Ye et al., Biochimica et Biophysica Acta, 1339:39-52 (1997)).

In some embodiments, the TL-CP biosensor contains the caspase-3 recognition site comprising amino acids DEVD, at the junction between the TL. Upon interaction with caspase-3, the TL-CP biosensor is cleaved at the recognition site allowing the two TL fragments to form a more favorable, higher activity, conformation. In other embodiments, the TL-CP biosensor contains a recognition site for other proteases, e.g., caspase-8 recognition site (LETDG; SEQ ID NO:15), TEV protease recognition site (ENLYFQS; SEQ ID NO:16) or MMP-2 recognition site (PLGMWSR; SEQ ID NO: 75).

The amino acid sequence of the modified TL-CP biosensor is different than the amino acid sequence of a corresponding unmodified TL-CP biosensor (parental), e.g., a mutant luciferase with one or more substitutions in the luciferase sequences. In some embodiments, the luciferase sequences of the modified thermostable luciferase are circularly-permuted relative to the amino acid sequence of a corresponding unmodified thermostable luciferase (parental luciferase) wherein the permutation is at a site (residue) or in a region that is tolerant to modification. In some embodiments, the luciferase sequences of a circularly-permuted thermostable luciferases are modified relative to a non-permuted thermostable luciferase.

In some embodiments, the TL-CP biosensor has one or more discrete (isolated) heterologous amino acid sequences, at least one of which directly or indirectly interacts with a target molecule, and optionally may include the deletion of one or more amino acids, e.g., at a site(s) or in a region(s) tolerant to modification including the N- and/or C-terminus of the unmodified thermostable luciferase, so long as the resulting TL-CP biosensor has bioluminescent activity before and/or after the interaction with the target, e.g., bioluminescent activity is altered after interaction with the target molecule, such as an alteration in light intensity, color or kinetic profile.

In some embodiments, a TL-CP of the invention comprises an amino acid sequence which is circularly-permuted relative to the amino acid sequence of a corresponding thermostable luciferase, such as an unmodified thermostable luciferase, resulting in a new N- and C-terminus in the circularly-permuted thermostable luciferase, at least one of which is at a site or in a region which is tolerant to modification, and is engineered to have functionality by introducing a sensor region comprising an amino acid sequence which directly or indirectly interacts with a target molecule. In other embodiments, the circularly-permuted thermostable luciferase includes other modifications, including but not limited to, insertions and/or deletions internal to the N- or C-terminus of the circularly-permuted thermostable luciferase, for instance, another insertion and/or a deletion, e.g., at or near the N- and C-terminus of the corresponding unmodified thermostable luciferase such as at residues corresponding to residues 1 to about 10 or about 30, or any integer in between, of the N-terminus and/or corresponding to the last residue or about the last 30, e.g., last 15, or any integer in between 1 and 30, residues of the C-terminus of the corresponding unmodified thermostable luciferase.

In some embodiments, a thermostable beetle luciferase may be circularly-permuted at a residue, for instance, residue 7, 37, 47, 75, 83, 107, 121, 144, 160, 174, 188, 198, 205, 225, 233, 242, 255, 268, 308, 316, 358, 377, 403, 435, 490 or 540, or in a region corresponding to residue 2 to 12; residue 32 to 53, e.g., residue 32 to 43 or residue 42 to 52; residue 70 to 88, e.g., residue 70 to 80 or residue 78 to 88; residue 102 to 126, e.g., residue 102 to 112 or residue 116 to 126; residue 139 to 165; residue 183 to 203; residue 220 to 247, e.g., residue 228 to 238; residue 262 to 273; residue 303 to 313; residue 353 to 408; residue 485 to 495; or residue 535 to 546 of a firefly luciferase, such as one of SEQ ID NOs:2 or 4. The residue numbering is based on that of an unmodified (native) firefly luciferase sequence. Corresponding positions may be identified by aligning luciferase sequences using, for instance, sequence alignment programs. Residues or regions in a luciferase tolerant to modification may be employed as sites to circularly permute the luciferase or for an insertion.

In some embodiments, the invention provides a polynucleotide encoding a biosensor comprising a modified circularly-permuted thermostable luciferase and a linker. In some embodiments, the thermostable luciferase is based on a version of *Photuris pennsylvanica* luciferase Ppe2 (SEQ ID NOs: 1 and 2) comprising amino acid substitutions which confer improved properties such as thermostability (SEQ ID NOs:3 and 4). The linker links the C-terminal portion of the modified thermostable luciferase to the N-terminal portion of the modified thermostable luciferase. The linker has a sensor region capable of interacting with a target molecule in a cell. The modified thermostable luciferase biosensor has an enhanced response after interaction of the biosensor with the target relative to an unmodified thermostable luciferase biosensor.

In some embodiments, the modified circularly-permuted thermostable luciferase biosensor has enhanced response after interaction with a target molecule in cells. The modified circularly-permuted thermostable luciferase biosensor include a substitution of at least one amino acid corresponding to positions 5, 17, 21, 23, 26, 39, 44, 51, 81, 101, 103, 110, 114, 115, 119, 123, 126, 128, 133, 137, 186, 191, 192, 193, 196, 208, 211, 214, 226, 228, 230, 233, 264, 273, 275, 286, 287, 294, 295, 297, 302, 303, 304, 306, 308, 309, 313, 324, 329, 331, 343, 348, 353, 364, 374, 385, 389, 409, 420, 426, 427, 428, 431, 449, 456, 460, 461, 465, 466, 468, 471, 473, 482, 484, 485, 489, 493, 494, 497, 503, 507, 509, 510, 513, 516, 517, 521, 522, 523, 526, 530, 533, 536, 537, 542, or 543 of SEQ ID NO: 2, or combinations thereof.

In some embodiments, a TL-CP has a linker containing a sensor region connecting the N- and C-terminals of the thermostable luciferase, where the sensor region comprises an amino acid sequence, e.g., a protease recognition site or a kinase site, which directly interacts with a target molecule, e.g., a protease or kinase.

In some embodiments, the amino acid sequence that interacts with the target molecule is flanked by at least one linker, e.g., flanked at each end, such as a peptide linker, which linkers may be the same or different, which optionally improve luminescence and/or response upon interaction with a target molecule. In some embodiments, the amino acid sequence that interacts with the target molecule is flanked by at least one linker at the N-terminus, which optionally improves luminescence and/or response upon interaction with a target molecule. In some embodiments, the linker has at least one of the following sequences:

G S S G G S G G S G G G, (SEQ ID NO: 23)

G S S S D S D S S A G S, (SEQ ID NO: 24)

G S N D S S G G S E G G, (SEQ ID NO: 25)

G S N G G F D S S E G G, (SEQ ID NO: 26)

G S I R W S G L S G G D, (SEQ ID NO: 27)

G S R G G S V Y S E G G, (SEQ ID NO: 28)

G S S E G S S D F G G D, (SEQ ID NO: 29)

G S I V V S C S S E G G, (SEQ ID NO: 30)

G S N W D S G C S R E G, (SEQ ID NO: 31)

G S N W D S G C S R E C, (SEQ ID NO: 32)

G S S G C T G D A G G S, (SEQ ID NO: 33)

G S N W D S G C S R Q C, (SEQ ID NO: 34)

G S S/N S/D/G D/S/G S/F D/G S/G S A/E G S/G, (SEQ ID NO: 35)

G S I/R/S R/G/E W/G S G/V/S L/Y/D S/F G/E G D/G, (SEQ ID NO: 36)

G S I/N/S V/W/G V/D/C S/T C/G S/C/D S/A E/R/G G/E G/S, (SEQ ID NO: 37)

G S I/S V/G/A V/G S/C G/D G/D/S S/A G/E G/E G/N , (SEQ ID NO: 38)

G S I/N/S V/W/G/A V/D/C/G S/T/C C/G S/C/D S/A E/R/G G/E G/S, (SEQ ID NO: 39)

G S I A G C G D A G E G, (SEQ ID NO: 40)

G S N W D S G C S R E, (SEQ ID NO: 41)

```
                                                    (SEQ ID NO: 42)
G S I A G C G D A G E G, (SEQ ID NO: 43)
G S N W D S G C S R E G, (SEQ ID NO: 44)
N W D S G C S R E G,
or (SEQ ID NO: 45)
I A G C G D A G E G.
```

The "/" mark indicates that the amino acid before or after the "/" may be used in that position. A linker employed in the biosensor of the invention is an amino acid sequence, the presence of which in the biosensor does not substantially decrease the activity of that biosensor, e.g., does not decrease the activity by more than 10-fold, such as by no more that 4-fold, or no more than 2-fold, relative to a corresponding biosensor that lacks the linker(s), and/or the presence of the linker employed in the biosensor of the invention increases luminescence or response to interacting with its target, relative to a corresponding biosensor that lacks the linker(s) or a corresponding biosensor having the linker(s) GSSGGSGGSGGG (SEQ ID NO:23), or relative to both corresponding biosensors.

In some embodiments, a peptide linker of the invention is positioned N-terminal to a sensor region of the invention and is capable of directly or indirectly interacting with a target molecule, e.g., a molecule to be detected. In some embodiments, a peptide linker of the invention is positioned C-terminal to that peptide sequence in a biosensor of the invention. In some embodiments, a peptide linker of the invention is positioned N-terminal and C-terminal to peptide sequence which is capable of directly or indirectly interacting with a target molecule to be detected.

In some embodiments, in the absence of a target molecule, the activity of a modified circularly-permuted thermostable luciferase biosensor of the invention is less than the activity of a corresponding parental (unmodified) circularly-permuted thermostable luciferase biosensor, e.g., the luminescence activity of the modified circularly-permuted thermostable luciferase biosensor is about 0.001%, 0.01%, 0.1%, 1%, 10%, 20%, 50%, 70% or more, but less than 100% that of a corresponding parental (unmodified) circularly-permuted thermostable luciferase biosensor, the activity of which circularly-permuted modified thermostable luciferase biosensor is optionally detectable. In other embodiments, in the absence of the target, the activity of a modified circularly-permuted thermostable luciferase biosensor of the invention is substantially the same or greater than the activity of a parental (unmodified) circularly-permuted thermostable luciferase biosensor, e.g., the luminescence activity of the modified circularly-permuted thermostable luciferase biosensor of the invention is about 1.5-fold, e.g., at least 2-, 3- or 5-fold or more, that of a parental (unmodified) circularly-permuted thermostable luciferase biosensor. In the presence of the target molecule, the activity of the modified circularly-permuted thermostable luciferase biosensor of the invention is detectably altered. For instance, a detectable alteration in activity of a modified circularly-permuted thermostable luciferase biosensor in the presence of a target molecule is an alteration of at least 0.001%, 0.01%, 0.1%, 1%, 10%, or 100%, and up to 2-fold, 4-fold, 10-fold, 100-fold, 1.000-fold, 10.000-fold or more, relative to the activity of the modified circularly-permuted thermostable luciferase biosensor in the absence of the target. Thus, the physical proximity of a target molecule which interacts with a sensor region present in the modified circularly-permuted thermostable luciferase biosensor but not the parental (unmodified) circularly-permuted thermostable luciferase biosensor, alters, e.g., decreases, eliminates, or increases, the activity of the modified circularly-permuted thermostable luciferase biosensor. In some embodiments, the luminescent signal of a modified circularly-permuted thermostable luciferase biosensor of the invention in the presence of the target is increased relative to the luminescent signal of a corresponding parental (unmodified) circularly-permuted thermostable luciferase biosensor luciferase in the presence of a target molecule.

The invention includes circularly-permuted biosensors, which luciferase sequence may include deletions of residues at the original (wild type) N- or C-termini, or both, e.g., deletion of 1 to 3 or more residues at the N-terminus and 1 to 6 or more residues at the C-terminus, as well as a sensor region which interacts with a target molecule or are affected by post-translational modifications (sensors). The luciferase sequences of a modified circularly-permuted thermostable luciferase are the same or are substantially the same as the amino acid sequence of an unmodified circularly-permuted thermostable luciferase biosensor. A polypeptide or peptide having substantially the same sequence means that an amino acid sequence is largely, but may not entirely be, the same and retains a functional activity of the sequence to which it is related. In general, two amino acid sequences are substantially the same or substantially homologous if they are at least 80% identical, e.g., have at least 85%, 90%, 95%, 99%, or more identity.

In some embodiments, the modification may be the introduction of a recognition site for a hydrolase including but not limited to proteases, peptidases, esterases (e.g., cholesterol esterase), phosphatases (e.g., alkaline phosphatase), and the like. For instance, hydrolases include, but are not limited to, enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism. For example, a modified thermostable beetle luciferase of the invention may comprise an enterokinase cleavage site, a caspase cleavage site, a coronavirus protease site (STLQ-SGLRKMA; SEQ ID NO:46), a kinase site, a HIV-1 protease site (SQNY-PIVQ or KAVRL-AEAMS; SEQ ID NO:47 and SEQ ID NO:48, respectively), a HCV protease site (AEDV-VCC-SMSYS; SEQ ID NO:49) (see, e.g., Lee et al., 2003), a SARS virus protease site (e.g., QTSITSAVLQSGFRKMA-FPS; SEQ ID NO:50, or VRQCSGVTFQGKFKKIVKGT; SEQ ID NO:51), a Granzyme B site, a rhinovirus protease site, e.g., rhinovirus 3C protease site, a prohormone convertase site, an interleukin-1β-converting enzyme site, a CMV assembling site, a leishmandysin site, *B. anthracis* lethal factor, a botulinum neurotoxin light chain protease site, a beta-secretase site for amyloid precursor protein (VKM-DAEF; SEQ ID NO:56), prostate specific antigen sequence, a thrombin site, a renin and angiotensin-converting enzyme site, a cathepsin D site, a matrix metalloproteinase site, a uPA site, a plasmin site, a binding site for a cation, such as a calcium binding domain, a calmodulin binding domain, a cellulose binding domain, a chitin binding domain, a maltose binding protein domain, or a biotin binding domain. In another embodiment, a modified thermostable beetle luciferase of the invention may comprise a sequence recognized by a ligand such as an antibody or a metal such as calcium.

The invention also includes a stable cell line that expresses a modified circularly-permuted thermostable luciferase biosensor, comprises an expression cassette comprising a nucleic acid molecule encoding the modified circularly-permuted thermostable luciferase biosensor of the invention, and/or comprises a vector (e.g., a plasmid, virus, or defective viral particles) capable of expressing the nucleic acid molecule of the invention in a host cell. In one embodiment, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or modified circularly-permuted thermostable luciferase biosensor of the invention.

For instance, a vector encoding a modified circularly-permuted thermostable luciferase biosensor is mixed with a sample, e.g., a cell, cell lysate, in vitro transcription/translation mixture, or supernatant, and the activity of the modified circularly-permuted thermostable luciferase biosensor in the sample detected or determined, e.g., optionally at one or more time points, or relative to a control sample without the target or having a differing amount of the target. An alteration in luminescent activity in the sample, for instance, over time, and/or relative to a control, e.g., a cell having a specified amount of a target molecule, indicates the presence or amount of the target molecule in the sample, or change in amount of the target molecule related to experimental condition. In some embodiment, a cell is contacted with a vector comprising a promoter, e.g., a regulatable or constitutive promoter, and a nucleic acid sequence encoding a modified circularly-permuted thermostable luciferase of the invention which comprises a sensor region which interacts with a cyclic nucleotide. In some embodiments, a transfected cell is cultured under conditions in which the promoter induces transient expression of the modified circularly-permuted thermostable luciferase biosensor, and the presence or amount of luminescence determined. In other embodiments, a modified circularly-permuted thermostable luciferase biosensor of the invention comprising a sensor region which interacts with a target molecule and a sample suspected of having the target molecule are mixed, and the amount of luminescence determined.

A modified circularly-permuted thermostable luciferase biosensor of the invention may be employed in applications where unmodified circularly-permuted thermostable luciferase biosensor cannot, such as, as a functional reporter to measure or detect various conditions and/or target molecules in a cell or in an animal, e.g., a mouse. For instance, a vector encoding a modified circularly-permuted thermostable luciferase biosensor, or the modified circularly-permuted thermostable luciferase biosensor, is introduced to a cell, an animal, cell lysate, in vitro transcription/translation mixture, or supernatant, and the activity of the modified circularly-permuted thermostable luciferase biosensor detected or determined, e.g., at one or more time points and relative to a corresponding unmodified circularly-permuted thermostable luciferase biosensor. An alteration in luminescent activity in the cell, an animal, cell lysate, in vitro transcription/translation mixture, or supernatant over time, and/or relative to a control, e.g., a cell having the corresponding unmodified circularly-permuted thermostable luciferase biosensor, indicates the presence of the protease. For instance, the invention includes a method to detect a virus associated with severe acute respiratory syndrome. The method includes contacting a biological, e.g., a physiological tissue or fluid, sample with a modified circularly-permuted thermostable luciferase biosensor. The biosensor comprises an amino acid recognition sequence for a protease of the virus. It is detected or determined whether the activity of the modified circularly-permuted thermostable luciferase biosensor in the presence of the sample is altered, thereby indicating whether the sample contains the virus.

In some aspects, the disclosure provides a method to detect the presence or activity of a target molecule in a sample comprising contacting the sample with a modified circularly-permuted thermostable luciferase biosensor and a substrate for the modified circularly-permuted thermostable luciferase and measuring luminescence. In some embodiments, the modified circularly-permuted thermostable luciferase comprises a sensor region for the target molecule. The sensor region may contain but is not limited to a protease recognition site, a kinase recognition site, an antibody binding site, a metal binding site, an ion biding site, a cyclic nucleotide binding site or a nucleotide binding site. In some embodiments, the method may detect the presence or activity of target molecule which is a protease, a kinase, an antibody, a metal, an ion, a cyclic nucleotide or a nucleotide. In embodiments, the protease may be a caspase 3, caspase 8, TEV protease or MMP-2. In embodiments, the sample may be a cell, an animal, cell lysate, or an in vitro transcription/translation mixture. In some embodiments, the method further comprises adding a test compound wherein the test compound may alter (e.g., decreases, eliminates, or increases) the activity of the target molecule. In embodiments, the substrate for the modified circularly-permuted thermostable luciferase biosensor may be luciferin or a luciferin derivative.

The invention also provides a method of detecting the presence of a molecule of interest. For instance, a cell is contacted with a vector comprising a promoter, e.g., a regulatable promoter, and a nucleic acid sequence encoding a modified circularly-permuted thermostable luciferase biosensor of the invention which comprises an insertion/sensor region which interacts with the molecule of interest. In one embodiment, a transfected cell is cultured under conditions in which the promoter induces transient expression of the modified circularly-permuted thermostable luciferase biosensor, and a detectable activity of the modified circularly-permuted thermostable luciferase biosensor is determined. In another embodiment, an animal, e.g., a mouse, is contacted with a vector comprising a promoter, e.g., a regulatable promoter, and a nucleic acid sequence encoding a modified circularly-permuted thermostable luciferase biosensor of the invention which comprises an insertion/sensor region which interacts with the molecule of interest or a transfected cell expressing the modified circularly-permuted thermostable luciferase biosensor of the present invention. Detectable activity of the modified circularly-permuted thermostable luciferase biosensor is then determined.

The modified circularly-permuted thermostable luciferase biosensor of the invention comprises an amino acid sequence which interacts with a target molecule, i.e., molecule of interest, or is otherwise sensitive to conditions relative to the corresponding unmodified circularly-permuted thermostable luciferase biosensor. One or more mutated polynucleotides are selected which encode mutated modified circularly-permuted luciferase biosensors that have an altered interaction with the molecule of interest or altered activity under certain conditions relative to the interaction or activity of the modified circularly-permuted luciferase biosensor. In some embodiments, the invention provides a method which includes contacting a modified circularly-permuted thermostable luciferase biosensor of the invention with a library of molecules, and detecting or determining whether one or more molecules interacts with the sensor region in the modified circularly-permuted thermostable luciferase biosensor.

The invention also provides methods of screening for agents ("test" agents) capable of modulating the amount of the target molecule or molecule of interest present in a sample. "Modulation" refers to the capacity to either enhance or inhibit a functional property of biological activity or process (e.g., enzyme activity). Such enhancement or inhibition may be contingent on the occurrence of a specific event, such as activation of a signal transduction pathway, and/or may be manifest only in particular cell types. A "modulator" refers to an agent (naturally occurring or non-naturally occurring), such as, for example, a biological macromolecule (e.g., nucleic acid, protein, non-peptide, or organic molecule), small molecules, an extract made from biological materials such as bacteria, plants, fungi, or animal (particularly mammalian) cells or tissues, or any other agent. Modulators are evaluated for potential activity as inhibitors or activators (directly or indirectly) of a biological process or processes (e.g., agonist, partial antagonist, partial agonist, or antagonist) by inclusion in the screening assays described herein. The activities (or activity) of a modulator may be known, unknown or partially known. Such modulators can be screened using the methods of the invention. The term "test agent" or "test compound" refers to an agent or compound to be tested by one or more screening method(s) of the invention as a putative modulator. Usually, various predetermined concentrations are used for screening such as 0.01 µM, 0.1 µM, 1.0 µM, and 10.0 µM. Controls can include the measurement of a signal in the absence of the test agent or compound, comparison to an agent or compound known to modulate the target, or comparison to a sample (e.g., a cell, tissue, or organism) before, during, and/or after contacting with the test agent or compound.

In some embodiments, the method includes screening for agents or compounds that modulate protease activity. For example, in some embodiments, a method of identifying an agent or compound capable of modulating apoptosis is provided. Caspase family proteases have been associated with apoptosis. Thus, the method includes contacting a sample suspected of containing a caspase-family protease with an agent or compound suspected of modulating the caspase activity, and a modified circularly-permuted thermostable luciferase biosensor having a cleavage site cleavable by the caspase. The activity of the modified circularly-permuted thermostable luciferase biosensor is detected in the sample before and after contacting with the test agent or compound. An increase in activity after contacting with the agent is indicative of an agent or compound that inhibits apoptosis and a decrease is indicative of an agent that activates apoptosis.

Accordingly, the invention provides a screening system useful for identifying agents or compounds which modulate the cleavage of recognition sequence present in a modified circularly-permuted thermostable luciferase biosensor of the invention and detecting its activity. This allows one to rapidly screen for protease activity modulators. Utilization of the screening system described herein provides a sensitive and rapid means to identify agents or compounds which modulate (e.g., inhibit or activate) a protease, for example, a caspase family protease. In particular, the invention contemplates modified circularly-permuted thermostable luciferase biosensors in which the sensor region includes an amino acid sequence that is a cleavage site for an enzyme of interest. Thus, when the molecule of interest is a protease, the insertion comprises a peptide containing a cleavage recognition sequence for the protease. A cleavage recognition sequence for a protease is a specific amino acid sequence recognized by the protease during proteolytic cleavage. Accordingly, the invention provides methods to determine the amount of a protease in a sample by contacting the sample with a modified circularly-permuted thermostable luciferase biosensor of the invention comprising a sensor region for the protease and measuring changes in luciferase activity. The modified circularly-permuted thermostable luciferase biosensor of the invention can be used for, among other things, monitoring the activity of a protease inside a cell or an animal that expresses the modified circularly-permuted thermostable luciferase biosensor.

The assays of the invention can be used to screen drugs to identify agents or compounds that alter the activity of a protease that cleaves the modified circularly-permuted thermostable luciferase biosensor. In some embodiments, the assay is performed on a sample in vitro containing a protease. A sample containing a known amount of protease is mixed with a modified circularly-permuted thermostable luciferase biosensor of the invention and with a test agent. The amount of the protease activity in the sample is then determined as described above. The amount of activity per mole of protease in the presence of the test agent is compared with the activity per mole of protease in the absence of the test agent. A difference indicates that the test agent alters the activity of the protease. Accordingly, the alterations may be an increase in protease activity resulting in a decrease in modified circularly-permuted thermostable luciferase biosensor activity or a decrease in protease activity corresponding to an increase or maintenance of modified circularly-permuted thermostable luciferase biosensor activity.

In some embodiments, the ability of an agent to alter protease activity is determined. In this assay, cells are conditioned or contacted with an agent or compound suspected of modulating protease activity. The cell or cells in the culture are lysed and protease activity measured. For example, a lysed cell sample containing a known or unknown amount of protease is mixed with a modified circularly-permuted thermostable luciferase biosensor of the invention. The amount of the protease activity in the sample is then determined as above by determining the degree of modified circularly-permuted thermostable luciferase biosensor activity in a control or non-treated sample and the treated lysed cellular sample. The activity or inhibition can be calculated based on a per microgram or milligram protein in the sample. Accordingly, the modulation in protease activity includes an increase in protease activity resulting in a decrease in modified circularly-permuted thermostable luciferase biosensor activity or a decrease in protease activity corresponding to an increase or maintenance of modified circularly-permuted thermostable luciferase biosensor activity. Typically, the difference is calibrated against standard measurements to yield an absolute amount of protease activity. A test agent that inhibits or blocks the activity or expression of the protease can be detected by increased modified circularly-permuted thermostable luciferase biosensor activity in treated cells compared to untreated controls.

In other embodiments, the ability of an agent or compound to alter protease activity in vivo is determined. In an in vivo assay, cells transfected, either transiently or stably, with an expression vector encoding a modified circularly-permuted thermostable luciferase biosensor of the invention are exposed to different amounts of the test agent or test compound, and the effect of the test agent or test compound on luciferase activity in a cell can be determined. Typically, the difference is calibrated against standard measurements to yield an absolute amount of protease activity. A test agent that inhibits or blocks the activity or expression of the protease can be detected by increased modified circularly-permuted thermostable luciferase biosensor activity in treated cells compared to untreated controls.

In other embodiments, the ability of an agent or compound to alter protease activity in an animal is determined. In a whole animal assay, an animal, e.g., mouse, may be injected with cells that express a modified circularly-permuted thermostable luciferase biosensor of the invention, and the animal exposed to different amounts of a test agent or test compound. In some embodiments, cells that express a modified circularly-permuted thermostable luciferase biosensor of the invention may be implanted in an animal. In some embodiments, the substrate for the modified circularly-permuted thermostable luciferase is injected into the animal. In some embodiments, the substrate is injected into the cells of the animal. The effect of the test agent or test compound on luciferase activity in the animal can then be determined.

The disclosure also provides a method of immobilizing the modified circularly-permuted thermostable luciferase biosensor to a solid support, e.g., a particle, resin, column, solid surface (e.g., plate, slide, or well bottom), etc. The immobilized biosensor can then be used to detect the presence or activity of a molecule of interest. In some embodiments, the modified circularly-permuted thermostable luciferase biosensor of the invention, either in purified form or expressed in cell lysate, e.g., E. coli cell lysate, can be immobilized onto a solid support, e.g., resin or solid surface, and a molecule of interest detected. The molecule of interest can be purified form of the molecule or also be expressed in a cell lysate. Detectable activity of the modified circularly-permuted thermostable luciferase biosensor is then determined.

In some aspects, the disclosure provides a method to detect apoptosis in a sample comprising contacting the sample with a modified circularly-permuted thermostable luciferase biosensor and a substrate for the modified circularly-permuted thermostable luciferase and detecting luminescence in the sample. In some embodiments, the modified circularly-permuted thermostable luciferase biosensor contains a sensor region for a molecule involved in apoptosis.

In some aspects, the disclosure provides compositions and methods for a non-radioactive assay for cell-mediated cytotoxicity. The disclosure provides compositions and methods to detect or determine cytotoxicity mediated by cytotoxic lymphocytes, e.g., cytotoxic T lymphocytes (CTLs) and cytokine-activated natural killer (NK) cells. The disclosure also provides novel granzyme B recognition sequences and bioluminescent biosensors for detecting granzyme B activity. The disclosure further includes methods of detecting granzyme B activity in cell-based assays using the bioluminescent biosensors described herein.

In some embodiments, the method of the present invention utilizing a bioluminescent protease biosensor containing a novel or known granzyme B recognition sequence. In some embodiments, the method comprises transfecting a bioluminescent protease biosensor containing a granzyme B recognition sequence into a target cell, co-incubating the transfected target cells with a cytotoxic lymphocyte, e.g., a NK cell, and detecting luminescence. If granzyme B is successfully transferred to the transfected target cell, it will cleave the biosensor via the recognition sequence, and luminescence will be generated. Examples of a target cell include a tumor cell, such as K562 cell, EL4 cell, or Jurkat cell, virus-infected cells, cells infected with intracellular bacterial or protozoal parasites, and allografts, such as transplanted kidney, heart, lungs, In other embodiments, the method of the present invention can be used to test patient or patient-derived CTLs or NK cells to determine their cytotoxic function. In some embodiments, the method comprises transfecting a bioluminescent protease biosensor containing a granzyme B recognition sequence into a target cell, e.g., a tumor cell, co-incubating the transfected target cells with the patient or patient-derived CTLs or NK cells, and detecting luminescence. In some embodiments, the patient or patient-derived CTLs or NK cells have little or unknown cytotoxic function.

In other embodiments, the method of the present invention can be used to screen for inhibitors, e.g., siRNAs, or enhancers, e.g., small molecules, of the cytotoxic function of a cell. In some embodiments, the screening for inhibitors or enhancers can be done in a multi-well format, e.g., 96-, 384-, or 1536-wells.

The disclosure also provides novel granzyme B recognition sequences. In some embodiments, the novel granzyme B recognition sequence is GRIEADSE (SEQ ID NO:80) or KSVGPDFG (SEQ ID NO:81).

The disclosure also provides protease biosensors for the detection of cell-mediated cytotoxicity. The protease biosensors, as described in U.S. patent application Ser. No. 13/105, 648, incorporated by reference herein, encode a biosensor comprising a circularly-permuted, thermostable luciferase and a peptide linker. The peptide linker comprises a sensor region capable of interacting with a molecule of interest. In some embodiments, the protease biosensor sensor region comprises a granzyme B recognition sequence. In some embodiments, the granzyme B recognition sequence is a novel recognition sequence, e.g., GRIEADSE (SEQ ID NO:80) or KSVGPDFG (SEQ ID NO:81). In other embodiments, the granzyme B recognition sequence is a known recognition sequence, e.g., GIETDSG (SEQ ID NO:82).

The disclosure also provides methods for detecting granzyme B activity in cellular processes, e.g., beta-arrestin localization. In some embodiments, the granzyme B biosensor of the present invention would be used to determine the granzyme B activity in a cellular process.

The materials and composition for use in the assay of the invention are ideally suited for the preparation of a kit. Such a kit may comprise a carrier means containing one or more container means such as vials, tubes, and the like, each of the containers means comprising one of the separate elements to be used in the method. One of the containers comprises a modified circularly-permuted thermostable luciferase biosensor or polynucleotide (e.g., in the form of a vector) of the

EXAMPLES

Example I

Generation of a Modified Thermostable Luciferase Biosensor with Increased Responsivity in Cells The Caspase-3 BioSensor (CBS) is a thermostable *Photuris pennsylvanica* luciferase (TL), circularly-permuted (CP) at amino acid 358, with a caspase-3 recognition site, i.e., one containing the caspase-3 recognition site comprising amino acids DEVD, at the junction between the TL fragments. The specific CBS that was used as the starting template is termed TL-CP358-DEVD:DD. The amino acid sequence of this CBS can be represented as: M/TL residues 358-544/SDEVDGSL/TL residues 4-354/V (SEQ ID NO:6). The amino acid positions in the CP TL correlate to those of the non-CP TL sequence (provided in the attached appendix). Upon treatment with caspase-3, CBS is cleaved at the recognition site allowing the two TL fragments to form a more favorable, higher activity, conformation.

The utility of CBS is the differential activity before and after cleavage by caspase-3. The basal activity of CBS is defined as the activity at assay time (O), before caspase-3 has had time to cleave at the recognition site. The induced activity is defined as the activity at some later time (t) after CBS has been cleaved by caspase-3. The response or fold increase in activity, is the ratio of induced to basal activity. Substitutions in TL-CP358-DEVD:DD were generated to develop CBS variants with enhanced responsivity to induction using the error-prone, mutagenic PCR-based system GeneMorph II (Stratagene; Daugherty, PNAS USA 97(5):2029 (2000)), according to manufacturer's instructions.

The resulting library was expressed in *E. coli* and screened for luciferase activity with and without pre-treatment with recombinant caspase-3 (data not shown). CBS variants having the best signal and response characteristics were then evaluated in HEK293 cells by kinetic assay measuring the response to TNF-α-related apoptosis inducing ligand (TRAIL) treatment (Wiley, S. R. et al., Immunity 3:673 (1995); Niles, A. L. et al., Meth. Mol. Biol. 414:137 (2008)). TRAIL induces apoptosis via activation of the death receptor to form active caspase-8, which in turn activates procaspase 3 to produce caspase-3. The appearance of active caspase-3 should be accompanied by an increase in luminescence as the CBS variants are cleaved and activated. Briefly, HEK293 cells, plated at 15,000 cells/well in a 96-well plate, were transiently transfected using TransIT-LTI (Mires Bio) with plasmid DNAs encoding various CBS variants with amino acid substitutions in TL-CP358-DEVD:DD. The same plasmids also carried a gene for constitutive expression of *Renilla* luciferase to act as a transfection control. Cells were pre-treated with 2 mM luciferin for 2 hrs at 37° C. Cells were treated with 1 µg/mL TRAIL and assayed for 10 hrs at 37° C. Luminescence was monitored continuously over time (Luminometer: Varioskan Flash (Thermo) 1 sec integration time). Cells in replicate wells were lysed, at the time of TRAIL addition, i.e., time (0) and *Renilla* luciferase activity was measured. All biosensor data was then normalized for transfection efficiency using *Renilla* luciferase luminescence (Dual-GloAssay System; Promega Corporation).

Exemplary CBS variants include, but are not limited to those listed in Table 1. Table 1 lists the variants of TL-CP358-DEVD:DD, identified by clone name, showing improved response to TRAIL treatment. Improvements listed in Table 1 are normalized to the parental TL-CP358-DEVD:DD CBS. "BASAL" represents the normalized biosensor luminescence at TRAIL addition, i.e., time (0), "INDUCED" represents the normalized biosensor luminescence at roughly 10 hrs after TRAIL addition, and "RESPONSE" represents the fold-induction, i.e., the ratio of INDUCED to BASAL activity.

Standard sequencing techniques known in the art were used to identify the amino acid substitution in each clone (see Table 1). The amino acid position is based on parental TL, e.g., Pro at position 2 of the variants=TL 358; the residues to the N-terminus of the DEVD therefore represent TL residues 358-544(Gly); the residues to the C-terminus of the DEVD represent TL residues 4(Lys)-354(Gly) (See FIG. 1 for examples). Each amino acid substitution is indicated by the position corresponding to the amino acid position in the parental TL, not the TL-CP358-DEVD:DD sequence, whereby the first letter following the numerical position represents the corresponding amino acid in parental TL. If the amino acid is substituted with another amino acid, the second letter represents the amino acid substitution. If the amino acid is substituted with a stop codon, the substitution is indicated by "STOP."

TABLE 1

Summary of the fold improvement in responsivity of CBS variants over the corresponding TL-CP358-DEVD:DD

| CLONE | IMPROVEMENT OVER TL-CP358-DEVD:DD | | | | | | | | |
|---|---|---|---|---|---|---|---|---|---|
| | BASAL | INDUCED | RESPONSE | mut#1 | mut#2 | mut#3 | mut#4 | mut#5 | mut#6 |
| 01:E-12 | 0.35 | 0.71 | 2.04 | 021AD | | | | | |
| 01:G-12 | 0.00 | 0.00 | 2.11 | 044AD | | | | | |
| 01:G-03 | 0.47 | 0.59 | 1.26 | 128SP | | | | | |
| 01:E-11 | 0.4 | 0.6 | 1.3 | 193SP | | | | | |
| 09:A-11 | 0.69 | 1.17 | 1.69 | 273LQ | | | | | |
| 01:H-06 | 0.22 | 0.39 | 1.77 | 275SP | | | | | |
| 13:F-03 | 0.30 | 1.02 | 3.41 | 503DG | | | | | |
| 03:E-12 | 0.44 | 0.50 | 1.16 | 286LH | | | | | |
| 01:C-04 | 0.15 | 0.65 | 4.20 | 294LH | | | | | |
| 05:C-07 | 0.16 | 0.20 | 1.30 | 294LP | | | | | |
| 14:A-04 | 0.34 | 0.95 | 2.77 | 297SG | | | | | |

TABLE 1-continued

Summary of the fold improvement in responsivity of CBS variants over the corresponding TL-CP358-DEVD:DD

| | | IMPROVEMENT OVER TL-CP358-DEVD:DD | | | | | | |
|---|---|---|---|---|---|---|---|---|
| CLONE | BASAL | INDUCED | RESPONSE | mut#1 | mut#2 | mut#3 | mut#4 | mut#5 | mut#6 |
| 12:B-10 | 1.15 | 1.34 | 1.16 | 297SI | | | | | |
| 13:B-03 | 0.74 | 1.45 | 1.95 | 329RW | | | | | |
| 14:F-06 | 0.20 | 1.12 | 5.74 | 409AV | | | | | |
| 05:C-02 | 0.19 | 0.38 | 2.02 | 461PL | | | | | |
| 06:A-12 | 0.04 | 0.14 | 3.26 | 465DV | | | | | |
| 01:D-02 | 0.1 | 0.6 | 5.3 | 471IT | | | | | |
| 14:G-12 | 0.11 | 0.30 | 2.69 | 482AS | | | | | |
| 06:G-09 | 0.55 | 1.30 | 2.69 | 482AV | | | | | |
| 07:C-06 | 0.16 | 0.61 | 3.79 | 485VE | | | | | |
| 05:B-06 | 0.05 | 0.20 | 4.06 | 497VA | | | | | |
| 07:B-02 | 0.5 | 1.0 | 1.8 | 503SG | | | | | |
| 01:A-05 | 0.2 | 0.6 | 3.6 | 507TI | | | | | |
| 05:D-11 | 0.04 | 0.16 | 3.55 | 522PS | | | | | |
| 02:B-09 | 0.25 | 0.55 | 2.39 | 526TS | | | | | |
| 06:D-04 | 0.18 | 0.45 | 2.42 | 530DV | | | | | |
| 01:F-02 | 0.58 | 0.67 | 1.15 | 543NS | | | | | |
| 05:E-06 | 0.12 | 0.41 | 3.51 | 017EG | 513GA | | | | |
| 09:D-10 | 0.19 | 0.43 | 2.21 | 026FY | 530DG | | | | |
| 13:B-04 | 0.51 | 1.26 | 2.48 | 051LS | 193SP | | | | |
| 01:H-08 | 0.34 | 0.67 | 1.96 | 110EV | 304DA | | | | |
| 11:A-11 | 0.71 | 1.16 | 1.63 | 115HY | 521IV | | | | |
| 05:G-10 | 0.43 | 0.82 | 1.92 | 123RH | 303YD | | | | |
| 04:A-05 | 0.21 | 0.45 | 2.20 | 128SP | 523KQ | | | | |
| 12:D-08 | 330.89 | 764.74 | 2.31 | 192AT | 389LS | | | | |
| 05:D-06 | 0.55 | 1.03 | 1.87 | 193SP | 114IK | | | | |
| 15:E-10 | 0.06 | 0.17 | 2.73 | 196FY | 530DG | | | | |
| 11:F-07 | 0.23 | 0.69 | 2.96 | 208MK | 466AG | | | | |
| 04:H-08 | 0.06 | 0.17 | 3.03 | 226FY | 509KT | | | | |
| 07:C-02 | 0.29 | 0.78 | 2.66 | 264MT | 303YN | | | | |
| 01:E-04 | 0.22 | 0.57 | 2.63 | 294LH | 304DE | | | | |
| 13:C-09 | 0.55 | 1.36 | 2.46 | 294LH | 308LI | | | | |
| 04:H-07 | 0.14 | 0.25 | 1.80 | 294LP | 510WR | | | | |
| 14:G-10 | 0.23 | 0.50 | 2.17 | 302KE | 530DV | | | | |
| 01:B-08 | 0.07 | 0.15 | 2.20 | 308LS | 343E(STOP) | | | | |
| 13:G-12 | 0.37 | 1.06 | 2.89 | 309KN | 331KI | | | | |
| 16:D-12 | 0.2 | 0.6 | 2.4 | 329RQ | 530DV | | | | |
| 05:A-07 | 0.29 | 0.61 | 2.10 | 353K(STOP) | 530DA | | | | |
| 09:E-03 | 0.54 | 1.26 | 2.33 | 364IM | 530DA | | | | |
| 18:C-05 | 0.07 | 0.29 | 4.24 | 374DY | 431FL | | | | |
| 13:A-05 | 0.09 | 0.18 | 2.67 | 374DY | 431FS | | | | |
| 08:A-12 | 0.24 | 0.75 | 3.13 | 385EG | 465DG | | | | |
| 01:C-11 | 0.01 | 0.10 | 8.50 | 420GR | 489GR | | | | |
| 04:A-08 | 0.01 | 0.03 | 3.92 | 468VI | 484VL | | | | |
| 04:G-10 | 0.17 | 0.53 | 3.14 | 484VI | 516KN | | | | |
| 04:D-01 | 0.66 | 0.79 | 1.21 | 543NS | 494EV | | | | |
| 04:E-11 | 0.14 | 0.42 | 3.07 | 081SC | 374DV | 517FC | | | |
| 01:H-11 | 0.03 | 0.07 | 2.15 | 101VA | 286LP | 364IL | | | |
| 05:C-06 | 0.21 | 0.41 | 2.01 | 119IN | 294LH | 542TP | | | |
| 04:B-09 | 0.10 | 0.16 | 1.66 | 128SP | 211HL | 287VA | | | |
| 11:D-05 | 0.20 | 0.46 | 2.25 | 137NY | 493NY | 507TI | | | |
| 10:D-04 | 0.17 | 0.41 | 2.33 | 196FY | 228NT | 530DG | | | |
| 11:B-03 | 0.04 | 0.19 | 4.57 | 208ML | 230IT | 273LP | | | |
| 07:B-04 | 0.24 | 0.61 | 2.54 | 295AV | 449AT | 537ML | | | |
| 04:C-03 | 0.2 | 0.7 | 2.9 | 523KI | 533VA | 536QR | | | |
| 10:D-11 | 0.51 | 1.31 | 2.58 | 005ND | 133QL | 228NT | 294LH | | |
| 15:D-11 | 0.27 | 1.00 | 3.64 | 021AS | 426DN | 428DG | 526TS | | |
| 11:A-06 | 0.23 | 0.85 | 3.73 | 039IT | 214IV | 348VA | 507TI | | |
| 14:H-06 | 0.16 | 0.69 | 4.24 | 186NI | 233TM | 427ND | 465DG | | |
| 05:F-11 | 0.94 | 1.50 | 1.58 | 103PS | 191VA | 306SP | 313ST | 473DV | |
| 11:B-10 | 0.53 | 1.19 | 2.25 | 126FC | 466AV | 471IM | 536QR | 543NK | |
| 10:D-03 | 0.34 | 1.06 | 3.09 | 023EG | 228NT | 309KE | 324EG | 456IV | 460HL |

Example II

Evaluation of Specific Combinations of Mutations in Thermostable Luciferase Caspase-3 Biosensors Additional CBS variants were generated using the oligo-based site-directed mutagenesis kit Quik Change (Stratagene; Kunkel, PNAS USA 82(2):488 (1985)), according to the manufacturer's instructions. The amino acid substitutions identified in those variants from Example I with the most improved response, specifically clones 12:B-10, 01:A-05, 04:C-03, 01:E-11, 16:D-12, 01:D-02 and 07:B-02, were combined and evaluated in HEK293 cells as in Example I. The amino acid substitutions used to generate the additional CBS variants were 193SP, 297SI, 329RQ, 4711T, 503SG, 507TI, 523KI, 533VA, and 536QR corresponding to SEQ ID NO:2. Exemplary CBS variants include, but are not limited to, those listed in Table 2. Table 2 identifies the clone ("NEW #"), the amino acid substitutions found in the clone indicated by an X in the column which indicate the amino acid substitution, 193SP, 297SI, 329RQ, 4711T, 503SG, 507TI, 523KI, 533VA, and 536QR, the improvement in Basal, Induced and Response over the corresponding starting TL-CP358-DEVD:DD.

sequence and the positions corrected for the circular permutation sites (see also Table 3). The top cartoon in FIG. 1 indicates the location of the substitutions based on sequential numbering of the primary amino acid sequence. The bottom cartoon in FIG. 1 indicates the codon designations based on the parental TL-CP358-DEVD:DD. The nucleotide changes are as follows: 471: ata>aca; 503: agt>ggt; 507: aca>ata; 193: tcg>ccg.

TABLE 2

Summary of the fold improvement in responsivity of CBS variants with specific amino acid substitution combinations over the corresponding TL-CP358-DEVD:DD

| NEW # | 193SP | 297SI | 329RQ | 471IT | 503SG | 507TI | 523KI | 533VA | 536QR | BASAL | INDUCED | RESPONSE |
|---|---|---|---|---|---|---|---|---|---|---|---|---|
| FC7: 02 | X | X | | X | X | X | X | | | 0.023 | 0.070 | 3.112 |
| FC7: 05 | X | X | X | X | X | X | | | | 0.028 | 0.089 | 3.197 |
| FC7: 06 | X | X | X | X | X | | X | | | 0.007 | 0.016 | 2.444 |
| FC7: 07 | X | X | X | | X | X | X | | | 0.005 | 0.008 | 1.483 |
| FC7: 08 | X | | | X | X | X | X | | | 0.007 | 0.009 | 1.365 |
| FC7: 12 | X | | X | X | X | X | | | | 0.077 | 0.168 | 2.186 |
| FC7: 15 | X | | X | X | X | | X | | | 0.038 | 0.048 | 1.253 |
| FC7: 16 | | X | X | X | X | | X | | | 0.010 | 0.019 | 2.014 |
| FC7: 17 | X | X | X | X | X | | | | | 0.060 | 0.153 | 2.543 |
| FC7: 18 | X | X | | | X | X | X | | | 0.070 | 0.168 | 2.411 |
| FC7: 19 | X | | X | | X | X | X | | | 0.161 | 0.353 | 2.194 |
| FC7: 21 | X | X | X | | X | X | | | | 0.123 | 0.235 | 1.920 |
| FC7: 22 | X | X | X | | X | | X | | | 0.044 | 0.143 | 3.263 |
| FC7: 24 | X | | | X | X | X | | | | 0.035 | 0.191 | 5.480 |
| FC7: 26 | | X | X | X | X | | | | | 0.065 | 0.186 | 2.843 |
| FC7: 27 | X | | | X | X | | X | | | 0.033 | 0.069 | 2.093 |
| FC7: 28 | | X | | X | X | | X | | | 0.019 | 0.044 | 2.400 |
| FC7: 30 | X | X | | X | X | | | | | 0.110 | 0.288 | 2.614 |
| FC7: 31 | X | | X | X | X | | | | | 0.241 | 0.496 | 2.053 |
| FC7: 32 | | X | X | X | X | | | | | 0.090 | 0.225 | 2.485 |
| FC7: 33 | X | | | | X | X | X | | | 0.070 | 0.344 | 4.886 |
| FC7: 36 | X | X | | | X | X | | | | 0.218 | 0.390 | 1.789 |
| FC7: 37 | X | | X | | X | X | | | | 0.435 | 0.775 | 1.781 |
| FC7: 39 | X | X | | | X | | X | | | 0.147 | 0.294 | 2.000 |
| FC7: 40 | X | | X | | X | | X | | | 0.273 | 0.477 | 1.749 |
| FC7: 41 | | X | X | | X | | X | | | 0.186 | 0.573 | 3.081 |
| FC7: 42 | X | X | X | | X | | | | | 0.131 | 0.235 | 1.803 |
| FC7: 43 | | | | X | X | X | | | | 0.028 | 0.189 | 6.735 |
| FC7: 44 | | | | X | X | | X | | | 0.015 | 0.021 | 1.390 |
| FC7: 45 | X | | | X | X | | | | | 0.184 | 0.559 | 3.041 |
| FC7: 46 | | X | | X | X | | | | | 0.125 | 0.349 | 2.782 |
| FC7: 47 | | | X | X | X | | | | | 0.141 | 0.392 | 2.782 |
| FC7: 49 | X | | | | X | X | | | | 0.167 | 0.852 | 5.115 |
| FC7: 50 | | X | | | X | X | | | | 0.192 | 0.724 | 3.765 |
| FC7: 52 | X | | | | X | | X | | | 0.178 | 0.369 | 2.077 |
| FC7: 54 | | X | | | X | | X | | | 0.345 | 0.728 | 2.109 |
| FC7: 55 | X | X | | | X | | | | | 0.356 | 0.460 | 1.292 |
| FC7: 56 | X | | X | | X | | | | | 0.644 | 0.818 | 1.271 |
| FC7: 58 | | | | X | X | | | | | 0.110 | 0.347 | 3.153 |
| FC7: 59 | | | | | X | X | | | | 0.198 | 0.704 | 3.549 |
| FC7: 60 | | | | | X | | X | | | 0.145 | 0.497 | 3.429 |
| FC7: 61 | X | | | | X | | | | | 0.505 | 0.926 | 1.833 |
| FC7: 62 | | X | | | X | | | | | 0.460 | 0.955 | 2.078 |
| FC7: 63 | | | X | | X | | | | | 0.407 | 0.694 | 1.705 |
| FC7: 64 | | | | | X | | X | X | X | 0.213 | 0.669 | 3.139 |
| FC7: 65 | X | | X | | X | | | | | 0.048 | 0.091 | 1.882 |

Many of the combinations of substitutions tested demonstrated increased responsivity as compared to the parental TL-CP358-DEVD:DD biosensor or the variants disclosed in Table 1. Four CBS variants, namely 01:A-05, FC7:24, FC7:43 and FC7:49, were of particular interest, (see FIG. 1 and Table 3). FIG. 1 shows the position of the four amino acid substitutions, I471T, S503G, T507I, and S193P, incorporated into these variants in the parental TL-CP358-DEVD:DD

TABLE 3

Summary of amino acid substitutions found in clones 01:1-05, FC7:24, FC7:43 and FC7:43

| Clone | Substitution(s) | | | |
|---|---|---|---|---|
| 01:A-05 | T507I | | | |
| FC7:24 | I471T | S503G | T507I | S193P |

TABLE 3-continued

Summary of amino acid substitutions found in clones 01:1-05, FC7:24, FC7:43 and FC7:43

| Clone | Substitution(s) | | |
|---|---|---|---|
| FC7:43 | I471T | S503G | T507I |
| FC7:49 | S503G | T507I | S193P |

Figure 2:
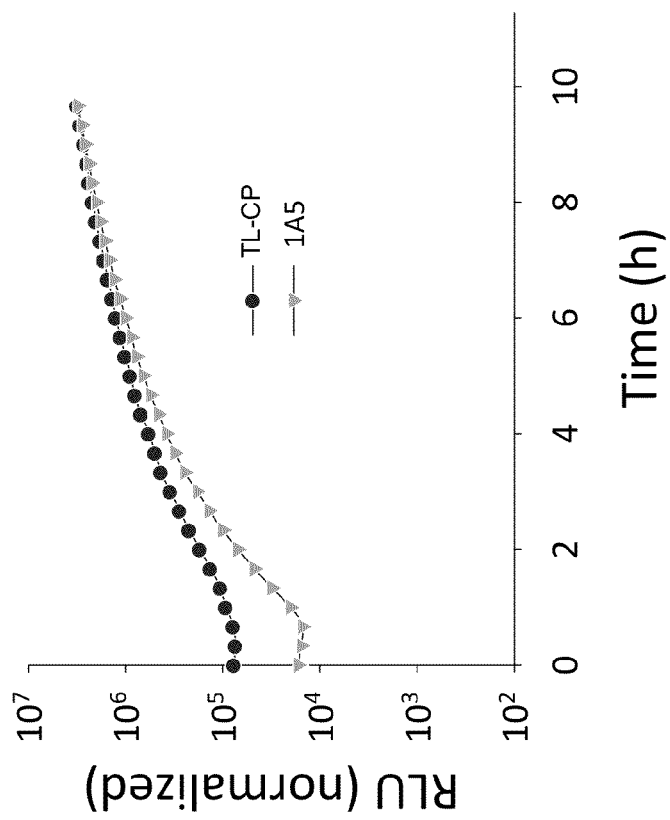
FIGS. 2A-B show the normalized RLU for the variant 01:A-05 and the corresponding starting sequence TL-CP358-DEVD:DD after treatment with TNF-α-related apoptosis inducing ligand (TRAIL) treatment (FIG. 2A) and the fold-induction (response) after 2 and 10 hrs (FIG. 2B).
Figure 3:
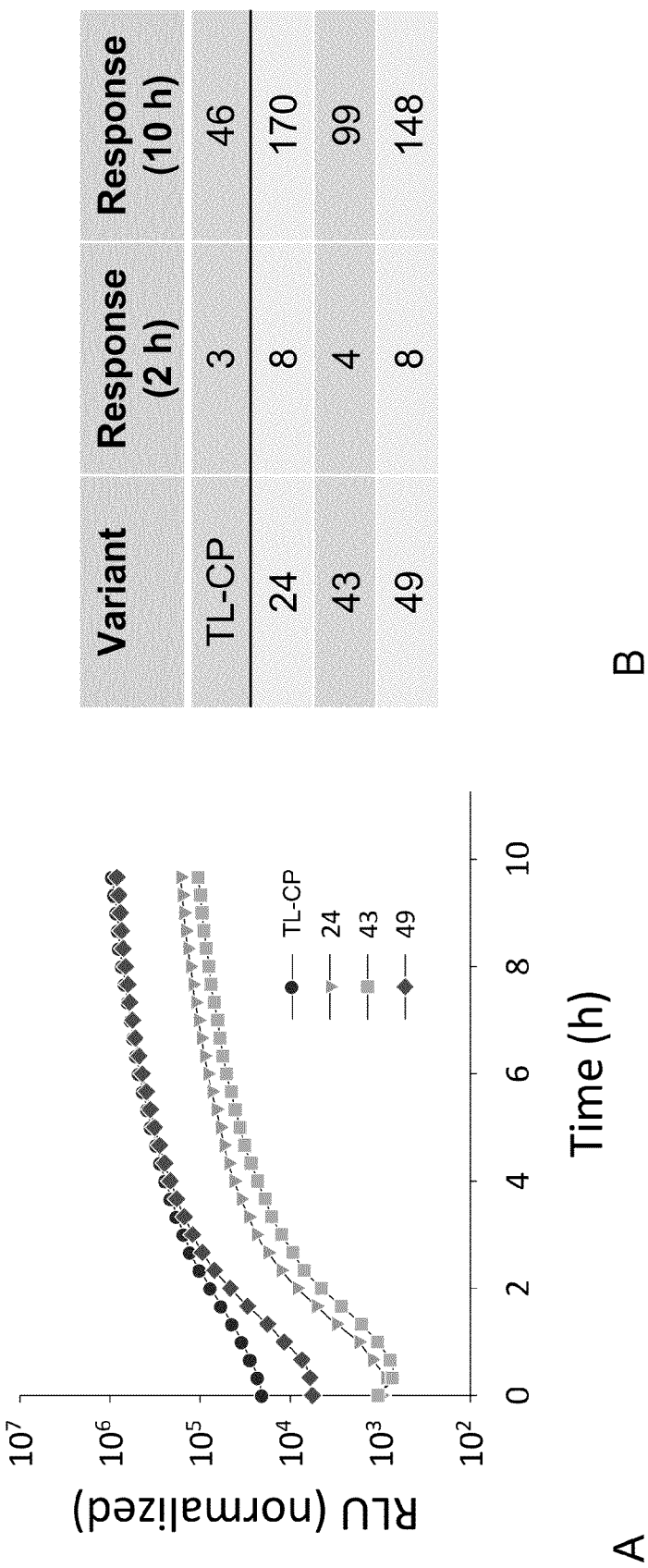
FIGS. 3A-B show the normalized RLU for the variants FC7:24, FC7:43, and FC7:49, compared to corresponding starting sequence TL-CP358-DEVD:DD after treatment with TRAIL (FIG. 3A) and the fold-induction (response) after 2 and 10 hrs (FIG. 3B).

The response to TRAIL in live cells in the improved CBS variants 01:A-05, FC7:24, FC7:43 and FC7:49 ("1A5", "24", "43", and "49", respectively) was compared to the parental TL-CP358-DEVD:DD ("TL-CP") in FIGS. 2A-B and 3A-B over a 10 hr time period. Variant 01:A-05 had 2 times and about 4.8 times greater RESPONSE after 2 and 10 hrs TRAIL treatment, respectively, compared with TL-CP358-DEVD:DD (FIGS. 2A and 2B). After 2 hrs, variants FC7:24 and FC7:49 had about 2 times greater response than TL-CP358-DEVD:DD and variant 43 (FIGS. 3A and 3B). After 10 hrs, variants FC7:24 and FC7:49 had about 3.2-3.7 times greater response than TL-CP358-DEVD:DD (FIGS. 3A and 3B), while variant FC7:43 had about 2.2 times greater response. These data demonstrates that CBS biosensors can be generated to have improved response by incorporating one or more of these four amino acid substitutions, I471T, S503G, T507I, and S193P.

Example III

Additional CBS variants were generated to have different linker sequences, such as SSDEVDGSSG (SEQ ID NO:52), SSGSDEVDGSLSSG (SEQ ID NO:53), SDEVDGSL (SEQ ID NO:54), or DEVDG (SEQ ID NO:55). The CBS variants were evaluated in HEK293 cells as in Example I. Exemplary CBS variants include, but are not limited to, those listed in FIG. 4. All biosensor data was then normalized for transfection efficiency using *Renilla* luciferase luminescence as in Example I. FIG. 4 identifies the clone by the linker sequence it contains ("Linker") and shows the luminescence in RLUs at TRAIL addition, i.e., time (0), ("Basal (t=0)"), at roughly 10 hrs after TRAIL addition ("Induced (10 h)") and the fold-induction, i.e., the ration of Induced to Basal Activity ("Response (10 h)"). The common linker clone between the two experiments is #2 (i.e., SSGSDEVDGSLSSG). The difference in the numbers is typical variation between experiments. Linker #3 is the same linker found in the clone referred to as "TL-CP358-DEVD:DD."

Example IV

Evaluation of the Mutant Thermostable Luciferase Biosensors to Detect Caspase-8

To evaluate whether the mutant thermostable luciferase biosensors of the present invention can be used to detect Caspase-8 activity in cells, biosensors were generated that contained the Caspase-8 cleavage site, LETDG (SEQ ID NO:15). Two different biosensors, TL-CP358-Caspase-8 and TL-CP233-Caspase-8 were used. As controls, the firefly (*Photinus pyralis*; Ppy) luciferase biosensors FF-CP234-Caspase-8 (M/Ppy residues 234-544/LETDG/Ppy residues 4-230/V), FF-CP359-Caspase-8 (M/Ppy residues 359-544/LETDG/Ppy residues 4-355/V), and TL-CP358-DEVD. Table 4 provides sequence details of the biosensors.

TABLE 4

| Construct | Caspase Cleavage site with linker | Luciferase | Fragments |
|---|---|---|---|
| TL-CP358-Caspase 8 (SEQ ID NOs: 59 and 60) | GSSLETDSSG (SEQ ID NO: 76) | TL Ppe | 358-543 and 4-354 |
| TL-CP233-Caspase 8 (SEQ ID NOs: 57 and 58) | GSSLETDSSG (SEQ ID NO: 76) | TL Ppe | 233-543 and 4-232 |
| FF-CP234-caspase-8 (SEQ ID NOs: 21 and 22) | GSSLETDSSG (SEQ ID NO: 76) | Ppy | 234-544 and 4-233 |
| FF-CP359-caspase-8 (SEQ ID NOs: 19 and 20) | GSSLETDSSG (SEQ ID NO: 76) | Ppy | 359-544 and 4-355 |
| TL-CP358-DEVD (SEQ ID NOs: 5 and 6) | GSSDEVDSSG (SEQ ID NO: 77) | TL Ppe | 358-543 and 4-354 |

All biosensors were transfected into HeLa cells. Cells were plated at a (10,000/well) into a 96-well tissue culture plate. Biosensor DNA was prepared for transfection into the cells as described in Table 4. Thirty 10 µL reactions were set up for each biosensor. TransIT® LTI (LTI; Mirus) transfection master mix was prepared by mixing 1650 µL DMEM with 49.5 µL LTI. The master mix was incubated for 15 min at room temperature. 300 µL of the master mix was then added to each biosensor DNA (enough for 30 reactions; 0.1 µg/reaction) and incubated for another 15 min at room temperature (Table 5). 10 µL of the biosensor DNA-transfection master mix solution was added to the cells in the appropriate wells. The cells were then incubated overnight at 37° C., 5% $CO_2$.

TABLE 5

|  | FF-CP234-caspase-8 | FF-CP359-caspase-8 | TL-CP233-caspase-8 | TL-CP358-caspase-8 |
|---|---|---|---|---|
| concentration DNA | 0.309 | 0.363 | 0.327 | 0.348 |
| amount for 30 reactions (0.1 µg/well) | 9.71 | 8.26 | 9.17 | 8.62 |
| volume of DMEM per 30 reactions (10 µL) | 300 | 300 | 300 | 300 |
| µL of Mirus LT1 per 30 reactions | 9 | 9 | 9 | 9 |

After overnight incubation, the media was removed from the cells and replaced with $CO_2$ Independent Media (Invitrogen Cat. No. 18045088) with 2 mM Luciferin EF (Promega Cat. No. E6551). Cells were pre-equilibrated with Luciferin EF for 2 hrs in a Varioskan luminometer with bioluminescence readings taken every 20 min. Following incubation, the cells were either induced with 1 µg/mL TRAIL in $CO_2$ Independent Media+10% Fetal Bovine Serum (FBS) or no compound (control; media+10% FBS only). The cells were again incubated at 37° C. in a Varioskan luminometer for 500+ min with bioluminescence measured every 20 min.

Figure 5:
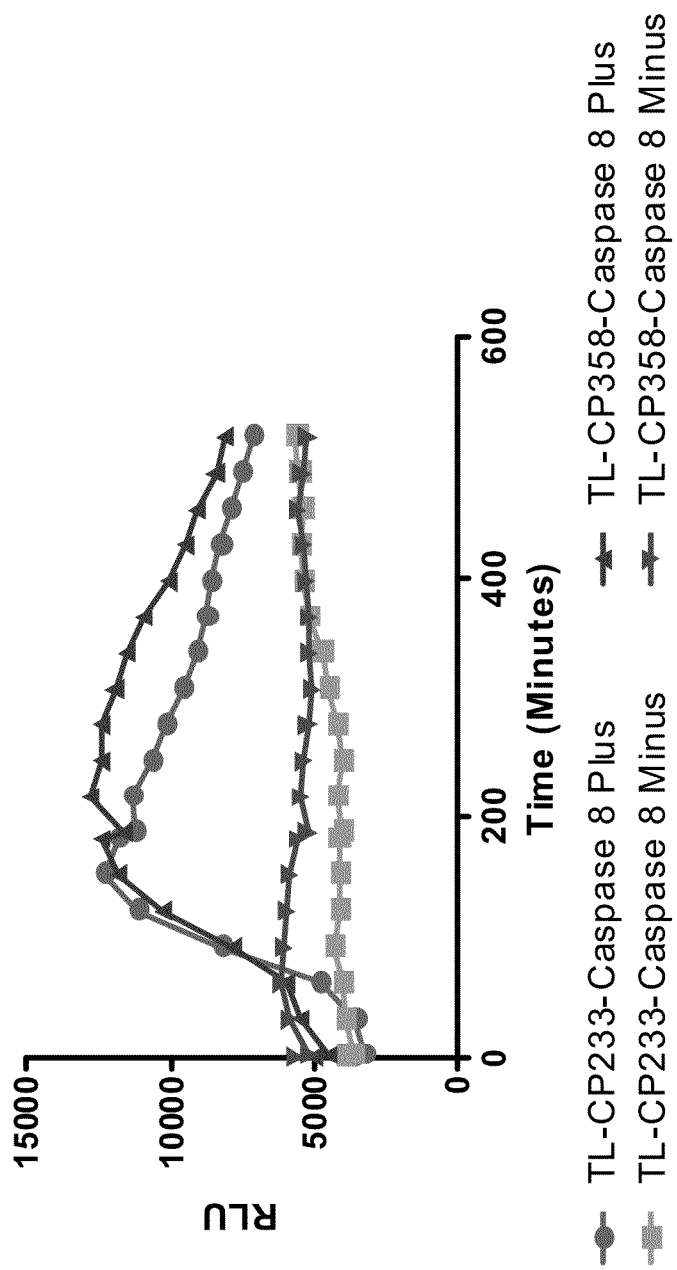
FIG. 5 shows the kinetic profile of Caspase 8 activation by TRAIL over time at 37° C. using TL-CP233-Caspase 8 and TL-CP358-Caspase 8 Biosensors.
Figure 6:
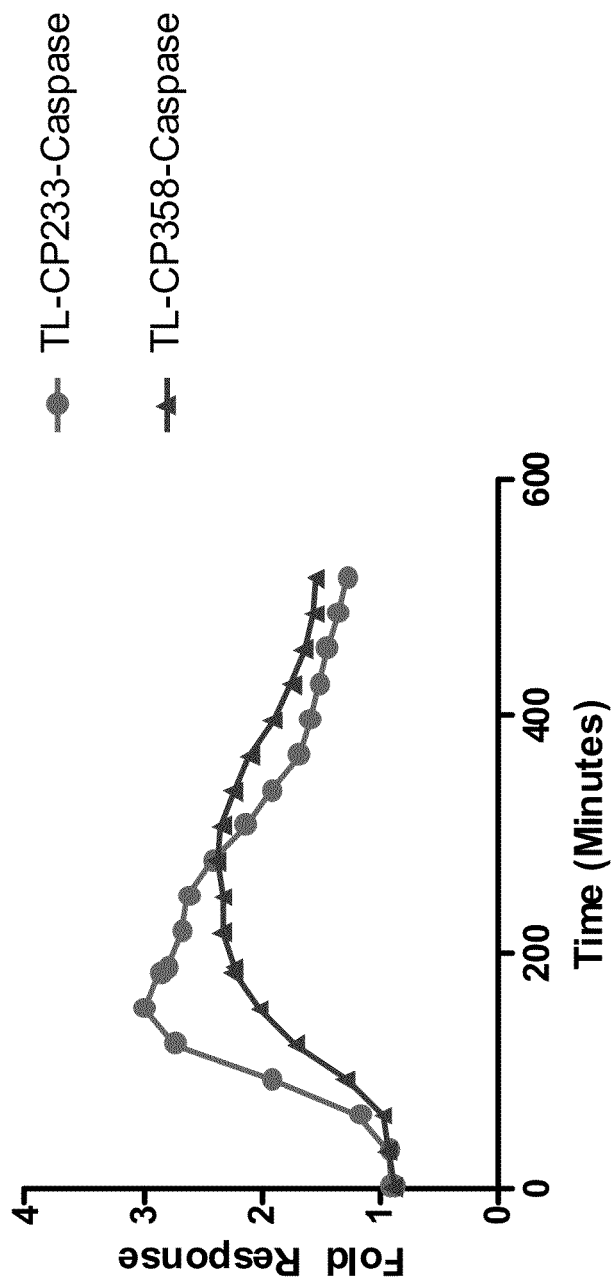
FIG. 6 shows the fold response of Caspase 8 activation by TRAIL over time using TL-CP233-Caspase 8 and TL-CP358-Caspase 8 Biosensors.
Figure 7:
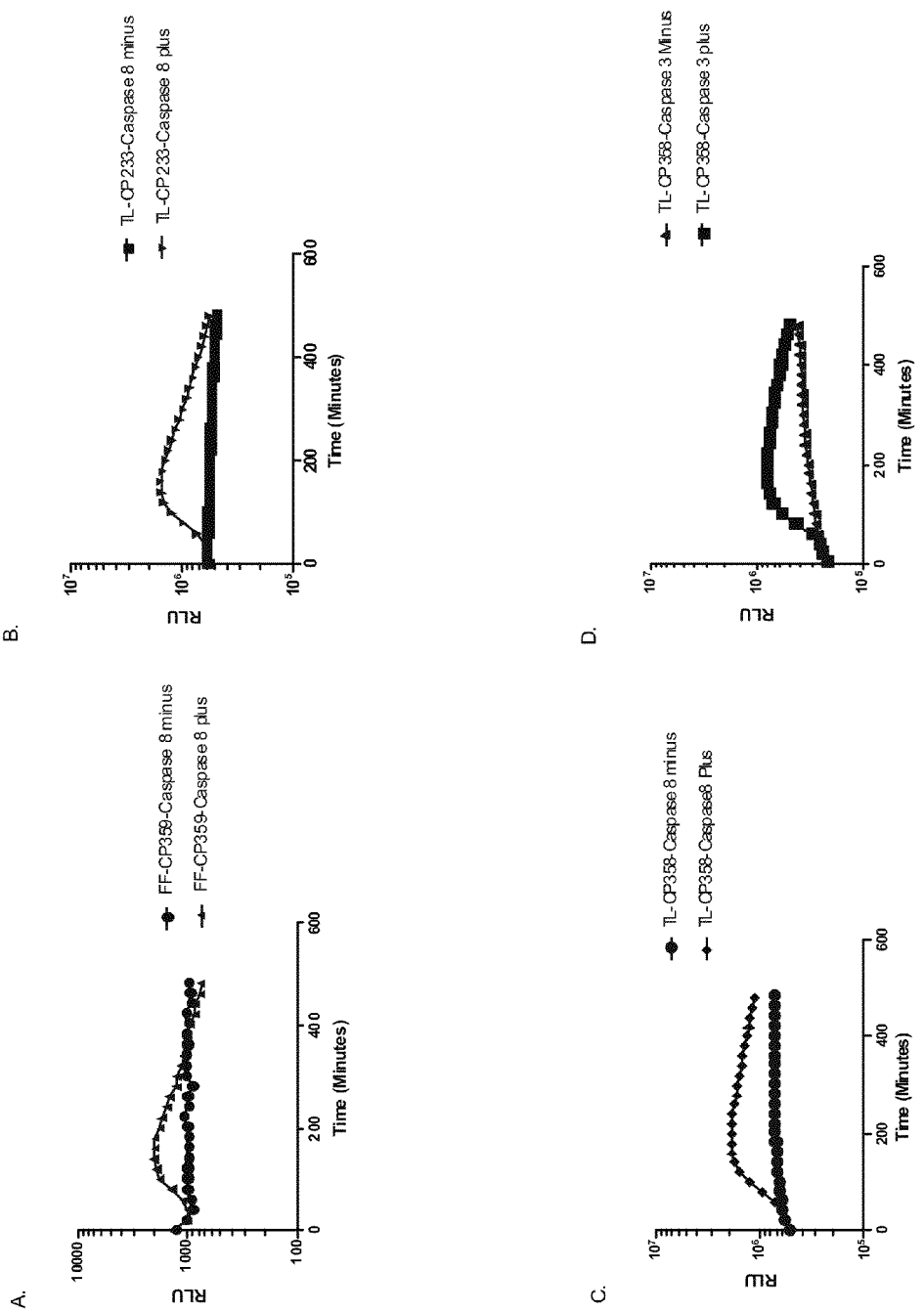
FIGS. 7A-D show the kinetic profile of Caspase 8 activation by TRAIL over time at 37° C. using FF-CP359 Caspase 8 (FIG. 7A), TL-CP233-Caspase 8 (FIG. 7B), TL-CP358-Caspase 8 (FIG. 7C), and TL-CP358-Caspase3 (FIG. 7C) Biosensors.
Figure 8:
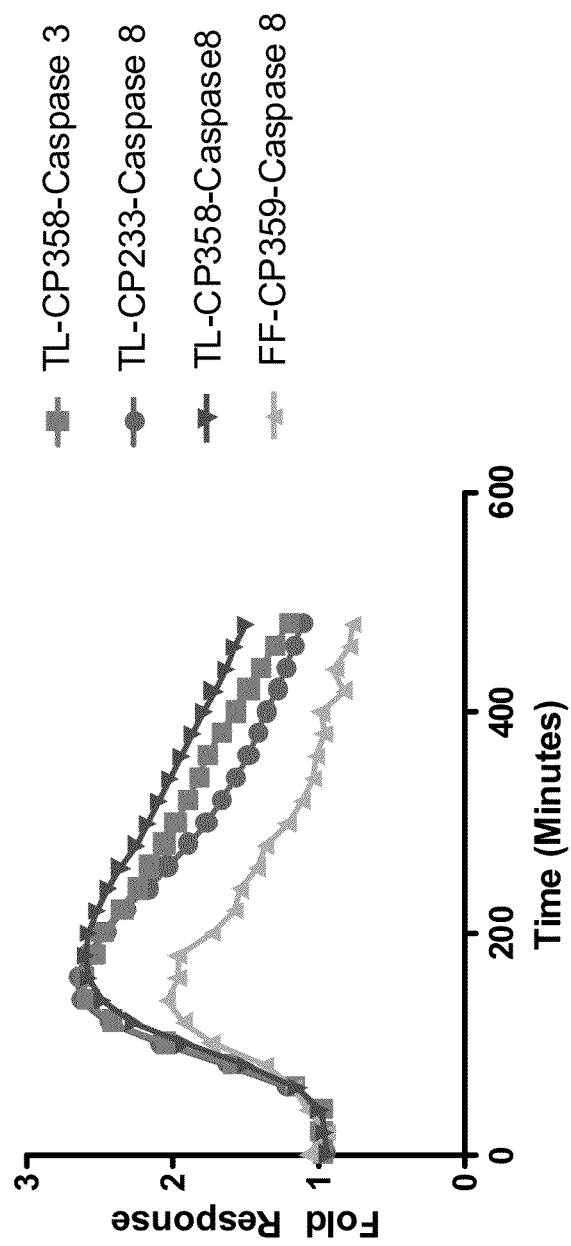
FIG. 8 shows fold response of Caspase 8 activation by TRAIL over time using TL-CP358-Caspase 3, TL-CP233-Caspase 8, TL-CP358-Caspase 8 and FF-CP359-Caspase 8 Biosensors.

FIGS. 5-8 demonstrate at TL-CP233-Caspase 8 and TL-CP358-Caspase 8 biosensors can detect Caspase 8 activation by TRAIL. FIGS. 5 and 7 identify the kinetic profiles of Caspase 8 activation by TRAIL over time at 37° C. FIGS. 6 and 8 identify the fold response of Caspase 8 activation by TRAIL over time. Fold induction of activation was calculated by dividing the signal of samples with TRAIL over the signals without trail at a given time point. FIGS. 7 and 8 show Caspase 3 induction by Trail as measured by TL-CP358-DEVD as well as Caspase 8 induction.

Example V

Activation of TEV Protease Mutant Thermostable Luciferase Biosensor

To evaluate whether the mutant thermostable luciferase biosensors of the present invention can detect TEV protease activity in cells, the TL-CP233 biosensor, TL-CP233-TEV, containing the TEV protease cleavage site GSS-ENLYFQS-SSG (SEQ ID NO:78) was generated. TL-CP233-TEV has an amino acid sequence that can be represented as: M/TL residues 233-544/GSS-ENLYFQS-SSG TL residues 4-233/V (SEQ ID NOs:61 and 62). As controls, the firefly (*Photinus pyralis*; Ppy) luciferase biosensors FF-CP235-TEV (M/Ppy residues 234-544/GSS-ENLYFQS-SSG/Ppy residues 4-233/V; SEQ ID NOs:63 and 64), FF-CP269-TEV (M/Ppy residues 269-544/GSS-ENLYFQS-SSG/Ppy residues 4-268/V; SEQ ID NOs:65 and 66), and FF-CP359-TEV (M/Ppy residues 359-544/GSS-ENLYFQS-SSG/Ppy residues 4-355/V; SEQ ID NOs:67 and 68) were used. For all transfections, TEV protease (Genbank accession no. BFB754) constitutively expressed from a CMV promoter was transfected (pF9a—BFB754). This construct also co-expresses *Renilla* luciferase for use as a transfection efficiency control.

Each of the biosensors and TEV protease constructs were transfected in Chinese Hamster Ovary (CHO) cells. Cells were plated at (15,000 cells per well) into a 96-well tissue culture plate. The transfection solution was prepared according to Table 6. Each sensor was co-transfected with either the TEV protease or a carrier vector (pF9α-null).

Figure 9:
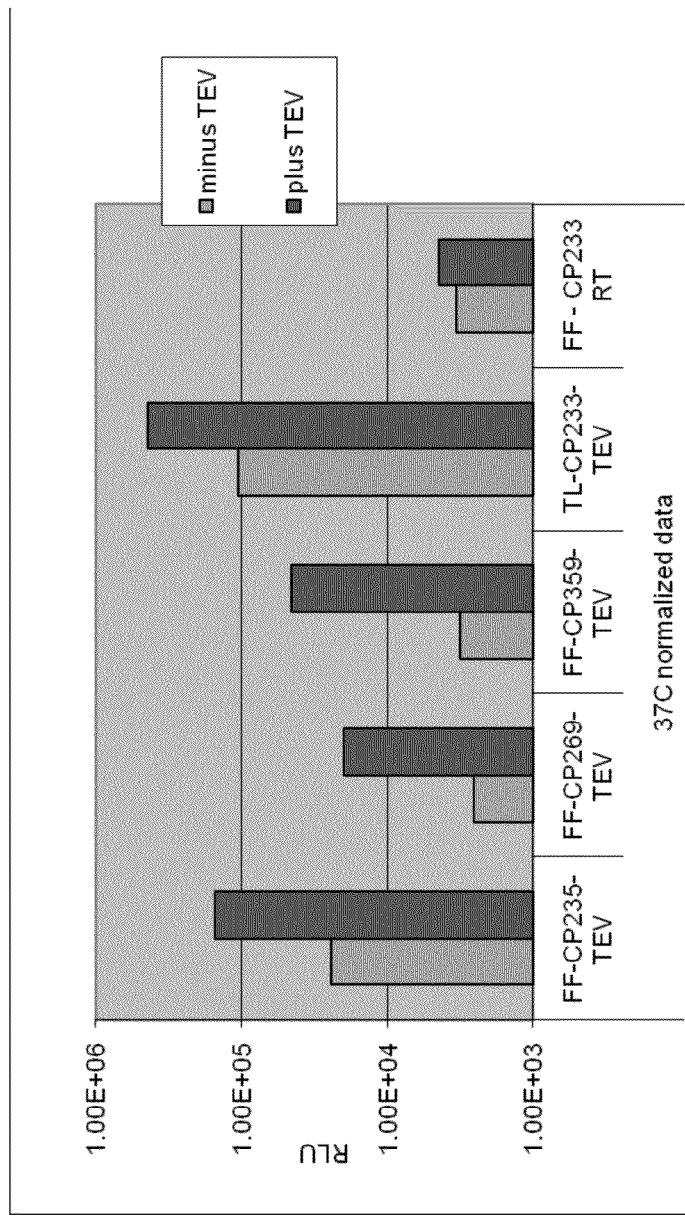
FIG. 9 shows TEV protease Biosensors detect TEV co-expressed in CHO cells.

The Biosensor without the TEV recognition sequence (FF-CP233-Read through; FF-CP233-RT) is not activated by TEV protease while the other biosensors were activated by TEV protease (FIG. 9).

Example VI

Molecular Imaging of Apoptosis in Glioma Cells

To demonstrate that the mutant thermostable biosensors of the present invention can be used to detect cell death in cells, the thermostable caspase 3 biosensors, TL-CP233-Caspase 3 ("233"; SEQ ID NOs:17 and 18), TL-CP358-Caspase 3 ("358V2"; SEQ ID NOs:5 and 6) and the mutant thermostable caspase 3 biosensors 1A5 ("358V3"; SEQ ID NOs:7 and 8), 24 ("358V4"; SEQ ID NOs:9 and 10), 43 ("358V5"; SEQ ID NOs:11 and 12) and 49 ("358V6"; SEQ ID NOs:13 and 14) were stably expressed in the glioma cell line D54-MG, the cells treated with TRAIL and bioluminescence measured to detect caspase 3 activity.

To derive cells stably expressing the thermostable biosensors, D54-MG cells were transfected with the biosensors. The biosensors were subcloned into pEF vector containing a neomycin resistance gene (Invitrogen) via PCR amplification and inserted into the multiple cloning site at the SalI and EcoRI restriction sites. Transfections were performed in 6-well tissue culture dishes using 3 µL Fugene 6 transfection reagent (Roche) and 1 µg plasmid DNA. Cells were placed in RPMI media (Gibco) containing 10% FBS (Gibco), Pen/Strep Glutamine (100×; Gibco) and 200 µg/mL geneticin (G418) for 48 hrs. Single clones were selected approximately 10 days after transfection using standard techniques known in the art. Briefly, the media was removed from the cells, and the cells were gently washed with PBS. Round filter papers were soaked in trypsin and placed on a single colony. The filter paper, which contained the attached cells, was removed and placed into a 24-well tissue culture dish. Each individual clone was tested approximately 2-3 weeks after selection for reporter expression by Western blotting using a luciferase antibody (Promega; Cat. No. G7451) and bioluminescence (100 µg/mL D-Luciferin reconstituted in PBS was add directly to the media and detected). Clones with similar bioluminescent activity (highest fold induction) and reporter expression (determined by Western blot) were selected for use in detecting cell death.

TABLE 6

| DNA | Amount for 60 wells of a 96-well plate (600 µL of media plus 18 µL Mirus LT1 plus DNA) | | | | | | |
|---|---|---|---|---|---|---|---|
| concentration | 0.202 | 0.177 | 0.38 | 0.342 | 0.261 | 0.214 | 0.214 |
| construct | pF9a-TEV protease | pF9a Null | FF-CP233-TEV | FF-CP268-TEV | FF-CP358-TEV | TL-CP233-TEV | Read Through |
| Amount per Tfx (µg) | 1.2 | 1.2 | 5.8 | 5.8 | 5.8 | 5.8 | 5.8 |
| Amount per Tfx (µL) | 5.9 | 6.8 | 15.3 | 17.0 | 22.2 | 27.1 | 27.1 |

Cells were incubated overnight for 24 hrs at 37° C., 5% $CO_2$. After overnight incubation, cells were equilibrated with media and 5 mM Luciferin EF for 2 hrs. Bioluminescence was then measured at 37° C. in a Varioskan luminometer. Results were normalized to *Renilla* to control for transfection efficiencies.

To detect cell death, the stable D54-MG cells were seeded at 10,000 cells/well into a 96-well assay plate and allowed to incubate for 24 hrs at 37° C., 5% $CO_2$. After overnight incubation, the cells were treated with 200 ng/mL TRAIL and 100 µg/mL D-luciferin (Promega). Live cell bioluminescence was imaged at 2, 4, and 6 hrs. Photon counts were taken at the different time points pre- and post-TRAIL treatment using the Envision luminometer (Perkin Elmer). Reporter expression and TRAIL-induced apoptosis was further detected by Western blotting against luciferase and Caspase-3.

Figure 10:
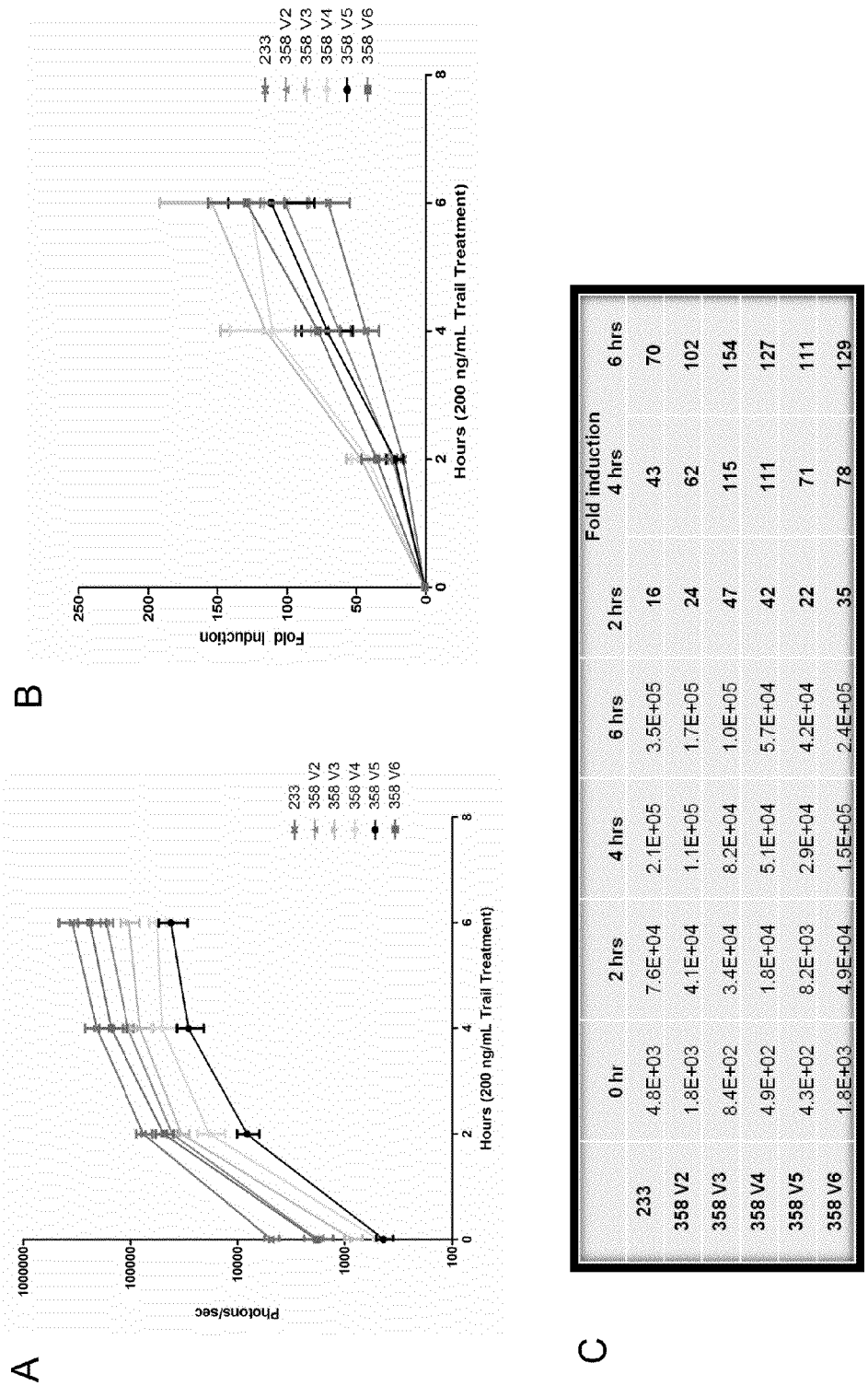
FIGS. 10A-D show the luminescence (photon counts/sec) of D54-MG cells expressing the various thermostable biosensors upon treatment with TRAIL at various time points (FIG. 10A), the fold induction (FIG. 10B), the average photon counts/sec at baseline, 2, 4 and 6 hrs post treatment (FIG. 10C) and a Western blot showing reporter expression (FIG. 10D).
Figure 10:
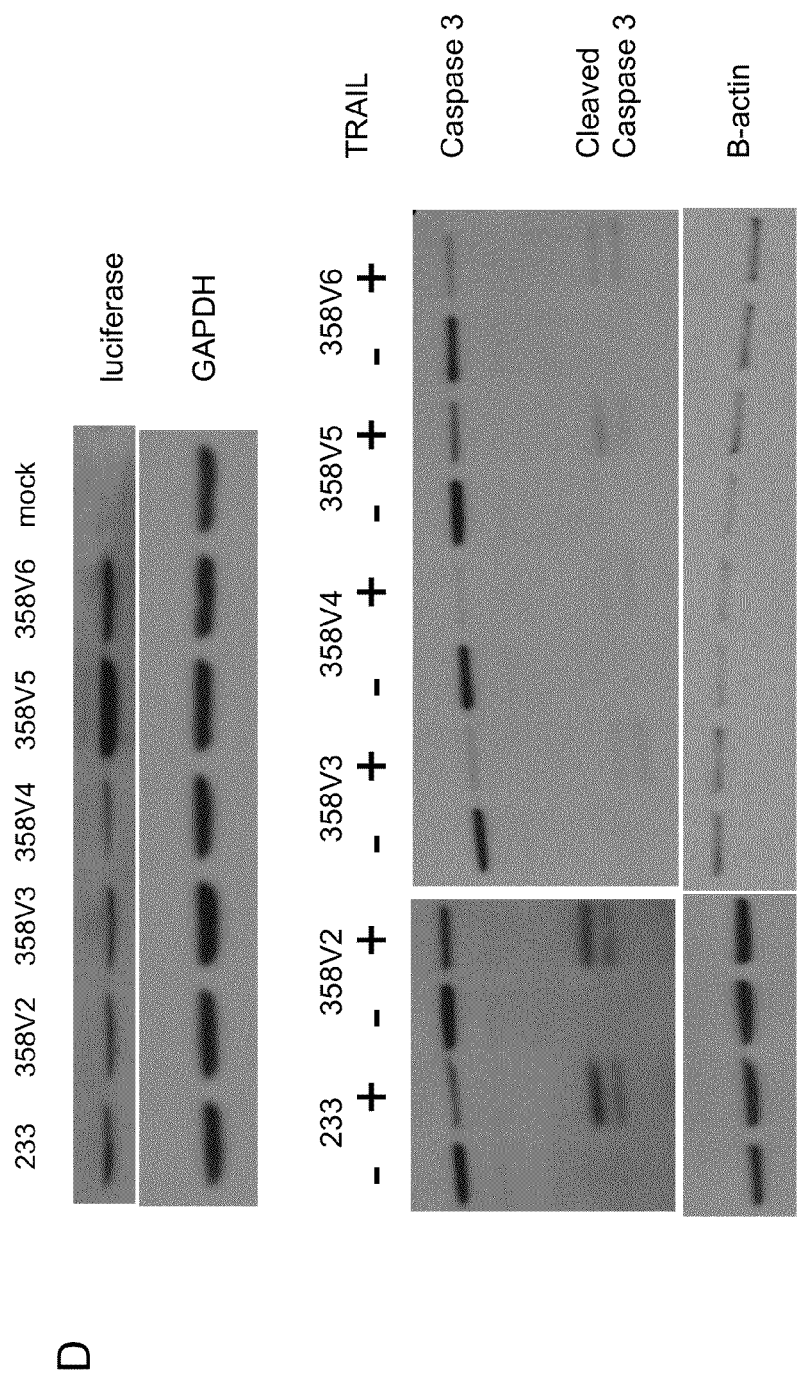

FIG. 10 demonstrates that upon treatment with TRAIL, D54-MG cells stably expressing the various thermostable biosensors resulted in a 100-200 fold induction in bioluminescent activity. D54-MG cells expressing different versions of the thermostable biosensors were untreated or treated with 200 ng/mL TRAIL and imaged at indicated time points; photon counts/sec were recorded at the indicated time points (FIG. 10A). The fold induction of D54-MG cells expressing different versions of the thermostable biosensors untreated or treated with 200 ng/mL TRAIL were calculated by normalizing the values (photons/sec) to baseline (time 0 hr) (FIG. 10B). The average photon counts/sec at baseline, 2 hrs, 4 hrs and 6 hrs post treatment in addition to fold changes achieved with different biosensor versions are depicted in FIG. 10C. FIG. 10D shows the detection of reporter expression and TRAIL induced apoptosis by Western blotting against luciferase and Caspase-3.

Example VII

Mutant Thermostable Biosensors Use

To demonstrate the use of the mutant thermostable biosensors to detect cell death in vivo, D54-MG cells stably expressing either TL-CP233-Caspase 3 ("233"; SEQ ID NOs: 17 and 18), TL-CP358-Caspase 3 ("358V2"; SEQ ID NOs:5 and 6), 1A5 ("358V3"; "3-S"; SEQ ID NOs:7 and 8), 43 ("358V5"; "5-R"; SEQ ID NOs:11 and 12) or 49 ("358V6"; "6-A"; SEQ ID NOs:13 and 14) were implanted into nude mice.

To establish a flank xenograft mouse model, $2 \times 10^6$ D54-MG cells stably expressing one of the biosensors listed above (as described in Example VI) were implanted subcutaneously into nude mice. Treatment with 8 mg/kg TRAIL started when tumors reached ~100 mm³ as assayed by electronic digital caliper measurement. For in vivo bioluminescence detection, mice were anesthetized using 2% isofluorane/air mixture and injected intraperitoneally with a single dose (150 mg/kg) D-luciferin. Photon counts/sec were acquired before and 6 hrs post-TRAIL treatment (FIG. 11A) using IVIS imaging system (Caliper Life Sciences). Fold induction (FIG. 11B) was calculated by normalizing post treatment values to pre-treatment values per mouse.

Figure 11:
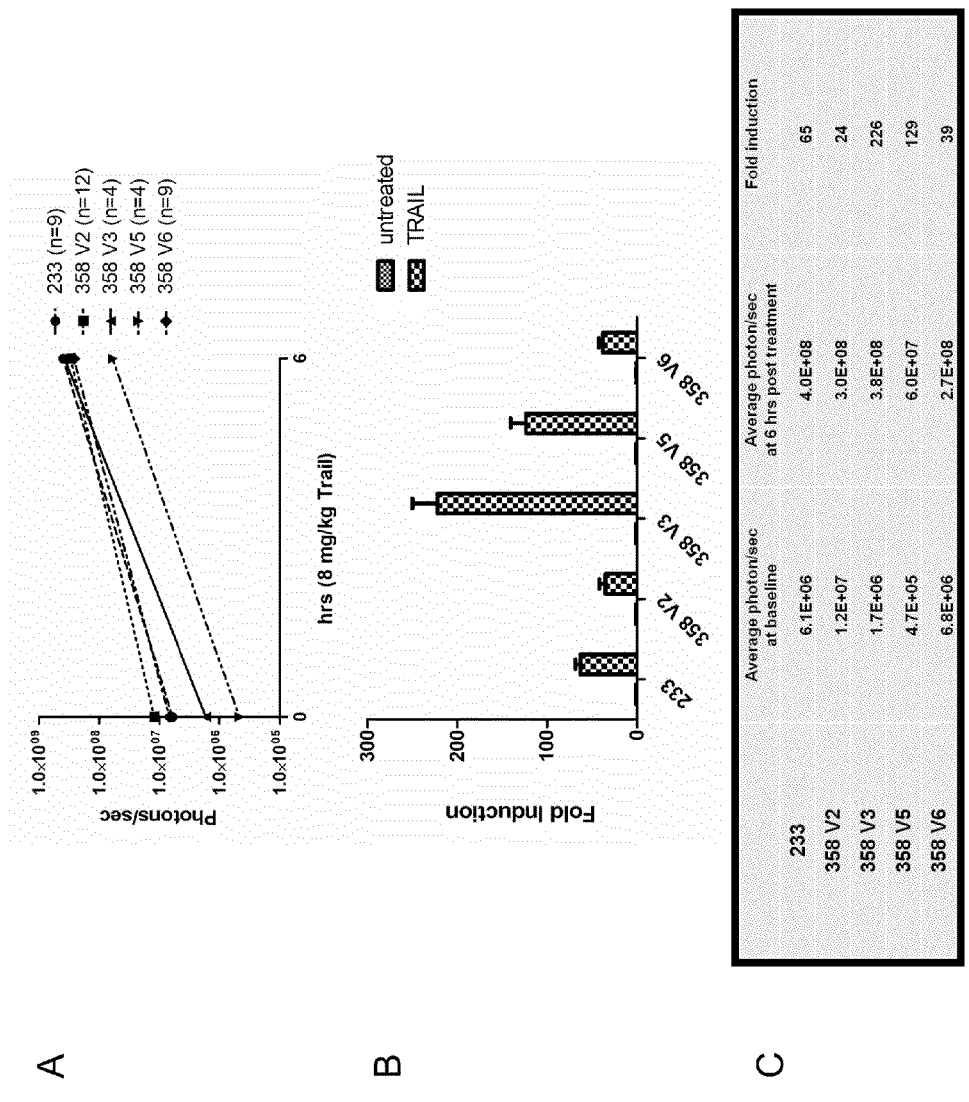
FIGS. 11A-C show the luminescence (photon counts/sec) of D54-MG reporter xenografted nude mice treated with 8 mg/kg of TRAIL (FIG. 11A), the fold induction (FIG. 11B), and average photon counts/sec at baseline and 6 hrs post treatment (FIG. 11C).

The data demonstrates that the mutant thermostable biosensors of the present invention are extremely sensitive as 100 fold bioluminescence activation upon TRAIL treatment was seen in the mouse xenograft model. D54-MG reporter xenografted nude mice were treated with 8 mg/kg of TRAIL. Photon counts/sec were acquired pre- and post-treatment (FIG. 11). The fold induction was calculated by normalizing post treatment values to pre treatment values per mouse (FIG. 11B). FIG. 11C shows a table depicting the average photon counts/sec at baseline and 6 hrs post treatment in addition to fold changes achieved with different biosensor versions.

Example VIII

Imaging of Cell Death in Breast Bone Metastasis

To demonstrate the use of the thermostable caspase-3 biosensors to detect cell death in animals, 100,000 MDA-MB231/1833 cells ("1833"; breast cancer cell line) stably expressing TL-CP233-Caspase-3 biosensor (derived as described in Example VI for glioma cells) were implanted into the tibia of nude mice. Tumor growth was followed by MRI and TRAIL treatment was initiated when the tumor reached 5-15 mm³

For in vivo bioluminescence detection, mice were anesthetized using 2% isofluorane/air mixture and injected intraperitoneally with a single dose (150 mg/kg) D-luciferin. Photon counts/sec were acquired before and 6 hrs post-TRAIL treatment or as indicated in FIG. 12A-D using IVIS imaging system (Caliper Life Sciences). Fold induction (FIG. 11B) was calculated by normalizing post treatment values to pre-treatment values per mouse.

Figure 12:
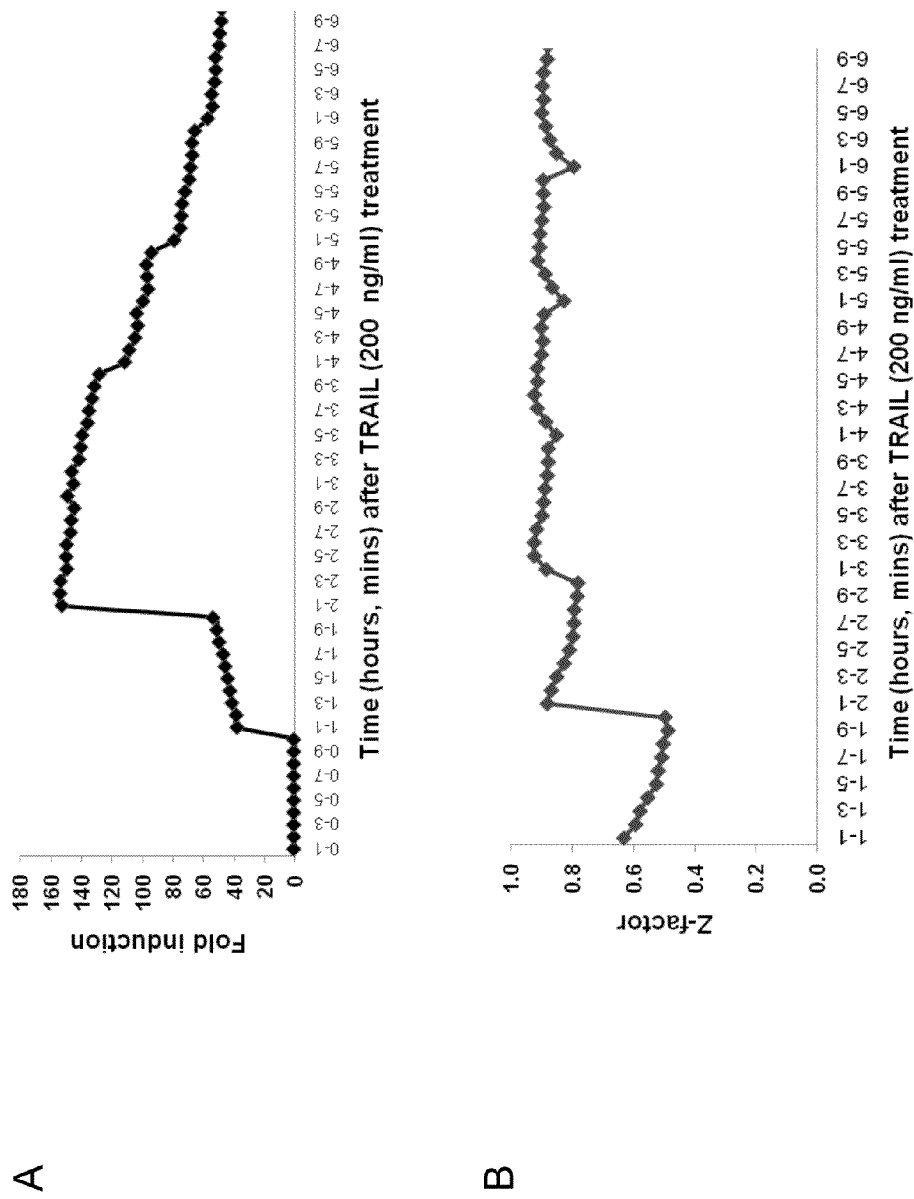
FIGS. 12A-D show the normalized data compared to pre-treatment values for intratibial implanted MDA-MB23101833 cells stably expressing TL-CP233-Caspase 3 treated with TRAIL (FIG. 12A), the Z factor calculated for every time point (FIG. 12B), representative images taken at the indicated time points (FIG. 12C), and fold induction of xenografted animals tested treated with TRAIL (FIG. 12D).
Figure 12:
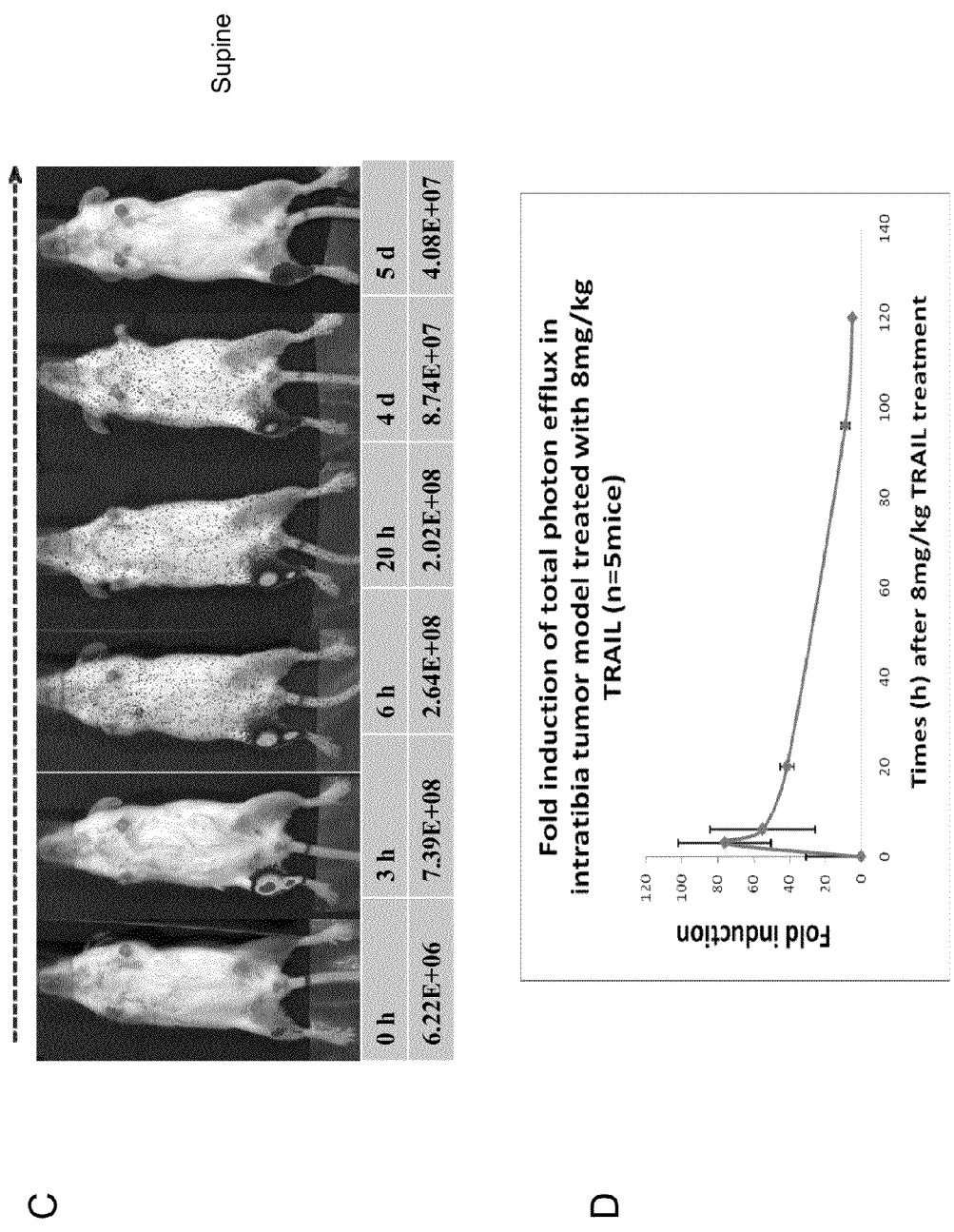

In FIG. 12A, intratibial implanted MDA-MB231/1833 cells stably expressing TL-CP233-Caspase-3 were treated with TRAIL (200 ng/mL) and imaged every hour for 10 consecutive min. Fold induction was calculated by normalizing data to pre-treatment value. In FIG. 12B, Z factors were calculated as described in Zhang et al (Biomol Screen. 4:67-73. 1999) for every time point, and an average Z factor of 0.82 sufficed assay suitability for high-throughput screening. In FIG. 12C, representative images taken at the indicated time points of intratibial implanted TL-CP233-Caspase-3 stably expressing MDA-MB231/1833 cells with the photons/sec. In FIG. 12D, fold induction of xenografted animals tested treated with TRAIL. This data highlights the usefulness of the thermostable biosensor for imaging cell death dynamically and over time in mouse models.

Example IX

Utility of the Thermostable Caspase Biosensor in High-Throughput Screening

To demonstrate the utility of the thermostable biosensors for high-throughput screening (HTS), the MDA-MB231/1833 ("1833") cells stably expressing TL-CP233-Caspase-3 from Example VIII were used to screen compounds in the NIH Clinical Collection Biofocus and TimTec Kinase Inhibitor libraries.

Figure 13:
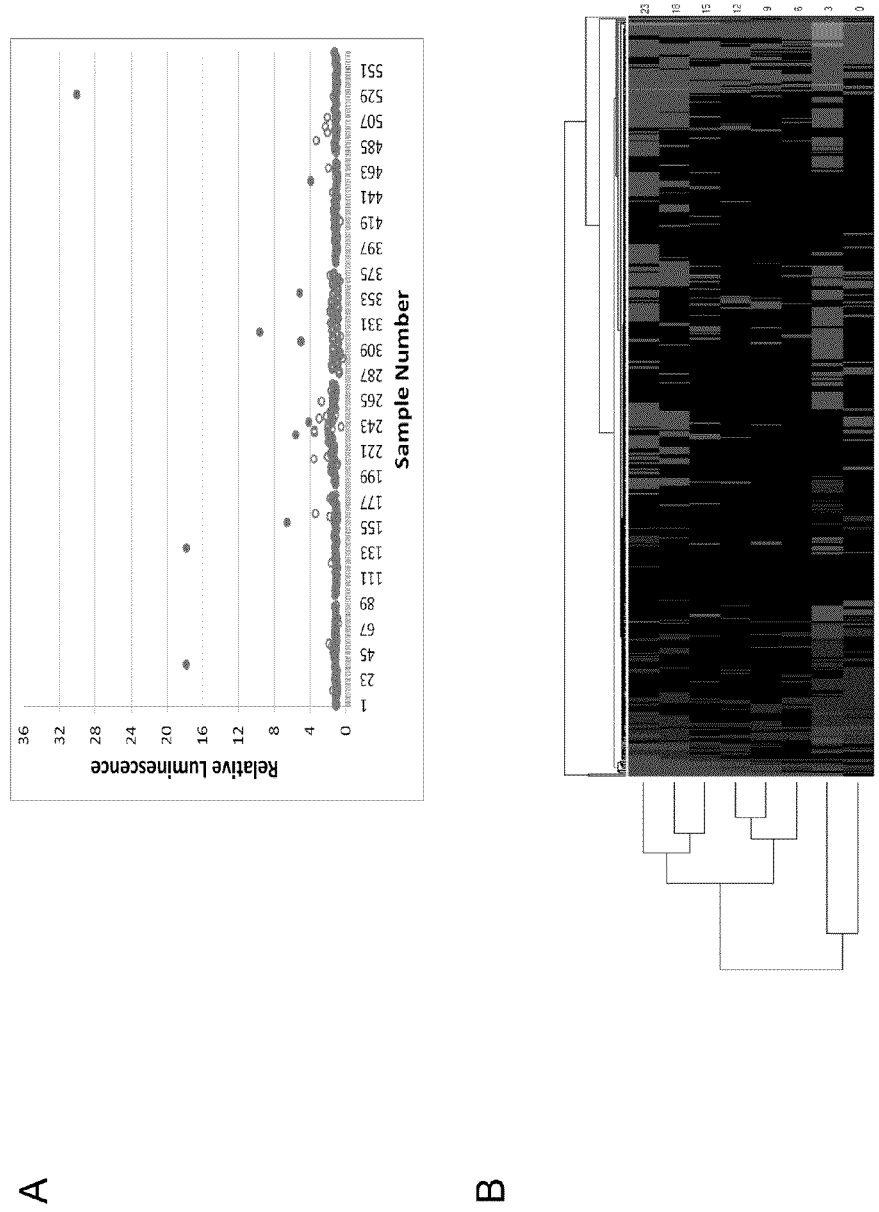
FIGS. 13A-D show the relative luminescence upon compound treatment (max) from compounds in the NIH Clinical Collection Biofocus Library (FIG. 13A) and the TimTec Kinase Inhibitor Library (FIG. 13C) and the heat map of data acquired for the NIH Clinical Collection Biofocus Library (FIG. 13B) and the TimTec Kinase Inhibitor Library (FIG. 13D).
Figure 13:
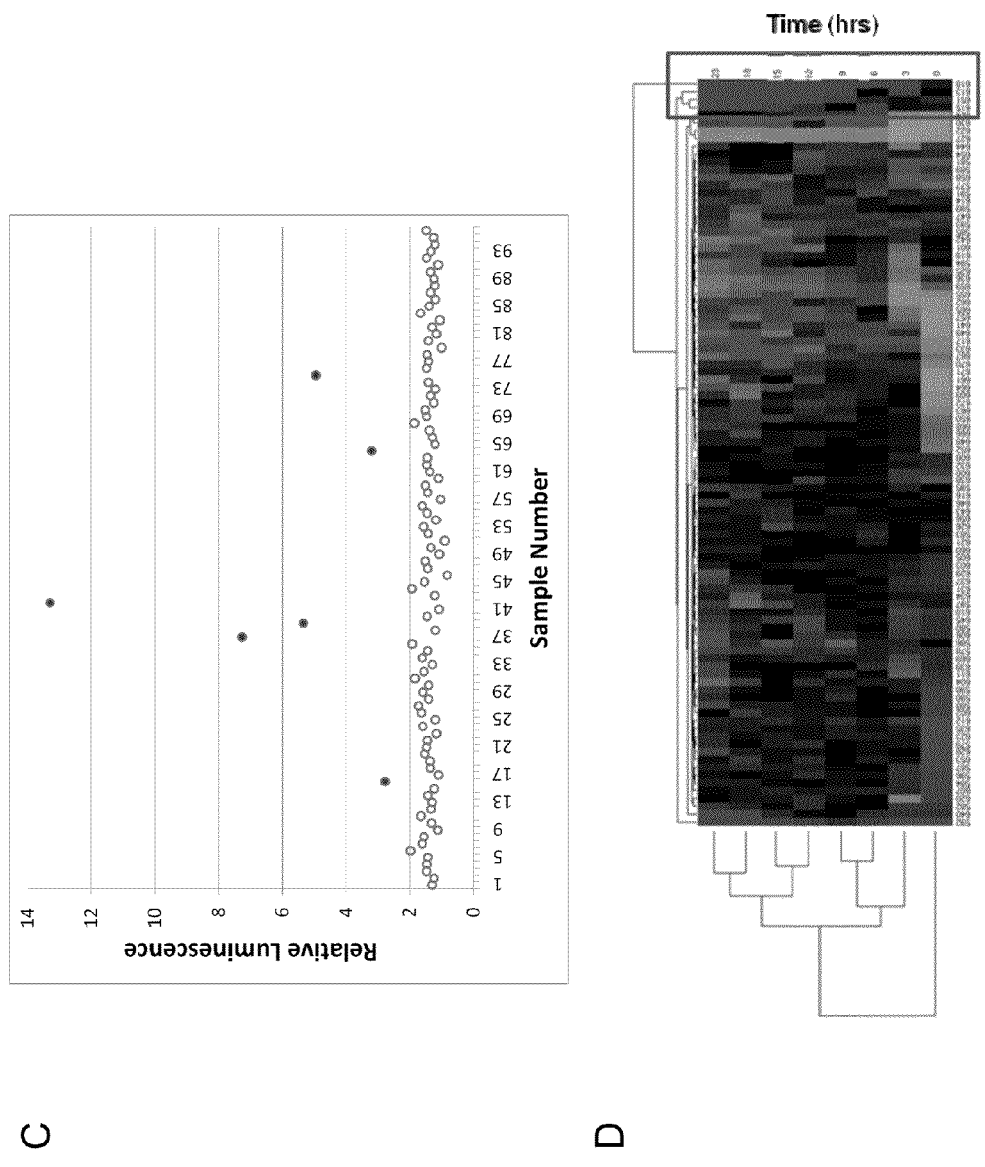

TL-CP233-Caspase-3 MDA-MB231/1833 cells were seeded at 10,000 cells/well in a 96-well plate. Forty-eight hrs post-seeding, the media was changed to $CO_2$ Independent Media containing 1% GloSensor cAMP Reagent (Promega; Cat. No. E1290) and incubated for 0-23 hrs with compound at a final concentration of 10 µM. A total of 483 compounds in the NIH Clinical Collection and 80 kinase inhibitors from the TimTec collection were tested. The addition of media and compound library was performed using a Titertek Multidrop Microplate Dispenser (ThermoFisher Scientific). Relative luminescence was calculated by normalizing values of compound treated wells to untreated wells. (FIGS. 13A and 13C). FIG. 13A shows the relative luminescence upon compound treatment (max) from compounds in the NIH Clinical Collection Biofocus Library. FIG. 13C shows the relative luminescence upon compound treatment (max) from compounds in the TimTec Kinase Inhibitor Library. Maximum values reaching above 4 were considered significant. Heat maps were generated using bioinformatics toolbox of Matlab Software and show correlation of biosensor activation over time. (FIGS. 13B and 13D). The Z-factor was calculated as previously described in Example VIII.

Due to the ability of repeated imaging of the thermostable biosensor, dynamics of apoptosis in response to various drugs could be imaged. This allowed for the identification of interesting death inducing compounds in the otherwise chemoresistant 1833 breast cancer cell line.

Example X

Purification of MMP-2 Sensor

The matrix metalloproteinases (MMP) are a homologous group of zinc enzymes that participate in the breakdown of the major protein components of the extracellular matrix. Five major MMP have been identified in humans and implicated in connective tissue turnover and destruction. These include the fibroblast-type and neutrophil-type interstitial collagenases that hydrolyze the type I, II, and III collagens that make up the majority of the matrix. Fibroblast collagenase also hydrolyzes native type VII and X collagens. The MMP are sometimes referred to by a numerical code in which the fibroblast-type and neutrophil-type collagenases are designated MMP-1 and MMP-8, respectively. A 72-kDa gelatinase (MMP-2) is produced by proliferating fibroblasts and tumor cells, while a distinct 92-kDa gelatinase (MMP-9) is produced by neutrophils, macrophages, and certain transformed cells.

The MMP-2 sensor (SEQ ID NOs:69 and 70) used herein contains the 1A5 variant backbone and the human MMP-2 recognition site, PLGMWSR (SEQ ID NO:75). In addition, the MMP-2 sensor contains two purification tags: a GST tag on the N-terminus of the sensor that is separated from the sensor region by a TEV protease site (for removal of the GST tag from the purified MMP-2 sensor) and a 5×HQ (HQHQHQHQHQ; SEQ ID NO:79) tag on the C-terminus of the sensor.

Purification of the MMP-2 sensor was performed as follows using His and GST purification.

Figure 14:
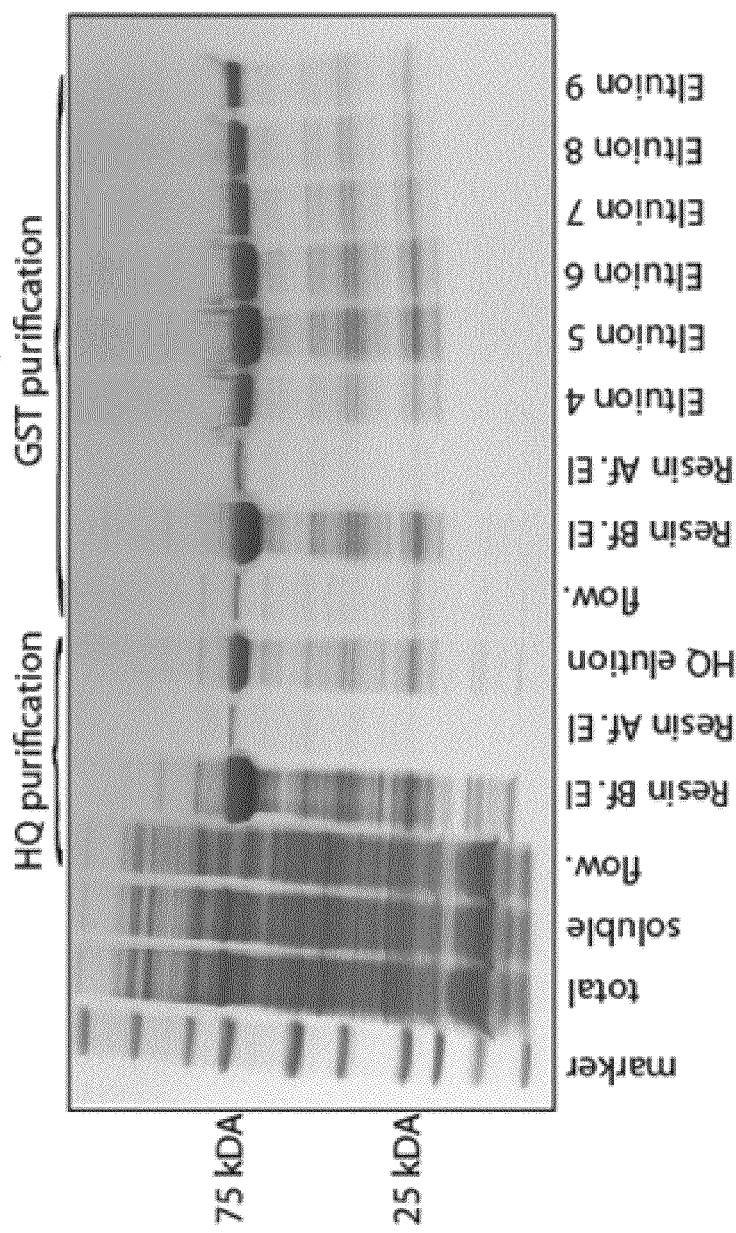
FIG. 14 shows SDS-PAGE gel analysis of the proteins at various stages during the purification process.

1. 2-5 mL cultures of *E. coli* KRX cells (Promega) containing the MMP-2 sensor were grown in LB/ampicillin with shaking at 37° C.
2. Each culture was diluted 1:100 in 1 L LB with 0.05% rhamnose and 0.05% glucose.
3. Incubated at 25° C. for 18-20 hrs.
4. Cells were harvested by centrifugation at 5000 g for 5 min (split 1 L into 2-500 mL aliquots), cell paste weight was determined, and placed at −20° C. overnight.
5. One of the 2 cell pastes was resuspended with 30 mL lysis buffer (8.5 mL/g cell paste; 50 mM $NaH_2PO_4$, 300 mM NaCl, 10 mM Imidazole and pH to 8.0 with NaOH). 1 mg/mL lysozyme was added, and the resuspension was incubated on ice, with inverting occasionally, for 30 min.
6. The lysis solution was sonicated at power 6.0 for 2 min (5 sec on, 5 sec off). 100 µl of the sample was saved as "total" sample.
7. The lysis solution was spun at 16,000 g for 20 min. 100 µl of the sample was saved as "soluble" sample.
8. 1 mL 50% Ni-NTA resin (Qiagen; pre-washed in lysis buffer) per 6 mL lysate (5 mLs total) was added and mixed at 4° C. for 1 hr.
9. Sample was spun at 700 rpm on a tabletop centrifuge for 2 min. 100 µl of the sample was saved as "flowthrough" sample with the supernatant discarded.
10. The resin was washed in 40 mL lysis buffer, mixed at 4° C. for 5 min, spun at 700 rpm on a tabletop centrifuge for 2 min, and the supernatant was discarded.
11. The resin was then washed in 40 mL wash buffer (lysis buffer with 20 mM Imidazole), spun at 700 rpm on a tabletop centrifuge for 2 min, and the supernatant was discarded.
12. 10 mL of wash buffer was added and mixed, and the supernatant was added to an empty column.
13. The column was washed with 50 mL wash buffer and 100 µL resin was removed and saved.
14. The sensor was eluted from the column with 10 mL elution buffer (lysis buffer with 250 mM Imidazole) with 0.5 mL fractions collected and directly assayed using the Bradford Assay.
15. 100 µL of the resin was removed and saved, the elution fractions were combined, and the combined fraction was diluted to 10 mL in lysis buffer.
16. The combined fraction was dialyzed (1 hr with 1 L twice) in GST binding/wash buffer (1×PBS).
17. The dialyzed protein was added to 5 mL glutathione-sepharose resin slurry (GE Cat #17-0756-01) prewashed in GST binding/wash buffer) and was incubated for 1 hr at 4° C.
18. The resin mixture was spun at 700 rpm in a tabletop centrifuge for 2 min, 100 µL was saved as "flowthrough", and the supernatant was discarded.
19. The resin was added to an empty column, washed with 50 mL GST binding/wash buffer, and 100 µL was removed.
20. The protein was eluted with elution buffer (1×PBS buffer with 10 mM reduced Glutathione). 0.5 mL fractions were collected and directly assayed using the Bradford assay. 100 µL of resin was removed and saved.
21. The saved fractions ("total", "soluble", "flowthrough" (his), His resin before elution, His resin after elution, after dialysis sample, flowthrough (GST), GST resin before elution, GST resin after elution and GST fractions) were analyzed on an SDS-PAGE gel (FIG. 14).
22. The GST fractions were combined and dialyzed in storage buffer (50 mM HEPES pH 7.5, 150 mM NaCl, 1 mM DTT, 50% glycerol).

Figure 15:
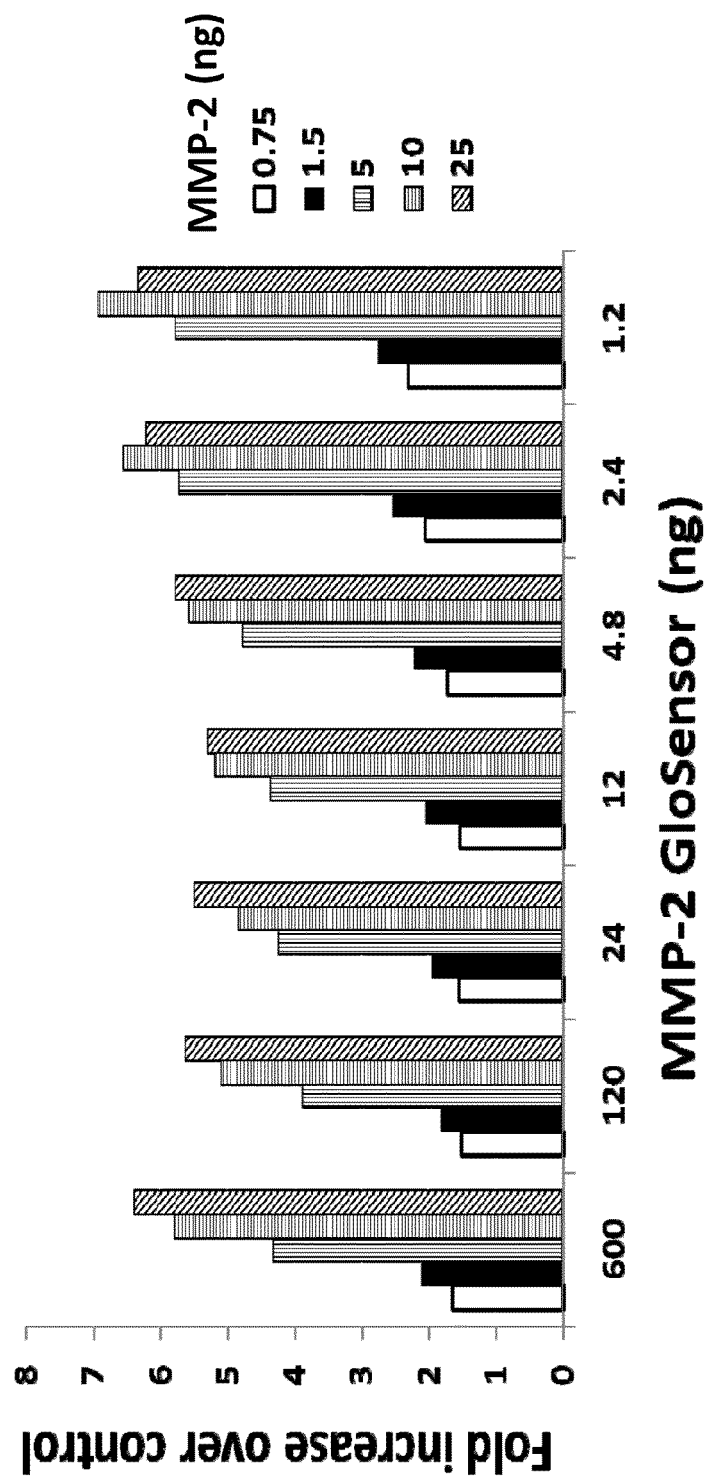
FIG. 15 shows the fold increase over control (background from MMP-2 sensor).

To demonstrate that the purified MMP-2 sensor can detect MMP-2, purified MMP-2 sensor (1.3 mg/mL) was diluted in buffer (50 mM Tris-HCl pH 7.5, 150 mM NaCl, 10 mM $CaCl_2$, and 0.05% Brij35) as described in FIG. 15. Activated MMP-2 (10 ng/µL; Anaspec) was added to the diluted MMP-2 sensor as described in FIG. 15. Total volume of the final reaction mixture was 50 µL. The mixture was incubated at 37° C. for 1 hr. Bright-Glo Assay Reagent (Promega) was prepared according to the manufacturer's instructions, and 50 µL added to the mixture. Luminescence was read immediately on a GloMax MultiPlus luminometer.

FIG. 15 presents the fold increase over control (background from MMP-2 sensor). The results demonstrate that a purified MMP-2 sensor according to the present invention can be used to detect as little as 0.75 ng protein.

Figure 16:
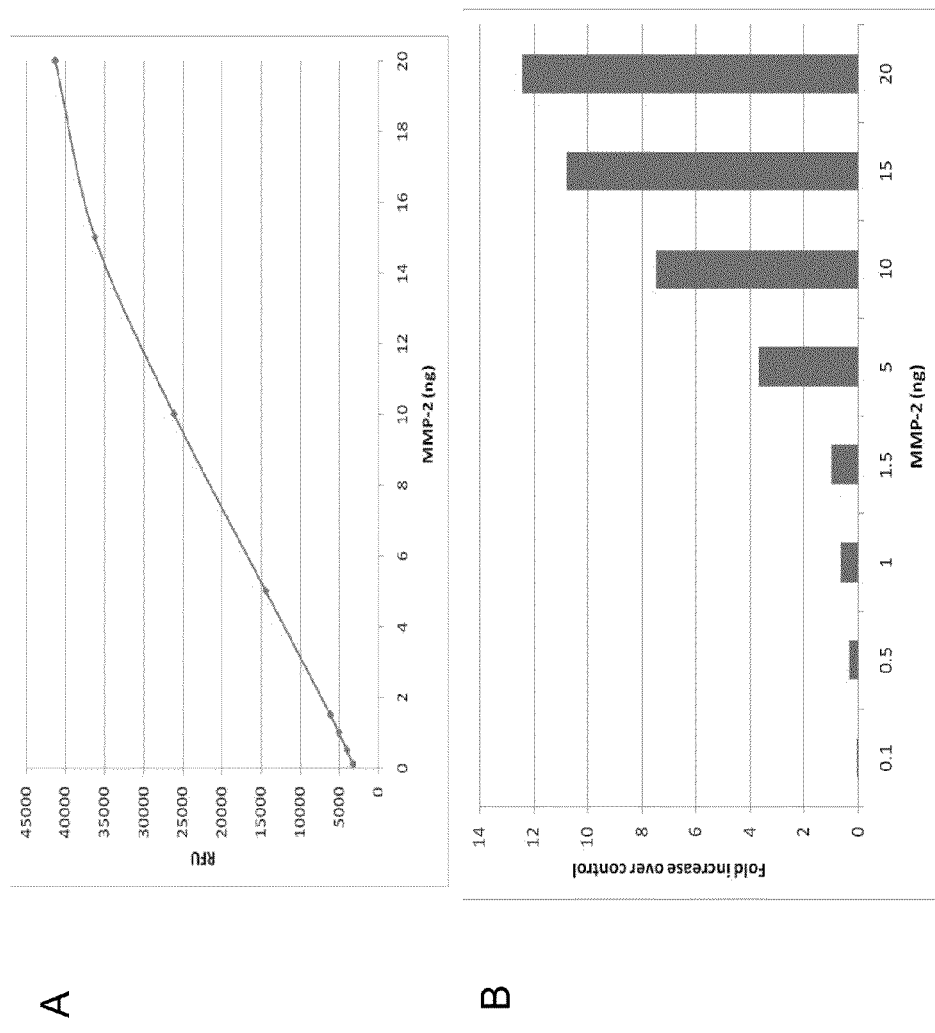
FIGS. 16A-B show the luminescence of the MMP-2 protein using the SensoLyte assay, (FIG. 16A) and the fold-induction (FIG. 16B).

To further demonstrate the sensitivity of the purified MMP-2 sensor, the fluorogenic SensoLyte 520 MMP-2 Assay (Anaspec) was also used to detect MMP-2 protein. The assay was performed according to the manufacturer's instructions. Fluorescence was detected on a Tecan fluorometer at Ex490 nm/Em520 nm. FIGS. 16A-B report detection of 1.5 ng MMP-2 protein using the SensoLyte assay.

Example XI

Cell-Free Expression of CBS

To demonstrate that the protease biosensor of the present invention can effectively and efficiently be cleaved by exogenous protease in a cell-free environment, the CBS variant 1A5 was expressed in wheat germ extract and used to detect Caspase-3.

The CBS variant 1A5 was cloned into the vector pFN19K HaloTag® (Promega Cat. No. G1841) to generate a CBS-HaloTag® (CBS-HT) fusion protein (SEQ ID NOs:71 and 72). 20 µl (8 µg) of the CBS-HT vector was added to 30 µl TnT® SP6 High-Yield Wheat Germ Expression System (Promega Cat. No. L3261) and incubated at 25° C. for 90 min.

For the CBS-HT caspase-3 cleavage reaction, one volume of the expression reaction was incubated with an equal volume of either an *E. coli* lysate containing caspase-3 or C(3) Lysis Buffer (0.8× FastBreak (Promega Cat. No. V857A), 10 mM DTT, 0.1% CHAPS, 0.8 mg/mL Lysozyme, 3 U/µL RQ1 DNase (Promega Cat. No. M610A)) and incubated for 60 min at room temperature. The *E. coli* lysate containing caspase-3 was prepared from KRX cells overexpressing recombinant caspase-3. Briefly, KRX cells were transformed with pTS1k: caspase-3(T/S). A starter culture (50 mL, LB Broth) was inoculated from a single colony and grown for 17-22 hrs at 37° C. with shaking (275 rpm). The starter culture was diluted (1:50) into fresh media and growth was continued for an additional 3 hrs. The incubation temperature was then lowered to 25° C. and, after 15 min, expression of caspase-3 was initiated by addition of rhamnose (0.2% final concentration). After 2 hr, cells were collected by centrifugation, re-suspended in 50 mL C(3) Lysis Buffer and incubated at ambient temperature (i.e. 22-24° C.) for 10 min. The lysate was clarified by centrifugation (20,000×g for 20 min at 4° C.) and used as the Caspase-3 source.

Figure 17:
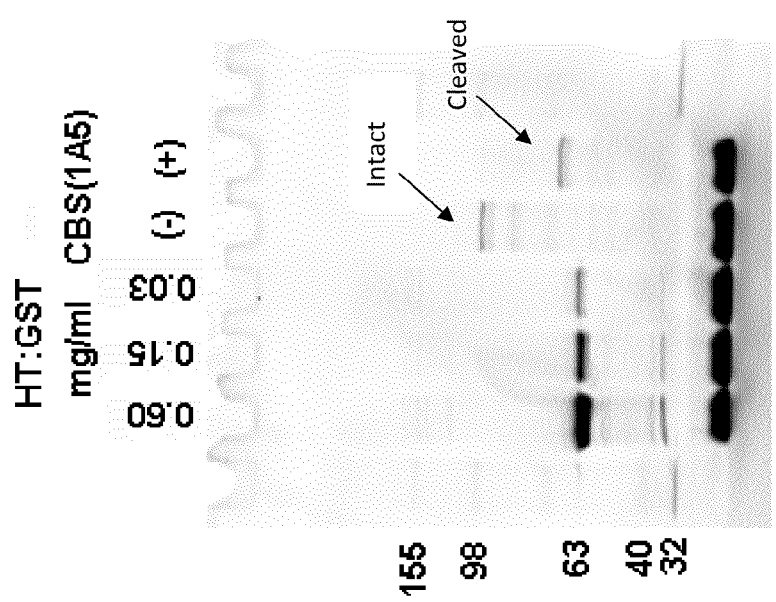
FIG. 17 shows cleavage of CBS-HT by Caspase-3 detected by SDS-PAGE gel analysis.

Cleavage of CBS-HT by Caspase-3 was detected in two different ways: by SDS-PAGE analysis and luminescence detection. For SDS-PAGE analysis, cleavage reaction samples were first labeled with the fluorescent marker CA-TAM (chloro alkane-TAMRA ligand (Promega Cat. No. G825A). 20 µl of the sample was added to 20 µL CA-TAM (diluted 1:100 in buffer (1×PBS, 0.05% IGEPAL)) and incubated for 30 min at room temperature. To this sample, 40 µL SDS-PAGE Loading Buffer (120 mM Tris Buffer (pH7.4), 1% SDS, 25.2% Glycerol, 1.5 mM Bromophenol Blue, 100 mM DTT) was added. The resulting solution was incubated at 65° C. for 30 min. 10 µL was loaded onto an SDS-PAGE gel. As a control, 0.60, 0.15 and 0.03 mg/mL HT:GST (HaloTag®-GST (Promega Cat. No. G449A) fusion was also loaded onto the gel (FIG. 17). After electrophoresis, CA-TAM labeled species were detected by fluorescent imaging (ex:532, Em:580; FIG. 17). For detection via luminescence, 40 µL of the cleavage reaction samples were added to 60 µL buffer (50 mM HEPES (pH 7.5) and 100 µL Bright-Glo assay reagent. Luminescence was detected as previously described (Table 7).

TABLE 7

| | WG(HY) | | |
|---|---|---|---|
| MIN. | BASAL | INDUCED | RESPONSE |
| 5 | 10,494 | 4,626,173 | 441 |

Example XII

Immobilization of CBS

To demonstrate that the protease biosensor of the present invention when expressed in a cell-free environment maintains activity when immobilized on a solid support, the CBS-HT fusion expressed in wheat germ extract (Example XI) was immobilized to a solid support (resin and plate) and used to detect Caspase-3.

Figure 18:
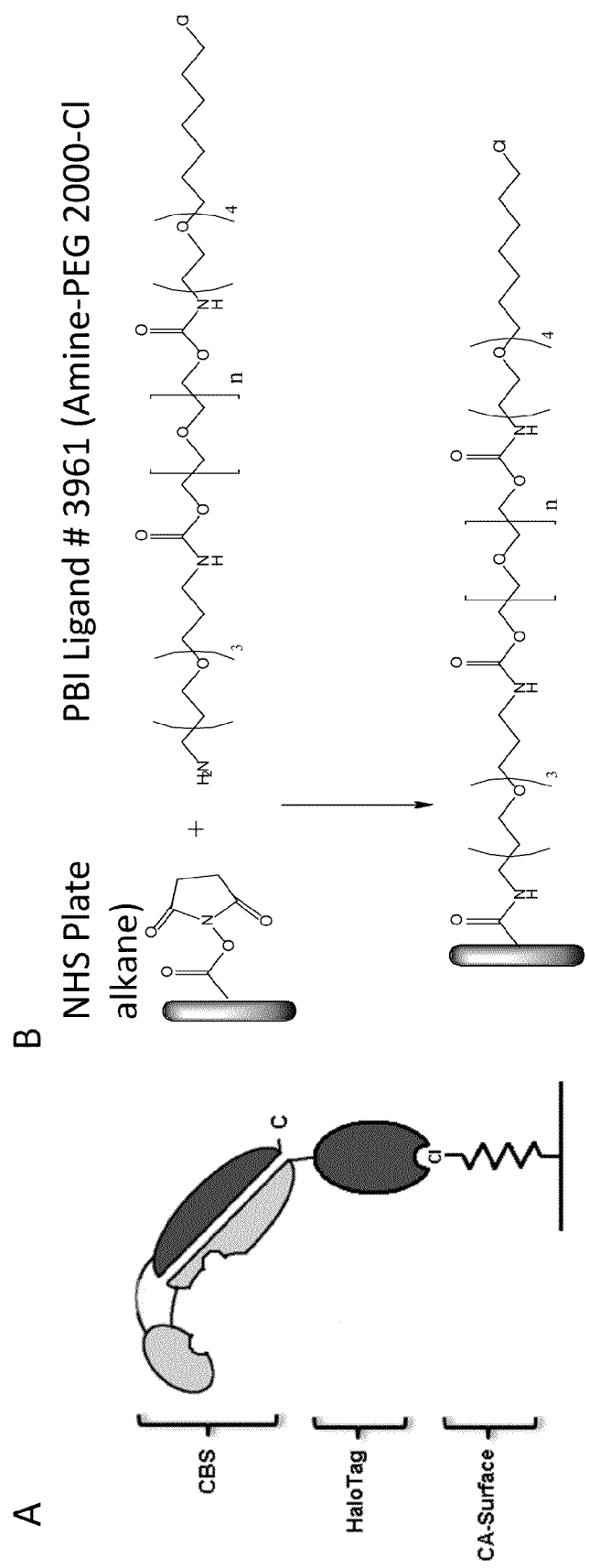
FIGS. 18A-B show illustrations of the immobilization of CBS to a HaloLink resin (FIG. 18A) or a microtiter plate (FIG. 18B).

For immobilization to a resin (FIG. 18A), HaloLink resin (25% slurry, Promega Cat. No. G1912) was first equilibrated with HTPB Buffer (50 mM HEPES (pH 7.5), 150 mM NaCl, 1 mM DTT and 0.5 mM EDTA). Resin from one volume of slurry was collected by centrifugation (5 min at 1000×g), and the storage buffer was removed. The resin pellet was re-suspended in 2 volumes of HTPB and mixed. This process was repeated for a total of three HTPB washes. 100 µL of the CBS-HT fusion from Example XI (cell free expression reaction) was mixed with 25 µL washed resin (50% slurry in HTPB) and incubated overnight with mixing at 4° C. Incubation was continued at ambient temperature for 2 hrs. After incubation, the resin was washed to remove un-bound CBS. The resin was split into two 50 µl aliquots, and each aliquot was washed 3 times with HTPB. The final resin pellets were re-suspended in 50 µL HTPB.

Figure 19:
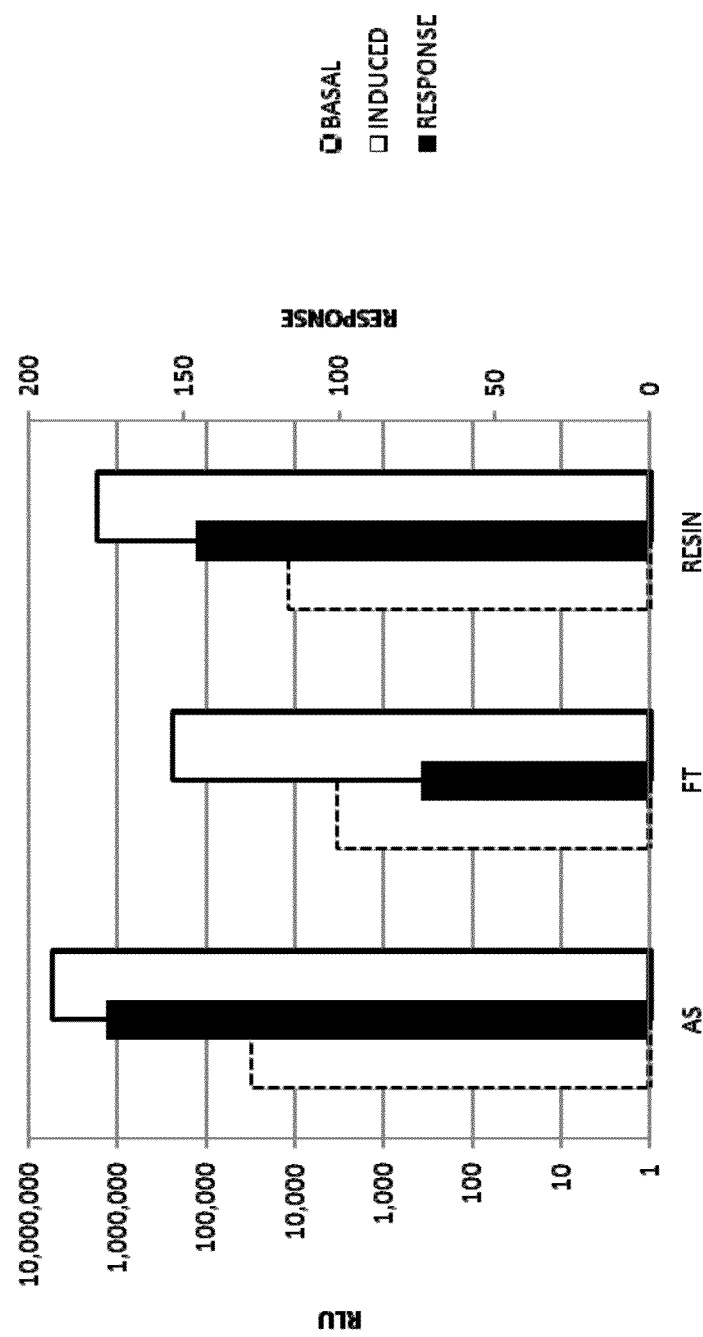
FIG. 19 shows the luminescence of protease biosensor expressed in a cell-free environment.

For the CBS caspase-3 cleavage reaction, 20 µl of the washed resin was mixed with 20 µL of either *E. coli* lysate containing caspase-3 or C(3) Lysis Buffer (as in Example XI) and incubated for 30 min at ambient temperature. 60 µl HEPES pH 7.5 was added to the samples, followed by the addition of 100 µl Bright-Glo Assay Reagent. Luminescence was detected as previously described (Table 8 and FIG. 19).

TABLE 8

| | BASAL | INDUCED | RESPONSE |
|---|---|---|---|
| BLANK | 10 | 70 | 7 |
| AS | 29,553 | 5,162,108 | 175 |
| FT | 3,170 | 232,117 | 73 |
| RESIN | 11,219 | 1,635,259 | 146 |

For immobilization to a plate (FIG. 18B), a microtiter plate was prepared containing HaloTag® ligand for immobilizing the CBS-HT fusion protein. Briefly, bicarbonate buffer pH 8.5 (100 µL), containing amine-PEG 2000-Cl alkane HaloTag® ligand (0.25 mM (final concentration; PBI 3961 and methoxy-PEG-NH$_2$ (0.75 mM final concentration) were added to wells of a NHS microtiter plate and incubated for 1 hr at room temperature. The wells were then washed 3 times with PBS containing 0.05% Tween-20. After washing, 50 mM ethanolamine was added, and the plates were incubated for 30 min at room temperature and washed again 3 times with PBS containing 0.05% Tween-20. The plate was then stored at 4° C. with PBS containing 0.05% Tween-20 in each well. For the assay, the wells were washed 3 times with 200 µl HPTB. 50 µl CBS-HT cell-free expression reaction (Example XI) was added to the wells, and incubated overnight at 4° C. Following incubation, the plate was washed 3 times with 200 µl PBSI (1×PBS with 0.05% IGEPAL). 100 µL *E. coli* lysate containing caspase-3 or C(3) lysis buffer (described above) were added and the plate was incubated for 60 min with mixing at room temperature. The wells were then washed with 100 µl PBSI. 100 µL HEPES pH 7.5 and 100 µl Bright-Glo Assay Reagent were added and luminescence was detected as previously described (Table 9).

TABLE 9

| MIN. | BASAL | INDUCED | RESPONSE |
|---|---|---|---|
| 0 | 66 | 1,226 | 19 |
| 1 | 16 | 1,636 | 102 |
| 2 | 106 | 2,267 | 21 |
| 3 | 66 | 2,147 | 33 |
| 4 | 126 | 2,297 | 18 |
| 5 | 126 | 2,857 | 23 |
| 6 | 76 | 3,107 | 41 |
| 7 | 56 | 3,377 | 60 |
| 8 | 136 | 3,037 | 22 |
| 9 | 116 | 3,667 | 32 |

Example XIII

CBS Expression in *E. coli*

To demonstrate that the protease biosensor of the present invention can be expressed and function in *E. coli*, the CBS variant 1A5 was expressed in *E. coli* and used to detect Caspase-3.

Figure 20:
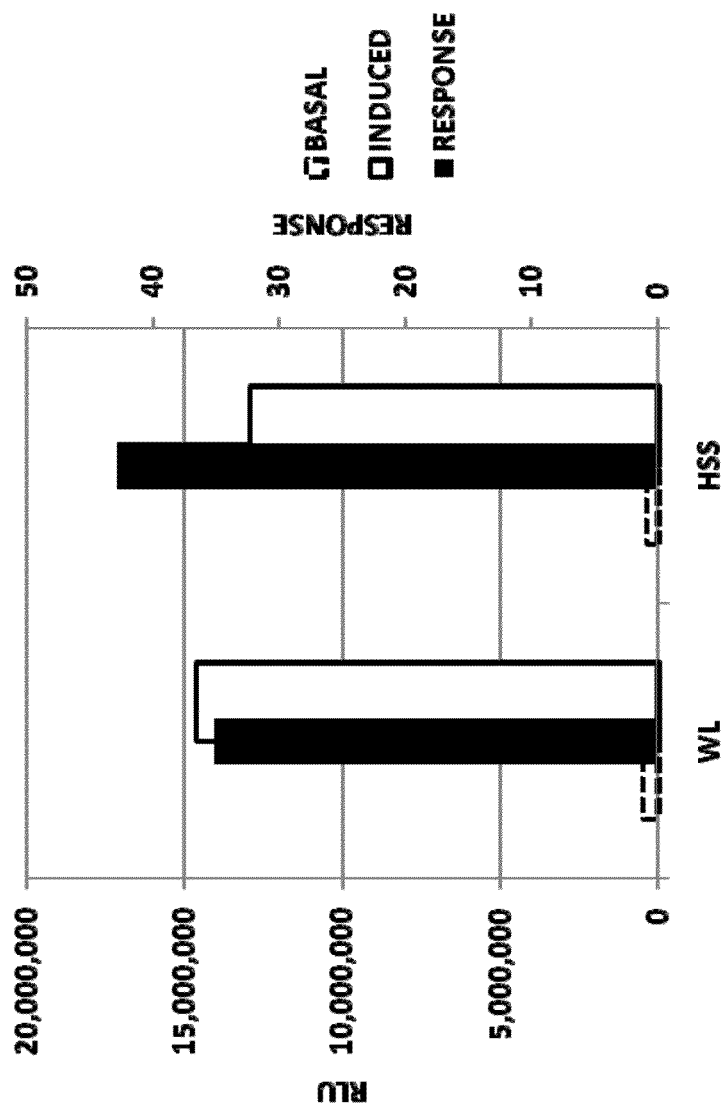
FIG. 20 shows the luminescence of protease biosensor expressed in E. coli.

The CBS variant 1A5 was cloned into a bacterial expression vector (pFNA:HQ(5×):CBS:HT(7); SEQ ID NOs:73 and 74) containing HaloTag® (C-terminal to the CBS) and a 5×HQ tag (N-terminal to CBS). The fusion protein was expressed in *E. coli* as follows: *E. coli* (KRX) was transformed with the vector. A starter culture (50 mL, LB Broth) was inoculated from a single colony and grown for 17-22 hrs at 37° C. with shaking (275 rpm). The starter culture was diluted (1:50) into induction media (500 mL, LB Broth with 0.05% glucose and 0.02% rhamnose) and growth was continued for another 17-22 hrs at 25° C. with shaking (275 rpm). The culture was divided into two 250 mL aliquots, and cells were collected by centrifugation (5,000×g for 20 min at 4° C.). One cell pellet was re-suspended in Lysis Buffer (25 mL, 50 mM HEPES (pH 7.5), 0.2× FastBreak, 2 mM DTT, 0.05% CHAPS, 50 mM Arginine, 50 mM Glutamic acid, 0.2 mg/mL Lysozyme, 10 U/mL RQ1 DNase, and Protease Inhibitors (Beckton/Dickenson Cat. No. 544779)) and incubated on ice for 30 min. After incubation, the sample was sonicated (Misonix Sonicator-3000, 4 mM total, 5 sec on, 5 sec rest, Power Setting 5). The crude lysate was clarified by centrifugation (20,000×g for 20 min at 4° C.), and the supernatant (cleared lysate) was used as the CBS source. For the caspase-3 cleavage reaction, 20 µl of the cleared lysate was mixed with 20 µL *E. coli* lysate expressing caspase-3 (Example XII) and incubated at room temperature for 30 min. 60 µL HEPES pH 7.5 was added, followed by the addition of 100 µL Bright-Glo Assay Reagent. Luminescence was detected as previously described above (FIG. 20).

Example XIV

Purification of CBS from *E. coli*

To demonstrate the ability to purify a functional protease biosensor of the present invention from *E. coli*, the CBS expressed in Example XIII was purified using HisLink (Promega Cat. No.V8821)) column chromatography according to the manufacturer's instructions. Briefly, 25 mL of cleared lysate was made 0.5 M in NaCl (final concentration) and applied to 2 mL of settled HisLink resin that had been equilibrated with Binding Buffer (100 mM HEPES (pH7.5), 10 mM Imidazole, 500 mM NaCl). The resin was washed with 12 mL of Binding Buffer followed by washing with Elution Buffer (100 mM HEPES (pH 7.5), 1000 mM Imidazole). 1.75 mL fractions were collected.

Figure 21:
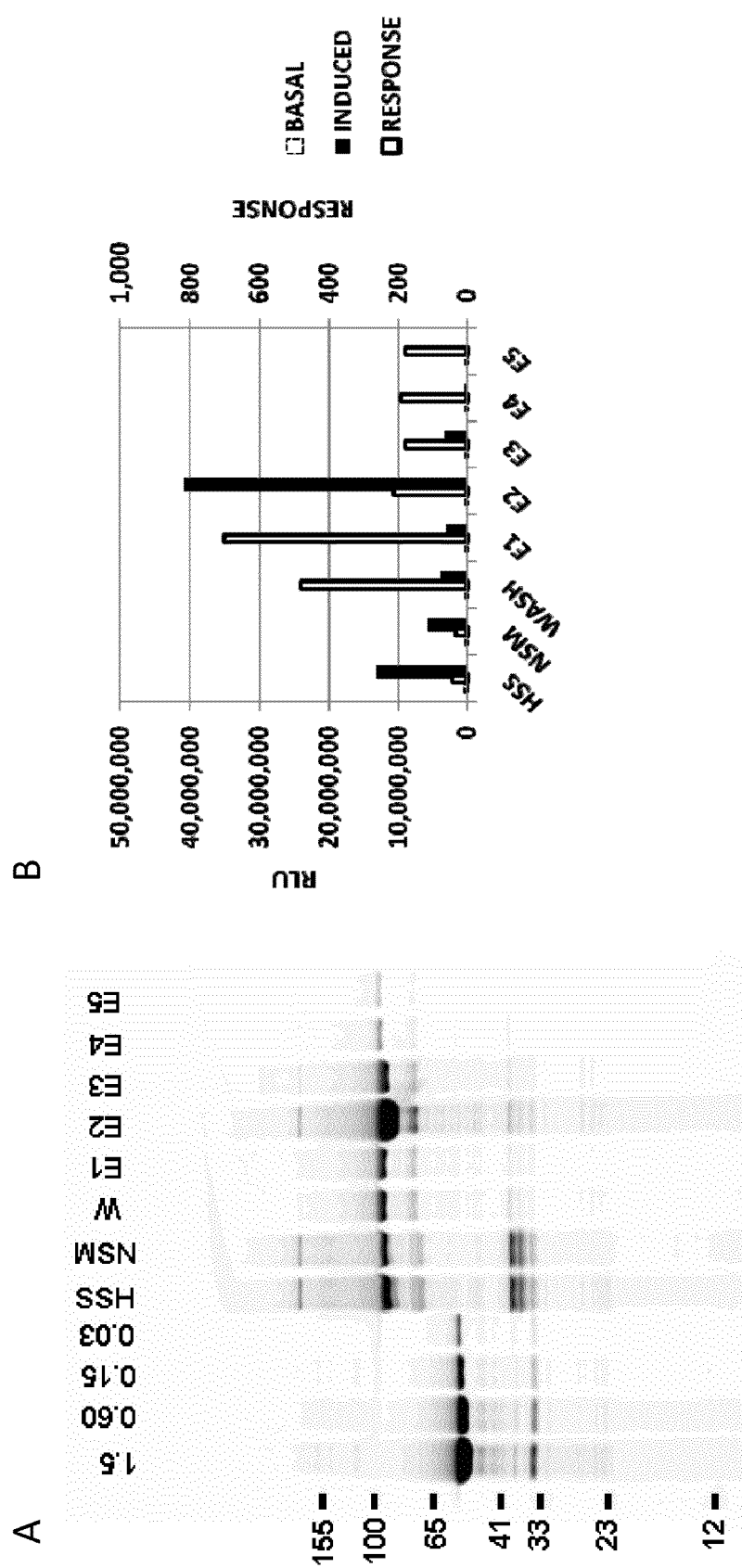
FIGS. 21A-B show SDS-PAGE analysis of samples labeled with CA-TAM (FIG. 21A) and the luminescence of purified protease biosensor (FIG. 21B).

For SDS-PAGE gel analysis, samples were labeled with CA-TAM and analyzed as described previously (FIG. 21A). For caspase-3 cleavage reaction, 20 µl of each sample was mixed with 20 µL *E. coli* lysate expressing Caspase-3 (Example XII) and incubated at room temperature for 30 min. 60 µL HEPES pH 7.5 was added, followed by the addition of 100 µL Bright-Glo Assay Reagent. Luminescence was detected as previously described above (Table 10 and FIG. 21B).

TABLE 10

|  | HSS | NSM | WASH | E1 | E2 | E3 | E4 | E5 |
| --- | --- | --- | --- | --- | --- | --- | --- | --- |
| BASAL | 301,304 | 176,259 | 7,734 | 4,221 | 193,268 | 18,454 | 1,130 | 270 |
| INDUCED | 12,875,742 | 5,822,003 | 3,706,541 | 2,951,899 | 40,913,496 | 3,287,059 | 215,580 | 48,068 |
| RESPONSE | 43 | 33 | 479 | 699 | 212 | 178 | 191 | 178 |

Example XV

Immobilization of *E. coli* Expressed CBS

Figure 22:
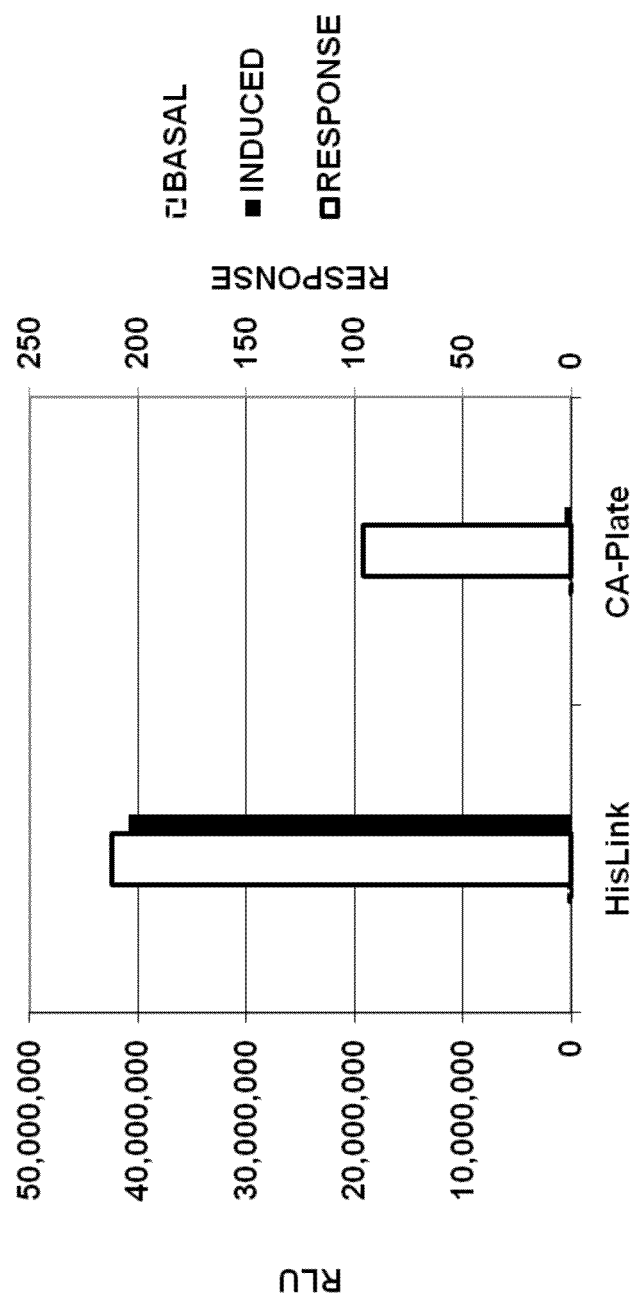
FIG. 22 shows the luminescence of the protease biosensor immobilized to a solid support.

To demonstrate that the protease biosensor expressed in *E. coli* can be immobilized to a solid support while maintaining the ability to detect protease, purified HQ:CBS:HT (5×HQ tag:CBS: HaloTag) was immobilized on HaloLink resin and HaloLink plates and assayed for activation by Caspase-3. For immobilization on HaloLink resin, 100 µL of purified HQ:CBS:HT was added to 30 µL of settled HaloLink resin (pre-equilibrated with HTPB as described previously) and incubated for 2 hrs at ambient temperature. The resin was washed 3 times with 300 µL HTPB, and the final resin pellet was re-suspended in 300 µL HTPB. 50 µL washed resin was added to 50 µL *E. coli* Lysate containing Caspase-3 or 50 µL C(3) Lysis Buffer and incubated for 30 min at ambient temperature. 100 µL of Bright-Glo Assay Reagent was added and luminescence was detected as previously described (Table 11 and FIG. 22).

For immobilization on HaloLink plates, 100 µL of purified HQ:CBS:HT was added to a microtiter plate containing immobilized HaloTag® ligand (Example XII). The plate was incubated at room temperature with mixing for 2 hrs. The plate was then washed 3 times in 1×PBSI (1×PBS with 0.05% IGEPAL) and incubated with 100 µL of *E. coli* Lysate containing Caspase-3 (prepared as described previously) for 30 min at room temperature. 100 µL Bright-Glo Assay Reagent was added, and luminescence detected as previously described (Table 11 and FIG. 22).

TABLE 11

|  | HisLink | HaloLink-Plate |
| --- | --- | --- |
| BASAL | 193,268 | 6,880 |
| INDUCED | 40,913,496 | 661,597 |
| RESPONSE | 212 | 96 |

Example XVI

Kinetic Study of NK92 Cells with Different Target Cells

To determine whether the granzyme B biosensors of the present invention can be used to detect cell-mediated cytotoxicity, protease biosensors containing 1 of 3 granzyme B recognition sites or 1 of 4 control recognition sites were generated.

Granzyme B Cleavage Site Design:

1. Search for protease sites for known granzyme B target proteins.
2. Create the corresponding non-cleavable control sequences as well.

Site B (BID): GRIEADSE (SEQ ID NO:80) and negative control: IEAA (SEQ ID NO:83) (grB and caspase 10)

Site C (Casp3): GIETDSG (SEQ ID NO:82) and negative control: IETA (SEQ ID NO:84) (grB and caspase 8)

Site D (DDPK): KSVGPDFG (SEQ ID NO:81) and negative control: VGPA (SEQ ID NO:85) (grB specific)

Constructs were expressed in the target cells, K562 cells, and co-incubated with NK effector cells. Luminescence was detected. K562 target cells were transduced with one of the following vectors:

i) pGloSensor™-30E-GRIEADSE: Granzyme B sensor B ("B+");

ii) pGloSensor™-30F-IEAA: Negative control sensor B ("B−");

iii) pGloSensor™-30E-GIETSDG: Granzyme B sensor C ("C+");

iv) pGloSensor™-30F-IETA: Negative control sensor C ("C−");

v) pGloSensor™-30E-KSVGPDFG: Granzyme B sensor D ("D+");

vi) pGloSensor™-30E-IVGPA: Negative control sensor D ("D−"); or vii) pGloSensor™-30E-DEVD: Positive control sensor ("DEVD").

Cells expressing the granzyme B sensors or control sensors were selected using G418. Once selected, the granzyme B sensor or control sensor target cells were incubated with NK92 effectors cells. Cells were then co-incubated, a luciferase detection reagent added, and luminescence detected on a Veritas luminometer. The DEVD construct was used as a positive control as an apoptosis-substrate for activated caspase 3/7 as it will activate with all inducers of apoptosis.

Figure 23:
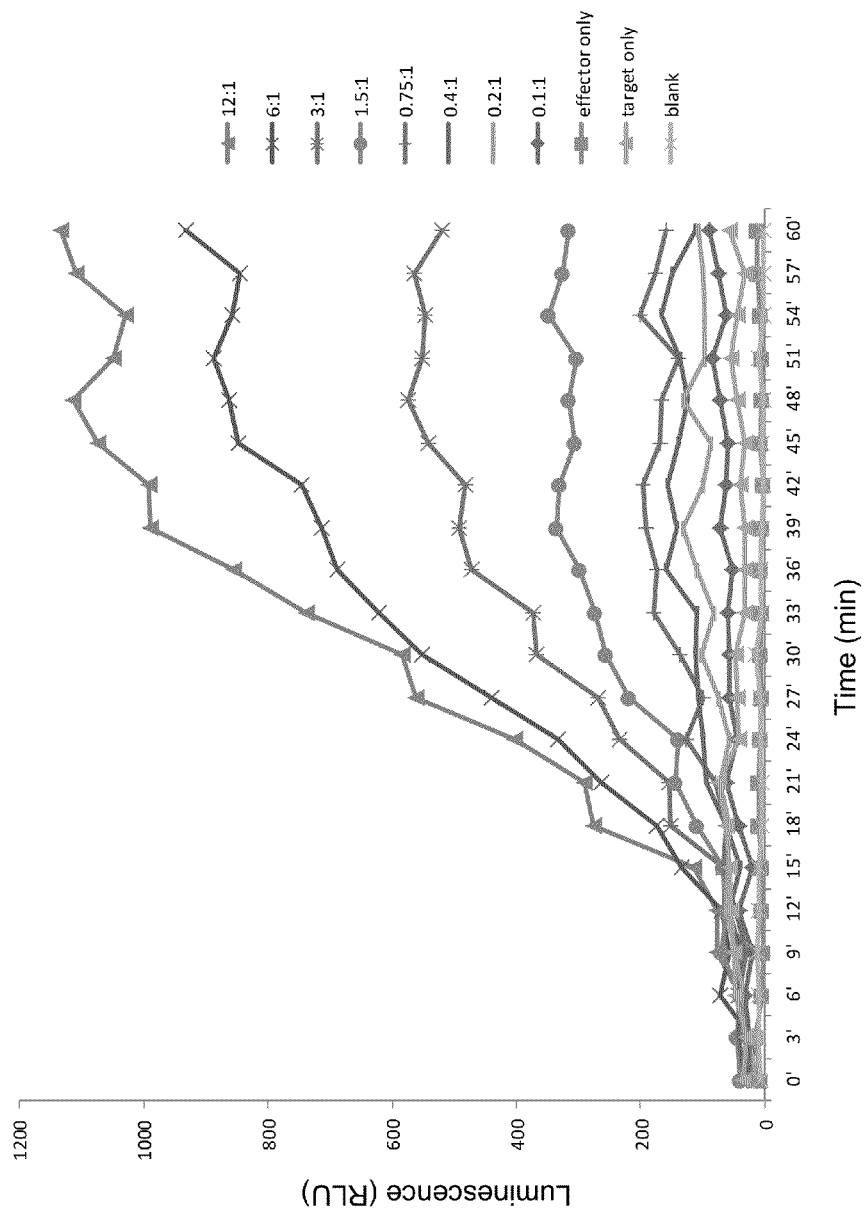
FIG. 23 shows the kinetic data using NK92 cells and the DEVD construct at 37° C. measured with a Biotek Reader.
Figure 24:
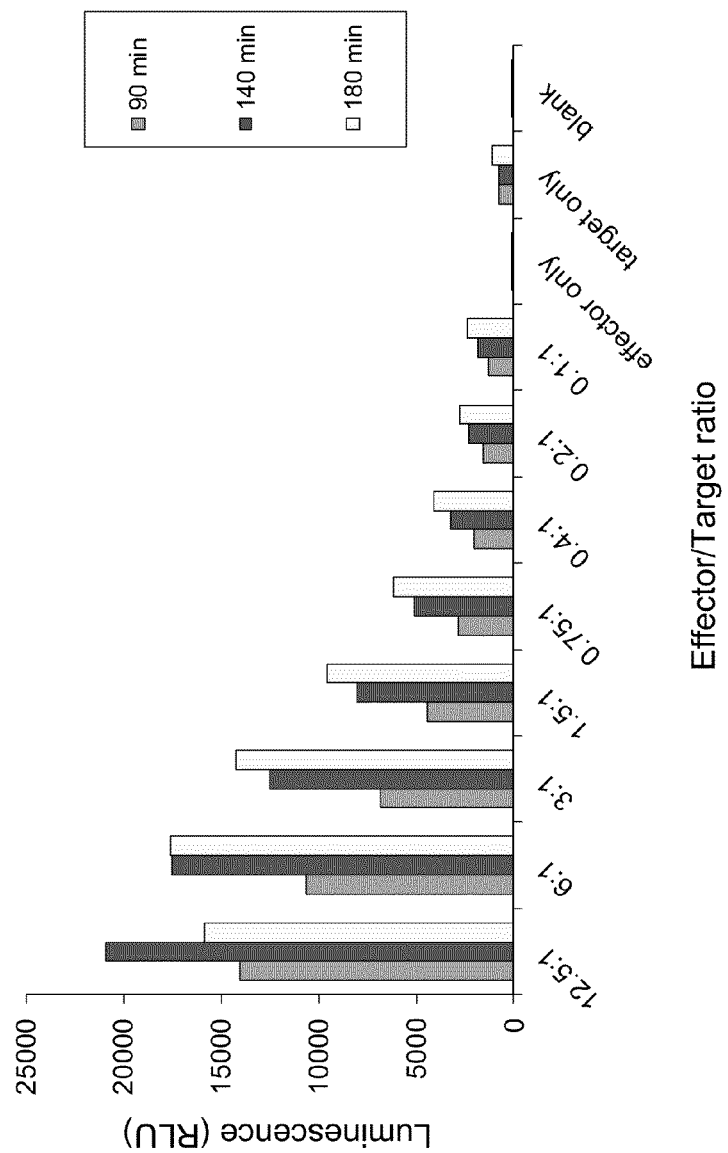
FIG. 24 shows luminescence of NK92 cells and the DEVD construct at room temperature measured with a Veritas reader.

To establish the capacity for a positive control to work with the control effector cell line NK92, K562 cells were transfected with the caspase 3/7 cleaved firefly ("DEVD") biosensor construct. A stable transfectant was obtained by limiting dilution in G418. After incubation with luciferin (2%) for 30 min, the K562 cells were added to wells of a 96-well round bottom, white plate at 30,000 cells/well. NK92 cells were then added to the wells at decreasing Effector/Target (E/T) ratios (from 50:1 to 0.1:1). After centrifugation of the plate at 200×g for 5 min, luminescence was measured at 37° C. every 3 min for a total of 60 min on a Biotek luminometer. FIG. 23 shows an increase of the luminescent signal 6 min after the incubation and a signal plateau at about 40-45 min. An increase of the luminescent signal can be seen in E/T ratios as low as 0.75:1. Control K562 target alone had a low basal signal. NK92 and K562 cells expressing the DEVD biosensor construct were co-incubated at 37° C. in a 5% CO$_2$ incubator for 90 min, 140 min, and 180 min, respectively. The plates were cooled at room temperature for 10 min, and luminescence measured on a Veritas plate reader. FIG. 24 shows an induction of luminescent signal in all different E/T ratios as compared with the target alone. Longer incubation (180 min) at 37° C. resulted in higher luminescent signal. FIGS. 23 and 24 show the capacity for the positive control to work with the control effector cell line, NK92.

Figure 25:
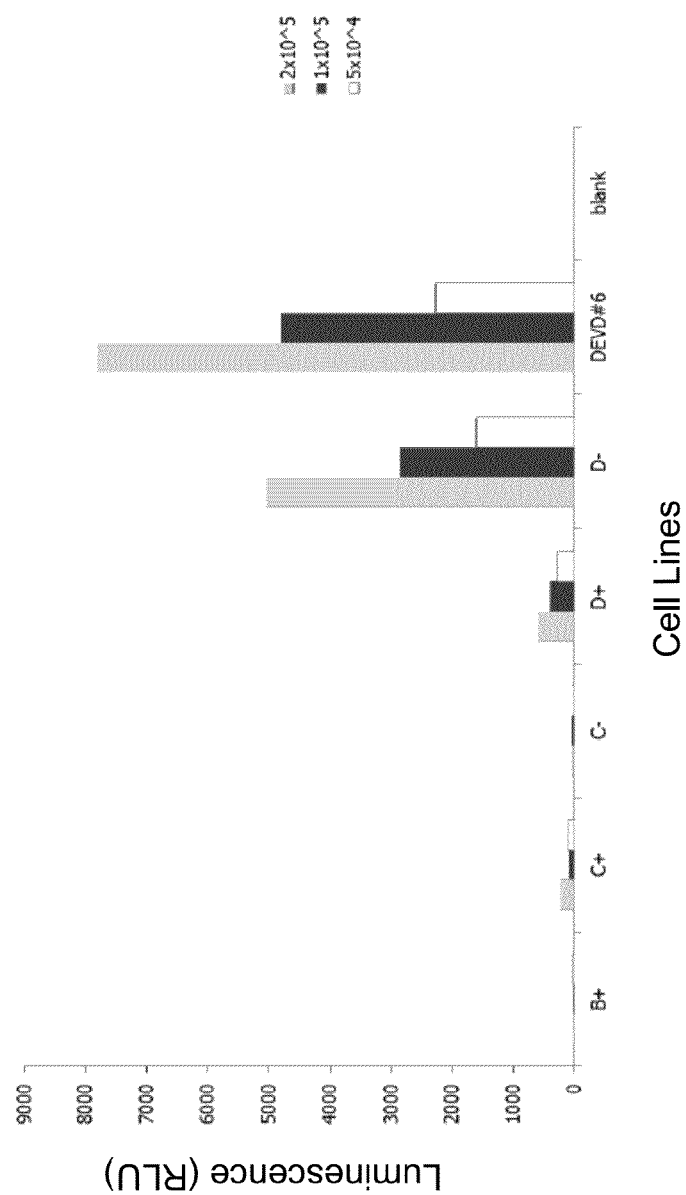
FIG. 25 shows the luminescence of the basal signal (i.e., no effectors) of the granzyme B constructs compared to the controls measured with a Veritas reader.

The granzyme B biosensors, B+, C+, C−, D+, and D−, were transfected into K562 cells and selected using G418 selection. The caspase 3/7 biosensor transfected cells (K562-DEVD clone #6; "K562-DEVD #6") were treated the same way as described above and served as a comparison. Cells were harvested and resuspended in 2% luciferin substrate and aliquoted into wells of a 96-well round bottom, white plate at 2×10$^5$, 1×10$^5$, and 5×10$^4$ cells per well, respectively. Plates were incubated at 37° C. for 30 min and cooled at room temperature for 10 min. Luminescence was read on a Veritas plate reader. FIG. 25 shows that K562-DEVD #6 and K562-D− (a negative control for K562-D+ construct cells) target cells have a higher basal luminescence (i.e., no effectors) than other granzyme B constructs target cells. FIG. 25 also shows that the co-incubation of target cells expressing the granzyme B sensors with the NK92 effector cells lead to the generation of luminescence when NK cell signaling occurs. In addition, the data demonstrated that the luminescence generated was easily detected in as little as 30,000 target cells/well with a 6:1 ratio of effector to target cells in a 96-well plate.

Figure 26:
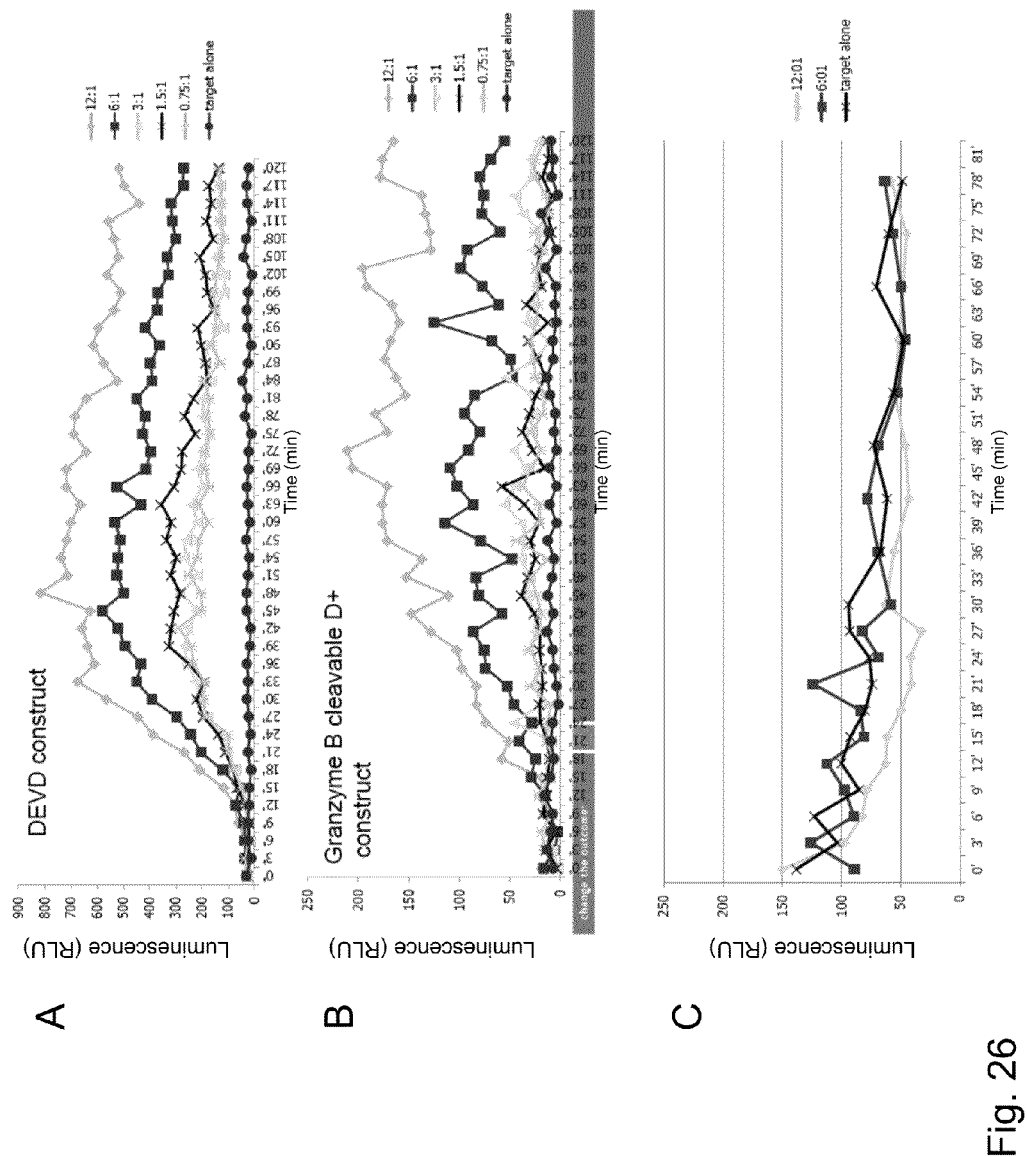
FIGS. 26A-E show the kinetic data of the DEVD construct (FIG. 26A and FIG. 26E), the granzyme B cleavable D+ construct (FIG. 26B and FIG. 26D), and the granzyme B negative control (D−) construct (FIG. 26C).
Figure 26:
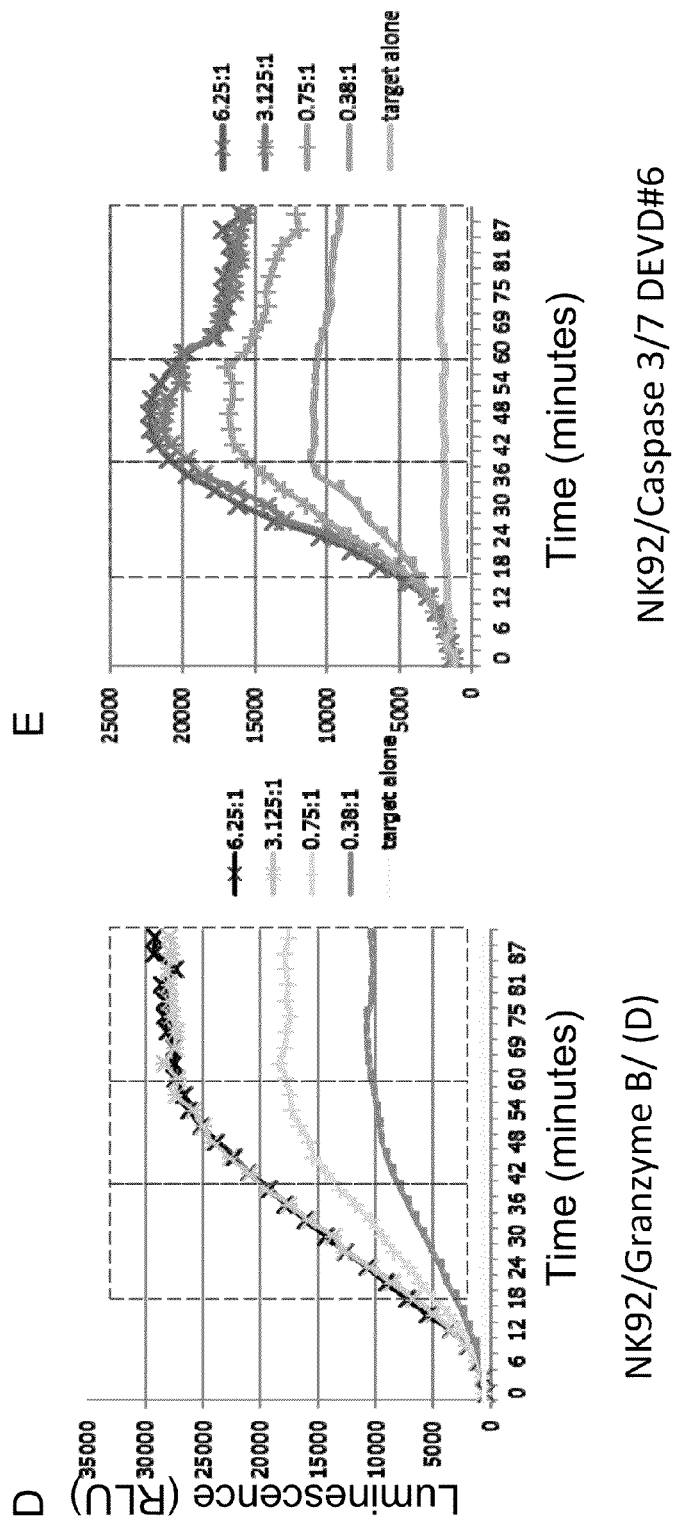

The K562-DEVD #6, granzyme B cleavable (D+) construct, and the granzyme B negative control (D−) construct target cells were examined Transfected K562 target cells (K562-DEVD clone #6 in FIGS. 26A and 26E, K562-D+ parental line in FIGS. 26B and 26D, K562-D-parental line in FIG. 26C) were incubated with 2% luciferin substrate at 37° C. in a 5% CO$_2$ incubator for 30 min. Cells were aliquot into wells of a 96-well round bottom, white plate at 30,000 cells/well. A titration of effector NK92 cells was then added to the wells at various Effector/Target (E/T) ratios (from 12:1 to 0.75:1). The plate was centrifuged at 200×g for 5 min and incubated in a Biotek luminometer at 37° C. Luminescence was measured every 3 min for a total of 120 minutes. FIGS. 26A-C show induction of luminescent signal in K562-DEVD #6 (FIG. 26A) and K562-D+ target cells (FIG. 26B) when effector NK92 cells were added, but no induction of luminescent signal in K562-D-target cells (FIG. 26C). FIGS. 26D and 26E show an increase in luminescent signal 6 min after incubation and a signal plateau at about 40-45 min, similar to the results shown in FIG. 23. Also, FIGS. 26D and 26E show that an increase of the luminescent signal can be seen in E/T ratio as low as 0.75:1 and the control. K562 target cells alone had low basal signal.

Example XVII

Figure 27:
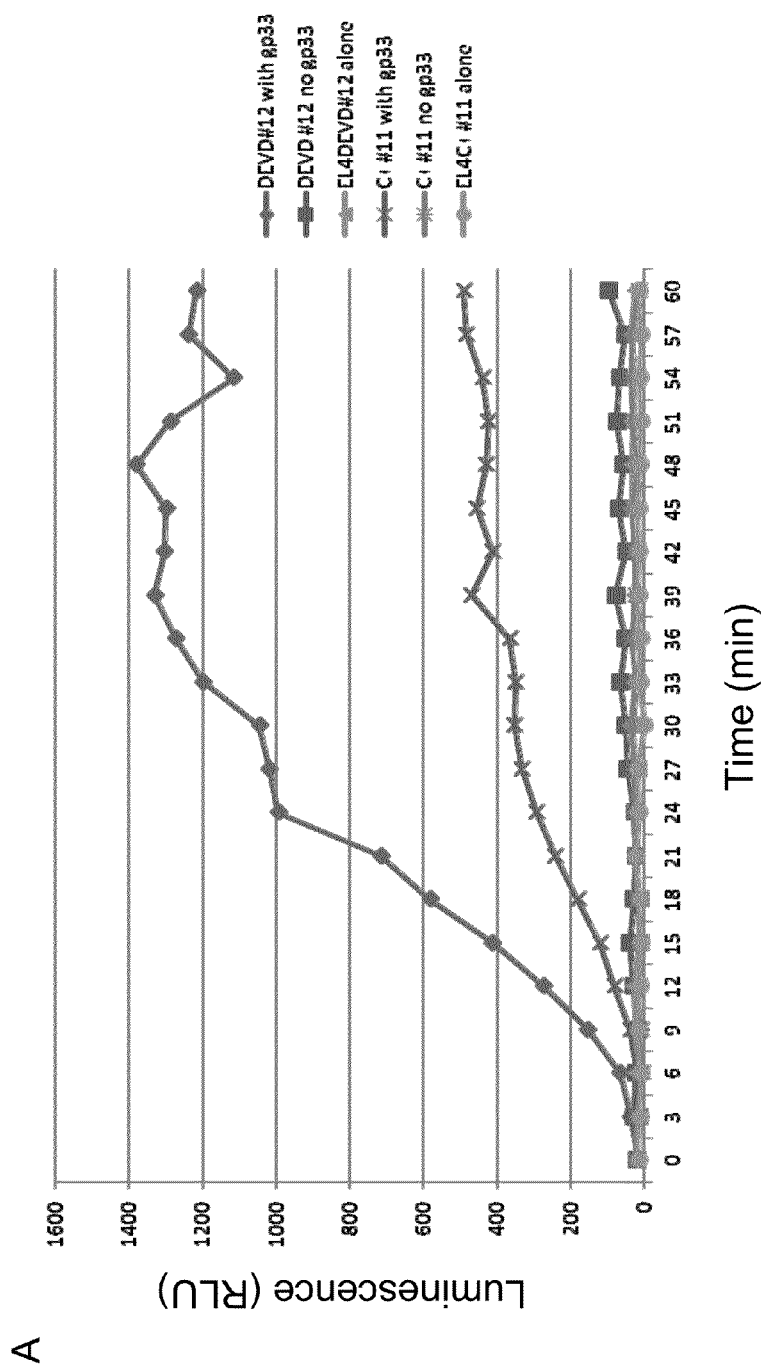
FIGS. 27A-B show that activated cytotoxic T cells (CTL) from P14 mice trigger caspase 3/7 and granzyme B (C+) biosensor in murine EL4 target cells through antigen specific recognition.
Figure 27:
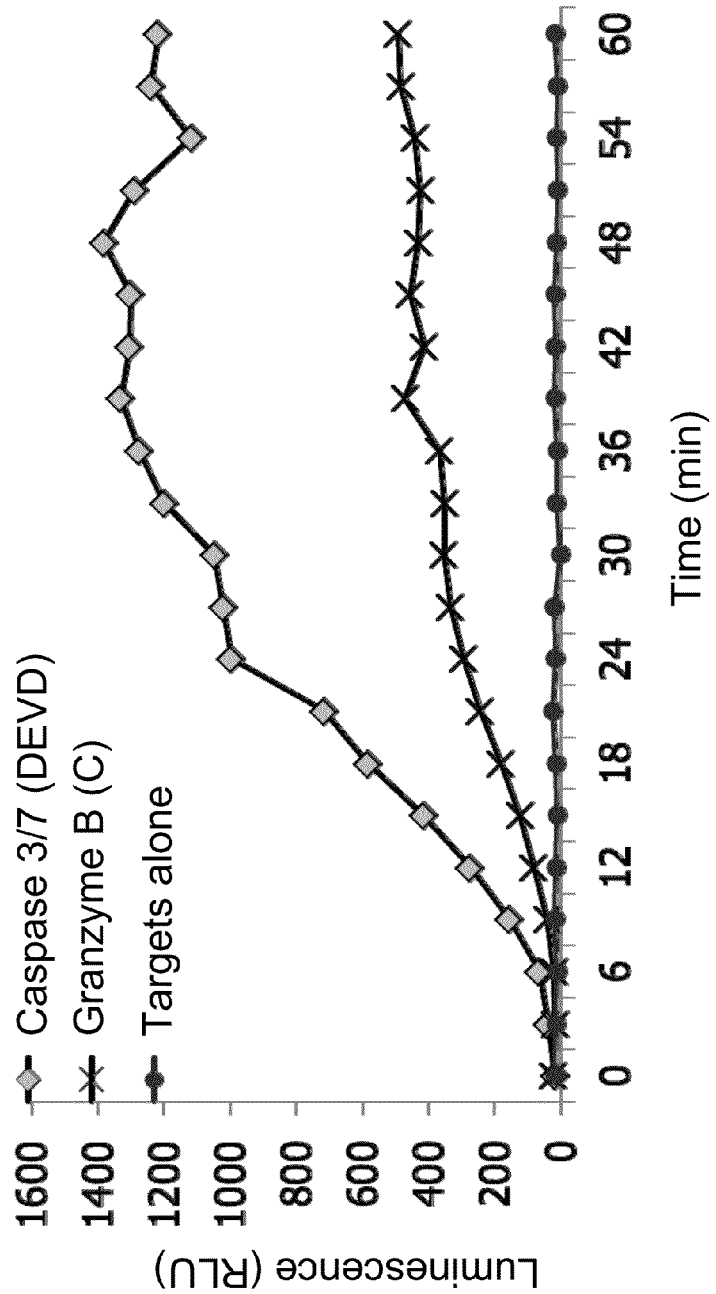

The granzyme B biosensors described above were tested with EL4 target cells (ATCC Manassas, Va.) using mouse cytotoxic T cells (CTLs) as effectors to determine if the sensors work with different target cells and effector cells. Splenocytes from T-cell receptor (TCR) transgenic P14 mice (available through A.T.C.C.) were stimulated in vitro with Lymphocytic Choriomeningitis (LCMV) gp33 peptide for 3 (FIG. 27A) or 2 (FIG. 27B) days followed by expansion in IL-2 for 2 or 3 days, respectively. The CTL effector cells were isolated and added to plates containing 20,000 per well of EL4 target cells preincubated with 2% GloSensor cAMP reagent in an effector/target ratio of 12:1. The plate was centrifuged at 200×g for 5 min, and luminescence measured on a Biotek luminometer at 37° C. for 60 min. As shown in FIGS. 27A and 27B, activated CTL cells from P14 mice triggered caspase 3/7 (DEVD) and granzyme B (C+) biosensors in murine EL4 cells through antigen specific recognition.

Example XVIII

Figure 28:
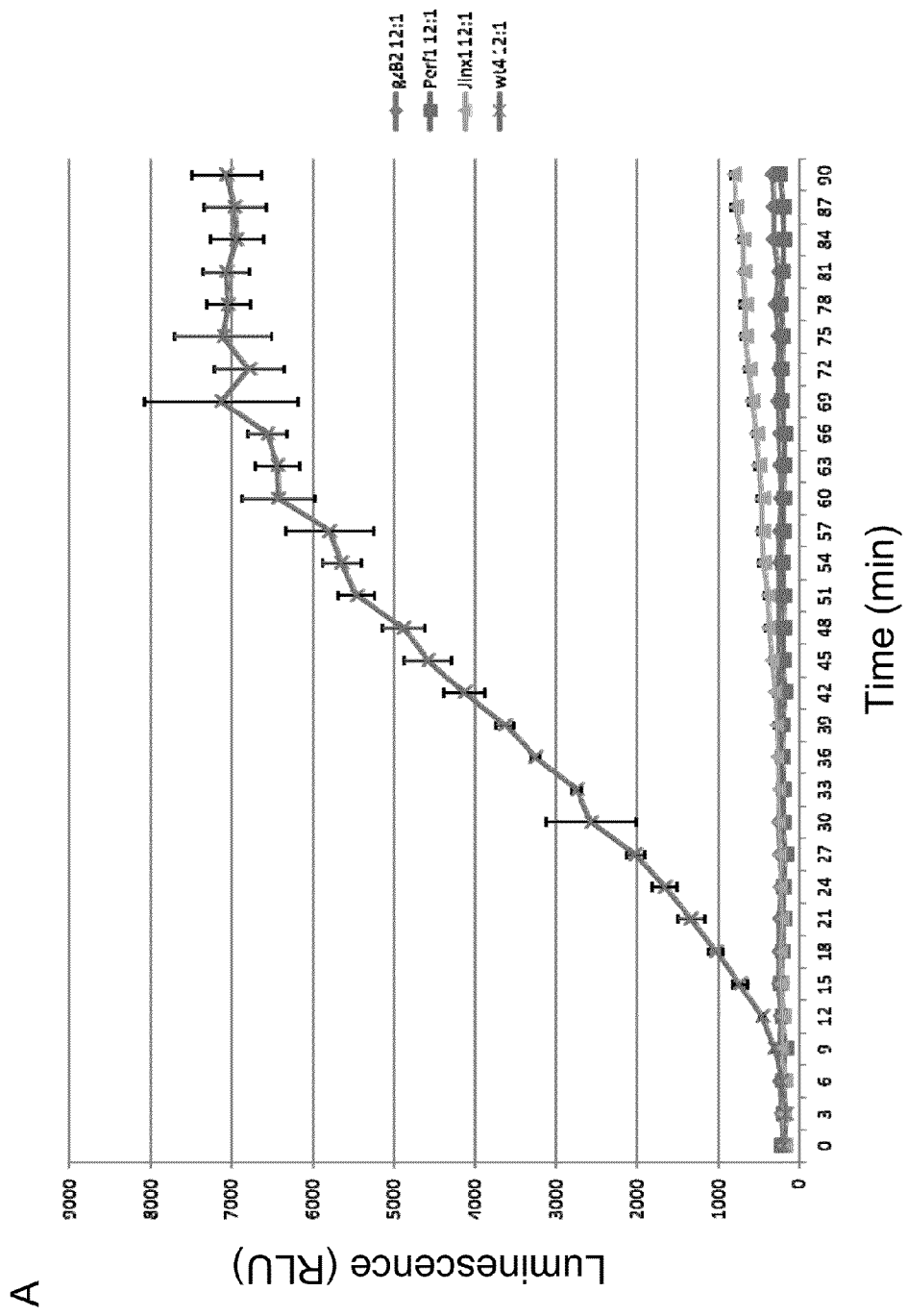
FIGS. 28A-B show that the caspase 3/7 biosensor (DEVD) is dependent on the delivery of granzyme B into the target cells and perforin.
Figure 28:
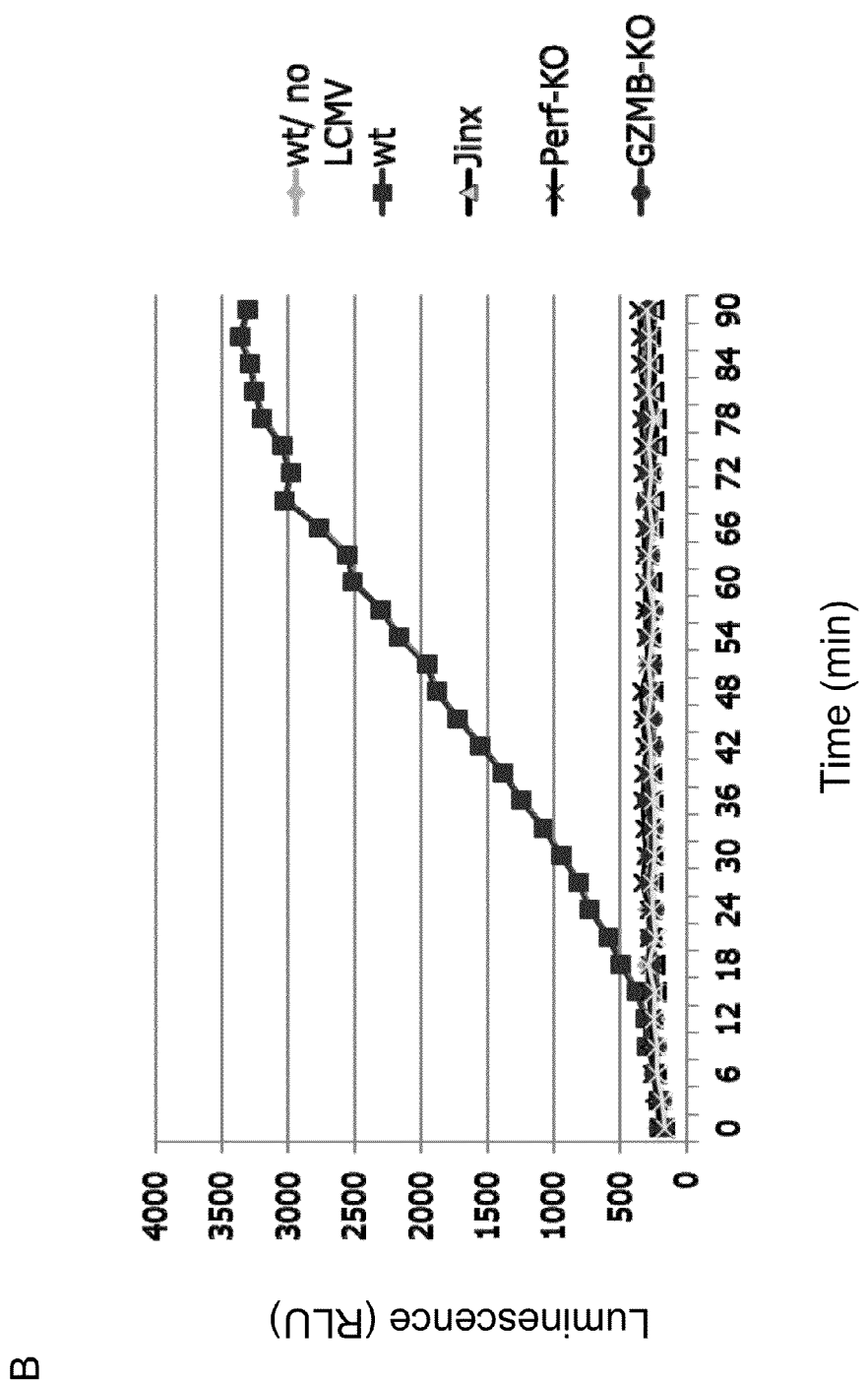
Figure 29:
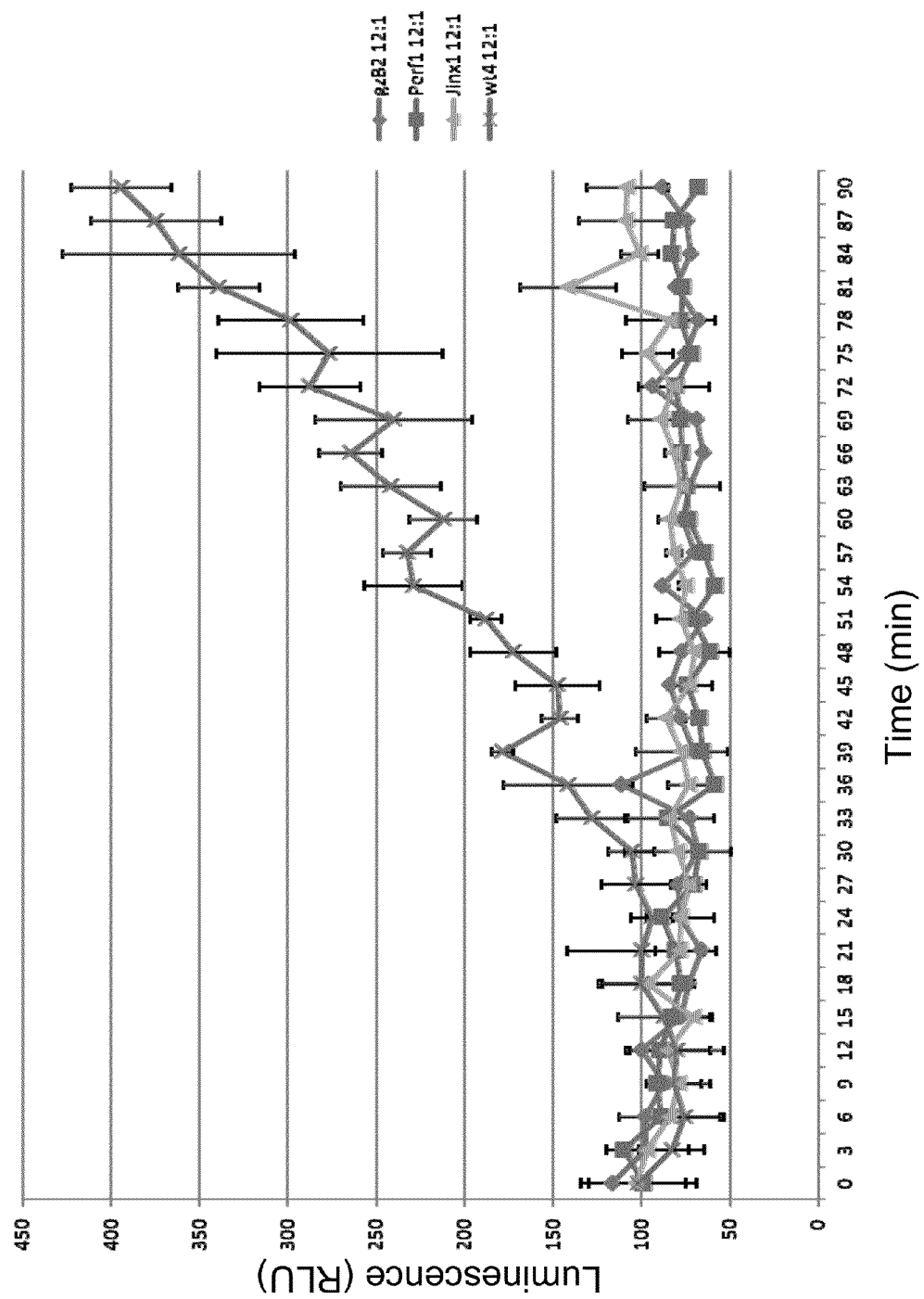
FIG. 29 shows that the granzyme B biosensor (C+) is dependent on delivery of granzyme B into the target cells.

The granzyme B sensors described above were tested to determine if the sensors were granzyme and/or perforin dependent. Granzyme B knockout, perforin knockout and Jinx mice were used and are described in Lykens et al., Blood 118:618-626 (2011). The mice (three granzyme B knockout mice, three perforin knockout mice, three Jinx mice, and five wild type mice) were infected with LCMV (see Lykens et al., Blood 118:618-626 (2011)). On day 7 after the infection, splenocytes were harvested and co-incubated with gp33-pulsed EL4 target cells transfected as described above with the caspase 3/7 biosensor or the granzyme B biosensor at a 12:1 ratio. The gp33 peptide is the dominant LCMV epitope and used to present antigen to effector T cells. Luminescence was measured at 37° C. with a Glomax luminometer for 90 min. FIGS. 28A and 28B show that caspase 3/7 biosensor is dependent on delivery of granzyme B into the target cells and on perforin. FIG. 29 shows that the granzyme B biosensor (C+) is dependent on delivery of granzyme B into the target cells.

Figure 33:
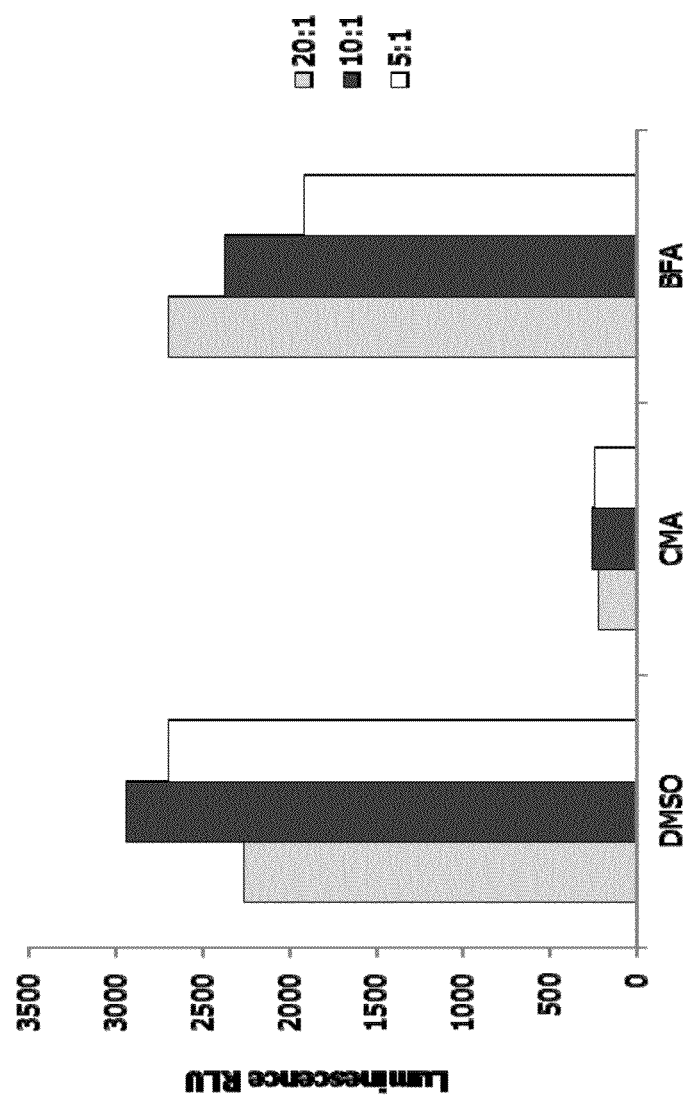
FIG. 33 shows that the inhibition of perforin-dependent killing blocks activation of the granzyme B biosensor by granzyme B.

NK92 and K562 cells expressing granzyme B sensor (D+) were used to determine if inhibition of perforin-dependent killing blocks the granzyme B signal. NK92 cells were incubated with concanamycin A (CMA), Brefeldin (BFA), or control (DMSO). The luminescence signal was measured on Veritas luminometer following a 60 min co-incubation at varying E/T ratios at 37° C. FIG. 33 shows the secretory granule/perforin dependence of the signal generated.

Example XIX

Figure 30:
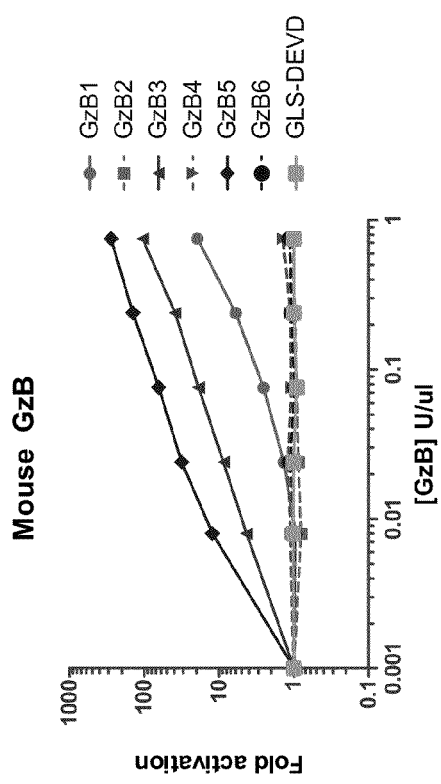
FIGS. 30A-B show that constructs with granzyme B cleavage sites have dose dependent increases in luminescence with increasing concentrations of granzyme B enzyme.
Figure 30:
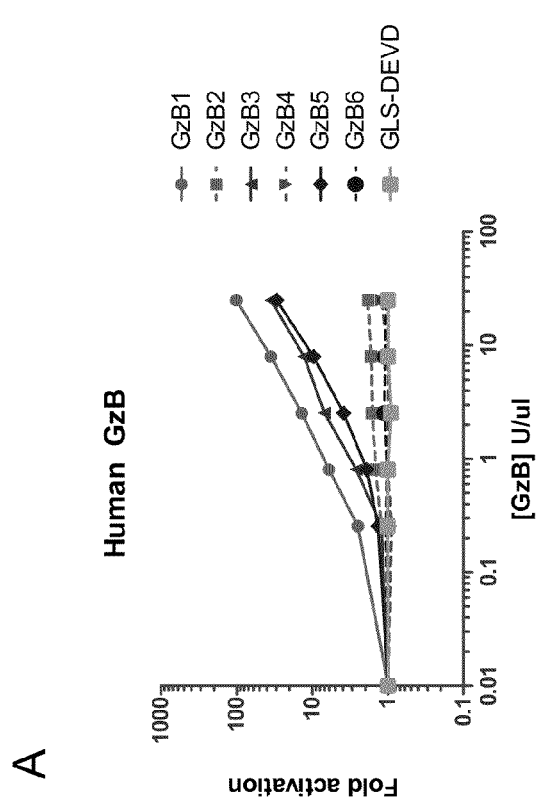

To confirm activation and specificity, biosensor constructs encoding GRIEADSE ("GzB1"), KSVGPDFG ("GzB5"), GIETDSG ("GzB3") or DEVDG ("GLS-DEVD") recognition and cleavage sites, together with non-cleavable control constructs encoding GRIEAASE ("GzB2"), KSVPPAFG ("GzB6"), GIETASG ("GzB4"), were expressed in vitro and treated with mouse or human granzyme B (see Table 12). Biosensor constructs were transcribed and translated in wheat germ extract (Promega cat #L4140) plus Fluorotect (Promega cat #L5001) following the manufacturer's recommended protocol for two hours at 30° C. Human granzyme B (Enzo BML-SE238) or mouse granzyme B (Sigma G9278) were serially diluted in assay buffer (100 mM HEPES, pH=7.4; 200 mM NaCl; 0.2% CHAPS; 2 mM EDTA; 20% glycerol, 1 mM DTT). Serially diluted enzymes were mixed 1:1 with cell-free expression extract, and samples were allowed to incubate at 37° C. for 1 hour. After 1 hour, 10 µL of reaction mixture was transferred in triplicate to a new plate, followed by injection of 100 µL of Luciferase Assay Reagent (Promega cat #E1500) and measurement of luminescence on a GloMax Multi Plus luminometer (Promega; 0.5 second integration time). FIGS. 30A and 30B show that constructs with granzyme B cleavage sites showed a dose dependent increase in luminescence with increasing concentrations of enzyme, but control constructs lacking the P1 aspartic acid residue or containing the caspase-3/7 cleavage site (DEVDG) showed no dose dependent increase in luminescence.

TABLE 12

| Vector Name | Biosensor Constructs |
| --- | --- |
| pGLSGZB1 | pF9aAg3-V3P-CP358/GRIEADSE |
| pGLSGZB2 | pF9aAg3-V3P-CP358/GRIEAASE [pGLSGZB1 control] |
| pGLSGZB3 | pF9aAg3-V3P-CP358/GIETDSG |

TABLE 12-continued

| Vector Name | Biosensor Constructs |
| --- | --- |
| pGLSGZB4 | pF9aAg3-V3P-CP358/GIETASG [pGLSGZB3 control] |
| pGLSGZB5 | pF9aAg3-V3P-CP358/KSVGPDFG |
| pGLSGZB6 | pF9aAg3-V3P-CP358/KSVGPDFG [pGLSGZB5 control] |

Example XX

Figure 31:
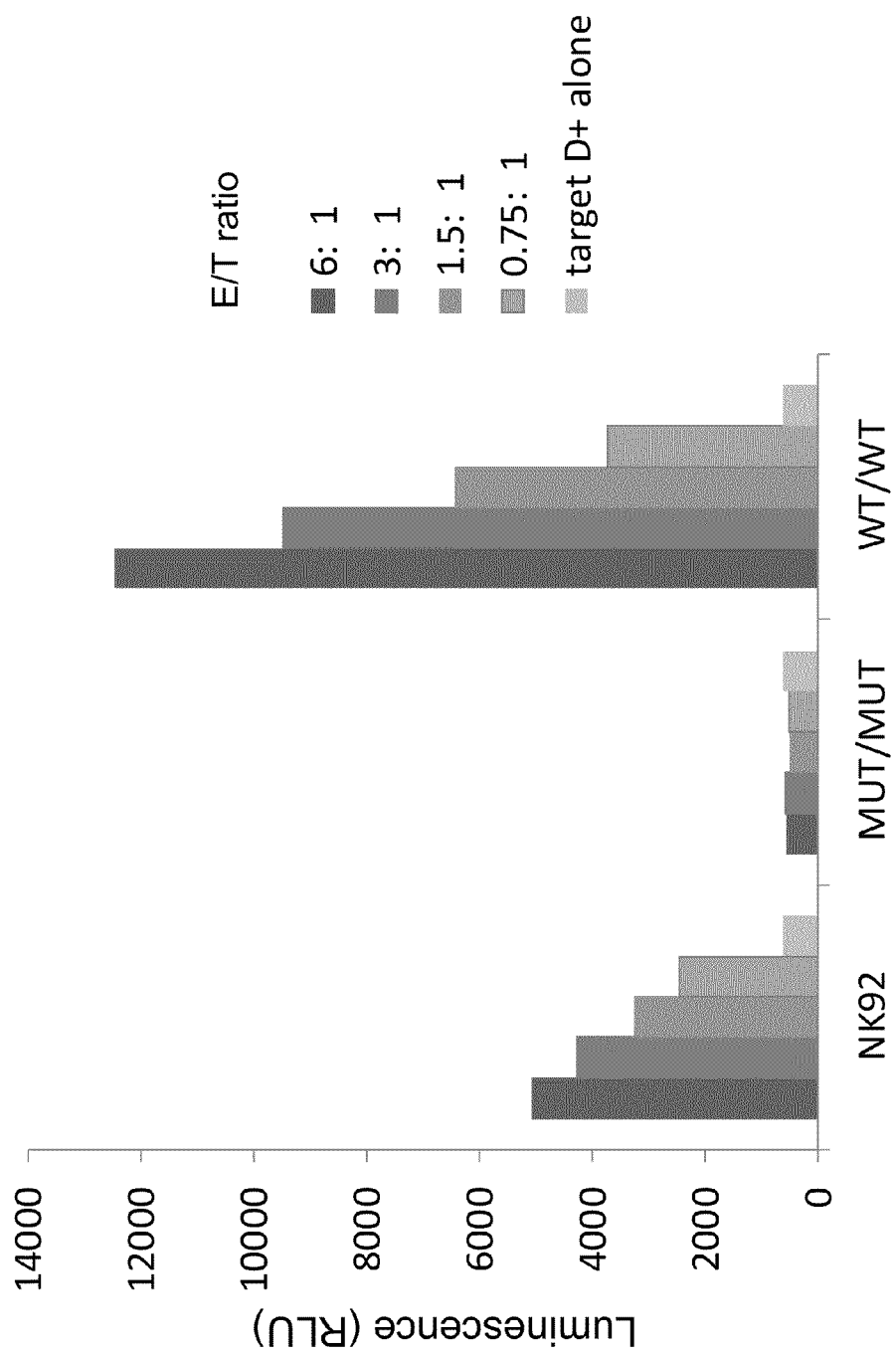
FIG. 31 shows granzyme B delivery induced luminescence in IL-2 activated NK cell lines from healthy control (WT/WT) and patient with biallelic perforin mutations (MUT/MUT).

Herpes Saimiri Virus (HSV)-transformed, IL-2 activated NK cells from a healthy control patient (WT/WT) and a patient with a biallelic perforin mutation (Mut/Mut) were co-incubated at various E/T ratios with K562 target cells containing the granzyme B biosensor B+, C+, C−, D+, and D−, and were selected with G418. Cells were harvested and resuspended in 2% luciferin substrate and aliquoted into wells of a 96-well bottom plate at 2×10$^5$, 1×10$^5$, and 5×10$^4$ cells per well, respectively. Plates were incubated at 37° C. for 30 min and cooled at room temperature for 10 min. Luminescence was read on a Veritas luminometer plate reader. FIG. 31 shows granzyme B delivery induced luminescence in IL-2 activated NK cell lines from healthy control (WT/WT) and patient with biallelic perforin mutations (MUT/MUT). FIG. 31 shows the perforin dependence of the luminescent signal generated.

Example XXI

Figure 34:
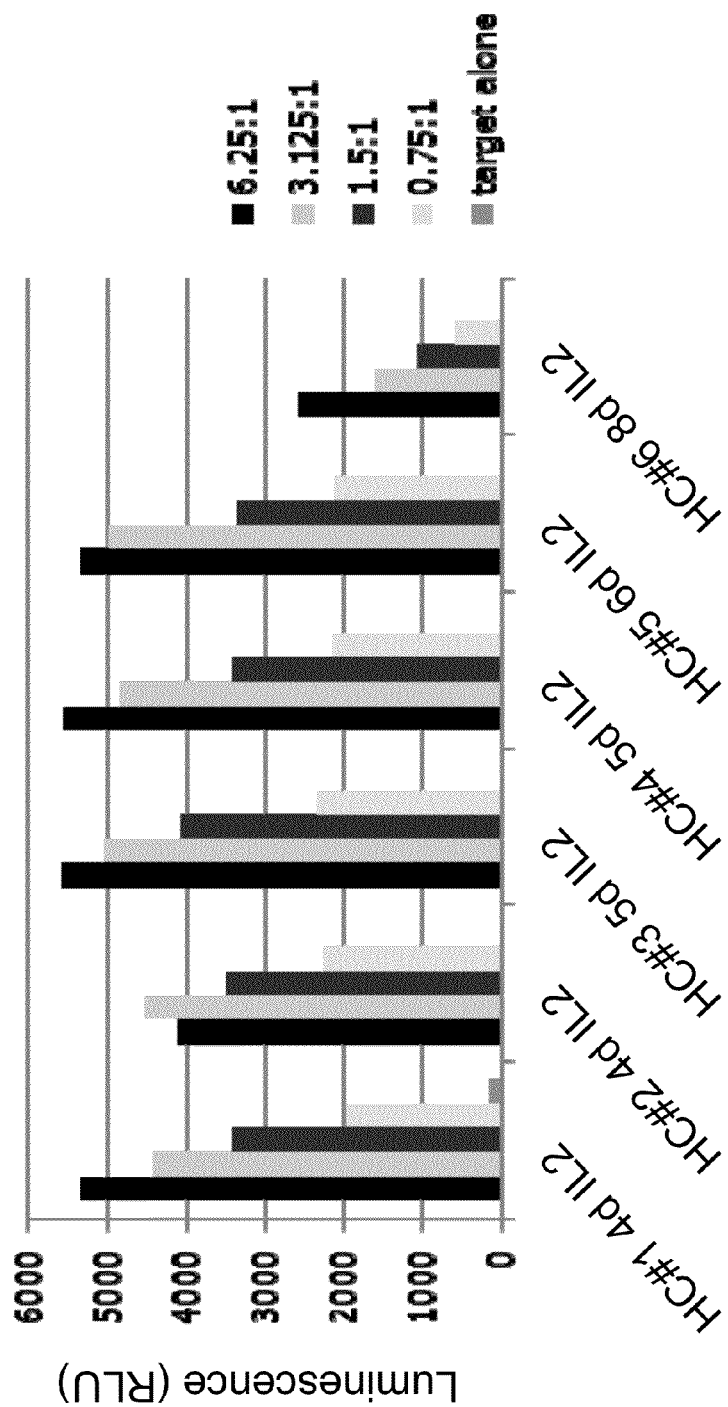
FIG. 34 shows NKs are able to activate luminescence from a Granzyme B biosensor after prolonged culture with IL-2.

PBMC cells from healthy donors (n=5) were cultured with high dose IL-2 (1000 U/mL) for 4-8 days. At 4, 5, 6, and 8 days, the cells were co-incubated at various E/T ratios with K562 target cells transfected with the granzyme B biosensor D+ for 60 min at 37° C. Luminescence was measured on a Veritas luminometer as described above. FIG. 34 shows that NK cells are able to activate luminescence from a granzyme B biosensor after prolonged exposure to IL-2.

Example XXII

Figure 35:
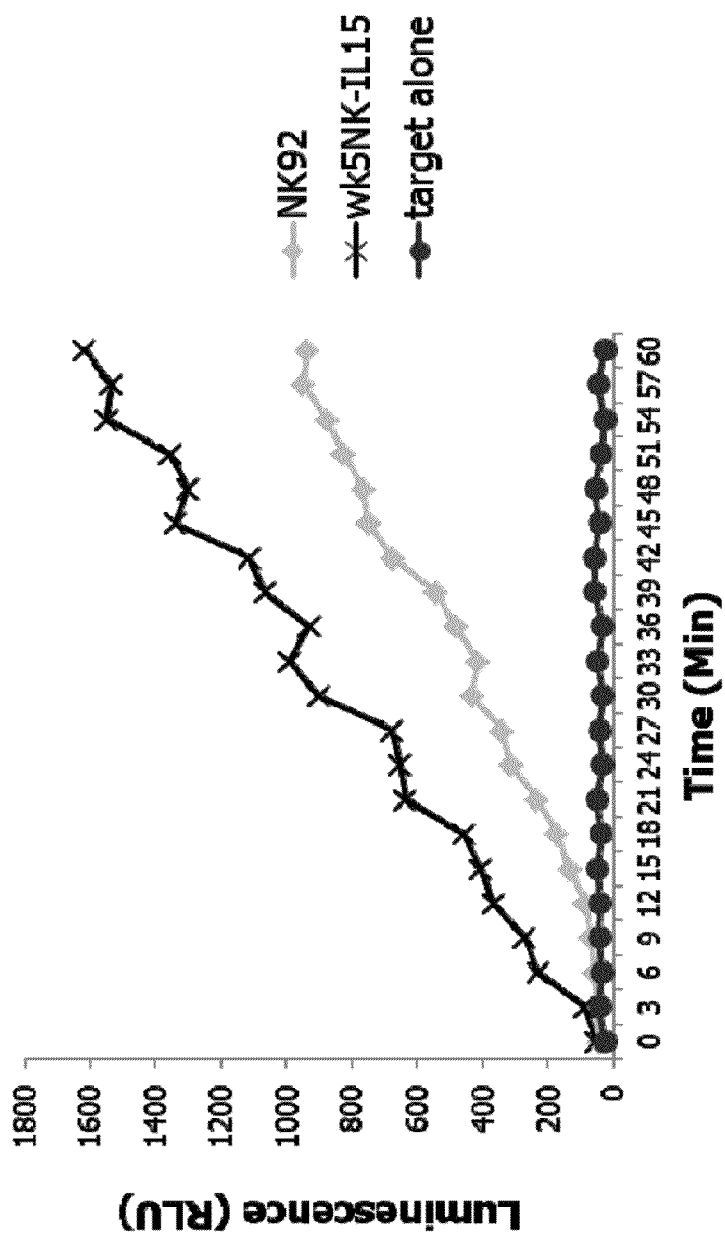
FIG. 35 shows umbilical cord derived, IL-15 stimulated cells are capable of releasing Granzyme B and activating luminescence from target cells containing a Granzyme B biosensor.

Human CD34 cells were isolated from umbilical cord blood (healthy donor) and cultured on stromal cells (MS5) in IL-15 and stem cell factor (SCF) for 5 weeks before testing cytotoxicity against K562 cells expressing granzyme B biosensor D+. Luminescence was measured as described above on a Biotek luminometer at 37° C. FIG. 35 shows that umbilical cord-derived, IL-15 stimulated cells are capable of releasing and delivering granzyme B to target cells containing a granzyme B biosensor and activating luminescence from the biosensor.

Example XXIII

Figure 32:
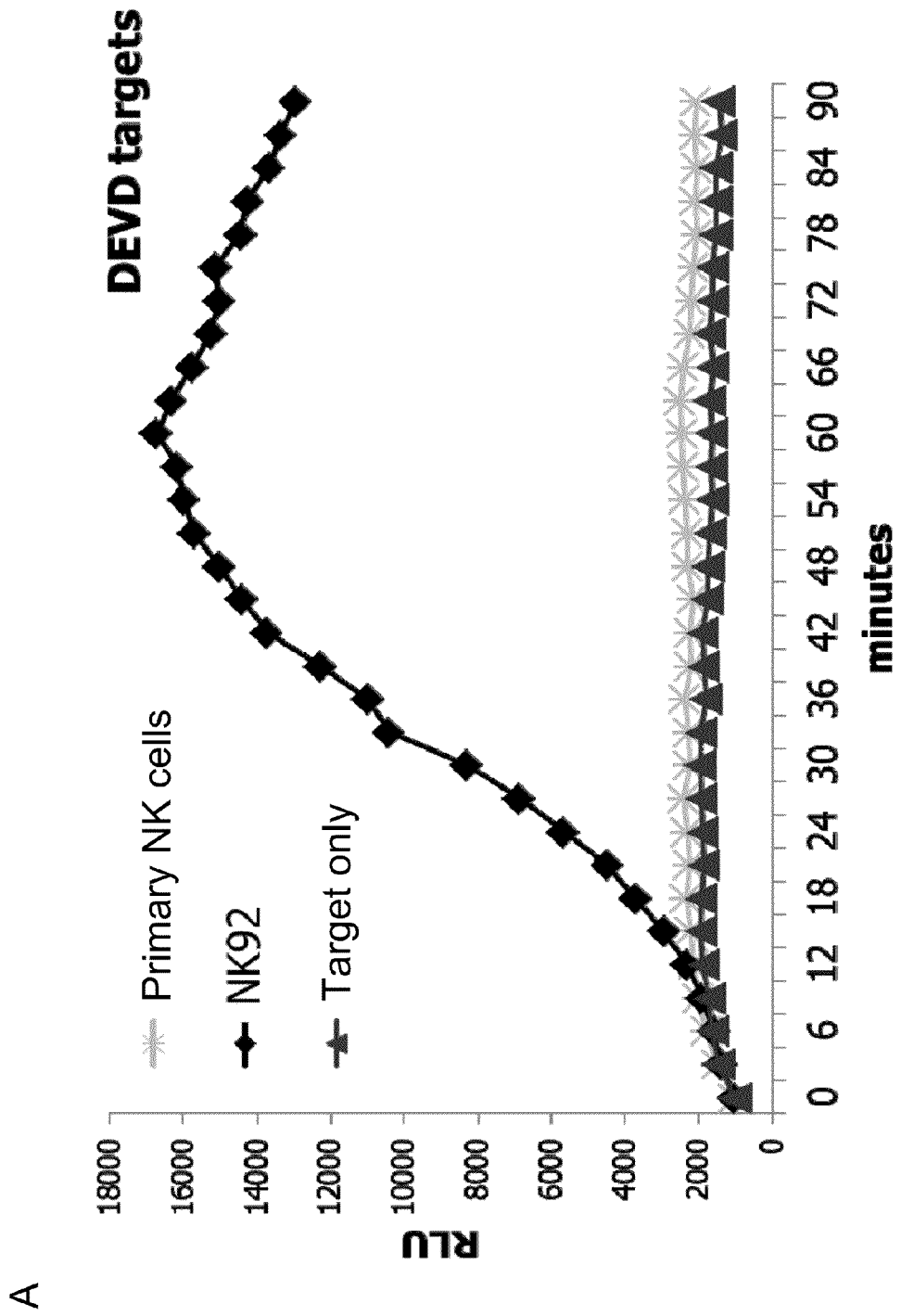
FIGS. 32A-B show the use of caspase 3/7 biosensor and the granzyme B biosensor with primary NK and NK92 cells
Figure 32:
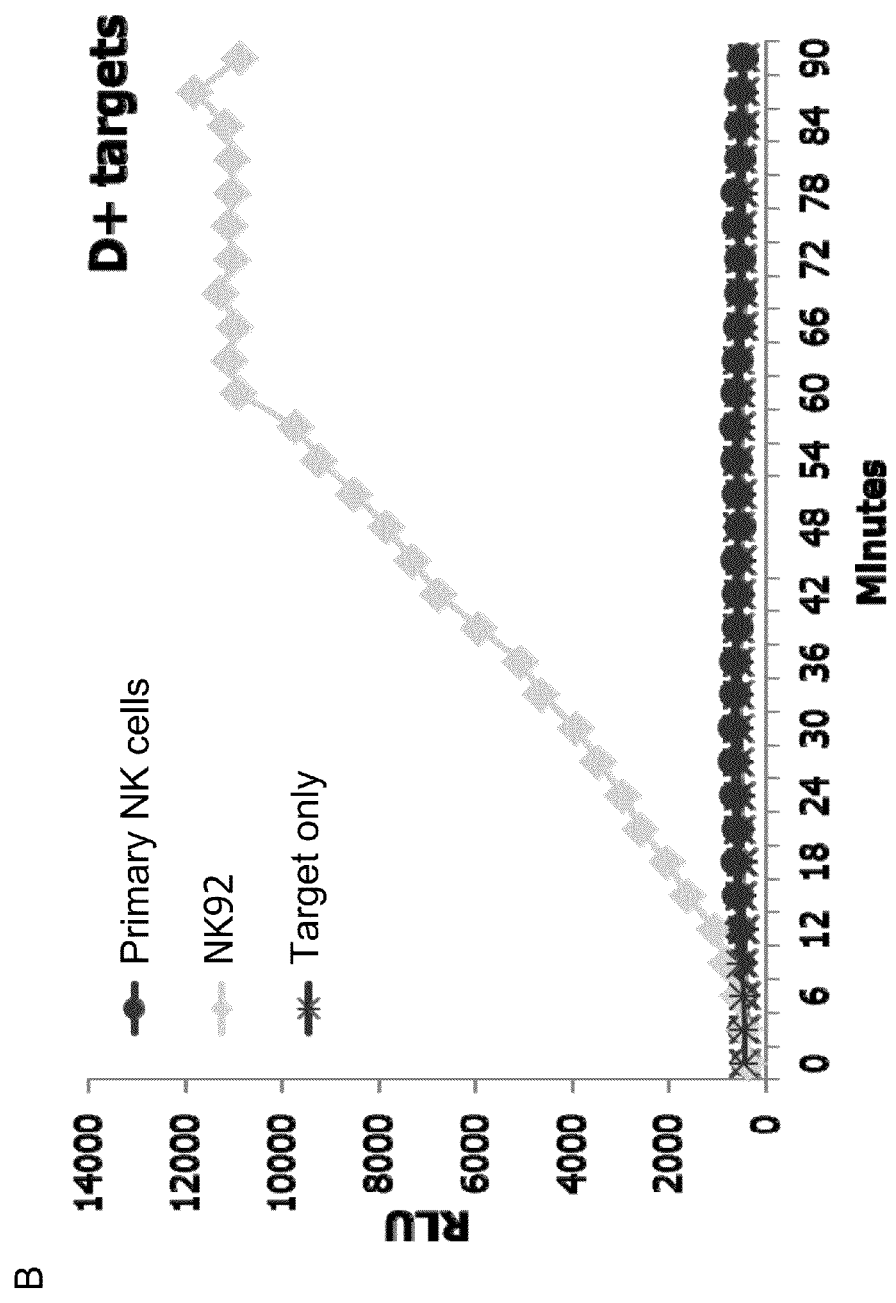
Figure 36:
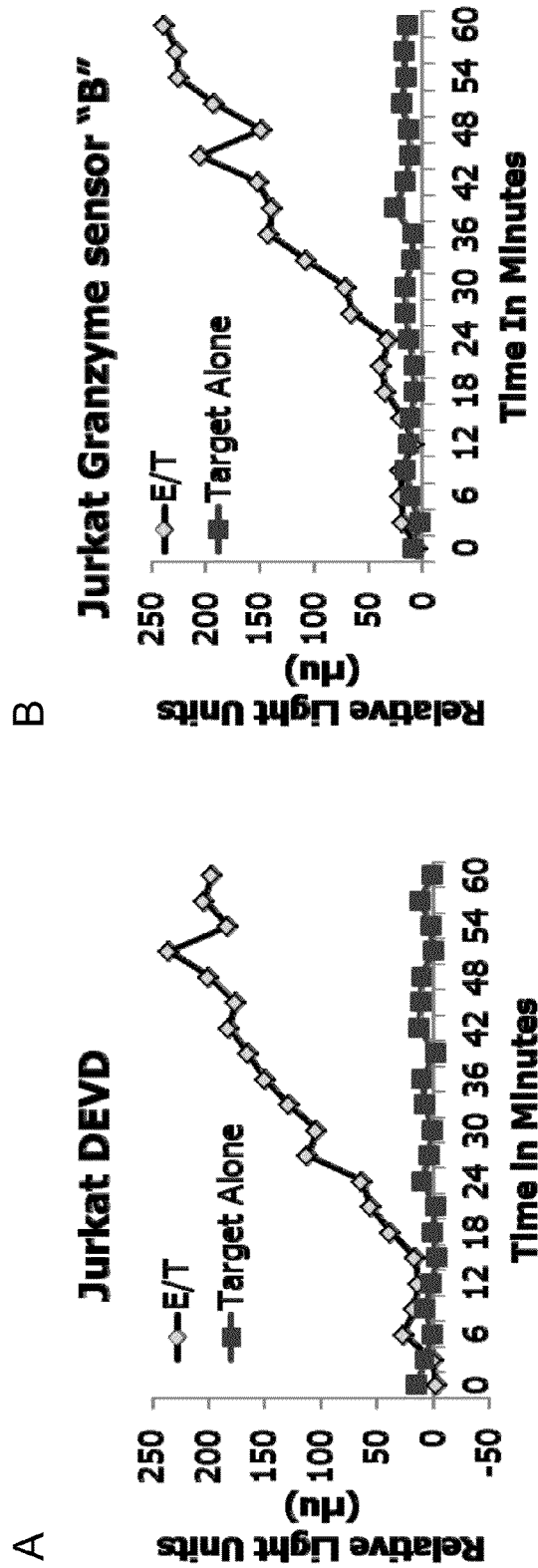
FIGS. 36A-B show the use of caspase 3/7 biosensor and the granzyme B biosensor in Jurkat target cells.

FIGS. 32A-B show the use of caspase 3/7 biosensor and the granzyme B biosensor with primary NK and NK92 cells. FIGS. 36A-B show the use of caspase 3/7 biosensor and the granzyme B biosensor in Jurkat target cells.

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

Thus, the invention provides, among other things, a modified circularly-permuted thermostable luciferase biosensor with enhanced response to a target molecule. Various features and advantages of the invention are set forth in the following claims.

What is claimed is:

1. A polynucleotide encoding a circularly-permuted thermostable luciferase comprising a peptide linker linking the original N- and C-termini of the non-permuted thermostable luciferase, wherein the peptide linker comprises a granzyme B recognition site, wherein the circularly-permuted thermostable luciferase has increased luminescence following cleavage by granzyme B when compared to an uncleaved circularly-permuted thermostable luciferase, wherein the granzyme B recognition site is selected from the group consisting of GRIEADSE (SEQ ID NO:80), KSVGPDFG (SEQ ID NO:81), and GIETDSG (SEQ ID NO:82), and wherein the non-permuted thermostable luciferase has at least 90% identity to the amino acid sequence of SEQ ID NO:2 or at least 90% identity to the amino acid sequence of SEQ ID NO:4.

2. The polynucleotide of claim 1, wherein the granzyme B recognition site is flanked by peptide linkers.

3. A vector comprising the polynucleotide of claim 1.

4. A cell comprising the vector of claim 3.

5. A kit comprising the polynucleotide of claim 1.

* * * * *

SEQUENCE LISTING

<160> NUMBER OF SEQ ID NOS: 85

<210> SEQ ID NO 1
<211> LENGTH: 1635
<212> TYPE: DNA
<213> ORGANISM: Photuris pennsylvanica

<400> SEQUENCE: 1

```
atggaagata aaatattttt atatggacct gaaccatttc atcccttggc tgatgggacg        60
gctggagaac agatgtttta cgcattatct cggtatgcag atatttcagg atgcattgca       120
ttgacaaatg ctcatacaaa agaaaatgtt ttatatgaag aattttttaaa attgtcgtgt      180 cgtttagcgg aaagttttaa aaagtatgga ttaaaacaaa acgacacaat agcggtgtgt       240
agtgaaaatg gtttgcaatt tttccttcct ttaattgcat cattgtatct tggaataatt      300
gcagcacctg ttagtgataa atacattgaa cgtgaattaa tacacagtct tggtattgta       360
aaaccacgca taatttttg ttccaagaat acttttcaaa agtactgaa tgtaaaatct        420 aaattaaaat atgtagaaac tattattata ttagacttaa atgaagactt aggaggttat      480
caatgcctca acaactttat ttctcaaaat tccgatatta atcttgacgt aaagaaattt       540
aaaccaaatt cttttaatcg agacgatcag gttgcgttgg taatgttttc ttctggtaca       600
actggtgttt ctaagggagt catgctaact cacaagaata ttgttgcacg atttctcat       660 tgcaaagatc ctacttttgg taacgcaatt aatccaacga cagcaatttt aacagtaata       720
ccattccacc atggttttgg tatgactacc acattaggat actttacttg tggattccga       780
gttgctctaa tgcacacgtt tgaagaaaaa ctattttac aatcattaca agattataaa         840
gtggaaagta ctttacttgt accaacatta atggcatttt ttccaaaaag tgcgttagtt       900
gaaaagtacg atttatcgca cttaaaagaa attgcatctg gtggcgcacc tttatcaaaa       960
gaaattgggg agatggtgaa aaaacggttt aaattaaact ttgtcaggca agggtatgga     1020
ttaacagaaa ccacttcggc tgtttttaatt acaccggaca ctgacgtcag accgggatca     1080
actggtaaaa tagtaccatt tcacgctgtt aaagttgtgg atcctacaac aggaaaaatt     1140
ttggggccaa atgaaactgg agaattgtat tttaaaggcg acatgataat gaaaagttat     1200
tataataatg aagaagctac taaagcaatt attaacaaag acggatggtt gcgctctggt     1260
gatattgctt attatgacaa tgatggccat ttttatattg tggacaggct gaagtcatta     1320
attaaatata aaggttatca ggttgcacct gctgaaattg agggaatact cttacaacac     1380
ccgtatattg ttgatgccgg cgttactggt ataccggatg aagccgcggg cgagcttcca     1440
gctgcaggtg ttgtagtaca gactggaaaa tatctaaacg aacaaatcgt acaaaatttt     1500
gtttccagtc aagtttcaac agccaaatgg ctacgtggtg gggtgaaatt tttggatgaa     1560
attcccaaag gatcaactgg aaaaattgac agaaaagtgt taagacaaat gtttgaaaaa     1620
cacaaatcta agctg                                                      1635
```

<210> SEQ ID NO 2
<211> LENGTH: 545
<212> TYPE: PRT
<213> ORGANISM: Photuris pennsylvanica

<400> SEQUENCE: 2

```
Met Glu Asp Lys Asn Ile Leu Tyr Gly Pro Glu Pro Phe His Pro Leu
  1               5                  10                  15

Ala Asp Gly Thr Ala Gly Glu Gln Met Phe Tyr Ala Leu Ser Arg Tyr
             20                  25                  30
```

```
Ala Asp Ile Ser Gly Cys Ile Ala Leu Thr Asn Ala His Thr Lys Glu
         35                  40                  45

Asn Val Leu Tyr Glu Glu Phe Leu Lys Leu Ser Cys Arg Leu Ala Glu
 50                      55                  60

Ser Phe Lys Lys Tyr Gly Leu Lys Gln Asn Asp Thr Ile Ala Val Cys
 65                  70                  75                  80

Ser Glu Asn Gly Leu Gln Phe Phe Leu Pro Leu Ile Ala Ser Leu Tyr
                 85                  90                  95

Leu Gly Ile Ile Ala Ala Pro Val Ser Asp Lys Tyr Ile Glu Arg Glu
                100                 105                 110

Leu Ile His Ser Leu Gly Ile Val Lys Pro Arg Ile Ile Phe Cys Ser
            115                 120                 125

Lys Asn Thr Phe Gln Lys Val Leu Asn Val Lys Ser Lys Leu Lys Tyr
        130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Asn Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser His Cys Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Thr Thr Thr Leu Gly Tyr Phe Thr
                245                 250                 255

Cys Gly Phe Arg Val Ala Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Phe Pro Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asp Thr Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Thr Gly Glu Leu Tyr Phe Lys Gly Asp Met Ile Met Lys Ser Tyr
385                 390                 395                 400

Tyr Asn Asn Glu Glu Ala Thr Lys Ala Ile Ile Asn Lys Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445
```

```
Ala Pro Ala Glu Ile Glu Gly Ile Leu Leu Gln His Pro Tyr Ile Val
    450                 455                 460
Asp Ala Gly Val Thr Gly Ile Pro Asp Glu Ala Ala Gly Glu Leu Pro
465                 470                 475                 480
Ala Ala Gly Val Val Gln Thr Gly Lys Tyr Leu Asn Glu Gln Ile
                485                 490                 495
Val Gln Asn Phe Val Ser Ser Gln Val Ser Thr Ala Lys Trp Leu Arg
            500                 505                 510
Gly Gly Val Lys Phe Leu Asp Glu Ile Pro Lys Gly Ser Thr Gly Lys
        515                 520                 525
Ile Asp Arg Lys Val Leu Arg Gln Met Phe Glu Lys His Lys Ser Lys
530                 535                 540
Leu
545

<210> SEQ ID NO 3
<211> LENGTH: 1632
<212> TYPE: DNA
<213> ORGANISM: Artificial
<220> FEATURE:
<223> OTHER INFORMATION: Synthetic

<400> SEQUENCE: 3
atggcagata taagaatatttt atatgggccc gaaccatttt atcccttgga agatgggacg      60
gctggagaac agatgtttga cgcattatct cgttatgcag ctattccggg ctgcatagca     120
ttgacaaatg ctcatacaaa agaaaatgtt ttatatgaag agtttctgaa actgtcgtgt     180
cgtttagcgg aaagttttaa aaagtatgga ttaaaacaaa acgacacaat agcggtgtgt     240
agcgaaaata gtctgcaatt tttccttcct gtaattgcat cattgtatct tggaataatt     300
gtggcacctg ttaacgataa atacattgaa cgtgaattaa tacacagtct tggtattgta     360
aaaccacgca tagttttttg ctccaagaat acttttcaaa aagtactgaa tgtaaaatct     420
aaattaaaat ctattgaaac tattattata ttagacttaa atgaagactt aggaggttat     480
caatgcctca acaactttat ttctcaaaat tccgatagta atctggacgt aaaaaaattt     540
aaaccctatt cttttaatcg agacgatcag gttgcgtcga ttatgttttc ttctggtaca     600
actggtctgc cgaagggagt catgctaact cacaagaata ttgttgcacg attttctatt     660
gcaaaagatc ctactttgg taacgcaatt aatcccacgt cagcaatttt aacggtaata     720
cctttccacc atggttttgg tatgatgacc acattaggat actttacttg tggattccga     780
gttgttctaa tgcacacgtt tgaagaaaaa ctatttctac aatcattaca agattataaa     840
gtggaaagta ctttacttgt accaacatta atggcatttc ttgcaaaaag tgcattagtt     900
gaaaagtacg atttatcgca cttaaaagaa attgcatctg tggcgcaccc tttatcaaaa     960
gaaattgggg agatggtgaa aaaacggttt aaattaaact tgtcaggca agggtatgga    1020 ttaacagaaa ccacttcggc tgtttttaatt acaccgaaag gtgacgccaa accgggatca    1080
actggtaaaa tagtaccatt acacgctgtt aaagttgtcg atcctacaac aggaaaaatt    1140
ttggggccaa atgaacctgg agaattgtat tttaaaggcc cgatgataat gaagggttat    1200
tataataatg aagaagctac taaagcaatt attgataatg acggatggtt gcgctctggt    1260
gatattgctt attatgacaa tgatggccat ttttatattg tggacaggct gaagtcactg    1320
attaaatata aaggttatca ggttgcacct gctgaaattg agggaatact cttacaacat    1380
ccgtatattg ttgatgccgg cgttactggt ataccggatg aagccgcggg cgagcttcca    1440
```

-continued

```
gctgcaggtg ttgtagtaca gactggaaaa tatctaaacg aacaaatcgt acaagattat    1500
gttgccagtc aagtttcaac agccaaatgg ctacgtggtg gggtgaaatt tttggatgaa    1560
attcccaaag gatcaactgg aaaaattgac agaaaagtgt taagacaaat gttagaaaaa    1620
cacaccaatg gg                                                        1632
```

```
<210> SEQ ID NO 4
<211> LENGTH: 544
<212> TYPE: PRT
<213> ORGANISM: Artificial
<220> FEATURE:
<223> OTHER INFORMATION: Synthetic

<400> SEQUENCE: 4

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30

Ala Ala Ile Pro Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
    210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
```

|  |  |  | 325 |  |  |  | 330 |  |  |  | 335 |  |
|--|--|--|--|--|--|--|--|--|--|--|--|--|

Gln Gly Tyr Gly Leu Thr Glu Thr Thr Ser Ala Val Leu Ile Thr Pro
         340            345            350

Lys Gly Asp Ala Lys Pro Gly Ser Thr Gly Lys Ile Val Pro Leu His
         355            360            365

Ala Val Lys Val Val Asp Pro Thr Thr Gly Lys Ile Leu Gly Pro Asn
         370            375            380

Glu Pro Gly Glu Leu Tyr Phe Lys Gly Pro Met Ile Met Lys Gly Tyr
385              390           395            400

Tyr Asn Asn Glu Glu Ala Thr Lys Ala Ile Ile Asp Asn Asp Gly Trp
         405            410            415

Leu Arg Ser Gly Asp Ile Ala Tyr Tyr Asp Asn Asp Gly His Phe Tyr
         420            425            430

Ile Val Asp Arg Leu Lys Ser Leu Ile Lys Tyr Lys Gly Tyr Gln Val
         435            440            445

Ala Pro Ala Glu Ile Glu Gly Ile Leu Leu Gln His Pro Tyr Ile Val
         450            455            460

Asp Ala Gly Val Thr Gly Ile Pro Asp Glu Ala Ala Gly Glu Leu Pro
465              470           475            480

Ala Ala Gly Val Val Gln Thr Gly Lys Tyr Leu Asn Glu Gln Ile
             485            490            495

Val Gln Asp Tyr Val Ala Ser Gln Val Ser Thr Ala Lys Trp Leu Arg
         500            505            510

Gly Gly Val Lys Phe Leu Asp Glu Ile Pro Lys Gly Ser Thr Gly Lys
         515            520            525

Ile Asp Arg Lys Val Leu Arg Gln Met Leu Glu Lys His Thr Asn Gly
         530            535            540

<210> SEQ ID NO 5
<211> LENGTH: 1644
<212> TYPE: DNA
<213> ORGANISM: Artificial
<220> FEATURE:
<223> OTHER INFORMATION: Synthetic

<400> SEQUENCE: 5

| | |
|---|---:|
| atgccgggat caactggtaa atagtacca ttacacgctg ttaaagttgt cgatcctaca | 60 |
| acaggaaaaa ttttggggcc aaatgaacct ggagaattgt attttaaagg cccgatgata | 120 |
| atgaagggtt attataataa tgaagaagct actaaagcaa ttattgataa tgacggatgg | 180 |
| ttgcgctctg gtgatattgc ttattatgac aatgatggcc attttatat tgtggacagg | 240 |
| ctgaagtcac tgattaaata taaggttat caggttgcac ctgctgaaat tgagggaata | 300 |
| ctcttacaac atccgtatat tgttgatgcc ggcgttactg gtataccgga tgaagccgcg | 360 |
| ggcgagcttc cagctgcagg tgttgtagta cagactggaa atatctaaa cgaacaaatc | 420 |
| gtacaagatt atgttgccag tcaagtttca cagccaaat ggctacgtgg tggggtgaaa | 480 |
| tttttggatg aaattcccaa aggatcaact ggaaaaattg acagaaaagt gttaagacaa | 540 |
| atgttagaaa acacaccaa tggatccgac gaggtggacg gaagcttgaa aaacatcctg | 600 |
| tatggtccgg aaccgttcta cccactggaa atggtaccg ctggtgaaca gatgtttgac | 660 |
| gcattatctc gttatgcagc tattccgggc tgcatagcat tgacaaatgc tcatacaaaa | 720 |
| gaaaatgttt tatatgaaga gtttctgaaa ctgtcgtgtc gttagcgga aagttttaaa | 780 |
| aagtatggat taaacaaaaa cgacacaata gcggtgtgta gcgaaaatag tctgcaattt | 840 |

```
ttccttcctg taattgcatc attgtatctt ggaataattg tggcacctgt taacgataaa    900
tacattgaac gtgaattaat acacagtctt ggtattgtaa aaccacgcat agttttttgc    960
tccaagaata cttttcaaaa agtactgaat gtaaaatcta aattaaaatc tattgaaact   1020
attattatat tagacttaaa tgaagactta ggaggttatc aatgcctcaa caactttatt   1080
tctcaaaatt ccgatagtaa tctggacgta aaaaaattta aaccctattc ttttaatcga   1140
gacgatcagg ttgcgtcgat tatgttttct tctggtacaa ctggtctgcc gaagggagtc   1200
atgctaactc acaagaatat tgttgcacga ttttctattg caaaagatcc tacttttggt   1260
aacgcaatta atcccacgtc agcaatttta acggtaatac ctttccacca tggttttggt   1320
atgatgacca cattaggata ctttacttgt ggattccgag ttgttctaat gcacacgttt   1380
gaagaaaaac tatttctaca atcattacaa gattataaag tggaaagtac tttacttgta   1440
ccaacattaa tggcatttct tgcaaaaagt gcattagttg aaaagtacga tttatcgcac   1500
ttaaaagaaa ttgcatctgg tggcgcacct ttatcaaaag aaattgggga gatggtgaaa   1560
aaacggttta aattaaactt tgtcaggcaa gggtatggat aacagaaaac cacttcggct   1620
gttttaatta caccgaaagg tgtt                                         1644
```

<210> SEQ ID NO 6
<211> LENGTH: 548
<212> TYPE: PRT
<213> ORGANISM: Artificial
<220> FEATURE:
<223> OTHER INFORMATION: Synthetic

<400> SEQUENCE: 6

```
Met Pro Gly Ser Thr Gly Lys Ile Val Pro Leu His Ala Val Lys Val
1               5                   10                  15
Val Asp Pro Thr Thr Gly Lys Ile Leu Gly Pro Asn Glu Pro Gly Glu
            20                  25                  30
Leu Tyr Phe Lys Gly Pro Met Ile Met Lys Gly Tyr Tyr Asn Asn Glu
        35                  40                  45
Glu Ala Thr Lys Ala Ile Ile Asp Asn Asp Gly Trp Leu Arg Ser Gly
    50                  55                  60
Asp Ile Ala Tyr Tyr Asp Asn Asp Gly His Phe Tyr Ile Val Asp Arg
65                  70                  75                  80
Leu Lys Ser Leu Ile Lys Tyr Lys Gly Tyr Gln Val Ala Pro Ala Glu
                85                  90                  95
Ile Glu Gly Ile Leu Leu Gln His Pro Tyr Ile Val Asp Ala Gly Val
            100                 105                 110
Thr Gly Ile Pro Asp Glu Ala Ala Gly Glu Leu Pro Ala Ala Gly Val
        115                 120                 125
Val Val Gln Thr Gly Lys Tyr Leu Asn Glu Gln Ile Val Gln Asp Tyr
    130                 135                 140
Val Ala Ser Gln Val Ser Thr Ala Lys Trp Leu Arg Gly Gly Val Lys
145                 150                 155                 160
Phe Leu Asp Glu Ile Pro Lys Gly Ser Thr Gly Lys Ile Asp Arg Lys
                165                 170                 175
Val Leu Arg Gln Met Leu Glu Lys His Thr Asn Gly Ser Asp Glu Val
            180                 185                 190
Asp Gly Ser Leu Lys Asn Ile Leu Tyr Gly Pro Glu Pro Phe Tyr Pro
        195                 200                 205
Leu Glu Asp Gly Thr Ala Gly Glu Gln Met Phe Asp Ala Leu Ser Arg
    210                 215                 220
```

| Tyr | Ala | Ala | Ile | Pro | Gly | Cys | Ile | Ala | Leu | Thr | Asn | Ala | His | Thr | Lys |
| 225 | | | | 230 | | | | | 235 | | | | | 240 | |

| Glu | Asn | Val | Leu | Tyr | Glu | Glu | Phe | Leu | Lys | Leu | Ser | Cys | Arg | Leu | Ala |
| | | | | 245 | | | | | 250 | | | | | 255 | |

| Glu | Ser | Phe | Lys | Lys | Tyr | Gly | Leu | Lys | Gln | Asn | Asp | Thr | Ile | Ala | Val |
| | | | 260 | | | | | 265 | | | | | 270 | | |

| Cys | Ser | Glu | Asn | Ser | Leu | Gln | Phe | Phe | Leu | Pro | Val | Ile | Ala | Ser | Leu |
| | | | 275 | | | | | 280 | | | | | 285 | | |

| Tyr | Leu | Gly | Ile | Ile | Val | Ala | Pro | Val | Asn | Asp | Lys | Tyr | Ile | Glu | Arg |
| | 290 | | | | | 295 | | | | | 300 | | | | |

| Glu | Leu | Ile | His | Ser | Leu | Gly | Ile | Val | Lys | Pro | Arg | Ile | Val | Phe | Cys |
| 305 | | | | | 310 | | | | | 315 | | | | | 320 |

| Ser | Lys | Asn | Thr | Phe | Gln | Lys | Val | Leu | Asn | Val | Lys | Ser | Lys | Leu | Lys |
| | | | | 325 | | | | | 330 | | | | | 335 | |

| Ser | Ile | Glu | Thr | Ile | Ile | Ile | Leu | Asp | Leu | Asn | Glu | Asp | Leu | Gly | Gly |
| | | | 340 | | | | | 345 | | | | | 350 | | |

| Tyr | Gln | Cys | Leu | Asn | Asn | Phe | Ile | Ser | Gln | Asn | Ser | Asp | Ser | Asn | Leu |
| | | 355 | | | | | 360 | | | | | 365 | | | |

| Asp | Val | Lys | Lys | Phe | Lys | Pro | Tyr | Ser | Phe | Asn | Arg | Asp | Asp | Gln | Val |
| | 370 | | | | | 375 | | | | | 380 | | | | |

| Ala | Ser | Ile | Met | Phe | Ser | Ser | Gly | Thr | Thr | Gly | Leu | Pro | Lys | Gly | Val |
| 385 | | | | | 390 | | | | | 395 | | | | | 400 |

| Met | Leu | Thr | His | Lys | Asn | Ile | Val | Ala | Arg | Phe | Ser | Ile | Ala | Lys | Asp |
| | | | | 405 | | | | | 410 | | | | | 415 | |

| Pro | Thr | Phe | Gly | Asn | Ala | Ile | Asn | Pro | Thr | Ser | Ala | Ile | Leu | Thr | Val |
| | | | 420 | | | | | 425 | | | | | 430 | | |

| Ile | Pro | Phe | His | His | Gly | Phe | Gly | Met | Met | Thr | Thr | Leu | Gly | Tyr | Phe |
| | | 435 | | | | | 440 | | | | | 445 | | | |

| Thr | Cys | Gly | Phe | Arg | Val | Val | Leu | Met | His | Thr | Phe | Glu | Glu | Lys | Leu |
| | 450 | | | | | 455 | | | | | 460 | | | | |

| Phe | Leu | Gln | Ser | Leu | Gln | Asp | Tyr | Lys | Val | Glu | Ser | Thr | Leu | Leu | Val |
| 465 | | | | | 470 | | | | | 475 | | | | | 480 |

| Pro | Thr | Leu | Met | Ala | Phe | Leu | Ala | Lys | Ser | Ala | Leu | Val | Glu | Lys | Tyr |
| | | | | 485 | | | | | 490 | | | | | 495 | |

| Asp | Leu | Ser | His | Leu | Lys | Glu | Ile | Ala | Ser | Gly | Gly | Ala | Pro | Leu | Ser |
| | | | 500 | | | | | 505 | | | | | 510 | | |

| Lys | Glu | Ile | Gly | Glu | Met | Val | Lys | Lys | Arg | Phe | Lys | Leu | Asn | Phe | Val |
| | | | 515 | | | | | 520 | | | | | 525 | | |

| Arg | Gln | Gly | Tyr | Gly | Leu | Thr | Glu | Thr | Thr | Ser | Ala | Val | Leu | Ile | Thr |
| | 530 | | | | | 535 | | | | | 540 | | | | |

| Pro | Lys | Gly | Val |
| 545 | | | |

<210> SEQ ID NO 7
<211> LENGTH: 1644
<212> TYPE: DNA
<213> ORGANISM: Artificial
<220> FEATURE:
<223> OTHER INFORMATION: Synthetic

<400> SEQUENCE: 7

```
atgccgggat caactggtaa aatagtacca ttcacgctg ttaaagttgt cgatcctaca        60
acaggaaaaa ttttgggcc aaatgaacct ggagaattgt attttaaagg cccgatgata       120 atgaaggtt attataataa tgaagaagct actaaagcaa ttattgataa tgacggatgg       180
```

```
ttgcgctctg gtgatattgc ttattatgac aatgatggcc atttttatat tgtggacagg      240
ctgaagtcac tgattaaata taaaggttat caggttgcac ctgctgaaat tgagggaata      300
ctcttacaac atccgtatat tgttgatgcc ggcgttactg gtataccgga tgaagccgcg      360
ggcgagcttc cagctgcagg tgttgtagta cagactggaa atatctaaa cgaacaaatc      420 gtacaagatt atgttgccag tcaagtttca atagccaaat ggctacgtgg tggggtgaaa      480
tttttggatg aaattcccaa aggatcaact ggaaaaattg acagaaaagt gttaagacaa      540
atgttagaaa acacaccaa tggatccgac gaggtggacg gaagcttgaa aaacatcctg      600
tatggtccgg aaccgttcta cccactgaa gatggtaccg ctggtgaaca gatgtttgac      660
gcattatctc gttatgcagc tattccgggc tgcatagcat tgacaaatgc tcatacaaaa      720
gaaaatgttt tatatgaaga gtttctgaaa ctgtcgtgtc gtttagcgga aagttttaaa      780
aagtatggat taaacaaaa cgacacaata gcggtgtgta gcgaaaatag tctgcaattt      840
ttccttcctg taattgcatc attgtatctt ggaataattg tggcacctgt aacgataaa      900 tacattgaac gtgaattaat acacagtctt ggtattgtaa aaccacgcat agttttttgc      960
tccaagaata cttttcaaaa agtactgaat gtaaaatcta aattaaaatc tattgaaact     1020
attattatat tagacttaaa tgaagactta ggaggttatc aatgcctcaa caactttatt     1080
tctcaaaatt ccgatagtaa tctggacgta aaaaaattta accctattc ttttaatcga     1140 gacgatcagg ttgcgtcgat tatgtttct tctggtacaa ctggtctgcc gaagggagtc     1200
atgctaactc acaagaatat tgttgcacga ttttctattg caaagatcc tacttttggt     1260 aacgcaatta atcccacgtc agcaatttta acggtaatac ctttccacca tggttttggt     1320
atgatgacca cattaggata ctttacttgt ggattccgag ttgttctaat gcacacgttt     1380
gaagaaaaac tatttctaca atcattacaa gattataaag tggaaagtac tttacttgta     1440
ccaacattaa tggcatttct tgcaaaaagt gcattagttg aaaagtacga tttatcgcac     1500
ttaaaagaaa ttgcatctgg tggcgcacct ttatcaaaag aaattgggga gatggtgaaa     1560
aaacggttta aattaaactt tgtcaggcaa gggtatggat taacagaaac cacttcggct     1620
gttttaatta caccgaaagg tgtt                                            1644
```

<210> SEQ ID NO 8
<211> LENGTH: 548
<212> TYPE: PRT
<213> ORGANISM: Artificial
<220> FEATURE:
<223> OTHER INFORMATION: Synthetic

<400> SEQUENCE: 8

```
Met Pro Gly Ser Thr Gly Lys Ile Val Pro Leu His Ala Val Lys Val
1               5                   10                  15

Val Asp Pro Thr Thr Gly Lys Ile Leu Gly Pro Asn Glu Pro Gly Glu
            20                  25                  30

Leu Tyr Phe Lys Gly Pro Met Ile Met Lys Gly Tyr Tyr Asn Asn Glu
        35                  40                  45

Glu Ala Thr Lys Ala Ile Ile Asp Asn Asp Gly Trp Leu Arg Ser Gly
    50                  55                  60

Asp Ile Ala Tyr Tyr Asp Asn Asp Gly His Phe Tyr Ile Val Asp Arg
65                  70                  75                  80

Leu Lys Ser Leu Ile Lys Tyr Lys Gly Tyr Gln Val Ala Pro Ala Glu
                85                  90                  95
```

```
Ile Glu Gly Ile Leu Leu Gln His Pro Tyr Ile Val Asp Ala Gly Val
            100                 105                 110

Thr Gly Ile Pro Asp Glu Ala Ala Gly Glu Leu Pro Ala Ala Gly Val
            115                 120                 125

Val Val Gln Thr Gly Lys Tyr Leu Asn Glu Gln Ile Val Gln Asp Tyr
130                 135                 140

Val Ala Ser Gln Val Ser Ile Ala Lys Trp Leu Arg Gly Gly Val Lys
145                 150                 155                 160

Phe Leu Asp Glu Ile Pro Lys Gly Ser Thr Gly Lys Ile Asp Arg Lys
                165                 170                 175

Val Leu Arg Gln Met Leu Glu Lys His Thr Asn Gly Ser Asp Glu Val
            180                 185                 190

Asp Gly Ser Leu Lys Asn Ile Leu Tyr Gly Pro Glu Pro Phe Tyr Pro
        195                 200                 205

Leu Glu Asp Gly Thr Ala Gly Glu Gln Met Phe Asp Ala Leu Ser Arg
    210                 215                 220

Tyr Ala Ala Ile Pro Gly Cys Ile Ala Leu Thr Asn Ala His Thr Lys
225                 230                 235                 240

Glu Asn Val Leu Tyr Glu Glu Phe Leu Lys Leu Ser Cys Arg Leu Ala
                245                 250                 255

Glu Ser Phe Lys Lys Tyr Gly Leu Lys Gln Asn Asp Thr Ile Ala Val
            260                 265                 270

Cys Ser Glu Asn Ser Leu Gln Phe Phe Leu Pro Val Ile Ala Ser Leu
        275                 280                 285

Tyr Leu Gly Ile Ile Val Ala Pro Val Asn Asp Lys Tyr Ile Glu Arg
    290                 295                 300

Glu Leu Ile His Ser Leu Gly Ile Val Lys Pro Arg Ile Val Phe Cys
305                 310                 315                 320

Ser Lys Asn Thr Phe Gln Lys Val Leu Asn Val Lys Ser Lys Leu Lys
                325                 330                 335

Ser Ile Glu Thr Ile Ile Ile Leu Asp Leu Asn Glu Asp Leu Gly Gly
            340                 345                 350

Tyr Gln Cys Leu Asn Asn Phe Ile Ser Gln Asn Ser Asp Ser Asn Leu
        355                 360                 365

Asp Val Lys Lys Phe Lys Pro Tyr Ser Phe Asn Arg Asp Asp Gln Val
    370                 375                 380

Ala Ser Ile Met Phe Ser Ser Gly Thr Thr Gly Leu Pro Lys Gly Val
385                 390                 395                 400

Met Leu Thr His Lys Asn Ile Val Ala Arg Phe Ser Ile Ala Lys Asp
                405                 410                 415

Pro Thr Phe Gly Asn Ala Ile Asn Pro Thr Ser Ala Ile Leu Thr Val
            420                 425                 430

Ile Pro Phe His His Gly Phe Gly Met Met Thr Thr Leu Gly Tyr Phe
        435                 440                 445

Thr Cys Gly Phe Arg Val Val Leu Met His Thr Phe Glu Glu Lys Leu
    450                 455                 460

Phe Leu Gln Ser Leu Gln Asp Tyr Lys Val Glu Ser Thr Leu Leu Val
465                 470                 475                 480

Pro Thr Leu Met Ala Phe Leu Ala Lys Ser Ala Leu Val Glu Lys Tyr
                485                 490                 495

Asp Leu Ser His Leu Lys Glu Ile Ala Ser Gly Gly Ala Pro Leu Ser
            500                 505                 510

Lys Glu Ile Gly Glu Met Val Lys Lys Arg Phe Lys Leu Asn Phe Val
```

515                 520                 525
Arg Gln Gly Tyr Gly Leu Thr Glu Thr Thr Ser Ala Val Leu Ile Thr
    530                 535                 540

Pro Lys Gly Val
545

<210> SEQ ID NO 9
<211> LENGTH: 1644
<212> TYPE: DNA
<213> ORGANISM: Artificial
<220> FEATURE:
<223> OTHER INFORMATION: Synthetic

<400> SEQUENCE: 9

```
atgccgggat caactggtaa aatagtacca ttacacgctg ttaaagttgt cgatcctaca      60
acaggaaaaa ttttggggcc aaatgaacct ggagaattgt attttaaagg cccgatgata     120
atgaagggtt attataataa tgaagaagct actaaagcaa ttattgataa tgacggatgg     180
ttgcgctctg gtgatattgc ttattatgac aatgatggcc attttttatat tgtggacagg    240
ctgaagtcac tgattaaata taaaggttat caggttgcac tgctgaaaat tgagggaata    300
ctcttacaac atccgtatat tgttgatgcc ggcgttactg gtacaccgga tgaagccgcg    360
ggcgagcttc cagctgcagg tgttgtagta cagactggaa aatatctaaa cgaacaaatc    420
gtacaagatt atgttgccgg tcaagtttca atagccaaat ggctacgtgg tggggtgaaa    480
tttttggatg aaattcccaa aggatcaact ggaaaaattg acagaaaagt gttaagacaa    540
atgttagaaa acacaccaa tggatccgac gaggtggacg gaagcttgaa aaacatcctg      600
tatggtccgg aaccgttcta cccactggaa gatggtaccg ctggtgaaca gatgtttgac    660
gcattatctc gttatgcagc tattccgggc tgcatagcat tgacaaatgc tcatacaaaa    720
gaaaatgttt tatatgaaga gtttctgaaa ctgtcgtgtc gtttagcgga agttttaaa    780
aagtatggat taaacaaaa cgacacaata gcggtgtgta gcgaaaatag tctgcaattt    840
ttccttcctg taattgcatc attgtatctt ggaataattg tggcacctgt taacgataaa    900
tacattgaac gtgaattaat acacagtctt ggtattgtaa aaccacgcat agttttttgc    960
tccaagaata cttttcaaaa agtactgaat gtaaaatcta attaaaatc tattgaaact    1020
attattatat tagacttaaa tgaagactta ggaggttatc aatgcctcaa caactttatt    1080
tctcaaaatt ccgatagtaa tctggacgta aaaaaattta acccctattc ttttaatcga    1140
gacgatcagg ttgcgccgat tatgtttttct tctggtacaa ctggtctgcc gaagggagtc    1200
atgctaactc acaagaatat tgttgcacga ttttctattg caaaagatcc tacttttggt    1260
aacgcaatta atcccacgtc agcaattta acggtaatac cttccacca tggttttggt      1320
atgatgacca cattaggata ctttacttgt ggattccgag ttgttctaat gcacgtttt     1380
gaagaaaaac tatttctaca atcattacaa gattataaag tggaaagtac tttacttgta    1440
ccaacattaa tggcatttct tgcaaaaagt gcattagttg aaaagtacga tttatcgcac    1500
ttaaaagaaa ttgcatctgg tggcgcacct ttatcaaaag aaattgggga gatggtgaaa    1560
aaacggttta aattaaactt tgtcaggcaa gggtatggat aacagaaaac cacttcggct    1620
gttttaatta caccgaaagg tgtt                                           1644
```

<210> SEQ ID NO 10
<211> LENGTH: 548
<212> TYPE: PRT
<213> ORGANISM: Artificial

<220> FEATURE:
<223> OTHER INFORMATION: Synthetic

<400> SEQUENCE: 10

```
Met Pro Gly Ser Thr Gly Lys Ile Val Pro Leu His Ala Val Lys Val
1               5                   10                  15

Val Asp Pro Thr Thr Gly Lys Ile Leu Gly Pro Asn Glu Pro Gly Glu
            20                  25                  30

Leu Tyr Phe Lys Gly Pro Met Ile Met Lys Gly Tyr Tyr Asn Asn Glu
        35                  40                  45

Glu Ala Thr Lys Ala Ile Ile Asp Asn Asp Gly Trp Leu Arg Ser Gly
    50                  55                  60

Asp Ile Ala Tyr Tyr Asp Asn Asp Gly His Phe Tyr Ile Val Asp Arg
65                  70                  75                  80

Leu Lys Ser Leu Ile Lys Tyr Lys Gly Tyr Gln Val Ala Pro Ala Glu
                85                  90                  95

Ile Glu Gly Ile Leu Leu Gln His Pro Tyr Ile Val Asp Ala Gly Val
            100                 105                 110

Thr Gly Thr Pro Asp Glu Ala Ala Gly Glu Leu Pro Ala Ala Gly Val
        115                 120                 125

Val Val Gln Thr Gly Lys Tyr Leu Asn Glu Gln Ile Val Gln Asp Tyr
130                 135                 140

Val Ala Gly Gln Val Ser Ile Ala Lys Trp Leu Arg Gly Gly Val Lys
145                 150                 155                 160

Phe Leu Asp Glu Ile Pro Lys Gly Ser Thr Gly Lys Ile Asp Arg Lys
                165                 170                 175

Val Leu Arg Gln Met Leu Glu Lys His Thr Asn Gly Ser Asp Glu Val
            180                 185                 190

Asp Gly Ser Leu Lys Asn Ile Leu Tyr Gly Pro Glu Pro Phe Tyr Pro
        195                 200                 205

Leu Glu Asp Gly Thr Ala Gly Glu Gln Met Phe Asp Ala Leu Ser Arg
    210                 215                 220

Tyr Ala Ala Ile Pro Gly Cys Ile Ala Leu Thr Asn Ala His Thr Lys
225                 230                 235                 240

Glu Asn Val Leu Tyr Glu Glu Phe Leu Lys Leu Ser Cys Arg Leu Ala
                245                 250                 255

Glu Ser Phe Lys Lys Tyr Gly Leu Lys Gln Asn Asp Thr Ile Ala Val
            260                 265                 270

Cys Ser Glu Asn Ser Leu Gln Phe Phe Leu Pro Val Ile Ala Ser Leu
        275                 280                 285

Tyr Leu Gly Ile Ile Val Ala Pro Val Asn Asp Lys Tyr Ile Glu Arg
    290                 295                 300

Glu Leu Ile His Ser Leu Gly Ile Val Lys Pro Arg Ile Val Phe Cys
305                 310                 315                 320

Ser Lys Asn Thr Phe Gln Lys Val Leu Asn Val Lys Ser Lys Leu Lys
                325                 330                 335

Ser Ile Glu Thr Ile Ile Ile Leu Asp Leu Asn Glu Asp Leu Gly Gly
            340                 345                 350

Tyr Gln Cys Leu Asn Asn Phe Ile Ser Gln Ser Asp Ser Asn Leu
        355                 360                 365

Asp Val Lys Lys Phe Lys Pro Tyr Ser Phe Asn Arg Asp Asp Gln Val
    370                 375                 380

Ala Pro Ile Met Phe Ser Ser Gly Thr Thr Gly Leu Pro Lys Gly Val
385                 390                 395                 400
```

```
Met Leu Thr His Lys Asn Ile Val Ala Arg Phe Ser Ile Ala Lys Asp
                405                 410                 415
Pro Thr Phe Gly Asn Ala Ile Asn Pro Thr Ser Ala Ile Leu Thr Val
            420                 425                 430
Ile Pro Phe His His Gly Phe Gly Met Met Thr Thr Leu Gly Tyr Phe
        435                 440                 445
Thr Cys Gly Phe Arg Val Val Leu Met His Thr Phe Glu Glu Lys Leu
    450                 455                 460
Phe Leu Gln Ser Leu Gln Asp Tyr Lys Val Glu Ser Thr Leu Leu Val
465                 470                 475                 480
Pro Thr Leu Met Ala Phe Leu Ala Lys Ser Ala Leu Val Glu Lys Tyr
                485                 490                 495
Asp Leu Ser His Leu Lys Glu Ile Ala Ser Gly Gly Ala Pro Leu Ser
            500                 505                 510
Lys Glu Ile Gly Glu Met Val Lys Lys Arg Phe Lys Leu Asn Phe Val
        515                 520                 525
Arg Gln Gly Tyr Gly Leu Thr Glu Thr Thr Ser Ala Val Leu Ile Thr
    530                 535                 540
Pro Lys Gly Val
545

<210> SEQ ID NO 11
<211> LENGTH: 1644
<212> TYPE: DNA
<213> ORGANISM: Artificial
<220> FEATURE:
<223> OTHER INFORMATION: Synthetic

<400> SEQUENCE: 11
atgccgggat caactggtaa aatagtacca ttacacgctg ttaaagttgt cgatcctaca      60
acaggaaaaa ttttggggcc aaatgaacct ggagaattgt attttaaagg cccgatgata     120
atgaagggtt attataataa tgaagaagct actaaagcaa ttattgataa tgacggatgg     180
ttgcgctctg gtgatattgc ttattatgac aatgatggcc attttatat tgtggacagg      240
ctgaagtcac tgattaaata taaaggttat caggttcac ctgctgaaat tgagggaata      300
ctcttacaac atccgtatat tgttgatgcc ggcgttactg gtacaccgga tgaagccgcg     360
ggcgagcttc cagctgcagg tgttgtagta cagactggaa aatatctaaa cgaacaaatc     420
gtacaagatt atgttgccgg tcaagtttca atagccaaat ggctacgtgg tgggtgaaa     480
tttttggatg aaatccccaa aggatcaact ggaaaaattg acagaaaagt gttaagacaa      540
atgttagaaa acacaccaa tggatccgac gaggtggacg gaagcttgaa aaacatcctg      600
tatggtccgg aaccgttcta cccactgaa atggtaccg ctggtgaaca atgtttgac        660
gcattatctc gttatgcagc tattccgggc tgcatagcat tgacaaatgc tcatacaaaa      720
gaaaatgttt tatatgaaga gtttctgaaa ctgtcgtgtc gttagcgga aagttttaaa       780
aagtatggat taaacaaaa cgacacaata gcggtgtgta gcgaaaatag tctgcaattt      840
ttccttcctg taattgcatc attgtatctt ggaataattg tggcacctgt taacgataaa      900
tacattgaac gtgaattaat acacagtctt ggtattgtaa aaccacgcat agttttttgc      960
tccaagaata cttttcaaaa agtactgaat gtaaaatcta aattaaaatc tattgaaact    1020
attattatat tagacttaaa tgaagactta ggaggttatc aatgcctcaa caactttatt    1080
tctcaaaatt ccgatagtaa tctggacgta aaaaaattta acccctattc ttttaatcga    1140
```

```
gacgatcagg ttgcgtcgat tatgttttct tctggtacaa ctggtctgcc gaagggagtc    1200
atgctaactc acaagaatat tgttgcacga ttttctattg caaaagatcc tacttttggt    1260
aacgcaatta atcccacgtc agcaatttta acggtaatac ctttccacca tggttttggt    1320
atgatgacca cattaggata ctttacttgt ggattccgag ttgttctaat gcacacgttt    1380
gaagaaaaac tatttctaca atcattacaa gattataaag tggaaagtac tttacttgta    1440
ccaacattaa tggcatttct tgcaaaaagt gcattagttg aaaagtacga tttatcgcac    1500
ttaaaagaaa ttgcatctgg tggcgcacct ttatcaaaag aaattgggga gatggtgaaa    1560
aaacggttta aattaaactt tgtcaggcaa gggtatggat aacagaaac cacttcggct    1620 gttttaatta caccgaaagg tgtt                                           1644
```

<210> SEQ ID NO 12
<211> LENGTH: 548
<212> TYPE: PRT
<213> ORGANISM: Artificial
<220> FEATURE:
<223> OTHER INFORMATION: Synthetic

<400> SEQUENCE: 12

```
Met Pro Gly Ser Thr Gly Lys Ile Val Pro Leu His Ala Val Lys Val
1               5                   10                  15

Val Asp Pro Thr Thr Gly Lys Ile Leu Gly Pro Asn Glu Pro Gly Glu
            20                  25                  30

Leu Tyr Phe Lys Gly Pro Met Ile Met Lys Gly Tyr Tyr Asn Asn Glu
        35                  40                  45

Glu Ala Thr Lys Ala Ile Ile Asp Asn Asp Gly Trp Leu Arg Ser Gly
    50                  55                  60

Asp Ile Ala Tyr Tyr Asp Asn Asp Gly His Phe Tyr Ile Val Asp Arg
65                  70                  75                  80

Leu Lys Ser Leu Ile Lys Tyr Lys Gly Tyr Gln Val Ala Pro Ala Glu
                85                  90                  95

Ile Glu Gly Ile Leu Leu Gln His Pro Tyr Ile Val Asp Ala Gly Val
            100                 105                 110

Thr Gly Thr Pro Asp Glu Ala Ala Gly Glu Leu Pro Ala Ala Gly Val
        115                 120                 125

Val Val Gln Thr Gly Lys Tyr Leu Asn Glu Gln Ile Val Gln Asp Tyr
    130                 135                 140

Val Ala Gly Gln Val Ser Ile Ala Lys Trp Leu Arg Gly Gly Val Lys
145                 150                 155                 160

Phe Leu Asp Glu Ile Pro Lys Gly Ser Thr Gly Lys Ile Asp Arg Lys
                165                 170                 175

Val Leu Arg Gln Met Leu Glu Lys His Thr Asn Gly Ser Asp Glu Val
            180                 185                 190

Asp Gly Ser Leu Lys Asn Ile Leu Tyr Gly Pro Glu Pro Phe Tyr Pro
        195                 200                 205

Leu Glu Asp Gly Thr Ala Gly Glu Gln Met Phe Asp Ala Leu Ser Arg
    210                 215                 220

Tyr Ala Ala Ile Pro Gly Cys Ile Ala Leu Thr Asn Ala His Thr Lys
225                 230                 235                 240

Glu Asn Val Leu Tyr Glu Glu Phe Leu Lys Leu Ser Cys Arg Leu Ala
                245                 250                 255

Glu Ser Phe Lys Lys Tyr Gly Leu Lys Gln Asn Asp Thr Ile Ala Val
            260                 265                 270
```

```
Cys Ser Glu Asn Ser Leu Gln Phe Leu Pro Val Ile Ala Ser Leu
            275                 280                 285

Tyr Leu Gly Ile Ile Val Ala Pro Val Asn Asp Lys Tyr Ile Glu Arg
        290                 295                 300

Glu Leu Ile His Ser Leu Gly Ile Val Lys Pro Arg Ile Val Phe Cys
305                 310                 315                 320

Ser Lys Asn Thr Phe Gln Lys Val Leu Asn Val Lys Ser Lys Leu Lys
                325                 330                 335

Ser Ile Glu Thr Ile Ile Ile Leu Asp Leu Asn Glu Asp Leu Gly Gly
                340                 345                 350

Tyr Gln Cys Leu Asn Asn Phe Ile Ser Gln Asn Ser Asp Ser Asn Leu
        355                 360                 365

Asp Val Lys Lys Phe Lys Pro Tyr Ser Phe Asn Arg Asp Asp Gln Val
370                 375                 380

Ala Ser Ile Met Phe Ser Ser Gly Thr Thr Gly Leu Pro Lys Gly Val
385                 390                 395                 400

Met Leu Thr His Lys Asn Ile Val Ala Arg Phe Ser Ile Ala Lys Asp
                405                 410                 415

Pro Thr Phe Gly Asn Ala Ile Asn Pro Thr Ser Ala Ile Leu Thr Val
                420                 425                 430

Ile Pro Phe His His Gly Phe Gly Met Met Thr Thr Leu Gly Tyr Phe
        435                 440                 445

Thr Cys Gly Phe Arg Val Val Leu Met His Thr Phe Glu Glu Lys Leu
        450                 455                 460

Phe Leu Gln Ser Leu Gln Asp Tyr Lys Val Glu Ser Thr Leu Leu Val
465                 470                 475                 480

Pro Thr Leu Met Ala Phe Leu Ala Lys Ser Ala Leu Val Glu Lys Tyr
                485                 490                 495

Asp Leu Ser His Leu Lys Glu Ile Ala Ser Gly Gly Ala Pro Leu Ser
                500                 505                 510

Lys Glu Ile Gly Glu Met Val Lys Lys Arg Phe Lys Leu Asn Phe Val
        515                 520                 525

Arg Gln Gly Tyr Gly Leu Thr Glu Thr Thr Ser Ala Val Leu Ile Thr
        530                 535                 540

Pro Lys Gly Val
545

<210> SEQ ID NO 13
<211> LENGTH: 1644
<212> TYPE: DNA
<213> ORGANISM: Artificial
<220> FEATURE:
<223> OTHER INFORMATION: Synthetic

<400> SEQUENCE: 13
atgccgggat caactggtaa aatagtacca ttacacgctg ttaaagttgt cgatcctaca      60
acaggaaaaa ttttgggggcc aaatgaacct ggagaattgt attttaaagg cccgatgata    120
atgaagggtt attataataa tgaagaagct actaaagcaa ttattgataa tgacggatgg    180
ttgcgctctg gtgatattgc ttattatgac aatgatggcc attttttatat tgtggacagg    240 ctgaagtcac tgattaaata taaaggttat caggttgcac tgctgaaat tgagggaata     300 ctcttacaac atccgtatat tgttgatgcc ggcgttactg gtataccgga tgaagccgcg    360
ggcgagcttc cagctgcagg tgttgtagta cagactggaa aatatctaaa cgaacaaatc    420
gtacaagatt atgttgccgg tcaagtttca atagccaaat ggctacgtgg tggggtgaaa    480
```

```
tttttggatg aaattcccaa aggatcaact ggaaaaattg acagaaaagt gttaagacaa    540
atgttagaaa aacacaccaa tggatccgac gaggtggacg aaagcttgaa aaacatcctg    600
tatggtccgg aaccgttcta cccactggaa gatggtaccg ctggtgaaca gatgtttgac    660
gcattatctc gttatgcagc tattccgggc tgcatagcat tgacaaatgc tcatacaaaa    720
gaaaatgttt tatatgaaga gtttctgaaa ctgtcgtgtc gtttagcgga aagttttaaa    780
aagtatggat taaacaaaa cgacacaata gcggtgtgta gcgaaaatag tctgcaattt    840
ttccttcctg taattgcatc attgtatctt ggaataattg tggcacctgt aacgataaa    900 tacattgaac gtgaattaat acacagtctt ggtattgtaa aaccacgcat agttttttgc    960
tccaagaata cttttcaaaa agtactgaat gtaaaatcta aattaaaatc tattgaaact   1020
attattatat tagacttaaa tgaagactta ggaggttatc aatgcctcaa caactttatt   1080
tctcaaaatt ccgatagtaa tctggacgta aaaaaattta accctattc ttttaatcga    1140 gacgatcagg ttgcgccgat tatgttttct tctggtacaa ctggtctgcc gaagggagtc   1200
atgctaactc acaagaatat tgttgcacga ttttctattg caaaagatcc tacttttggt   1260
aacgcaatta atcccacgtc agcaatttta acggtaatac ctttccacca tggttttggt   1320
atgatgacca cattaggata ctttacttgt ggattccgag ttgttctaat gcacacgttt   1380
gaagaaaaac tatttctaca atcattacaa gattataaag tggaaagtac tttacttgta   1440
ccaacattaa tggcatttct tgcaaaaagt gcattagttg aaaagtacga tttatcgcac   1500
ttaaaagaaa ttgcatctgg tggcgcacct ttatcaaaag aaattgggga gatggtgaaa   1560
aaacggttta aattaaactt tgtcaggcaa gggtatggat aacagaaac cacttcggct   1620 gttttaatta caccgaaagg tgtt                                         1644
```

<210> SEQ ID NO 14
<211> LENGTH: 548
<212> TYPE: PRT
<213> ORGANISM: Artificial
<220> FEATURE:
<223> OTHER INFORMATION: Synthetic

<400> SEQUENCE: 14

```
Met Pro Gly Ser Thr Gly Lys Ile Val Pro Leu His Ala Val Lys Val
1               5                   10                  15

Val Asp Pro Thr Thr Gly Lys Ile Leu Gly Pro Asn Glu Pro Gly Glu
            20                  25                  30

Leu Tyr Phe Lys Gly Pro Met Ile Met Lys Gly Tyr Tyr Asn Asn Glu
        35                  40                  45

Glu Ala Thr Lys Ala Ile Ile Asp Asn Asp Gly Trp Leu Arg Ser Gly
    50                  55                  60

Asp Ile Ala Tyr Tyr Asp Asn Asp Gly His Phe Tyr Ile Val Asp Arg
65                  70                  75                  80

Leu Lys Ser Leu Ile Lys Tyr Lys Gly Tyr Gln Val Ala Pro Ala Glu
                85                  90                  95

Ile Glu Gly Ile Leu Leu Gln His Pro Tyr Ile Val Asp Ala Gly Val
            100                 105                 110

Thr Gly Ile Pro Asp Glu Ala Ala Gly Glu Leu Pro Ala Ala Gly Val
        115                 120                 125

Val Val Gln Thr Gly Lys Tyr Leu Asn Glu Gln Ile Val Gln Asp Tyr
    130                 135                 140

Val Ala Gly Gln Val Ser Ile Ala Lys Trp Leu Arg Gly Gly Val Lys
```

```
            145                 150                 155                 160
        Phe Leu Asp Glu Ile Pro Lys Gly Ser Thr Gly Lys Ile Asp Arg Lys
                        165                 170                 175
        Val Leu Arg Gln Met Leu Glu Lys His Thr Asn Gly Ser Asp Glu Val
                        180                 185                 190
        Asp Gly Ser Leu Lys Asn Ile Leu Tyr Gly Pro Glu Pro Phe Tyr Pro
                        195                 200                 205
        Leu Glu Asp Gly Thr Ala Gly Glu Gln Met Phe Asp Ala Leu Ser Arg
                    210                 215                 220
        Tyr Ala Ala Ile Pro Gly Cys Ile Ala Leu Thr Asn Ala His Thr Lys
        225                 230                 235                 240
        Glu Asn Val Leu Tyr Glu Glu Phe Leu Lys Leu Ser Cys Arg Leu Ala
                            245                 250                 255
        Glu Ser Phe Lys Lys Tyr Gly Leu Lys Gln Asn Asp Thr Ile Ala Val
                        260                 265                 270
        Cys Ser Glu Asn Ser Leu Gln Phe Phe Leu Pro Val Ile Ala Ser Leu
                        275                 280                 285
        Tyr Leu Gly Ile Ile Val Ala Pro Val Asn Asp Lys Tyr Ile Glu Arg
                    290                 295                 300
        Glu Leu Ile His Ser Leu Gly Ile Val Lys Pro Arg Ile Val Phe Cys
        305                 310                 315                 320
        Ser Lys Asn Thr Phe Gln Lys Val Leu Asn Val Lys Ser Lys Leu Lys
                            325                 330                 335
        Ser Ile Glu Thr Ile Ile Leu Asp Leu Asn Glu Asp Leu Gly Gly
                        340                 345                 350
        Tyr Gln Cys Leu Asn Asn Phe Ile Ser Gln Asn Ser Asp Ser Asn Leu
                    355                 360                 365
        Asp Val Lys Lys Phe Lys Pro Tyr Ser Phe Asn Arg Asp Asp Gln Val
                    370                 375                 380
        Ala Pro Ile Met Phe Ser Ser Gly Thr Thr Gly Leu Pro Lys Gly Val
        385                 390                 395                 400
        Met Leu Thr His Lys Asn Ile Val Ala Arg Phe Ser Ile Ala Lys Asp
                            405                 410                 415
        Pro Thr Phe Gly Asn Ala Ile Asn Pro Thr Ser Ala Ile Leu Thr Val
                        420                 425                 430
        Ile Pro Phe His His Gly Phe Gly Met Met Thr Thr Leu Gly Tyr Phe
                    435                 440                 445
        Thr Cys Gly Phe Arg Val Val Leu Met His Thr Phe Glu Glu Lys Leu
                    450                 455                 460
        Phe Leu Gln Ser Leu Gln Asp Tyr Lys Val Glu Ser Thr Leu Leu Val
        465                 470                 475                 480
        Pro Thr Leu Met Ala Phe Leu Ala Lys Ser Ala Leu Val Glu Lys Tyr
                            485                 490                 495
        Asp Leu Ser His Leu Lys Glu Ile Ala Ser Gly Gly Ala Pro Leu Ser
                        500                 505                 510
        Lys Glu Ile Gly Glu Met Val Lys Lys Arg Phe Lys Leu Asn Phe Val
                    515                 520                 525
        Arg Gln Gly Tyr Gly Leu Thr Glu Thr Thr Ser Ala Val Leu Ile Thr
                    530                 535                 540
        Pro Lys Gly Val
        545

<210> SEQ ID NO 15
```

<211> LENGTH: 5
<212> TYPE: PRT
<213> ORGANISM: Artificial
<220> FEATURE:
<223> OTHER INFORMATION: Synthetic

<400> SEQUENCE: 15

Leu Glu Thr Asp Gly
1               5

<210> SEQ ID NO 16
<211> LENGTH: 7
<212> TYPE: PRT
<213> ORGANISM: Artificial
<220> FEATURE:
<223> OTHER INFORMATION: Synthetic

<400> SEQUENCE: 16

Glu Asn Leu Tyr Phe Gln Ser
1               5

<210> SEQ ID NO 17
<211> LENGTH: 1665
<212> TYPE: DNA
<213> ORGANISM: Artificial
<220> FEATURE:
<223> OTHER INFORMATION: Synthetic

<400> SEQUENCE: 17

| | | | | | |
|---|---|---|---|---|---|
| atgacgtcag | caattttaac | ggtaatacct | ttccaccatg | gttttggtat | gatgaccaca | 60 |
| ttaggatact | ttacttgtgg | attccgagtt | gttctaatgc | acacgtttga | agaaaaacta | 120 |
| tttctacaat | cattacaaga | ttataaagtg | aaagtactt | tacttgtacc | aacattaatg | 180 |
| gcatttcttg | caaaaagtgc | attagttgaa | aagtacgatt | tatcgcactt | aaaagaaatt | 240 |
| gcatctggtg | gcgcaccttt | atcaaaagaa | attggggaga | tggtgaaaaa | acggtttaaa | 300 |
| ttaaactttg | tcaggcaagg | gtatggatta | acagaaacca | cttcggctgt | tttaattaca | 360 |
| ccgaaaggtg | acgccaaacc | gggatcaact | ggtaaaatag | taccattaca | cgctgttaaa | 420 |
| gttgtcgatc | ctacaacagg | aaaaattttg | gggccaaatg | aacctggaga | attgtatttt | 480 |
| aaaggcccga | tgataatgaa | gggttattat | aataatgaag | aagctactaa | agcaattatt | 540 |
| gataatgacg | gatggttgcg | ctctggtgat | attgcttatt | atgacaatga | tggccatttt | 600 |
| tatattgtgg | acaggctgaa | gtcactgatt | aaatataaag | gttatcaggt | tgcacctgct | 660 |
| gaaattgagg | aatactctt | acaacatccg | tatattgttg | atgccggcgt | tactggtata | 720 |
| ccggatgaag | ccgcgggcga | gcttccagct | gcaggtgttg | tagtacagac | tggaaaatat | 780 |
| ctaaacgaac | aaatcgtaca | agattatgtt | gccagtcaag | tttcaacagc | caaatggcta | 840 |
| cgtggtgggg | tgaaattttt | ggatgaaatt | cccaaaggat | caactggaaa | aattgacaga | 900 |
| aaagtgttaa | gacaaatgtt | agaaaaacac | accaatggct | cgagcgacga | ggtggacggg | 960 |
| agctccggtg | ataagaatat | tttatatggg | cccgaaccat | tttatccctt | ggaagatggg | 1020 |
| acggctggag | aacagatgtt | tgacgcatta | tctcgttatg | cagctattcc | gggctgcata | 1080 |
| gcattgacaa | atgctcatac | aaaagaaaat | gttttatatg | aagagtttct | gaaactgtcg | 1140 |
| tgtcgtttag | cggaaagttt | taaaaagtat | ggattaaaac | aaaacgacac | aatagcggtg | 1200 |
| tgtagcgaaa | atagtctgca | attttttcctt | cctgtaattg | catcattgta | tcttggaata | 1260 |
| attgtggcac | tgttaacga | taatacatt | gaacgtgaat | taatacacag | tcttggtatt | 1320 |
| gtaaaaccac | gcatagtttt | ttgctccaag | aatacttttc | aaaaagtact | gaatgtaaaa | 1380 |

-continued

```
tctaaattaa aatctattga aactattatt atattagact taaatgaaga cttaggaggt    1440
tatcaatgcc tcaacaactt tatttctcaa aattccgata gtaatctgga cgtaaaaaaa    1500
tttaaaccct attcttttaa tcgagacgat caggttgcgt cgattatgtt ttcttctggt    1560
acaactggtc tgccgaaggg agtcatgcta actcacaaga atattgttgc acgattttct    1620
attgcaaaag atcctacttt tggtaacgca attaatcccg tttaa                   1665
```

<210> SEQ ID NO 18
<211> LENGTH: 554
<212> TYPE: PRT
<213> ORGANISM: Artificial
<220> FEATURE:
<223> OTHER INFORMATION: Synthetic

<400> SEQUENCE: 18

```
Met Thr Ser Ala Ile Leu Thr Val Ile Pro Phe His His Gly Phe Gly
1               5                   10                  15

Met Met Thr Thr Leu Gly Tyr Phe Thr Cys Gly Phe Arg Val Val Leu
            20                  25                  30

Met His Thr Phe Glu Glu Lys Leu Phe Leu Gln Ser Leu Gln Asp Tyr
        35                  40                  45

Lys Val Glu Ser Thr Leu Leu Val Pro Thr Leu Met Ala Phe Leu Ala
    50                  55                  60

Lys Ser Ala Leu Val Glu Lys Tyr Asp Leu Ser His Leu Lys Glu Ile
65                  70                  75                  80

Ala Ser Gly Gly Ala Pro Leu Ser Lys Glu Ile Gly Glu Met Val Lys
                85                  90                  95

Lys Arg Phe Lys Leu Asn Phe Val Arg Gln Gly Tyr Gly Leu Thr Glu
            100                 105                 110

Thr Thr Ser Ala Val Leu Ile Thr Pro Lys Gly Asp Ala Lys Pro Gly
        115                 120                 125

Ser Thr Gly Lys Ile Val Pro Leu His Ala Val Lys Val Val Asp Pro
    130                 135                 140

Thr Thr Gly Lys Ile Leu Gly Pro Asn Glu Pro Gly Glu Leu Tyr Phe
145                 150                 155                 160

Lys Gly Pro Met Ile Met Lys Gly Tyr Tyr Asn Asn Glu Glu Ala Thr
                165                 170                 175

Lys Ala Ile Ile Asp Asn Asp Gly Trp Leu Arg Ser Gly Asp Ile Ala
            180                 185                 190

Tyr Tyr Asp Asn Asp Gly His Phe Tyr Ile Val Asp Arg Leu Lys Ser
        195                 200                 205

Leu Ile Lys Tyr Lys Gly Tyr Gln Val Ala Pro Ala Glu Ile Glu Gly
    210                 215                 220

Ile Leu Leu Gln His Pro Tyr Ile Val Asp Ala Gly Val Thr Gly Ile
225                 230                 235                 240

Pro Asp Glu Ala Ala Gly Glu Leu Pro Ala Ala Gly Val Val Gln
                245                 250                 255

Thr Gly Lys Tyr Leu Asn Glu Gln Ile Val Gln Asp Tyr Val Ala Ser
            260                 265                 270

Gln Val Ser Thr Ala Lys Trp Leu Arg Gly Gly Val Lys Phe Leu Asp
        275                 280                 285

Glu Ile Pro Lys Gly Ser Thr Gly Lys Ile Asp Arg Lys Val Leu Arg
    290                 295                 300

Gln Met Leu Glu Lys His Thr Asn Gly Ser Ser Asp Glu Val Asp Gly
```

```
                305                 310                 315                 320
Ser Ser Gly Asp Lys Asn Ile Leu Tyr Gly Pro Glu Pro Phe Tyr Pro
            325                 330                 335

Leu Glu Asp Gly Thr Ala Gly Glu Gln Met Phe Asp Ala Leu Ser Arg
            340                 345                 350

Tyr Ala Ala Ile Pro Gly Cys Ile Ala Leu Thr Asn Ala His Thr Lys
            355                 360                 365

Glu Asn Val Leu Tyr Glu Glu Phe Leu Lys Leu Ser Cys Arg Leu Ala
            370                 375                 380

Glu Ser Phe Lys Lys Tyr Gly Leu Lys Gln Asn Asp Thr Ile Ala Val
385                 390                 395                 400

Cys Ser Glu Asn Ser Leu Gln Phe Phe Leu Pro Val Ile Ala Ser Leu
                405                 410                 415

Tyr Leu Gly Ile Ile Val Ala Pro Val Asn Asp Lys Tyr Ile Glu Arg
            420                 425                 430

Glu Leu Ile His Ser Leu Gly Ile Val Lys Pro Arg Ile Val Phe Cys
            435                 440                 445

Ser Lys Asn Thr Phe Gln Lys Val Leu Asn Val Lys Ser Lys Leu Lys
            450                 455                 460

Ser Ile Glu Thr Ile Ile Ile Leu Asp Leu Asn Glu Asp Leu Gly Gly
465                 470                 475                 480

Tyr Gln Cys Leu Asn Asn Phe Ile Ser Gln Asn Ser Asp Ser Asn Leu
                485                 490                 495

Asp Val Lys Lys Phe Lys Pro Tyr Ser Phe Asn Arg Asp Asp Gln Val
            500                 505                 510

Ala Ser Ile Met Phe Ser Ser Gly Thr Thr Gly Leu Pro Lys Gly Val
            515                 520                 525

Met Leu Thr His Lys Asn Ile Val Ala Arg Phe Ser Ile Ala Lys Asp
            530                 535                 540

Pro Thr Phe Gly Asn Ala Ile Asn Pro Val
545                 550

<210> SEQ ID NO 19
<211> LENGTH: 1656
<212> TYPE: DNA
<213> ORGANISM: Artificial
<220> FEATURE:
<223> OTHER INFORMATION: Synthetic

<400> SEQUENCE: 19
atgcctggcg cagtaggcaa ggtggtgccc ttcttcgagg ctaaggtggt ggacttggac      60
actggtaaga cactgggtgt gaaccagcgc ggcgagctgt gcgtccgtgg ccccatgatc     120
atgagcggct acgttaacaa ccccgaggct acaaacgctc tcatcgacaa ggacggctgg     180
ctgcacagcg gcgacatcgc ctactgggac gaggacgagc acttcttcat cgtggaccgg     240
ctgaagagcc tgatcaaata caagggctac caggtagccc cagccgaact ggagagcatc     300
ctgctgcaac accccaacat cttcgacgcc ggggtcgccg gcctgcccga cgacgatgcc     360
ggcgagctgc cgccgcagt cgtcgtgctg aacacggta aaaccatgac cgagaaggag     420
atcgtggact atgtggccag ccaggttaca accgccaaga gctgcgcgg tgtgttgtg     480 ttcgtggacg aggtgcctaa aggactgacc ggcaagttgg acgcccgcaa gatccgcgag     540
attctcatta aggccaagaa gggctcgagc ctggagaccg acggcagctc cggtgccaaa     600
aacattaaga agggcccagc gccattctac ccactcgaag acgggaccgc cggcgagcag     660
```

```
ctgcacaaag ccatgaagcg ctacgccctg gtgcccggca ccatcgcctt taccgacgca     720
catatcgagg tggacattac ctacgccgag tacttcgaga tgagcgttcg gctggcagaa     780
gctatgaagc gctatgggct gaatacaaac catcggatcg tggtgtgcag cgagaatagc     840
ttgcagttct tcatgcccgt gttgggtgcc ctgttcatcg tgtgtggctgt ggccccagct    900 aacgacatct acaacgagcg cgagctgctg aacagcatgg gcatcagcca gcccaccgtc     960
gtattcgtga gcaagaaagg gctgcaaaag atcctcaacg tgcaaaagaa gctaccgatc    1020
atacaaaaga tcatcatcat ggatagcaag accgactacc agggcttcca aagcatgtac    1080
accttcgtga cttcccattt gccacccggc ttcaacgagt acgacttcgt gcccgagagc    1140
ttcgaccggg acaaaaccat cgccctgatc atgaacagta gtggcagtac cggattgccc    1200
aagggcgtag ccctaccgca ccgcaccgct tgtgtccgat tcagtcatgc ccgcgacccc    1260
atcttcggca accagatcat ccccgacacc gctatcctca gcgtggtgcc atttcaccac    1320
ggcttcggca tgttcaccac gctgggctac ttgatctgcg gctttcgggt cgtgctcatg    1380
taccgcttcg aggaggagct attcttgcgc agcttgcaag actataagat tcaatctgcc    1440
ctgctggtgc ccacactatt tagcttcttc gctaagagca ctctcatcga caagtacgac    1500
ctaagcaact tgcacgagat cgccagcggc ggggcgccgc tcagcaagga ggtaggtgag    1560
gccgtggcca aacgcttcca cctaccaggc atccgccagg gctacggcct gacagaaaca    1620
accagcgcca ttctgatcac tccagaaggg gtttaa                              1656
```

<210> SEQ ID NO 20
<211> LENGTH: 551
<212> TYPE: PRT
<213> ORGANISM: Artificial
<220> FEATURE:
<223> OTHER INFORMATION: Synthetic

<400> SEQUENCE: 20

Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Leu Glu
            180                 185                 190

Thr Asp Gly Ser Ser Gly Ala Lys Asn Ile Lys Lys Gly Pro Ala Pro
        195                 200                 205

Phe Tyr Pro Leu Glu Asp Gly Thr Ala Gly Glu Gln Leu His Lys Ala
210                 215                 220

Met Lys Arg Tyr Ala Leu Val Pro Gly Thr Ile Ala Phe Thr Asp Ala
225                 230                 235                 240

His Ile Glu Val Asp Ile Thr Tyr Ala Glu Tyr Phe Glu Met Ser Val
                245                 250                 255

Arg Leu Ala Glu Ala Met Lys Arg Tyr Gly Leu Asn Thr Asn His Arg
            260                 265                 270

Ile Val Val Cys Ser Glu Asn Ser Leu Gln Phe Phe Met Pro Val Leu
        275                 280                 285

Gly Ala Leu Phe Ile Gly Val Ala Val Ala Pro Ala Asn Asp Ile Tyr
290                 295                 300

Asn Glu Arg Glu Leu Leu Asn Ser Met Gly Ile Ser Gln Pro Thr Val
305                 310                 315                 320

Val Phe Val Ser Lys Lys Gly Leu Gln Lys Ile Leu Asn Val Gln Lys
                325                 330                 335

Lys Leu Pro Ile Ile Gln Lys Ile Ile Met Asp Ser Lys Thr Asp
            340                 345                 350

Tyr Gln Gly Phe Gln Ser Met Tyr Thr Phe Val Thr Ser His Leu Pro
        355                 360                 365

Pro Gly Phe Asn Glu Tyr Asp Phe Val Pro Glu Ser Phe Asp Arg Asp
370                 375                 380

Lys Thr Ile Ala Leu Ile Met Asn Ser Ser Gly Ser Thr Gly Leu Pro
385                 390                 395                 400

Lys Gly Val Ala Leu Pro His Arg Thr Ala Cys Val Arg Phe Ser His
                405                 410                 415

Ala Arg Asp Pro Ile Phe Gly Asn Gln Ile Ile Pro Asp Thr Ala Ile
            420                 425                 430

Leu Ser Val Val Pro Phe His His Gly Phe Gly Met Phe Thr Thr Leu
        435                 440                 445

Gly Tyr Leu Ile Cys Gly Phe Arg Val Val Leu Met Tyr Arg Phe Glu
450                 455                 460

Glu Glu Leu Phe Leu Arg Ser Leu Gln Asp Tyr Lys Ile Gln Ser Ala
465                 470                 475                 480

Leu Leu Val Pro Thr Leu Phe Ser Phe Phe Ala Lys Ser Thr Leu Ile
                485                 490                 495

Asp Lys Tyr Asp Leu Ser Asn Leu His Glu Ile Ala Ser Gly Gly Ala
            500                 505                 510

Pro Leu Ser Lys Glu Val Gly Glu Ala Val Ala Lys Arg Phe His Leu
        515                 520                 525

Pro Gly Ile Arg Gln Gly Tyr Gly Leu Thr Glu Thr Thr Ser Ala Ile
530                 535                 540

Leu Ile Thr Pro Glu Gly Val
545                 550

<210> SEQ ID NO 21
<211> LENGTH: 1665
<212> TYPE: DNA
<213> ORGANISM: Artificial
<220> FEATURE:
<223> OTHER INFORMATION: Synthetic

<400> SEQUENCE: 21

```
atggacaccg ctatcctcag cgtggtgcca tttcaccacg gcttcggcat gttcaccacg      60
ctgggctact tgatctgcgg ctttcgggtc gtgctcatgt accgcttcga ggaggagcta     120
ttcttgcgca gcttgcaaga ctataagatt caatctgccc tgctggtgcc cacactattt     180
agcttcttcg ctaagagcac tctcatcgac aagtacgacc taagcaactt gcacgagatc     240
gccagcggcg gggcgccgct cagcaaggag gtaggtgagg ccgtggccaa acgcttccac     300
ctaccaggca tccgccaggg ctacggcctg acagaaacaa ccagcgccat tctgatcacc     360
cccgaagggg acgacaagcc tggcgcagta ggcaaggtgg tgcccttctt cgaggctaag     420
gtggtggact tggacactgg taagacactg ggtgtgaacc agcgcggcga gctgtgcgtc     480
cgtggcccca tgatcatgag cggctacgtt aacaaccccg aggctacaaa cgctctcatc     540
gacaaggacg gctggctgca cagcggcgac atcgcctact gggacgagga cgagcacttc     600
ttcatcgtgg accggctgaa gagcctgatc aaatacaagg gctaccaggt agccccagcc     660
gaactggaga gcatcctgct gcaacacccc aacatcttcg acgccgggcgt cgccggcctg     720
cccgacgacg atgccggcga gctgcccgcc gcagtcgtcg tgctggaaca cggtaaaacc     780
atgaccgaga aggagatcgt ggactatgtg gccagccagg ttacaaccgc caagaagctg     840
cgcggtggtg ttgtgttcgt ggacgaggtg cctaaaggac tgaccggcaa gttggacgcc     900
cgcaagatcc gcgagattct cattaaggcc aagaagggct cgagcctgga gccgacggc     960
agctccggtg ccaaaaacat taagaagggc ccagcgccat tctacccact gaagacggg    1020
accgccggcg agcagctgca caaagccatg aagcgctacg ccctggtgcc cggcaccatc    1080
gcctttaccg acgcacatat cgaggtggac attacctacg ccgagtactt cgagatgagc    1140
gttcggctgg cagaagctat gaagcgctat gggctgaata caaaccatcg atcgtggtg    1200
tgcagcgaga atagcttgca gttcttcatg ccgtgttgg gtgccctgtt catcggtgtg    1260
gctgtggccc cagctaacga catctacaac gagcgcgagc tgctgaacag catgggcatc    1320
agccagccca ccgtcgtatt cgtgagcaag aaagggctgc aaaagatcct caacgtgcaa    1380
aagaagctac cgatcataca aaagatcatc atcatggata gcaagaccga ctaccagggc    1440
ttccaaagca tgtacacctt cgtgacttcc catttgccac ccggcttcaa cgagtacgac    1500
ttcgtgcccg agagcttcga ccgggacaaa accatcgccc tgatcatgaa cagtagtggc    1560
agtaccggat tgcccaaggg cgtagcccta ccgcaccgca ccgcttgtgt ccgattcagt    1620
catgcccgcg accccatctt cggcaaccag atcatccccg tttaa                    1665
```

<210> SEQ ID NO 22
<211> LENGTH: 554
<212> TYPE: PRT
<213> ORGANISM: Artificial
<220> FEATURE:
<223> OTHER INFORMATION: Synthetic

<400> SEQUENCE: 22

Met Asp Thr Ala Ile Leu Ser Val Val Pro Phe His His Gly Phe Gly
1               5                   10                  15

Met Phe Thr Thr Leu Gly Tyr Leu Ile Cys Gly Phe Arg Val Val Leu
            20                  25                  30

Met Tyr Arg Phe Glu Glu Glu Leu Phe Leu Arg Ser Leu Gln Asp Tyr
        35                  40                  45

Lys Ile Gln Ser Ala Leu Leu Val Pro Thr Leu Phe Ser Phe Phe Ala
    50                  55                  60

```
Lys Ser Thr Leu Ile Asp Lys Tyr Asp Leu Ser Asn Leu His Glu Ile
 65                  70                  75                  80

Ala Ser Gly Gly Ala Pro Leu Ser Lys Glu Val Gly Glu Ala Val Ala
                 85                  90                  95

Lys Arg Phe His Leu Pro Gly Ile Arg Gln Gly Tyr Gly Leu Thr Glu
            100                 105                 110

Thr Thr Ser Ala Ile Leu Ile Thr Pro Glu Gly Asp Lys Pro Gly
            115                 120                 125

Ala Val Gly Lys Val Val Pro Phe Phe Glu Ala Lys Val Val Asp Leu
        130                 135                 140

Asp Thr Gly Lys Thr Leu Gly Val Asn Gln Arg Gly Glu Leu Cys Val
145                 150                 155                 160

Arg Gly Pro Met Ile Met Ser Gly Tyr Val Asn Asn Pro Glu Ala Thr
                165                 170                 175

Asn Ala Leu Ile Asp Lys Asp Gly Trp Leu His Ser Gly Asp Ile Ala
            180                 185                 190

Tyr Trp Asp Glu Asp Glu His Phe Phe Ile Val Asp Arg Leu Lys Ser
        195                 200                 205

Leu Ile Lys Tyr Lys Gly Tyr Gln Val Ala Pro Ala Glu Leu Glu Ser
210                 215                 220

Ile Leu Leu Gln His Pro Asn Ile Phe Asp Ala Gly Val Ala Gly Leu
225                 230                 235                 240

Pro Asp Asp Asp Ala Gly Glu Leu Pro Ala Ala Val Val Val Leu Glu
                245                 250                 255

His Gly Lys Thr Met Thr Glu Lys Glu Ile Val Asp Tyr Val Ala Ser
            260                 265                 270

Gln Val Thr Thr Ala Lys Lys Leu Arg Gly Gly Val Val Phe Val Asp
        275                 280                 285

Glu Val Pro Lys Gly Leu Thr Gly Lys Leu Asp Ala Arg Lys Ile Arg
290                 295                 300

Glu Ile Leu Ile Lys Ala Lys Lys Gly Ser Ser Leu Glu Thr Asp Gly
305                 310                 315                 320

Ser Ser Gly Ala Lys Asn Ile Lys Lys Gly Pro Ala Pro Phe Tyr Pro
                325                 330                 335

Leu Glu Asp Gly Thr Ala Gly Glu Gln Leu His Lys Ala Met Lys Arg
            340                 345                 350

Tyr Ala Leu Val Pro Gly Thr Ile Ala Phe Thr Asp Ala His Ile Glu
        355                 360                 365

Val Asp Ile Thr Tyr Ala Glu Tyr Phe Glu Met Ser Val Arg Leu Ala
370                 375                 380

Glu Ala Met Lys Arg Tyr Gly Leu Asn Thr Asn His Arg Ile Val Val
385                 390                 395                 400

Cys Ser Glu Asn Ser Leu Gln Phe Phe Met Pro Val Leu Gly Ala Leu
                405                 410                 415

Phe Ile Gly Val Ala Val Ala Pro Ala Asn Asp Ile Tyr Asn Glu Arg
            420                 425                 430

Glu Leu Leu Asn Ser Met Gly Ile Ser Gln Pro Thr Val Val Phe Val
        435                 440                 445

Ser Lys Lys Gly Leu Gln Lys Ile Leu Asn Val Gln Lys Lys Leu Pro
450                 455                 460

Ile Ile Gln Lys Ile Ile Ile Met Asp Ser Lys Thr Asp Tyr Gln Gly
465                 470                 475                 480

Phe Gln Ser Met Tyr Thr Phe Val Thr Ser His Leu Pro Pro Gly Phe
```

```
                        485                 490                 495
Asn Glu Tyr Asp Phe Val Pro Glu Ser Phe Asp Arg Asp Lys Thr Ile
            500                 505                 510

Ala Leu Ile Met Asn Ser Ser Gly Ser Thr Gly Leu Pro Lys Gly Val
        515                 520                 525

Ala Leu Pro His Arg Thr Ala Cys Val Arg Phe Ser His Ala Arg Asp
    530                 535                 540

Pro Ile Phe Gly Asn Gln Ile Ile Pro Val
545                 550

<210> SEQ ID NO 23
<211> LENGTH: 12
<212> TYPE: PRT
<213> ORGANISM: Artificial
<220> FEATURE:
<223> OTHER INFORMATION: Synthetic

<400> SEQUENCE: 23

Gly Ser Ser Gly Gly Ser Gly Gly Ser Gly Gly Gly
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic

<400> SEQUENCE: 24

Gly Ser Ser Ser Asp Ser Asp Ser Ser Ala Gly Ser
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

Gly Ser Asn Asp Ser Ser Gly Gly Ser Glu Gly Gly
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic

<400> SEQUENCE: 26

Gly Ser Asn Gly Gly Phe Asp Ser Ser Glu Gly Gly
1               5                   10

<210> SEQ ID NO 27
<211> LENGTH: 12
<212> TYPE: PRT
<213> ORGANISM: Artificial
<220> FEATURE:
<223> OTHER INFORMATION: Synthetic

<400> SEQUENCE: 27

Gly Ser Ile Arg Trp Ser Gly Leu Ser Gly Gly Asp
1               5                   10
```

```
<210> SEQ ID NO 28
<211> LENGTH: 12
<212> TYPE: PRT
<213> ORGANISM: Artificial
<220> FEATURE:
<223> OTHER INFORMATION: Synthetic

<400> SEQUENCE: 28

Gly Ser Arg Gly Gly Ser Val Tyr Ser Glu Gly Gly
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic

<400> SEQUENCE: 29

Gly Ser Ser Glu Gly Ser Ser Asp Phe Gly Gly Asp
1               5                   10

<210> SEQ ID NO 30
<211> LENGTH: 12
<212> TYPE: PRT
<213> ORGANISM: Artificial
<220> FEATURE:
<223> OTHER INFORMATION: Synthetic

<400> SEQUENCE: 30

Gly Ser Ile Val Val Ser Cys Ser Ser Glu Gly Gly
1               5                   10

<210> SEQ ID NO 31
<211> LENGTH: 12
<212> TYPE: PRT
<213> ORGANISM: Artificial
<220> FEATURE:
<223> OTHER INFORMATION: Synthetic

<400> SEQUENCE: 31

Gly Ser Asn Trp Asp Ser Gly Cys Ser Arg Glu Gly
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic

<400> SEQUENCE: 32

Gly Ser Asn Trp Asp Ser Gly Cys Ser Arg Glu Cys
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic

<400> SEQUENCE: 33

Gly Ser Ser Gly Cys Thr Gly Asp Ala Gly Gly Ser
1               5                   10
```

```
<210> SEQ ID NO 34
<211> LENGTH: 12
<212> TYPE: PRT
<213> ORGANISM: Artificial
<220> FEATURE:
<223> OTHER INFORMATION: Synthetic

<400> SEQUENCE: 34

Gly Ser Asn Trp Asp Ser Gly Cys Ser Arg Gln Cys
1               5                   10

<210> SEQ ID NO 35
<211> LENGTH: 22
<212> TYPE: PRT
<213> ORGANISM: Artificial
<220> FEATURE:
<223> OTHER INFORMATION: Synthetic

<400> SEQUENCE: 35

Gly Ser Ser Asn Ser Asp Gly Asp Ser Gly Ser Phe Asp Gly Ser Gly
1               5                   10                  15

Ser Ala Glu Gly Ser Gly
            20

<210> SEQ ID NO 36
<211> LENGTH: 24
<212> TYPE: PRT
<213> ORGANISM: Artificial
<220> FEATURE:
<223> OTHER INFORMATION: Synthetic

<400> SEQUENCE: 36

Gly Ser Ile Arg Ser Arg Gly Glu Trp Gly Ser Gly Val Ser Leu Tyr
1               5                   10                  15

Asp Ser Phe Gly Glu Gly Asp Gly
            20

<210> SEQ ID NO 37
<211> LENGTH: 27
<212> TYPE: PRT
<213> ORGANISM: Artificial
<220> FEATURE:
<223> OTHER INFORMATION: Synthetic

<400> SEQUENCE: 37

Gly Ser Ile Asn Ser Val Trp Gly Val Asp Cys Ser Thr Cys Gly Ser
1               5                   10                  15

Cys Asp Ser Ala Glu Arg Gly Gly Glu Gly Ser
            20                  25

<210> SEQ ID NO 38
<211> LENGTH: 24
<212> TYPE: PRT
<213> ORGANISM: Artificial
<220> FEATURE:
<223> OTHER INFORMATION: Synthetic

<400> SEQUENCE: 38

Gly Ser Ile Ser Val Gly Ala Val Gly Ser Cys Gly Asp Gly Asp Ser
1               5                   10                  15

Ser Ala Gly Glu Gly Glu Gly Asn
            20

<210> SEQ ID NO 39
<211> LENGTH: 30
```

```
<212> TYPE: PRT
<213> ORGANISM: Artificial
<220> FEATURE:
<223> OTHER INFORMATION: Synthetic

<400> SEQUENCE: 39

Gly Ser Ile Asn Ser Val Trp Gly Ala Val Asp Cys Gly Ser Thr Cys
1               5                   10                  15

Cys Gly Ser Cys Asp Ser Ala Glu Arg Gly Gly Glu Gly Ser
            20                  25                  30

<210> SEQ ID NO 40
<211> LENGTH: 12
<212> TYPE: PRT
<213> ORGANISM: Artificial
<220> FEATURE:
<223> OTHER INFORMATION: Synthetic

<400> SEQUENCE: 40

Gly Ser Ile Ala Gly Cys Gly Asp Ala Gly Glu Gly
1               5                   10

<210> SEQ ID NO 41
<211> LENGTH: 11
<212> TYPE: PRT
<213> ORGANISM: Artificial
<220> FEATURE:
<223> OTHER INFORMATION: Synthetic

<400> SEQUENCE: 41

Gly Ser Asn Trp Asp Ser Gly Cys Ser Arg Glu
1               5                   10

<210> SEQ ID NO 42
<211> LENGTH: 12
<212> TYPE: PRT
<213> ORGANISM: Artificial
<220> FEATURE:
<223> OTHER INFORMATION: Synthetic

<400> SEQUENCE: 42

Gly Ser Ile Ala Gly Cys Gly Asp Ala Gly Glu Gly
1               5                   10

<210> SEQ ID NO 43
<211> LENGTH: 12
<212> TYPE: PRT
<213> ORGANISM: Artificial
<220> FEATURE:
<223> OTHER INFORMATION: Synthetic

<400> SEQUENCE: 43

Gly Ser Asn Trp Asp Ser Gly Cys Ser Arg Glu Gly
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic

<400> SEQUENCE: 44

Asn Trp Asp Ser Gly Cys Ser Arg Glu Gly
1               5                   10
```

```
<210> SEQ ID NO 45
<211> LENGTH: 10
<212> TYPE: PRT
<213> ORGANISM: Artificial
<220> FEATURE:
<223> OTHER INFORMATION: Synthetic

<400> SEQUENCE: 45

Ile Ala Gly Cys Gly Asp Ala Gly Glu Gly
1               5                   10

<210> SEQ ID NO 46
<211> LENGTH: 11
<212> TYPE: PRT
<213> ORGANISM: Artificial
<220> FEATURE:
<223> OTHER INFORMATION: Synthetic

<400> SEQUENCE: 46

Ser Thr Leu Gln Ser Gly Leu Arg Lys Met Ala
1               5                   10

<210> SEQ ID NO 47
<211> LENGTH: 8
<212> TYPE: PRT
<213> ORGANISM: Artificial
<220> FEATURE:
<223> OTHER INFORMATION: Synthetic

<400> SEQUENCE: 47

Ser Gln Asn Tyr Pro Ile Val Gln
1               5

<210> SEQ ID NO 48
<211> LENGTH: 10
<212> TYPE: PRT
<213> ORGANISM: Artificial
<220> FEATURE:
<223> OTHER INFORMATION: Synthetic

<400> SEQUENCE: 48

Lys Ala Val Arg Leu Ala Glu Ala Met Ser
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic

<400> SEQUENCE: 49

Ala Glu Asp Val Val Cys Cys Ser Met Ser Tyr Ser
1               5                   10

<210> SEQ ID NO 50
<211> LENGTH: 20
<212> TYPE: PRT
<213> ORGANISM: Artificial
<220> FEATURE:
<223> OTHER INFORMATION: Synthetic

<400> SEQUENCE: 50

Gln Thr Ser Ile Thr Ser Ala Val Leu Gln Ser Gly Phe Arg Lys Met
1               5                   10                  15

Ala Phe Pro Ser
            20
```

<210> SEQ ID NO 51
<211> LENGTH: 20
<212> TYPE: PRT
<213> ORGANISM: Artificial
<220> FEATURE:
<223> OTHER INFORMATION: Synthetic

<400> SEQUENCE: 51

Val Arg Gln Cys Ser Gly Val Thr Phe Gln Gly Lys Phe Lys Lys Ile
1               5                   10                  15

Val Lys Gly Thr
            20

<210> SEQ ID NO 52
<211> LENGTH: 10
<212> TYPE: PRT
<213> ORGANISM: Artificial
<220> FEATURE:
<223> OTHER INFORMATION: Synthetic

<400> SEQUENCE: 52

Ser Ser Asp Glu Val Asp Gly Ser Ser Gly
1               5                   10

<210> SEQ ID NO 53
<211> LENGTH: 14
<212> TYPE: PRT
<213> ORGANISM: Artificial
<220> FEATURE:
<223> OTHER INFORMATION: Synthetic

<400> SEQUENCE: 53

Ser Ser Gly Ser Asp Glu Val Asp Gly Ser Leu Ser Ser Gly
1               5                   10

<210> SEQ ID NO 54
<211> LENGTH: 8
<212> TYPE: PRT
<213> ORGANISM: Artificial
<220> FEATURE:
<223> OTHER INFORMATION: Synthetic

<400> SEQUENCE: 54

Ser Asp Glu Val Asp Gly Ser Leu
1               5

<210> SEQ ID NO 55
<211> LENGTH: 5
<212> TYPE: PRT
<213> ORGANISM: Artificial
<220> FEATURE:
<223> OTHER INFORMATION: Synthetic

<400> SEQUENCE: 55

Asp Glu Val Asp Gly
1               5

<210> SEQ ID NO 56
<211> LENGTH: 7
<212> TYPE: PRT
<213> ORGANISM: Artificial
<220> FEATURE:
<223> OTHER INFORMATION: Synthetic

<400> SEQUENCE: 56

Val Lys Met Asp Ala Glu Phe
1               5

<210> SEQ ID NO 57
<211> LENGTH: 1665
<212> TYPE: DNA
<213> ORGANISM: Artificial
<220> FEATURE:
<223> OTHER INFORMATION: Synthetic

<400> SEQUENCE: 57

```
atgacgtcag caattttaac ggtaatacct ttccaccatg gttttggtat gatgaccaca      60
ttaggatact ttacttgtgg attccgagtt gttctaatgc acacgtttga agaaaaacta     120
tttctacaat cattacaaga ttataaagtg gaaagtactt tacttgtacc aacattaatg     180
gcatttcttg caaaaagtgc attagttgaa agtacgatt tatcgcactt aaaagaaatt      240
gcatctggtg gcgcaccttt atcaaagaa attggggaga tggtgaaaaa acggtttaaa      300
ttaaactttg tcaggcaagg gtatggatta acagaaacca cttcggctgt tttaattaca     360
ccgaaaggtg acgccaaacc gggatcaact ggtaaaatag taccattaca cgctgttaaa     420
gttgtcgatc ctacaacagg aaaaattttg gggccaaatg aacctggaga attgtatttt     480
aaaggcccga tgataatgaa gggttattat aataatgaag aagctactaa agcaattatt     540
gataatgacg gatggttgcg ctctggtgat attgcttatt atgacaatga tggccatttt     600
tatattgtgg acaggctgaa gtcactgatt aaatataaag gttatcaggt tgcacctgct     660
gaaattgagg aatactcttt acaacatccg tatattgttg atgccggcgt tactggtata     720
ccggatgaag ccgcgggcga gcttccagct gcaggtgttg tagtacagac tggaaaatat     780
ctaaacgaac aaatcgtaca agattatgtt gccagtcaag tttcaacagc caaatggcta     840
cgtggtgggg tgaaattttt ggatgaaatt cccaaaggat caactggaaa aattgacaga     900
aaagtgttaa gacaaatgtt agaaaaacac accaatggct cgagcctgga gaccgacggc     960
agctccggtg ataagaatat tttatatggg cccgaaccat tttatccctt ggaagatggg    1020
acggctggag aacagatgtt tgacgcatta tctcgttatg cagctattcc gggctgcata    1080
gcattgacaa atgctcatac aaaagaaaat gttttatatg aagagtttct gaaactgtcg    1140
tgtcgtttag cggaaagttt taaaagtat ggattaaaac aaaacgacac aatagcggtg    1200
tgtagcgaaa atagtctgca attttttcctt cctgtaattg catcattgta tcttggaata    1260
attgtggcac ctgttaacga taaatacatt gaacgtgaat taatacacag tcttggtatt    1320
gtaaaaccac gcatagtttt ttgctccaag aatactttc aaaaagtact gaatgtaaaa     1380
tctaaattaa aatctattga aactattatt atattagact taaatgaaga cttaggaggt    1440
tatcaatgcc tcaacaactt tatttctcaa aattccgata gtaatctgga cgtaaaaaaa    1500
tttaaaccct attctttttaa tcgagacgat caggttgcgt cgattatgtt ttcttctggt    1560
acaactggtc tgccgaaggg agtcatgcta actcacaaga atattgttgc acgattttct    1620
attgcaaaag atcctacttt tggtaacgca attaatcccg tttaa                     1665
```

<210> SEQ ID NO 58
<211> LENGTH: 554
<212> TYPE: PRT
<213> ORGANISM: Artificial
<220> FEATURE:
<223> OTHER INFORMATION: Synthetic

<400> SEQUENCE: 58

```
Met Thr Ser Ala Ile Leu Thr Val Ile Pro Phe His His Gly Phe Gly
1               5                   10                  15

Met Met Thr Thr Leu Gly Tyr Phe Thr Cys Gly Phe Arg Val Val Leu
            20                  25                  30

Met His Thr Phe Glu Glu Lys Leu Phe Leu Gln Ser Leu Gln Asp Tyr
        35                  40                  45

Lys Val Glu Ser Thr Leu Leu Val Pro Thr Leu Met Ala Phe Leu Ala
50                  55                  60

Lys Ser Ala Leu Val Glu Lys Tyr Asp Leu Ser His Leu Lys Glu Ile
65                  70                  75                  80

Ala Ser Gly Gly Ala Pro Leu Ser Lys Glu Ile Gly Glu Met Val Lys
                85                  90                  95

Lys Arg Phe Lys Leu Asn Phe Val Arg Gln Gly Tyr Gly Leu Thr Glu
            100                 105                 110

Thr Thr Ser Ala Val Leu Ile Thr Pro Lys Gly Asp Ala Lys Pro Gly
            115                 120                 125

Ser Thr Gly Lys Ile Val Pro Leu His Ala Val Lys Val Val Asp Pro
        130                 135                 140

Thr Thr Gly Lys Ile Leu Gly Pro Asn Glu Pro Gly Glu Leu Tyr Phe
145                 150                 155                 160

Lys Gly Pro Met Ile Met Lys Gly Tyr Tyr Asn Asn Glu Glu Ala Thr
                165                 170                 175

Lys Ala Ile Ile Asp Asn Asp Gly Trp Leu Arg Ser Gly Asp Ile Ala
            180                 185                 190

Tyr Tyr Asp Asn Asp Gly His Phe Tyr Ile Val Asp Arg Leu Lys Ser
        195                 200                 205

Leu Ile Lys Tyr Lys Gly Tyr Gln Val Ala Pro Ala Glu Ile Glu Gly
210                 215                 220

Ile Leu Leu Gln His Pro Tyr Ile Val Asp Ala Gly Val Thr Gly Ile
225                 230                 235                 240

Pro Asp Glu Ala Ala Gly Glu Leu Pro Ala Ala Gly Val Val Val Gln
                245                 250                 255

Thr Gly Lys Tyr Leu Asn Glu Gln Ile Val Gln Asp Tyr Val Ala Ser
            260                 265                 270

Gln Val Ser Thr Ala Lys Trp Leu Arg Gly Gly Val Lys Phe Leu Asp
        275                 280                 285

Glu Ile Pro Lys Gly Ser Thr Gly Lys Ile Asp Arg Lys Val Leu Arg
        290                 295                 300

Gln Met Leu Glu Lys His Thr Asn Gly Ser Ser Leu Glu Thr Asp Gly
305                 310                 315                 320

Ser Ser Gly Asp Lys Asn Ile Leu Tyr Gly Pro Glu Pro Phe Tyr Pro
                325                 330                 335

Leu Glu Asp Gly Thr Ala Gly Glu Gln Met Phe Asp Ala Leu Ser Arg
            340                 345                 350

Tyr Ala Ala Ile Pro Gly Cys Ile Ala Leu Thr Asn Ala His Thr Lys
            355                 360                 365

Glu Asn Val Leu Tyr Glu Glu Phe Leu Lys Leu Ser Cys Arg Leu Ala
370                 375                 380

Glu Ser Phe Lys Lys Tyr Gly Leu Lys Gln Asn Asp Thr Ile Ala Val
385                 390                 395                 400

Cys Ser Glu Asn Ser Leu Gln Phe Phe Leu Pro Val Ile Ala Ser Leu
                405                 410                 415

Tyr Leu Gly Ile Ile Val Ala Pro Val Asn Asp Lys Tyr Ile Glu Arg
```

|  |  | 420 |  |  |  | 425 |  |  |  | 430 |  |
|--|--|--|--|--|--|--|--|--|--|--|--|

Glu Leu Ile His Ser Leu Gly Ile Val Lys Pro Arg Ile Val Phe Cys
                435                 440                 445

Ser Lys Asn Thr Phe Gln Lys Val Leu Asn Val Lys Ser Lys Leu Lys
            450                 455                 460

Ser Ile Glu Thr Ile Ile Ile Leu Asp Leu Asn Glu Asp Leu Gly Gly
465                 470                 475                 480

Tyr Gln Cys Leu Asn Asn Phe Ile Ser Gln Asn Ser Asp Ser Asn Leu
                485                 490                 495

Asp Val Lys Lys Phe Lys Pro Tyr Ser Phe Asn Arg Asp Asp Gln Val
            500                 505                 510

Ala Ser Ile Met Phe Ser Ser Gly Thr Thr Gly Leu Pro Lys Gly Val
                515                 520                 525

Met Leu Thr His Lys Asn Ile Val Ala Arg Phe Ser Ile Ala Lys Asp
            530                 535                 540

Pro Thr Phe Gly Asn Ala Ile Asn Pro Val
545                 550

<210> SEQ ID NO 59
<211> LENGTH: 1653
<212> TYPE: DNA
<213> ORGANISM: Artificial
<220> FEATURE:
<223> OTHER INFORMATION: Synthetic

<400> SEQUENCE: 59

| atgccggqat | caactggtaa | aatagtacca | ttacacgctg | ttaaagttgt | cgatcctaca | 60 |
|---|---|---|---|---|---|---|
| acaggaaaaa | ttttggggcc | aaatgaacct | ggagaattgt | attttaaagg | cccgatgata | 120 |
| atgaagggtt | attataataa | tgaagaagct | actaaagcaa | ttattgataa | tgacggatgg | 180 |
| ttgcgctctg | gtgatattgc | ttattatgac | aatgatggcc | attttatat | tgtggacagg | 240 |
| ctgaagtcac | tgattaaata | taaaggttat | caggttgcac | ctgctgaaat | tgagggaata | 300 |
| ctcttacaac | atccgtatat | tgttgatgcc | ggcgttactg | gtataccgga | tgaagccgcg | 360 |
| ggcgagcttc | cagctgcagg | tgttgtagta | cagactggaa | aatatctaaa | cgaacaaatc | 420 |
| gtacaagatt | atgttgccag | tcaagtttca | acagccaaat | ggctacgtgg | tggggtgaaa | 480 |
| tttttggatg | aaaattccca | aggatcaact | ggaaaaattg | acagaaaagt | gttaagacaa | 540 |
| atgttagaaa | acacaccaa | tggctcgagc | ctggagaccg | acggcagctc | cgggaaaaac | 600 |
| atcctgtatg | tccggaacc | gttctaccca | ctggaagatg | gtaccgctgg | tgaacagatg | 660 |
| tttgacgcat | tatctcgtta | tgcagctatt | ccgggctgca | tagcattgac | aaatgctcat | 720 |
| acaaagaaa | atgttttata | tgaagagttt | ctgaaactgt | cgtgtcgttt | agcggaaagt | 780 |
| tttaaaaagt | atggattaaa | acaaaacgac | acaatagcgg | tgtgtagcga | aaatagtctg | 840 |
| caattttttcc | ttcctgtaat | tgcatcattg | tatcttggaa | taattgtggc | acctgttaac | 900 |
| gataaataca | ttgaacgtga | attaatacac | agtcttggta | ttgtaaaacc | acgcatagtt | 960 |
| ttttgctcca | gaatactttt | tcaaaaagta | ctgaatgtaa | aatctaaatt | aaaatctatt | 1020 |
| gaaactatta | ttatattaga | cttaaatgaa | gacttaggag | ttatcaatg | cctcaacaac | 1080 |
| tttatttctc | aaaattccga | tagtaatctg | acgtaaaaaa | aatttaaacc | ctattctttt | 1140 |
| aatcgagacg | atcaggttgc | gtcgattatg | ttttcttctg | gtacaactgg | tctgccgaag | 1200 |
| ggagtcatgc | taactcacaa | gaatattgtt | gcacgatttt | ctattgcaaa | agatcctact | 1260 |
| tttggtaacg | caattaatcc | cacgtcagca | attttaacgg | taatacctt | ccaccatggt | 1320 |

-continued

```
tttggtatga tgaccacatt aggatacttt acttgtggat tccgagttgt tctaatgcac   1380
acgtttgaag aaaaactatt tctacaatca ttacaagatt ataaagtgga aagtacttta   1440
cttgtaccaa cattaatggc atttcttgca aaaagtgcat tagttgaaaa gtacgattta   1500
tcgcacttaa aagaaattgc atctggtggc gcacctttat caaaagaaat tggggagatg   1560
gtgaaaaaac ggtttaaatt aaactttgtc aggcaagggt atggattaac agaaaccact   1620
tcggctgttt taattacacc gaaaggtgtt taa                                1653

<210> SEQ ID NO 60
<211> LENGTH: 550
<212> TYPE: PRT
<213> ORGANISM: Artificial
<220> FEATURE:
<223> OTHER INFORMATION: Synthetic

<400> SEQUENCE: 60

Met Pro Gly Ser Thr Gly Lys Ile Val Pro Leu His Ala Val Lys Val
1               5                   10                  15

Val Asp Pro Thr Thr Gly Lys Ile Leu Gly Pro Asn Glu Pro Gly Glu
                20                  25                  30

Leu Tyr Phe Lys Gly Pro Met Ile Met Lys Gly Tyr Tyr Asn Asn Glu
            35                  40                  45

Glu Ala Thr Lys Ala Ile Ile Asp Asn Asp Gly Trp Leu Arg Ser Gly
        50                  55                  60

Asp Ile Ala Tyr Tyr Asp Asn Asp Gly His Phe Tyr Ile Val Asp Arg
65                  70                  75                  80

Leu Lys Ser Leu Ile Lys Tyr Lys Gly Tyr Gln Val Ala Pro Ala Glu
                85                  90                  95

Ile Glu Gly Ile Leu Leu Gln His Pro Tyr Ile Val Asp Ala Gly Val
            100                 105                 110

Thr Gly Ile Pro Asp Glu Ala Ala Gly Glu Leu Pro Ala Ala Gly Val
        115                 120                 125

Val Val Gln Thr Gly Lys Tyr Leu Asn Glu Gln Ile Val Gln Asp Tyr
130                 135                 140

Val Ala Ser Gln Val Ser Thr Ala Lys Trp Leu Arg Gly Gly Val Lys
145                 150                 155                 160

Phe Leu Asp Glu Ile Pro Lys Gly Ser Thr Gly Lys Ile Asp Arg Lys
                165                 170                 175

Val Leu Arg Gln Met Leu Glu Lys His Thr Asn Gly Ser Ser Leu Glu
            180                 185                 190

Thr Asp Gly Ser Ser Gly Lys Asn Ile Leu Tyr Gly Pro Glu Pro Phe
        195                 200                 205

Tyr Pro Leu Glu Asp Gly Thr Ala Gly Glu Gln Met Phe Asp Ala Leu
    210                 215                 220

Ser Arg Tyr Ala Ala Ile Pro Gly Cys Ile Ala Leu Thr Asn Ala His
225                 230                 235                 240

Thr Lys Glu Asn Val Leu Tyr Glu Glu Phe Leu Lys Leu Ser Cys Arg
                245                 250                 255

Leu Ala Glu Ser Phe Lys Lys Tyr Gly Leu Lys Gln Asn Asp Thr Ile
            260                 265                 270

Ala Val Cys Ser Glu Asn Ser Leu Gln Phe Phe Leu Pro Val Ile Ala
        275                 280                 285

Ser Leu Tyr Leu Gly Ile Ile Val Ala Pro Val Asn Asp Lys Tyr Ile
    290                 295                 300
```

| | | | | | | | | | | | |
|---|---|---|---|---|---|---|---|---|---|---|---|
| Glu | Arg | Glu | Leu | Ile | His | Ser | Leu | Gly | Ile | Val | Lys | Pro | Arg | Ile | Val |
| 305 | | | | 310 | | | | | 315 | | | | | 320 | |

Glu Arg Glu Leu Ile His Ser Leu Gly Ile Val Lys Pro Arg Ile Val
305                 310                 315                 320

Phe Cys Ser Lys Asn Thr Phe Gln Lys Val Leu Asn Val Lys Ser Lys
            325                 330                 335

Leu Lys Ser Ile Glu Thr Ile Ile Ile Leu Asp Leu Asn Glu Asp Leu
        340                 345                 350

Gly Gly Tyr Gln Cys Leu Asn Asn Phe Ile Ser Gln Asn Ser Asp Ser
    355                 360                 365

Asn Leu Asp Val Lys Lys Phe Lys Pro Tyr Ser Phe Asn Arg Asp Asp
370                 375                 380

Gln Val Ala Ser Ile Met Phe Ser Ser Gly Thr Thr Gly Leu Pro Lys
385                 390                 395                 400

Gly Val Met Leu Thr His Lys Asn Ile Val Ala Arg Phe Ser Ile Ala
                405                 410                 415

Lys Asp Pro Thr Phe Gly Asn Ala Ile Asn Pro Thr Ser Ala Ile Leu
            420                 425                 430

Thr Val Ile Pro Phe His His Gly Phe Gly Met Met Thr Thr Leu Gly
        435                 440                 445

Tyr Phe Thr Cys Gly Phe Arg Val Val Leu Met His Thr Phe Glu Glu
    450                 455                 460

Lys Leu Phe Leu Gln Ser Leu Gln Asp Tyr Lys Val Glu Ser Thr Leu
465                 470                 475                 480

Leu Val Pro Thr Leu Met Ala Phe Leu Ala Lys Ser Ala Leu Val Glu
                485                 490                 495

Lys Tyr Asp Leu Ser His Leu Lys Glu Ile Ala Ser Gly Gly Ala Pro
            500                 505                 510

Leu Ser Lys Glu Ile Gly Glu Met Val Lys Lys Arg Phe Lys Leu Asn
        515                 520                 525

Phe Val Arg Gln Gly Tyr Gly Leu Thr Glu Thr Thr Ser Ala Val Leu
    530                 535                 540

Ile Thr Pro Lys Gly Val
545                 550

<210> SEQ ID NO 61
<211> LENGTH: 1671
<212> TYPE: DNA
<213> ORGANISM: Artificial
<220> FEATURE:
<223> OTHER INFORMATION: Synthetic

<400> SEQUENCE: 61
atgacgtcag caattttaac ggtaatacct ttccaccatg gttttggtat gatgaccaca      60
ttaggatact ttacttgtgg attccgagtt gttctaatgc acacgtttga agaaaaacta     120
tttctacaat cattacaaga ttataaagtg aaagtactt tacttgtacc aacattaatg      180
gcatttcttg caaaaagtgc attagttgaa aagtacgatt tatcgcactt aaaagaaatt     240
gcatctggtg gcgcaccttt atcaaaagaa attggggaga tggtgaaaaa acggtttaaa     300
ttaaactttg tcaggcaagg gtatggatta acagaaacca cttcggctgt tttaattaca     360
ccgaaaggtg acgccaaacc gggatcaact ggtaaaatag taccattaca cgctgttaaa     420
gttgtcgatc ctacaacagg aaaaattttg ggccaaatg aacctggaga attgtatttt      480
aaaggcccga tgataatgaa gggttattat aataatgaag aagctactaa agcaattatt     540
gataatgacg gatggttgcg ctctggtgat attgcttatt atgacaatga tggccatttt     600

-continued

```
tatattgtgg acaggctgaa gtcactgatt aaatataaag gttatcaggt tgcacctgct    660
gaaattgagg gaatactctt acaacatccg tatattgttg atgccggcgt tactggtata    720
ccggatgaag ccgcgggcga gcttccagct gcaggtgttg tagtacagac tggaaaatat    780
ctaaacgaac aaatcgtaca agattatgtt gccagtcaag tttcaacagc caaatggcta    840
cgtggtgggg tgaaatttt ggatgaaatt cccaaaggat caactggaaa aattgacaga    900
aaagtgttaa gacaaatgtt agaaaaacac accaatggct cgagcgagaa cctgtacttc    960
caatcgagct ccggtgataa gaatatttta tatgggcccg aaccatttta tcccttggaa    1020
gatgggacgg ctggagaaca gatgtttgac gcattatctc gttatgcagc tattccgggc    1080
tgcatagcat tgacaaatgc tcatacaaaa gaaaatgttt tatatgaaga gtttctgaaa    1140
ctgtcgtgtc gtttagcgga aagttttaaa aagtatggat aaaacaaaa cgacacaata    1200 gcggtgtgta gcgaaaatag tctgcaattt ttccttcctg taattgcatc attgtatctt    1260
ggaataattg tggcacctgt taacgataaa tacattgaac gtgaattaat acacagtctt    1320
ggtattgtaa aaccacgcat agttttttgc tccaagaata cttttcaaaa agtactgaat    1380
gtaaaatcta aattaaaatc tattgaaact attattatat tagacttaaa tgaagactta    1440
ggaggttatc aatgcctcaa caactttatt tctcaaaatt ccgatagtaa tctggacgta    1500
aaaaaattta acccctattc ttttaatcga gacgatcagg ttgcgtcgat tatgttttct    1560
tctggtacaa ctggtctgcc gaagggagtc atgctaactc acaagaatat tgttgcacga    1620
ttttctattg caaaagatcc tactttggt aacgcaatta atcccgttta a             1671
```

<210> SEQ ID NO 62
<211> LENGTH: 556
<212> TYPE: PRT
<213> ORGANISM: Artificial
<220> FEATURE:
<223> OTHER INFORMATION: Synthetic

<400> SEQUENCE: 62

```
Met Thr Ser Ala Ile Leu Thr Val Ile Pro Phe His His Gly Phe Gly
1               5                  10                  15

Met Met Thr Thr Leu Gly Tyr Phe Thr Cys Gly Phe Arg Val Val Leu
            20                  25                  30

Met His Thr Phe Glu Glu Lys Leu Phe Leu Gln Ser Leu Gln Asp Tyr
        35                  40                  45

Lys Val Glu Ser Thr Leu Leu Val Pro Thr Leu Met Ala Phe Leu Ala
    50                  55                  60

Lys Ser Ala Leu Val Glu Lys Tyr Asp Leu Ser His Leu Lys Glu Ile
65                  70                  75                  80

Ala Ser Gly Gly Ala Pro Leu Ser Lys Glu Ile Gly Glu Met Val Lys
                85                  90                  95

Lys Arg Phe Lys Leu Asn Phe Val Arg Gln Gly Tyr Gly Leu Thr Glu
            100                 105                 110

Thr Thr Ser Ala Val Leu Ile Thr Pro Lys Gly Asp Ala Lys Pro Gly
        115                 120                 125

Ser Thr Gly Lys Ile Val Pro Leu His Ala Val Lys Val Val Asp Pro
    130                 135                 140

Thr Thr Gly Lys Ile Leu Gly Pro Asn Glu Pro Gly Glu Leu Tyr Phe
145                 150                 155                 160

Lys Gly Pro Met Ile Met Lys Gly Tyr Tyr Asn Asn Glu Glu Ala Thr
                165                 170                 175
```

```
Lys Ala Ile Ile Asp Asn Asp Gly Trp Leu Arg Ser Gly Asp Ile Ala
                180                 185                 190

Tyr Tyr Asp Asn Asp Gly His Phe Tyr Ile Val Asp Arg Leu Lys Ser
            195                 200                 205

Leu Ile Lys Tyr Lys Gly Tyr Gln Val Ala Pro Ala Glu Ile Glu Gly
        210                 215                 220

Ile Leu Leu Gln His Pro Tyr Ile Val Asp Ala Gly Val Thr Gly Ile
225                 230                 235                 240

Pro Asp Glu Ala Ala Gly Glu Leu Pro Ala Gly Val Val Gln
                245                 250                 255

Thr Gly Lys Tyr Leu Asn Glu Gln Ile Val Gln Asp Tyr Val Ala Ser
            260                 265                 270

Gln Val Ser Thr Ala Lys Trp Leu Arg Gly Val Lys Phe Leu Asp
        275                 280                 285

Glu Ile Pro Lys Gly Ser Thr Gly Lys Ile Asp Arg Lys Val Leu Arg
            290                 295                 300

Gln Met Leu Glu Lys His Thr Asn Gly Ser Ser Glu Asn Leu Tyr Phe
305                 310                 315                 320

Gln Ser Ser Ser Gly Asp Lys Asn Ile Leu Tyr Gly Pro Glu Pro Phe
                325                 330                 335

Tyr Pro Leu Glu Asp Gly Thr Ala Gly Glu Gln Met Phe Asp Ala Leu
            340                 345                 350

Ser Arg Tyr Ala Ala Ile Pro Gly Cys Ile Ala Leu Thr Asn Ala His
        355                 360                 365

Thr Lys Glu Asn Val Leu Tyr Glu Glu Phe Leu Lys Leu Ser Cys Arg
370                 375                 380

Leu Ala Glu Ser Phe Lys Lys Tyr Gly Leu Lys Gln Asn Asp Thr Ile
385                 390                 395                 400

Ala Val Cys Ser Glu Asn Ser Leu Gln Phe Phe Leu Pro Val Ile Ala
                405                 410                 415

Ser Leu Tyr Leu Gly Ile Ile Val Ala Pro Val Asn Asp Lys Tyr Ile
            420                 425                 430

Glu Arg Glu Leu Ile His Ser Leu Gly Ile Val Lys Pro Arg Ile Val
        435                 440                 445

Phe Cys Ser Lys Asn Thr Phe Gln Lys Val Leu Asn Val Lys Ser Lys
450                 455                 460

Leu Lys Ser Ile Glu Thr Ile Ile Ile Leu Asp Leu Asn Glu Asp Leu
465                 470                 475                 480

Gly Gly Tyr Gln Cys Leu Asn Asn Phe Ile Ser Gln Asn Ser Asp Ser
                485                 490                 495

Asn Leu Asp Val Lys Lys Phe Lys Pro Tyr Ser Phe Asn Arg Asp Asp
            500                 505                 510

Gln Val Ala Ser Ile Met Phe Ser Ser Gly Thr Thr Gly Leu Pro Lys
        515                 520                 525

Gly Val Met Leu Thr His Lys Asn Ile Val Ala Arg Phe Ser Ile Ala
530                 535                 540

Lys Asp Pro Thr Phe Gly Asn Ala Ile Asn Pro Val
545                 550                 555
```

<210> SEQ ID NO 63
<211> LENGTH: 1671
<212> TYPE: DNA
<213> ORGANISM: Artificial
<220> FEATURE:
<223> OTHER INFORMATION: Synthetic

<400> SEQUENCE: 63

```
atgaccgcta tcctcagcgt ggtgccattt caccacggct tcggcatgtt caccacgctg      60
ggctacttga tctgcggctt tcgggtcgtg ctcatgtacc gcttcgagga ggagctattc     120
ttgcgcagct tgcaagacta taagattcaa tctgccctgc tggtgcccac actatttagc     180
ttcttcgcta agagcactct catcgacaag tacgacctaa gcaacttgca cgagatcgcc     240
agcggcgggg cgccgctcag caaggaggta ggtgaggccg tggccaaacg cttccaccta     300
ccaggcatcc gccagggcta cggcctgaca gaaacaacca gcgccattct gatcaccccc     360
gaaggggacg acaagcctgg cgcagtaggc aaggtggtgc ccttcttcga ggctaaggtg     420
gtggacttgg acaccggtaa gacactgggt gtgaaccagc gcggcgagct gtgcgtccgt     480
ggccccatga tcatgagcgg ctacgttaac aaccccgagg ctacaaacgc tctcatcgac     540
aaggacggct ggctgcacag cggcgacatc gcctactggg acgaggacga gcacttcttc     600
atcgtggacc ggctgaagag cctgatcaaa tacaagggct accaggtagc cccagccgaa     660
ctggagagca tcctgctgca cacccccaac atcttcgacg ccggggtcgc cggcctgccc     720
gacgacgatg ccgcgagct gcccgccgca gtcgtcgtgc tggaacacgg taaaaccatg     780
accgagaagg agatcgtgga ctatgtggcc agccaggtta caaccgccaa gaagctgcgc     840
ggtggtgttg tgttcgtgga cgaggtgcct aaaggactga ccggcaagtt ggacgcccgc     900
aagatccgcg agattctcat taaggccaag aagggctcga gcgagaacct gtacttccaa     960
tcgagctccg gtgccaaaaa cattaagaag ggcccagcgc cattctaccc actcgaagac    1020
gggaccgccg gcgagcagct gcacaaagcc atgaagcgct acgccctggt gcccggcacc    1080
atcgccttta ccgacgcaca tatcgaggtg acattacct acgccgagta cttcgagatg    1140
agcgttcggc tggcagaagc tatgaagcgc tatgggctga atacaaacca tcggatcgtg    1200
gtgtgcagcg agaatagctt gcagttcttc atgcccgtgt gggtgccct gttcatcggt    1260
gtggctgtgg ccccagctaa cgacatctac aacgagcgcg agctgctgaa cagcatgggc    1320
atcagccagc ccaccgtcgt attcgtgagc aagaaagggc tgcaaaagat cctcaacgtg    1380
caaaagaagc taccgatcat acaaaagatc atcatcatgg atagcaagac cgactaccag    1440
ggcttccaaa gcatgtacac cttcgtgact tcccatttgc acccggctt caacgagtac    1500
gacttcgtgc ccgagagctt cgaccgggac aaaaccatcg ccctgatcat gaacagtagt    1560
ggcagtaccg gattgcccaa gggcgtagcc ctaccgcacc gcaccgcttg tgtccgattc    1620
agtcatgccc gcgaccccat cttcggcaac cagatcatcc cctgagttta a            1671
```

<210> SEQ ID NO 64  
<211> LENGTH: 554  
<212> TYPE: PRT  
<213> ORGANISM: Artificial  
<220> FEATURE:  
<223> OTHER INFORMATION: Synthetic

<400> SEQUENCE: 64

```
Met Thr Ala Ile Leu Ser Val Val Pro Phe His His Gly Phe Gly Met
1               5                   10                  15

Phe Thr Thr Leu Gly Tyr Leu Ile Cys Gly Phe Arg Val Val Leu Met
            20                  25                  30

Tyr Arg Phe Glu Glu Glu Leu Phe Leu Arg Ser Leu Gln Asp Tyr Lys
        35                  40                  45

Ile Gln Ser Ala Leu Leu Val Pro Thr Leu Phe Ser Phe Phe Ala Lys
```

```
            50                  55                  60
Ser Thr Leu Ile Asp Lys Tyr Asp Leu Ser Asn Leu His Glu Ile Ala
 65                  70                  75                  80

Ser Gly Gly Ala Pro Leu Ser Lys Glu Val Gly Ala Val Ala Lys
                 85                  90                  95

Arg Phe His Leu Pro Gly Ile Arg Gln Gly Tyr Gly Leu Thr Glu Thr
                100                 105                 110

Thr Ser Ala Ile Leu Ile Thr Pro Glu Gly Asp Asp Lys Pro Gly Ala
                115                 120                 125

Val Gly Lys Val Val Pro Phe Phe Glu Ala Lys Val Val Asp Leu Asp
    130                 135                 140

Thr Gly Lys Thr Leu Gly Val Asn Gln Arg Gly Glu Leu Cys Val Arg
145                 150                 155                 160

Gly Pro Met Ile Met Ser Gly Tyr Val Asn Asn Pro Glu Ala Thr Asn
                165                 170                 175

Ala Leu Ile Asp Lys Asp Gly Trp Leu His Ser Gly Asp Ile Ala Tyr
                180                 185                 190

Trp Asp Glu Asp Glu His Phe Phe Ile Val Asp Arg Leu Lys Ser Leu
                195                 200                 205

Ile Lys Tyr Lys Gly Tyr Gln Val Ala Pro Ala Glu Leu Glu Ser Ile
    210                 215                 220

Leu Leu Gln His Pro Asn Ile Phe Asp Ala Gly Val Ala Gly Leu Pro
225                 230                 235                 240

Asp Asp Asp Ala Gly Glu Leu Pro Ala Ala Val Val Val Leu Glu His
                245                 250                 255

Gly Lys Thr Met Thr Glu Lys Glu Ile Val Asp Tyr Val Ala Ser Gln
                260                 265                 270

Val Thr Thr Ala Lys Lys Leu Arg Gly Gly Val Val Phe Val Asp Glu
                275                 280                 285

Val Pro Lys Gly Leu Thr Gly Lys Leu Asp Ala Arg Lys Ile Arg Glu
    290                 295                 300

Ile Leu Ile Lys Ala Lys Lys Gly Ser Ser Glu Asn Leu Tyr Phe Gln
305                 310                 315                 320

Ser Ser Ser Gly Ala Lys Asn Ile Lys Lys Gly Pro Ala Pro Phe Tyr
                325                 330                 335

Pro Leu Glu Asp Gly Thr Ala Gly Glu Gln Leu His Lys Ala Met Lys
                340                 345                 350

Arg Tyr Ala Leu Val Pro Gly Thr Ile Ala Phe Thr Asp Ala His Ile
                355                 360                 365

Glu Val Asp Ile Thr Tyr Ala Glu Tyr Phe Glu Met Ser Val Arg Leu
                370                 375                 380

Ala Glu Ala Met Lys Arg Tyr Gly Leu Asn Thr Asn His Arg Ile Val
385                 390                 395                 400

Val Cys Ser Glu Asn Ser Leu Gln Phe Phe Met Pro Val Leu Gly Ala
                405                 410                 415

Leu Phe Ile Gly Val Ala Val Ala Pro Ala Asn Asp Ile Tyr Asn Glu
                420                 425                 430

Arg Glu Leu Leu Asn Ser Met Gly Ile Ser Gln Pro Thr Val Val Phe
                435                 440                 445

Val Ser Lys Lys Gly Leu Gln Lys Ile Leu Asn Val Gln Lys Lys Leu
    450                 455                 460

Pro Ile Ile Gln Lys Ile Ile Ile Met Asp Ser Lys Thr Asp Tyr Gln
465                 470                 475                 480
```

```
Gly Phe Gln Ser Met Tyr Thr Phe Val Thr Ser His Leu Pro Pro Gly
            485                 490                 495

Phe Asn Glu Tyr Asp Phe Val Pro Glu Ser Phe Asp Arg Asp Lys Thr
        500                 505                 510

Ile Ala Leu Ile Met Asn Ser Ser Gly Ser Thr Gly Leu Pro Lys Gly
        515                 520                 525

Val Ala Leu Pro His Arg Thr Ala Cys Val Arg Phe Ser His Ala Arg
        530                 535                 540

Asp Pro Ile Phe Gly Asn Gln Ile Ile Pro
545                 550
```

<210> SEQ ID NO 65
<211> LENGTH: 1671
<212> TYPE: DNA
<213> ORGANISM: Artificial
<220> FEATURE:
<223> OTHER INFORMATION: Synthetic

<400> SEQUENCE: 65

| | | | | | |
|---|---|---|---|---|---|
| atggaggagg | agctattctt | gcgcagcttg | caagactata | agattcaatc | tgccctgctg | 60 |
| gtgcccacac | tatttagctt | cttcgctaag | agcactctca | tcgacaagta | cgacctaagc | 120 |
| aacttgcacg | agatcgccag | cggcggggcg | ccgctcagca | aggaggtagg | tgaggccgtg | 180 |
| gccaaacgct | tccacctacc | aggcatccgc | cagggctacg | gcctgacaga | aacaaccagc | 240 |
| gccattctga | tcaccccga | aggggacgac | aagcctggcg | cagtaggcaa | ggtggtgccc | 300 |
| ttcttcgagg | ctaaggtggt | ggacttggac | accggtaaga | cactgggtgt | gaaccagcgc | 360 |
| ggcgagctgt | gcgtccgtgg | ccccatgatc | atgagcggct | acgttaacaa | ccccgaggct | 420 |
| acaaacgctc | tcatcgacaa | ggacggctgg | ctgcacagcg | gcgacatcgc | ctactgggac | 480 |
| gaggacgagc | acttcttcat | cgtggaccgg | ctgaagagcc | tgatcaaata | caagggctac | 540 |
| caggtagccc | cagccgaact | ggagagcatc | ctgctgcaac | accccaacat | cttcgacgcc | 600 |
| ggggtcgccg | gcctgcccga | cgacgatgcc | ggcgagctgc | cgccgcagt | cgtcgtgctg | 660 |
| gaacacggta | aaaccatgac | cgagaaggag | atcgtggact | atgtggccag | ccaggttaca | 720 |
| accgccaaga | agctgcgcgg | tggtgttgtg | ttcgtggacg | aggtgcctaa | aggactgacc | 780 |
| ggcaagttgg | acgcccgcaa | gatccgcgag | attctcatta | aggccaagaa | gggctcgagc | 840 |
| gagaacctgt | acttccaatc | gagctccggt | gccaaaaaca | ttaagaaggg | cccagcgcca | 900 |
| ttctacccac | tcgaagacgg | gaccgccggc | gagcagctgc | acaaagccat | gaagcgctac | 960 |
| gccctggtgc | ccggcaccat | cgcctttacc | gacgcacata | tcgaggtgga | cattacctac | 1020 |
| gccgagtact | tcgagatgag | cgttcggctg | gcagaagcta | tgaagcgcta | tgggctgaat | 1080 |
| acaaaccatc | ggatcgtggt | gtgcagcgag | aatagcttgc | agttcttcat | gcccgtgttg | 1140 |
| ggtgccctgt | tcatcggtgt | ggctgtggcc | ccagctaacg | acatctacaa | cgagcgcgag | 1200 |
| ctgctgaaca | gcatgggcat | cagccagccc | accgtcgtat | tcgtgagcaa | gaaagggctg | 1260 |
| caaaagatcc | tcaacgtgca | aaagaagcta | ccgatcatac | aaaagatcat | catcatggat | 1320 |
| agcaagaccg | actaccaggg | cttccaaagc | atgtacacct | tcgtgacttc | ccatttgcca | 1380 |
| cccggcttca | acgagtacga | cttcgtgccc | gagagcttcg | accgggacaa | aaccatcgcc | 1440 |
| ctgatcatga | acagtagtgg | cagtaccgga | ttgcccaagg | gcgtagccct | accgcaccgc | 1500 |
| accgcttgtg | tccgattcag | tcatgcccgc | gaccccatct | tcggcaacca | gatcatcccc | 1560 |
| gacaccgcta | tcctcagcgt | ggtgccattt | caccacggct | tcggcatgtt | caccacgctg | 1620 |

```
ggctacttga tctgcggctt tcgggtcgtg ctcatgtacc gctgagttta a          1671
```

<210> SEQ ID NO 66
<211> LENGTH: 554
<212> TYPE: PRT
<213> ORGANISM: Artificial
<220> FEATURE:
<223> OTHER INFORMATION: Synthetic

<400> SEQUENCE: 66

Met Glu Glu Glu Leu Phe Leu Arg Ser Leu Gln Asp Tyr Lys Ile Gln
1               5                   10                  15

Ser Ala Leu Leu Val Pro Thr Leu Phe Ser Phe Phe Ala Lys Ser Thr
            20                  25                  30

Leu Ile Asp Lys Tyr Asp Leu Ser Asn Leu His Glu Ile Ala Ser Gly
        35                  40                  45

Gly Ala Pro Leu Ser Lys Glu Val Gly Glu Ala Val Ala Lys Arg Phe
    50                  55                  60

His Leu Pro Gly Ile Arg Gln Gly Tyr Gly Leu Thr Glu Thr Thr Ser
65                  70                  75                  80

Ala Ile Leu Ile Thr Pro Glu Gly Asp Asp Lys Pro Gly Ala Val Gly
                85                  90                  95

Lys Val Val Pro Phe Phe Glu Ala Lys Val Val Asp Leu Asp Thr Gly
            100                 105                 110

Lys Thr Leu Gly Val Asn Gln Arg Gly Glu Leu Cys Val Arg Gly Pro
        115                 120                 125

Met Ile Met Ser Gly Tyr Val Asn Asn Pro Glu Ala Thr Asn Ala Leu
    130                 135                 140

Ile Asp Lys Asp Gly Trp Leu His Ser Gly Asp Ile Ala Tyr Trp Asp
145                 150                 155                 160

Glu Asp Glu His Phe Phe Ile Val Asp Arg Leu Lys Ser Leu Ile Lys
                165                 170                 175

Tyr Lys Gly Tyr Gln Val Ala Pro Ala Glu Leu Glu Ser Ile Leu Leu
            180                 185                 190

Gln His Pro Asn Ile Phe Asp Ala Gly Val Ala Gly Leu Pro Asp Asp
        195                 200                 205

Asp Ala Gly Glu Leu Pro Ala Ala Val Val Val Leu Glu His Gly Lys
    210                 215                 220

Thr Met Thr Glu Lys Glu Ile Val Asp Tyr Val Ala Ser Gln Val Thr
225                 230                 235                 240

Thr Ala Lys Lys Leu Arg Gly Gly Val Val Phe Val Asp Glu Val Pro
                245                 250                 255

Lys Gly Leu Thr Gly Lys Leu Asp Ala Arg Lys Ile Arg Glu Ile Leu
            260                 265                 270

Ile Lys Ala Lys Lys Gly Ser Ser Glu Asn Leu Tyr Phe Gln Ser Ser
        275                 280                 285

Ser Gly Ala Lys Asn Ile Lys Lys Gly Pro Ala Pro Phe Tyr Pro Leu
    290                 295                 300

Glu Asp Gly Thr Ala Gly Glu Gln Leu His Lys Ala Met Lys Arg Tyr
305                 310                 315                 320

Ala Leu Val Pro Gly Thr Ile Ala Phe Thr Asp Ala His Ile Glu Val
                325                 330                 335

Asp Ile Thr Tyr Ala Glu Tyr Phe Glu Met Ser Val Arg Leu Ala Glu
            340                 345                 350

Ala Met Lys Arg Tyr Gly Leu Asn Thr Asn His Arg Ile Val Val Cys
            355                 360                 365

Ser Glu Asn Ser Leu Gln Phe Phe Met Pro Val Leu Gly Ala Leu Phe
    370                 375                 380

Ile Gly Val Ala Val Ala Pro Ala Asn Asp Ile Tyr Asn Glu Arg Glu
385                 390                 395                 400

Leu Leu Asn Ser Met Gly Ile Ser Gln Pro Thr Val Val Phe Val Ser
                405                 410                 415

Lys Lys Gly Leu Gln Lys Ile Leu Asn Val Gln Lys Lys Leu Pro Ile
                420                 425                 430

Ile Gln Lys Ile Ile Ile Met Asp Ser Lys Thr Asp Tyr Gln Gly Phe
            435                 440                 445

Gln Ser Met Tyr Thr Phe Val Thr Ser His Leu Pro Pro Gly Phe Asn
    450                 455                 460

Glu Tyr Asp Phe Val Pro Glu Ser Phe Asp Arg Asp Lys Thr Ile Ala
465                 470                 475                 480

Leu Ile Met Asn Ser Ser Gly Ser Thr Gly Leu Pro Lys Gly Val Ala
                485                 490                 495

Leu Pro His Arg Thr Ala Cys Val Arg Phe Ser His Ala Arg Asp Pro
                500                 505                 510

Ile Phe Gly Asn Gln Ile Ile Pro Asp Thr Ala Ile Leu Ser Val Val
            515                 520                 525

Pro Phe His His Gly Phe Gly Met Phe Thr Thr Leu Gly Tyr Leu Ile
    530                 535                 540

Cys Gly Phe Arg Val Val Leu Met Tyr Arg
545                 550

<210> SEQ ID NO 67
<211> LENGTH: 1662
<212> TYPE: DNA
<213> ORGANISM: Artificial
<220> FEATURE:
<223> OTHER INFORMATION: Synthetic

<400> SEQUENCE: 67
atgcctggcg cagtaggcaa ggtggtgccc ttcttcgagg ctaaggtggt ggacttggac      60
actggtaaga cactgggtgt gaaccagcgc ggcgagctgt gcgtccgtgg ccccatgatc     120
atgagcggct acgttaacaa ccccgaggct acaaacgctc tcatcgacaa ggacggctgg     180
ctgcacagcg gcgacatcgc ctactgggac gaggacgagc acttcttcat cgtggaccgg     240
ctgaagagcc tgatcaaata caagggctac caggtagccc cagccgaact ggagagcatc     300
ctgctgcaac accccaacat cttcgacgcc ggggtcgccg cctgcccga cgacgatgcc      360 ggcgagctgc ccgccgcagt cgtcgtgctg aacacggta aaaccatgac cgagaaggag      420
atcgtggact atgtggccag ccaggttaca accgccaaga agctgcgcgg tggtgttgtg     480
ttcgtggacg aggtgcctaa aggactgacc ggcaagttgg acgcccgcaa gatccgcgag     540
attctcatta aggccaagaa gggctcgagc gagaacctgt acttccaatc gagctccggt     600
gccaaaaaca ttaagaaggg cccagcgcca ttctacccac tcgaagacgg gaccgccggc     660
gagcagctgc acaaagccat gaagcgctac gccctggtgc ccggcaccat cgcctttacc     720
gacgcacata tcgaggtgga cattacctac gccgagtact tcgagatgag cgttcggctg     780
gcagaagcta tgaagcgcta tgggctgaat acaaaccatc ggatcgtggt gtgcagcgag     840
aatagcttgc agttcttcat gcccgtgttg ggtgcccctgt tcatcggtgt ggctgtggcc     900

```
ccagctaacg acatctacaa cgagcgcgag ctgctgaaca gcatgggcat cagccagccc    960
accgtcgtat tcgtgagcaa gaaagggctg caaaagatcc tcaacgtgca aaagaagcta   1020
ccgatcatac aaaagatcat catcatggat agcaagaccg actaccaggg cttccaaagc   1080
atgtacacct tcgtgacttc ccatttgcca cccggcttca acgagtacga cttcgtgccc   1140
gagagcttcg accgggacaa aaccatcgcc ctgatcatga acagtagtgg cagtaccgga   1200
ttgcccaagg gcgtagccct accgcaccgc accgcttgtg tccgattcag tcatgcccgc   1260
gaccccatct tcggcaacca gatcatcccc gacaccgcta tcctcagcgt ggtgccattt   1320
caccacggct tcggcatgtt caccacgctg ggctacttga tctgcggctt tcgggtcgtg   1380
ctcatgtacc gcttcgagga ggagctattc ttgcgcagct gcaagactaa taagattcaa   1440
tctgccctgc tggtgcccac actatttagc ttcttcgcta agagcactct catcgacaag   1500
tacgacctaa gcaacttgca cgagatcgcc agcggcgggg cgccgctcag caaggaggta   1560
ggtgaggccg tggccaaacg cttccaccta ccaggcatcc gccagggcta cggcctgaca   1620
gaaacaacca gcgccattct gatcactcca gaagggggttt aa                    1662
```

<210> SEQ ID NO 68
<211> LENGTH: 553
<212> TYPE: PRT
<213> ORGANISM: Artificial
<220> FEATURE:
<223> OTHER INFORMATION: Synthetic

<400> SEQUENCE: 68

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Glu Asn
            180                 185                 190

Leu Tyr Phe Gln Ser Ser Ser Gly Ala Lys Asn Ile Lys Lys Gly Pro
        195                 200                 205

Ala Pro Phe Tyr Pro Leu Glu Asp Gly Thr Ala Gly Glu Gln Leu His
    210                 215                 220

Lys Ala Met Lys Arg Tyr Ala Leu Val Pro Gly Thr Ile Ala Phe Thr
```

```
                225                 230                 235                 240
Asp Ala His Ile Glu Val Asp Ile Thr Tyr Ala Glu Tyr Phe Glu Met
                    245                 250                 255
Ser Val Arg Leu Ala Glu Ala Met Lys Arg Tyr Gly Leu Asn Thr Asn
                260                 265                 270
His Arg Ile Val Val Cys Ser Glu Asn Ser Leu Gln Phe Met Pro
            275                 280                 285
Val Leu Gly Ala Leu Phe Ile Gly Val Ala Val Ala Pro Ala Asn Asp
        290                 295                 300
Ile Tyr Asn Glu Arg Glu Leu Leu Asn Ser Met Gly Ile Ser Gln Pro
305                 310                 315                 320
Thr Val Val Phe Val Ser Lys Lys Gly Leu Gln Lys Ile Leu Asn Val
                325                 330                 335
Gln Lys Lys Leu Pro Ile Ile Gln Lys Ile Ile Met Asp Ser Lys
                340                 345                 350
Thr Asp Tyr Gln Gly Phe Gln Ser Met Tyr Thr Phe Val Thr Ser His
                355                 360                 365
Leu Pro Pro Gly Phe Asn Glu Tyr Asp Phe Val Pro Glu Ser Phe Asp
    370                 375                 380
Arg Asp Lys Thr Ile Ala Leu Ile Met Asn Ser Ser Gly Ser Thr Gly
385                 390                 395                 400
Leu Pro Lys Gly Val Ala Leu Pro His Arg Thr Ala Cys Val Arg Phe
                405                 410                 415
Ser His Ala Arg Asp Pro Ile Phe Gly Asn Gln Ile Ile Pro Asp Thr
            420                 425                 430
Ala Ile Leu Ser Val Val Pro Phe His His Gly Phe Gly Met Phe Thr
        435                 440                 445
Thr Leu Gly Tyr Leu Ile Cys Gly Phe Arg Val Val Leu Met Tyr Arg
    450                 455                 460
Phe Glu Glu Glu Leu Phe Leu Arg Ser Leu Gln Asp Tyr Lys Ile Gln
465                 470                 475                 480
Ser Ala Leu Leu Val Pro Thr Leu Phe Ser Phe Phe Ala Lys Ser Thr
                485                 490                 495
Leu Ile Asp Lys Tyr Asp Leu Ser Asn Leu His Glu Ile Ala Ser Gly
                500                 505                 510
Gly Ala Pro Leu Ser Lys Glu Val Gly Glu Ala Val Ala Lys Arg Phe
            515                 520                 525
His Leu Pro Gly Ile Arg Gln Gly Tyr Gly Leu Thr Glu Thr Thr Ser
        530                 535                 540
Ala Ile Leu Ile Thr Pro Glu Gly Val
545                 550

<210> SEQ ID NO 69
<211> LENGTH: 2385
<212> TYPE: DNA
<213> ORGANISM: Artificial
<220> FEATURE:
<223> OTHER INFORMATION: Synthetic

<400> SEQUENCE: 69
atgtccccta ctaggttta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attggggttg gagtttccca atcttcctta ttatattgat     180
ggtgatgtta aattaacaca gtctatggcc atcatacgtt atatagctga caagcacaac     240
```

```
atgttgggtg gttgtccaaa agagcgtgca gagatttcaa tgcttgaagg agcggttttg      300
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttga atggtgatca tgtaacccat cctgacttca tgttgtatga cgctcttgat      480
gttgttttat acatggaccc aatgtgcctg gatgcgttcc caaaattagt ttgtttcaaa      540
aaacgtattg aagctatccc acaaattgat aagtacttga atccagcaa gtatatagca       600 tggcctttgc agggctggca agccacgttt ggtggtggcg accatcctcc aaaatccgga      660
ggtggtggcg gagaaaacct gtacttccaa gcgatcgcca tgccgggatc aactggtaaa      720
atagtaccat tacacgctgt taaagttgtc gatcctacaa caggaaaaat tttggggcca      780
aatgaacctg gagaattgta ttttaaaggc ccgatgataa tgaagggtta ttataataat      840
gaagaagcta ctaaagcaat tattgataat gacggatggt tgcgctctgg tgatattgct      900
tattatgaca atgatggcca ttttatatt gtggacaggc tgaagtcact gattaaatat       960
aaaggttatc aggttgcacc tgctgaaatt gagggaatac tcttacaaca tccgtatatt     1020
gttgatgccg gcgttactgg tataccggat gaagccgcgg gcgagcttcc agctgcaggt     1080
gttgtagtac agactggaaa atatctaaac gaacaaatcg tacaagatta tgttgccagt     1140
caagtttcaa tagccaaatg gctacgtggt ggggtgaaat tttggatga aattcccaaa      1200 ggatcaactg gaaaaattga cagaaaagtg ttaagacaaa tgttagaaaa acacaccaat     1260
ggatccccgt tgggaatgtg gagtcgaagc ttgaaaaaca tcctgtatgg tccggaaccg     1320
ttctacccac tggaagatgg taccgctggt gaacagatgt ttgacgcatt atctcgttat     1380
gcagctattc cgggctgcat agcattgaca aatgctcata caaagaaaa tgttttatat     1440 gaagagtttc tgaaactgtc gtgtcgttta gcggaaagtt ttaaaagta tggattaaaa      1500 caaaacgaca caatagcggt gtgtagcgaa aatagtctgc aattttttcct tcctgtaatt    1560 gcatcattgt atcttggaat aattgtggca cctgttaacg ataaatacat tgaacgtgaa     1620
ttaatacaca gtcttggtat tgtaaaacca cgcatagttt tttgctccaa gaatactttt     1680
caaaaagtac tgaatgtaaa atctaaatta aaatctattg aaactattat tatattagac     1740
ttaaatgaag acttaggagg ttatcaatgc ctcaacaact ttatttctca aaattccgat     1800
agtaatctgg acgtaaaaaa atttaaaccc tattctttta atcgagacga tcaggttgcg     1860
tcgattatgt tttcttctgg tacaactggt ctgccgaagg gagtcatgct aactcacaag     1920
aatattgttg cacgattttc tattgcaaaa gatcctactt tggtaacgc aattaatccc      1980 acgtcagcaa ttttaacggt aataccttc caccatggtt ttggtatgat gaccacatta      2040
ggatacttta cttgtggatt ccgagttgtt ctaatgcaca cgtttgaaga aaactatttt     2100
ctacaatcat tacaagatta taagtggaa agtactttac ttgtaccaac attaatggca      2160
tttcttgcaa aaagtgcatt agttgaaaag tacgatttat cgcacttaaa agaaattgca     2220
tctggtggcg cacctttatc aaaagaaatt ggggagatgg tgaaaaaacg gtttaaatta     2280
aactttgtca ggcaagggta tggattaaca gaaccacttc ggctgttttt aattacaccg     2340
aaaggtgttt ctcaccaaca ccaacaccag caccaacacc agtaa                     2385
```

<210> SEQ ID NO 70
<211> LENGTH: 794
<212> TYPE: PRT
<213> ORGANISM: Artificial
<220> FEATURE:

<223> OTHER INFORMATION: Synthetic

<400> SEQUENCE: 70

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Gly Gly Gly Gly
    210                 215                 220

Glu Asn Leu Tyr Phe Gln Ala Ile Ala Met Pro Gly Ser Thr Gly Lys
225                 230                 235                 240

Ile Val Pro Leu His Ala Val Lys Val Val Asp Pro Thr Thr Gly Lys
                245                 250                 255

Ile Leu Gly Pro Asn Glu Pro Gly Glu Leu Tyr Phe Lys Gly Pro Met
            260                 265                 270

Ile Met Lys Gly Tyr Tyr Asn Asn Glu Glu Ala Thr Lys Ala Ile Ile
        275                 280                 285

Asp Asn Asp Gly Trp Leu Arg Ser Gly Asp Ile Ala Tyr Tyr Asp Asn
    290                 295                 300

Asp Gly His Phe Tyr Ile Val Asp Arg Leu Lys Ser Leu Ile Lys Tyr
305                 310                 315                 320

Lys Gly Tyr Gln Val Ala Pro Ala Glu Ile Glu Gly Ile Leu Leu Gln
                325                 330                 335

His Pro Tyr Ile Val Asp Ala Gly Val Thr Gly Ile Pro Asp Glu Ala
            340                 345                 350

Ala Gly Glu Leu Pro Ala Ala Gly Val Val Gln Thr Gly Lys Tyr
        355                 360                 365

Leu Asn Glu Gln Ile Val Gln Asp Tyr Val Ala Ser Gln Val Ser Ile
    370                 375                 380

Ala Lys Trp Leu Arg Gly Gly Val Lys Phe Leu Asp Glu Ile Pro Lys
385                 390                 395                 400
```

Gly Ser Thr Gly Lys Ile Asp Arg Lys Val Leu Arg Gln Met Leu Glu
            405                 410                 415

Lys His Thr Asn Gly Ser Pro Leu Gly Met Trp Ser Arg Ser Leu Lys
        420                 425                 430

Asn Ile Leu Tyr Gly Pro Glu Pro Phe Tyr Pro Leu Glu Asp Gly Thr
            435                 440                 445

Ala Gly Glu Gln Met Phe Asp Ala Leu Ser Arg Tyr Ala Ala Ile Pro
450                 455                 460

Gly Cys Ile Ala Leu Thr Asn Ala His Thr Lys Glu Asn Val Leu Tyr
465                 470                 475                 480

Glu Glu Phe Leu Lys Leu Ser Cys Arg Leu Ala Glu Ser Phe Lys Lys
            485                 490                 495

Tyr Gly Leu Lys Gln Asn Asp Thr Ile Ala Val Cys Ser Glu Asn Ser
            500                 505                 510

Leu Gln Phe Phe Leu Pro Val Ile Ala Ser Leu Tyr Leu Gly Ile Ile
            515                 520                 525

Val Ala Pro Val Asn Asp Lys Tyr Ile Glu Arg Glu Leu Ile His Ser
            530                 535                 540

Leu Gly Ile Val Lys Pro Arg Ile Val Phe Cys Ser Lys Asn Thr Phe
545                 550                 555                 560

Gln Lys Val Leu Asn Val Lys Ser Lys Leu Lys Ser Ile Glu Thr Ile
            565                 570                 575

Ile Ile Leu Asp Leu Asn Glu Asp Leu Gly Gly Tyr Gln Cys Leu Asn
            580                 585                 590

Asn Phe Ile Ser Gln Asn Ser Asp Ser Asn Leu Asp Val Lys Lys Phe
            595                 600                 605

Lys Pro Tyr Ser Phe Asn Arg Asp Asp Gln Val Ala Ser Ile Met Phe
            610                 615                 620

Ser Ser Gly Thr Thr Gly Leu Pro Lys Gly Val Met Leu Thr His Lys
625                 630                 635                 640

Asn Ile Val Ala Arg Phe Ser Ile Ala Lys Asp Pro Thr Phe Gly Asn
            645                 650                 655

Ala Ile Asn Pro Thr Ser Ala Ile Leu Thr Val Ile Pro Phe His His
            660                 665                 670

Gly Phe Gly Met Met Thr Thr Leu Gly Tyr Phe Thr Cys Gly Phe Arg
            675                 680                 685

Val Val Leu Met His Thr Phe Glu Glu Lys Leu Phe Leu Gln Ser Leu
            690                 695                 700

Gln Asp Tyr Lys Val Glu Ser Thr Leu Leu Val Pro Thr Leu Met Ala
705                 710                 715                 720

Phe Leu Ala Lys Ser Ala Leu Val Glu Lys Tyr Asp Leu Ser His Leu
            725                 730                 735

Lys Glu Ile Ala Ser Gly Gly Ala Pro Leu Ser Lys Glu Ile Gly Glu
            740                 745                 750

Met Val Lys Lys Arg Phe Lys Leu Asn Phe Val Arg Gln Gly Tyr Gly
            755                 760                 765

Leu Thr Glu Thr Thr Ser Ala Val Leu Ile Thr Pro Lys Gly Val Ser
            770                 775                 780

His Gln His Gln His Gln His Gln
785                 790

<210> SEQ ID NO 71
<211> LENGTH: 2583
<212> TYPE: DNA

<213> ORGANISM: Artificial
<220> FEATURE:
<223> OTHER INFORMATION: Synthetic

<400> SEQUENCE: 71

| | | | | | |
|---|---|---|---|---|---|
| atggcagaaa | tcggtactgg | ctttccattc | gaccccatt | atgtggaagt | cctgggcgag | 60 |
| cgcatgcact | acgtcgatgt | tggtccgcgc | gatggcaccc | ctgtgctgtt | cctgcacggt | 120 |
| aacccgacct | cctcctacgt | gtggcgcaac | atcatcccgc | atgttgcacc | gacccatcgc | 180 |
| tgcattgctc | cagacctgat | cggtatgggc | aaatccgaca | accagacct | ggttatttc | 240 |
| ttcgacgacc | acgtccgctt | catggatgcc | ttcatcgaag | ccctgggtct | ggaagaggtc | 300 |
| gtcctggtca | ttcacgactg | gggctccgct | ctgggtttcc | actgggccaa | gcgcaatcca | 360 |
| gagcgcgtca | aggtattgc | atttatggag | ttcatccgcc | ctatcccgac | ctgggacgaa | 420 |
| tggccagaat | tgcccgcga | gaccttccag | gccttccgca | ccaccgacgt | cggccgcaag | 480 |
| ctgatcatcg | atcagaacgt | ttttatcgag | ggtacgctgc | cgatgggtgt | cgtccgcccg | 540 |
| ctgactgaag | tcgagatgga | ccattaccgc | gagccgttcc | tgaatcctgt | tgaccgcgag | 600 |
| ccactgtggc | gcttcccaaa | cgagctgcca | atcgccggtg | agccagcgaa | catcgtcgcg | 660 |
| ctggtcgaag | aatacatgga | ctggctgcac | cagtcccctg | tcccgaagct | gctgttctgg | 720 |
| ggcaccccag | gcgttctgat | cccaccggcc | gaagccgctc | gcctggccaa | agcctgcct | 780 |
| aactgcaagg | ctgtggacat | cggcccgggt | ctgaatctgc | tgcaagaaga | caacccggac | 840 |
| ctgatcggca | gcgagatcgc | gcgctggctg | tcgacgctcg | agatttccgg | cgagccaacc | 900 |
| actgaggatc | tgtactttca | gagcgataac | gcgatcgcca | tgccgggatc | aactggtaaa | 960 |
| atagtaccat | tacacgctgt | taaagttgtc | gatcctacaa | caggaaaaat | tttggggcca | 1020 |
| aatgaacctg | gagaattgta | ttttaaaggc | ccgatgataa | tgaagggtta | ttataataat | 1080 |
| gaagaagcta | ctaaagcaat | tattgataat | gacggatggt | gcgctctgg | tgatattgct | 1140 |
| tattatgaca | atgatggcca | ttttatatt | gtggacaggc | tgaagtcact | gattaaatat | 1200 |
| aaaggttatc | aggttgcacc | tgctgaaatt | gagggaatac | tcttacaaca | tccgtatatt | 1260 |
| gttgatgccg | gcgttactgg | tataccggat | gaagccgcgg | gcgagcttcc | agctgcaggt | 1320 |
| gttgtagtac | agactggaaa | atatctaaac | gaacaaatcg | tacaagatta | tgttgccagt | 1380 |
| caagtttcaa | tagccaaatg | gctacgtggt | ggggtgaaat | ttttggatga | aattcccaaa | 1440 |
| ggatcaactg | gaaaaattga | cagaaaagtg | ttaagacaaa | tgttagaaaa | acacaccaat | 1500 |
| ggatccgacg | aggtggacgg | aagcttgaaa | aacatcctgt | atggtccgga | accgttctac | 1560 |
| ccactggaag | atggtaccgc | tggtgaacag | atgtttgacg | cattatctcg | ttatgcagct | 1620 |
| attccgggct | gcatagcatt | gacaaatgct | catacaaaag | aaaatgtttt | atatgaagag | 1680 |
| tttctgaaac | tgtcgtgtcg | tttagcggaa | agttttaaaa | agtatggatt | aaaacaaaac | 1740 |
| gacacaatag | cggtgtgtag | cgaaaatagt | ctgcaatttt | tccttcctgt | aattgcatca | 1800 |
| ttgtatcttg | gaataattgt | ggcacctgtt | aacgataaat | acattgaacg | tgaattaata | 1860 |
| cacagtcttg | gtattgtaaa | accacgcata | gttttttgct | ccaagaatac | ttttcaaaaa | 1920 |
| gtactgaatg | taaaatctaa | attaaaatct | attgaaacta | ttattatatt | agacttaaat | 1980 |
| gaagacttag | gaggttatca | atgcctcaac | aactttattt | ctcaaaattc | cgatagtaat | 2040 |
| ctggacgtaa | aaaaatttaa | accctattct | tttaatcgag | acgatcaggt | tgcgtcgatt | 2100 |
| atgttttctt | ctggtacaac | tggtctgccg | aagggagtca | tgctaactca | caagaatatt | 2160 |
| gttgcacgat | tttctattgc | aaaagatcct | acttttggta | acgcaattaa | tcccacgtca | 2220 |

```
gcaattttaa cggtaatacc tttccaccat ggtttggta tgatgaccac attaggatac    2280
tttacttgtg gattccgagt tgttctaatg cacacgtttg aagaaaaact atttctacaa    2340
tcattacaag attataaagt ggaaagtact ttacttgtac caacattaat ggcatttctt    2400
gcaaaaagtg cattagttga aaagtacgat ttatcgcact taaagaaat tgcatctggt    2460 ggcgcacctt tatcaaaaga aattggggag atggtgaaaa aacggtttaa attaaacttt    2520
gtcaggcaag ggtatggatt aacagaaacc acttcggctg ttttaattac accgaaaggt    2580
gtt                                                                  2583

<210> SEQ ID NO 72
<211> LENGTH: 861
<212> TYPE: PRT
<213> ORGANISM: Artificial
<220> FEATURE:
<223> OTHER INFORMATION: Synthetic

<400> SEQUENCE: 72

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285
```

-continued

```
Trp Leu Ser Thr Leu Glu Ile Ser Gly Glu Pro Thr Thr Glu Asp Leu
290                 295                 300

Tyr Phe Gln Ser Asp Asn Ala Ile Ala Met Pro Gly Ser Thr Gly Lys
305                 310                 315                 320

Ile Val Pro Leu His Ala Val Lys Val Val Asp Pro Thr Thr Gly Lys
            325                 330                 335

Ile Leu Gly Pro Asn Glu Pro Gly Glu Leu Tyr Phe Lys Gly Pro Met
            340                 345                 350

Ile Met Lys Gly Tyr Tyr Asn Glu Glu Ala Thr Lys Ala Ile Ile
            355                 360                 365

Asp Asn Asp Gly Trp Leu Arg Ser Gly Asp Ile Ala Tyr Tyr Asp Asn
370                 375                 380

Asp Gly His Phe Tyr Ile Val Asp Arg Leu Lys Ser Leu Ile Lys Tyr
385                 390                 395                 400

Lys Gly Tyr Gln Val Ala Pro Ala Glu Ile Glu Gly Ile Leu Leu Gln
                405                 410                 415

His Pro Tyr Ile Val Asp Ala Gly Val Thr Gly Ile Pro Asp Glu Ala
            420                 425                 430

Ala Gly Glu Leu Pro Ala Ala Gly Val Val Gln Thr Gly Lys Tyr
            435                 440                 445

Leu Asn Glu Gln Ile Val Gln Asp Tyr Val Ala Ser Gln Val Ser Ile
450                 455                 460

Ala Lys Trp Leu Arg Gly Val Lys Phe Leu Asp Glu Ile Pro Lys
465                 470                 475                 480

Gly Ser Thr Gly Lys Ile Asp Arg Lys Val Leu Arg Gln Met Leu Glu
                485                 490                 495

Lys His Thr Asn Gly Ser Asp Glu Val Asp Gly Ser Leu Lys Asn Ile
            500                 505                 510

Leu Tyr Gly Pro Glu Pro Phe Tyr Pro Leu Glu Asp Gly Thr Ala Gly
            515                 520                 525

Glu Gln Met Phe Asp Ala Leu Ser Arg Tyr Ala Ala Ile Pro Gly Cys
530                 535                 540

Ile Ala Leu Thr Asn Ala His Thr Lys Glu Asn Val Leu Tyr Glu Glu
545                 550                 555                 560

Phe Leu Lys Leu Ser Cys Arg Leu Ala Glu Ser Phe Lys Lys Tyr Gly
                565                 570                 575

Leu Lys Gln Asn Asp Thr Ile Ala Val Cys Ser Glu Asn Ser Leu Gln
            580                 585                 590

Phe Phe Leu Pro Val Ile Ala Ser Leu Tyr Leu Gly Ile Ile Val Ala
            595                 600                 605

Pro Val Asn Asp Lys Tyr Ile Glu Arg Glu Leu Ile His Ser Leu Gly
610                 615                 620

Ile Val Lys Pro Arg Ile Val Phe Cys Ser Lys Asn Thr Phe Gln Lys
625                 630                 635                 640

Val Leu Asn Val Lys Ser Lys Leu Lys Ser Ile Glu Thr Ile Ile Ile
                645                 650                 655

Leu Asp Leu Asn Glu Asp Leu Gly Gly Tyr Gln Cys Leu Asn Asn Phe
            660                 665                 670

Ile Ser Gln Asn Ser Asp Ser Asn Leu Asp Val Lys Lys Phe Lys Pro
            675                 680                 685

Tyr Ser Phe Asn Arg Asp Asp Gln Val Ala Ser Ile Met Phe Ser Ser
690                 695                 700

Gly Thr Thr Gly Leu Pro Lys Gly Val Met Leu Thr His Lys Asn Ile
```

```
                705                 710                 715                 720
Val Ala Arg Phe Ser Ile Ala Lys Asp Pro Thr Phe Gly Asn Ala Ile
                    725                 730                 735

Asn Pro Thr Ser Ala Ile Leu Thr Val Ile Pro Phe His His Gly Phe
                740                 745                 750

Gly Met Met Thr Thr Leu Gly Tyr Phe Thr Cys Gly Phe Arg Val Val
                    755                 760                 765

Leu Met His Thr Phe Glu Glu Lys Leu Phe Leu Gln Ser Leu Gln Asp
                770                 775                 780

Tyr Lys Val Glu Ser Thr Leu Leu Val Pro Thr Leu Met Ala Phe Leu
785                 790                 795                 800

Ala Lys Ser Ala Leu Val Glu Lys Tyr Asp Leu Ser His Leu Lys Glu
                    805                 810                 815

Ile Ala Ser Gly Gly Ala Pro Leu Ser Lys Glu Ile Gly Glu Met Val
                820                 825                 830

Lys Lys Arg Phe Lys Leu Asn Phe Val Arg Gln Gly Tyr Gly Leu Thr
                    835                 840                 845

Glu Thr Thr Ser Ala Val Leu Ile Thr Pro Lys Gly Val
                850                 855                 860

<210> SEQ ID NO 73
<211> LENGTH: 2616
<212> TYPE: DNA
<213> ORGANISM: Artificial
<220> FEATURE:
<223> OTHER INFORMATION: Synthetic

<400> SEQUENCE: 73
atgaaacatc aacatcagca ccaagcgatc gccatgccgg gatcaactgg taaaatagta     60
ccattacacg ctgttaaagt tgtcgatcct acaacaggaa aaattttggg gccaaatgaa    120
cctggagaat gtatttttaa aggcccgatg ataatgaagg ttattataa taatgaagaa     180 gctactaaag caattattga taatgacgga tggttgcgct ctggtgatat tgcttattat    240
gacaatgatg gccatttta tattgtggac aggctgaagt cactgattaa atataaaggt    300
tatcaggttg cacctgctga aattgaggga atactcttac aacatccgta tattgttgat    360
gccggcgtta ctggtatacc ggatgaagcc gcgggcgagc ttccagctgc aggtgttgta    420
gtacagactg aaaatatct aaacgaacaa atcgtacaag attatgttgc cagtcaagtt    480
tcaatagcca atggctacg tggtggggtg aaatttttgg atgaaattcc caaggatca    540 actgaaaaa ttgacagaaa agtgttaaga caaatgttag aaaaacacac caatggatcc    600
gacgaggtgg acggaagctt gaaaaacatc ctgtatggtc cggaaccgtt ctacccactg    660
gaagatggta ccgctggtga acagatgttt gacgcattat ctcgttatgc agctattccg    720
ggctgcatag cattgacaaa tgctcataca aagaaaatg ttttatatga gagtttctg    780 aaactgtcgt gtcgtttagc ggaaagtttt aaaagtatg gattaaaaca aaacgacaca    840
atagcggtgt gtagcgaaaa tagtctgcaa ttttccttc ctgtaattgc atcattgtat    900
cttggaataa ttgtggcacc tgttaacgat aaatacattg aacgtgaatt aatacacagt    960
cttggtattg taaaccacg catagttttt tgctccaaga atactttca aaaagtactg   1020 aatgtaaaat ctaaattaaa atctattgaa actattatta tattagactt aaatgaagac   1080
ttaggaggtt atcaatgcct caacaacttt atttctcaaa attccgatag taatctggac   1140 gtaaaaaat ttaaacccta ttcttttaat cgagacgatc aggttgcgtc gattatgttt   1200
```

```
tcttctggta caactggtct gccgaaggga gtcatgctaa ctcacaagaa tattgttgca    1260
cgattttcta ttgcaaaaga tcctactttt ggtaacgcaa ttaatcccac gtcagcaatt    1320
ttaacggtaa tacctttcca ccatggtttt ggtatgatga ccacattagg atactttact    1380
tgtggattcc gagttgttct aatgcacacg tttgaagaaa aactatttct acaatcatta    1440
caagattata aagtggaaag tactttactt gtaccaacat taatggcatt tcttgcaaaa    1500
agtgcattag ttgaaaagta cgatttatcg cacttaaaag aaattgcatc tggtggcgca    1560
cctttatcaa agaaattggg ggagatggtg aaaaaacggt ttaaattaaa ctttgtcagg    1620
caagggtatg gattaacaga aaccacttcg gctgttttaa ttacaccgaa aggtgtttct    1680
ctcgagccaa ccactgagga tctgtacttt cagagcgata cgatggatc cgaaatcggt    1740
actggctttc cattcgaccc ccattatgtg aagtcctgg gcgagcgcat gcactacgtc    1800
gatgttggtc cgcgcgatgg caccccctgtg ctgttcctgc acggtaaccc gacctcctcc    1860
tacgtgtggc gcaacatcat cccgcatgtt gcaccgaccc atcgctgcat tgctccagac    1920
ctgatcggta tgggcaaatc cgacaaacca gacctgggtt atttcttcga cgaccacgtc    1980
cgcttcatgg atgccttcat cgaagccctg gtctggaag aggtcgtcct ggtcattcac    2040
gactggggct ccgctctggg tttccactgg gccaagcgca atccagagcg cgtcaaaggt    2100
attgcattta tggagttcat ccgccctatc ccgacctggg acgaatggcc agaatttgcc    2160
cgcgagacct tccaggcctt ccgcaccacc gacgtcggcc gcaagctgat catcgatcag    2220
aacgttttta tcgagggtac gctgccgatg ggtgtcgtcc gcccgctgac tgaagtcgag    2280
atggaccatt accgcgagcc gttcctgaat cctgttgacc gcgagccact gtggcgcttc    2340
ccaaacgagc tgccaatcgc cggtgagcca gcgaacatcg tcgcgctggt cgaagaatac    2400
atggactggc tgcaccagtc ccctgtcccg aagctgctgt tctggggcac ccaggcgtt    2460
ctgatcccac cggccgaagc cgctcgcctg gccaaaagcc tgcctaactg caaggctgtg    2520
gacatcggcc cgggtctgaa tctgctgcaa gaagacaacc cggacctgat cggcagcgag    2580
atcgcgcgct ggctgtctac tctggagatt tccggt                              2616
```

<210> SEQ ID NO 74
<211> LENGTH: 872
<212> TYPE: PRT
<213> ORGANISM: Artificial
<220> FEATURE:
<223> OTHER INFORMATION: Synthetic

<400> SEQUENCE: 74

```
Met Lys His Gln His Gln His Gln Ala Ile Ala Met Pro Gly Ser Thr
1               5                   10                  15

Gly Lys Ile Val Pro Leu His Ala Val Lys Val Val Asp Pro Thr Thr
            20                  25                  30

Gly Lys Ile Leu Gly Pro Asn Glu Pro Gly Glu Leu Tyr Phe Lys Gly
        35                  40                  45

Pro Met Ile Met Lys Gly Tyr Tyr Asn Asn Glu Glu Ala Thr Lys Ala
    50                  55                  60

Ile Ile Asp Asn Asp Gly Trp Leu Arg Ser Gly Asp Ile Ala Tyr Tyr
65                  70                  75                  80

Asp Asn Asp Gly His Phe Tyr Ile Val Asp Arg Leu Lys Ser Leu Ile
                85                  90                  95

Lys Tyr Lys Gly Tyr Gln Val Pro Ala Glu Ile Glu Gly Ile Leu
            100                 105                 110
```

```
Leu Gln His Pro Tyr Ile Val Asp Ala Gly Val Thr Gly Ile Pro Asp
            115                 120                 125
Glu Ala Ala Gly Glu Leu Pro Ala Ala Gly Val Val Gln Thr Gly
        130                 135                 140
Lys Tyr Leu Asn Glu Gln Ile Val Gln Asp Tyr Val Ala Ser Gln Val
145                 150                 155                 160
Ser Ile Ala Lys Trp Leu Arg Gly Gly Val Lys Phe Leu Asp Glu Ile
                165                 170                 175
Pro Lys Gly Ser Thr Gly Lys Ile Asp Arg Lys Val Leu Arg Gln Met
            180                 185                 190
Leu Glu Lys His Thr Asn Gly Ser Asp Glu Val Asp Gly Ser Leu Lys
        195                 200                 205
Asn Ile Leu Tyr Gly Pro Glu Pro Phe Tyr Pro Leu Glu Asp Gly Thr
210                 215                 220
Ala Gly Glu Gln Met Phe Asp Ala Leu Ser Arg Tyr Ala Ala Ile Pro
225                 230                 235                 240
Gly Cys Ile Ala Leu Thr Asn Ala His Thr Lys Glu Asn Val Leu Tyr
                245                 250                 255
Glu Glu Phe Leu Lys Leu Ser Cys Arg Leu Ala Glu Ser Phe Lys Lys
            260                 265                 270
Tyr Gly Leu Lys Gln Asn Asp Thr Ile Ala Val Cys Ser Glu Asn Ser
        275                 280                 285
Leu Gln Phe Phe Leu Pro Val Ile Ala Ser Leu Tyr Leu Gly Ile Ile
        290                 295                 300
Val Ala Pro Val Asn Asp Lys Tyr Ile Glu Arg Glu Leu Ile His Ser
305                 310                 315                 320
Leu Gly Ile Val Lys Pro Arg Ile Val Phe Cys Ser Lys Asn Thr Phe
                325                 330                 335
Gln Lys Val Leu Asn Val Lys Ser Lys Leu Lys Ser Ile Glu Thr Ile
            340                 345                 350
Ile Ile Leu Asp Leu Asn Glu Asp Leu Gly Gly Tyr Gln Cys Leu Asn
        355                 360                 365
Asn Phe Ile Ser Gln Asn Ser Asp Ser Asn Leu Asp Val Lys Lys Phe
        370                 375                 380
Lys Pro Tyr Ser Phe Asn Arg Asp Asp Gln Val Ala Ser Ile Met Phe
385                 390                 395                 400
Ser Ser Gly Thr Thr Gly Leu Pro Lys Gly Val Met Leu Thr His Lys
                405                 410                 415
Asn Ile Val Ala Arg Phe Ser Ile Ala Lys Asp Pro Thr Phe Gly Asn
            420                 425                 430
Ala Ile Asn Pro Thr Ser Ala Ile Leu Thr Val Ile Pro Phe His His
        435                 440                 445
Gly Phe Gly Met Met Thr Thr Leu Gly Tyr Phe Thr Cys Gly Phe Arg
        450                 455                 460
Val Val Leu Met His Thr Phe Glu Glu Lys Leu Phe Leu Gln Ser Leu
465                 470                 475                 480
Gln Asp Tyr Lys Val Glu Ser Thr Leu Leu Val Pro Thr Leu Met Ala
                485                 490                 495
Phe Leu Ala Lys Ser Ala Leu Val Glu Lys Tyr Asp Leu Ser His Leu
            500                 505                 510
Lys Glu Ile Ala Ser Gly Gly Ala Pro Leu Ser Lys Glu Ile Gly Glu
        515                 520                 525
Met Val Lys Lys Arg Phe Lys Leu Asn Phe Val Arg Gln Gly Tyr Gly
```

```
                530                 535                 540
Leu Thr Glu Thr Thr Ser Ala Val Leu Ile Thr Pro Lys Gly Val Ser
545                 550                 555                 560

Leu Glu Pro Thr Thr Glu Asp Leu Tyr Phe Gln Ser Asp Asn Asp Gly
                565                 570                 575

Ser Glu Ile Gly Thr Gly Phe Pro Phe Asp Pro His Tyr Val Glu Val
                580                 585                 590

Leu Gly Glu Arg Met His Tyr Val Asp Val Gly Pro Arg Asp Gly Thr
                595                 600                 605

Pro Val Leu Phe Leu His Gly Asn Pro Thr Ser Ser Tyr Val Trp Arg
610                 615                 620

Asn Ile Ile Pro His Val Ala Pro Thr His Arg Cys Ile Ala Pro Asp
625                 630                 635                 640

Leu Ile Gly Met Gly Lys Ser Asp Lys Pro Asp Leu Gly Tyr Phe Phe
                645                 650                 655

Asp Asp His Val Arg Phe Met Asp Ala Phe Ile Glu Ala Leu Gly Leu
                660                 665                 670

Glu Glu Val Val Leu Val Ile His Asp Trp Gly Ser Ala Leu Gly Phe
                675                 680                 685

His Trp Ala Lys Arg Asn Pro Glu Arg Val Lys Gly Ile Ala Phe Met
690                 695                 700

Glu Phe Ile Arg Pro Ile Pro Thr Trp Asp Glu Trp Pro Glu Phe Ala
705                 710                 715                 720

Arg Glu Thr Phe Gln Ala Phe Arg Thr Thr Asp Val Gly Arg Lys Leu
                725                 730                 735

Ile Ile Asp Gln Asn Val Phe Ile Glu Gly Thr Leu Pro Met Gly Val
                740                 745                 750

Val Arg Pro Leu Thr Glu Val Glu Met Asp His Tyr Arg Glu Pro Phe
                755                 760                 765

Leu Asn Pro Val Asp Arg Glu Pro Leu Trp Arg Phe Pro Asn Glu Leu
                770                 775                 780

Pro Ile Ala Gly Glu Pro Ala Asn Ile Val Ala Leu Val Glu Glu Tyr
785                 790                 795                 800

Met Asp Trp Leu His Gln Ser Pro Val Pro Lys Leu Leu Phe Trp Gly
                805                 810                 815

Thr Pro Gly Val Leu Ile Pro Pro Ala Glu Ala Ala Arg Leu Ala Lys
                820                 825                 830

Ser Leu Pro Asn Cys Lys Ala Val Asp Ile Gly Pro Gly Leu Asn Leu
                835                 840                 845

Leu Gln Glu Asp Asn Pro Asp Leu Ile Gly Ser Glu Ile Ala Arg Trp
                850                 855                 860

Leu Ser Thr Leu Glu Ile Ser Gly
865                 870

<210> SEQ ID NO 75
<211> LENGTH: 7
<212> TYPE: PRT
<213> ORGANISM: Artificial
<220> FEATURE:
<223> OTHER INFORMATION: Synthetic

<400> SEQUENCE: 75

Pro Leu Gly Met Trp Ser Arg
1               5
```

```
<210> SEQ ID NO 76
<211> LENGTH: 10
<212> TYPE: PRT
<213> ORGANISM: Artificial
<220> FEATURE:
<223> OTHER INFORMATION: Synthetic

<400> SEQUENCE: 76

Gly Ser Ser Leu Glu Thr Asp Ser Ser Gly
1               5                   10

<210> SEQ ID NO 77
<211> LENGTH: 10
<212> TYPE: PRT
<213> ORGANISM: Artificial
<220> FEATURE:
<223> OTHER INFORMATION: Synthetic

<400> SEQUENCE: 77

Gly Ser Ser Asp Glu Val Asp Ser Ser Gly
1               5                   10

<210> SEQ ID NO 78
<211> LENGTH: 13
<212> TYPE: PRT
<213> ORGANISM: Artificial
<220> FEATURE:
<223> OTHER INFORMATION: Synthetic

<400> SEQUENCE: 78

Gly Ser Ser Glu Asn Leu Tyr Phe Gln Ser Ser Ser Gly
1               5                   10

<210> SEQ ID NO 79
<211> LENGTH: 10
<212> TYPE: PRT
<213> ORGANISM: Artificial
<220> FEATURE:
<223> OTHER INFORMATION: Synthetic

<400> SEQUENCE: 79

His Gln His Gln His Gln His Gln His Gln
1               5                   10

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Gly Arg Ile Glu Ala Asp Ser Glu
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Lys Ser Val Gly Pro Asp Phe Gly
1               5

<210> SEQ ID NO 82
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 82

Gly Ile Glu Thr Asp Ser Gly
1               5

<210> SEQ ID NO 83
<211> LENGTH: 4
<212> TYPE: PRT
<213> ORGANISM: Artificial Sequence
<220> FEATURE:
<223> OTHER INFORMATION: Synthetic

<400> SEQUENCE: 83

Ile Glu Ala Ala
1

<210> SEQ ID NO 84
<211> LENGTH: 4
<212> TYPE: PRT
<213> ORGANISM: Artificial Sequence
<220> FEATURE:
<223> OTHER INFORMATION: Synthetic

<400> SEQUENCE: 84

Ile Glu Thr Ala
1

<210> SEQ ID NO 85
<211> LENGTH: 4
<212> TYPE: PRT
<213> ORGANISM: Artificial Sequence
<220> FEATURE:
<223> OTHER INFORMATION: Synthetic

<400> SEQUENCE: 85

Val Gly Pro Ala
1
```